United States Patent
Morrow et al.

(10) Patent No.: US 11,260,079 B2
(45) Date of Patent: *Mar. 1, 2022

(54) DOSING REGIMENS FOR THE MOBILIZATION OF HEMATOPOIETIC STEM AND PROGENITOR CELLS

(71) Applicant: Magenta Therapeutics, Inc., Cambridge, MA (US)

(72) Inventors: Dwight Morrow, West Chester, PA (US); Patrick C. Falahee, Somerville, MA (US); Anthony Boitano, Newton, MA (US); Michael P. Cooke, Brookline, MA (US); Kevin A. Goncalves, Boston, MA (US)

(73) Assignee: Magenta Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/352,578

(22) Filed: Mar. 13, 2019

(65) Prior Publication Data

US 2019/0269735 A1 Sep. 5, 2019

Related U.S. Application Data

(63) Continuation of application No. PCT/US2018/064335, filed on Dec. 6, 2018, which is a continuation-in-part of application No. 16/101,676, filed on Aug. 13, 2018, which is a continuation of application No. 15/834,017, filed on Dec. 6, 2017, now Pat. No. 10,058,573.

(60) Provisional application No. 62/753,656, filed on Oct. 31, 2018, provisional application No. 62/773,954, filed on Nov. 30, 2018, provisional application No. 62/596,056, filed on Dec. 7, 2017.

(51) Int. Cl.
| | |
|---|---|
| *A61K 35/28* | (2015.01) |
| *A61P 37/00* | (2006.01) |
| *A61K 45/06* | (2006.01) |
| *A61K 31/4427* | (2006.01) |
| *A61K 35/12* | (2015.01) |
| *C12N 5/0789* | (2010.01) |

(52) U.S. Cl.
CPC .......... *A61K 35/28* (2013.01); *A61K 31/4427* (2013.01); *A61K 45/06* (2013.01); *A61P 37/00* (2018.01); *C12N 5/0647* (2013.01); *A61K 2035/124* (2013.01)

(58) Field of Classification Search
CPC .... A61K 35/28; A61K 45/06; A61K 31/4427; A61K 2035/124; A61K 38/19; A61K 31/395; A61P 37/00; C12N 5/0647
See application file for complete search history.

(56) References Cited

U.S. PATENT DOCUMENTS

| | | |
|---|---|---|
| 5,021,409 A | 6/1991 | Murrer et al. |
| 5,583,131 A | 12/1996 | Bridger et al. |
| 5,698,546 A | 12/1997 | Bridger et al. |
| 6,080,398 A | 6/2000 | Pelus et al. |
| 6,447,766 B1 | 9/2002 | Pelus et al. |
| 6,987,102 B2 | 1/2006 | Bridger et al. |
| 7,935,692 B2 | 5/2011 | Bridger et al. |
| 9,580,426 B2 | 2/2017 | Boitano et al. |
| 10,058,573 B1 | 8/2018 | Morrow et al. |
| 2006/0035829 A1 | 2/2006 | Bridger et al. |
| 2010/0178271 A1 | 7/2010 | Bridger et al. |
| 2019/0167726 A1 | 6/2019 | Morrow et al. |
| 2019/0269735 A1 | 9/2019 | Morrow et al. |
| 2019/0328706 A1 | 10/2019 | Ruminski et al. |
| 2019/0336536 A1 | 11/2019 | Morrow et al. |

FOREIGN PATENT DOCUMENTS

| | | |
|---|---|---|
| WO | WO-1999050461 A1 | 10/1999 |
| WO | WO-2000002870 A1 | 1/2000 |
| WO | WO-2000056729 A1 | 9/2000 |
| WO | WO-2001044229 A1 | 6/2001 |
| WO | WO-2001085196 A2 | 11/2001 |
| WO | WO-2001094420 A1 | 12/2001 |
| WO | WO-2003090512 A2 | 11/2003 |
| WO | WO-2005000333 A1 | 1/2005 |
| WO | WO-2007047882 A2 | 4/2007 |

(Continued)

OTHER PUBLICATIONS

Schroeder et al., Blood, 129(19):2680-2692 (2017) (Year: 2017).*
Invitation to Pay Additional Fees And, Where Applicable, Protest Fee dated Apr. 15, 2019, PCT/US2018/064335, 22 pages.
U.S. Appl. No. 15/834,017 (U.S. Pat. No. 10,058,573), Dosing Regimens for the Mobilization of Hematopoietic Stem Cells, filed Dec. 6, 2017.
U.S. Appl. No. 16/101,676, Dosing Regimens for the Mobilization of Hematopoietic Stem Cells, filed Aug. 13, 2018.
U.S. Appl. No. 16/212,497, Dosing Regimens for the Mobilization of Hematopoietic and Progenitor Stem Cells, filed Dec. 6, 2018.

(Continued)

*Primary Examiner* — Kade Ariani
(74) *Attorney, Agent, or Firm* — Goodwin Procter LLP

(57) ABSTRACT

The invention provides compositions and methods useful for mobilizing populations of hematopoietic stem and progenitor cells within a donor, as well as for determining whether samples of mobilized cells are suitable for release for ex vivo expansion and/or therapeutic use. In accordance with the compositions and methods described herein, mobilized hematopoietic stem and progenitor cells can be withdrawn from a donor and administered to a patient for the treatment of various stem cell disorders, including hematopoietic diseases, metabolic disorders, cancers, and autoimmune diseases, among others. In certain embodiments, the compositions and methods described herein lead to the mobilization of a population of $CD34^{dim}$ cells that have immunosuppressive effects and that can reduce the incidence of graft vs. host disease.

23 Claims, 32 Drawing Sheets

Specification includes a Sequence Listing.

(56) References Cited

FOREIGN PATENT DOCUMENTS

| WO | WO-2008017025 A2 | 2/2008 |
| WO | WO-2008019371 A1 | 2/2008 |
| WO | WO-2014134539 A1 | 9/2014 |
| WO | WO-2017147610 A1 | 8/2017 |
| WO | 2019113375 A2 | 6/2019 |
| WO | WO2021087406 | 5/2021 |

OTHER PUBLICATIONS

Dominietto et al. (2002) "Transplant-related mortality and long-term graft function are significantly influenced by cell dose in patients undergoing allogeneic marrow transplantation," Blood 100(12):3930-3934.

Arbez, et al., "Impact of donor hematopoietic cells mobilized with G-CSF and plerixafor on murine acute graft-versus-host-disease." Cytotherapy, (2015) vol. 17. pp. 948-955.

Bendall, et al., "G-CSF: From granulopoietic stimulant to bone marrow stem cell mobilizing agent,": Cytokine & Growth Factor Reviews, (2014) vol. 25, pp. 355-367.

Bonig, et al., "Hematopoietic stem cell mobilization: updated conceptual renditions," Spotlight Review Leukemia, (2013), vol. 27, pp. 24-31.

Broxmeyer, et al., "Rapid mobilization of murine and human hematopoietic stem and progenitor cells with AMD3100, a CXCR4 antagonist," The Journal of Experimental Medicine, (2005), vol. 207, No. 8, pp. 1307-1318.

Devine, et al. "Rapid mobilization of functional donor hematopoietic cells without G-CSF using AMD3100, an antagonist of the CXCR4/SDF-1 interaction," Blood, (2008) vol. 112, No. 4, pp. 990-998.

DiPersio, et al., "Phase III Prospective Randomized Double-Blind Placebo-Controlled Trial of Plerixafor Plus Granulocyte Colony-Stimulating Factor Compared with Placebo Plus Granulocyte Colony-Stimulating Factor for Autologous Stem-Cell Mobilization and Transplantation for Patients with Non-Hodgkin's Lymphoma," Journal of Clinical Oncology, (2009), vol. 27, No. 28, pp. 4767-4773.

DiPersio, et al., "Plerixafor and G-CSF versus placebo and G-CSF to mobilize hematopoietic stem cells for autologous stem cell transplantation in patients with multiple myeloma," Blood, (2009), vol. 113, No. 23, pp. 5720-5726.

Domingues, et al., "New agents in HSC mobilization," International Journal Hematol, (2017), vol. 105, pp. 141-152.

Donahue, et al., "Plerixafor (AMD3100) and granulocyte colony-stimulating factor (G-CSF) mobilize different CD34+ cell populations based on global gene and microRNA expression signatures," Blood, (2009), vol. 114, No. 12, pp. 2530-2541.

Fukuda, et al., "The chemokine GROβ mobilizes early hematopoietic stem cells characterized by enhanced homing and engraftment," Blood, (2007), vol. 110, No. 3, pp. 860-869.

Green, et al., "Plerixafor (a CXCR4 antagonist) following myeloablative allogeneic hematopoietic stem cell transplantation enhances hematopoietic recovery," Journal of Hematology & Oncology, (2016), vol. 9, No. 71, 10 pages.

Thaker, et al., "Plerixafor-mobilized stem cells alone are capable of inducing early engraftment across the MHC-haploidentical canine barrier," Blood, (2010), vol. 115, No. 4, pp. 916-917.

He et al., "FLT3L and Plerixafor Combination Increases Hematopoitic Stem Cell Mobilization and Leads to Improved Transplantation Outcome," Biol Blood Marrow Transplant, (2014), vol. 20, pp. 309-313.

Hendrix, et al., "Pharmacokinetics and Safety of AMD-3100, a Novel Antagonist of the CXCR-4 Chemokine Receptor, in Human Volunteers," Antimicrobial Agents and Chemotherapy, (2000), Vo. 44, No. 6, pp. 1667-1673.

Hoggatt, et al., "Prostaglandin E2 enhances long-term repopulation but does not permanently alter inherent stem cell competitiveness," Blood, (2013), vol. 122, No. 17, pp. 2997-3000.

Hoggatt et al., "Rapid Mobilization Reveals a Highly Engraftable Hematopoietic Stem Cell," Cell, (2018), vol. 172, pp. 1-14.

Kang, et al., "Selective Enhancement of Donor Hematopoietic Cell Engraftment by the CXCR4 Antagonist AMD3100 in a Mouse Transplantation Model," Plos One, (2010), vol. 5, Issue 6, pp. 1-14.

Karponi, et al., "Plerixafor+G-CSF-mobilized CD34+ cells represent an optimal graft source for thalassemia gene therapy," Blood, (2015), vol. 126, pp. 616-619.

Kean, et al., "Significant mobilization of both conventional and regulatory T cells with AMD3100," Blood, (2011), vol. 118, No. 25, pp. 6580-6590.

King, et al., "Identification of Unique Truncated KC/GRO β Chemokines with Potent Hematopoietic and Anti-Infective Activities," Journal of Immunology, (2000), vol. 164, pp. 3774-3782.

King, et al., "Rapid mobilization of murine hematopoietic stem cells with enhanced engraftment properties and evaluation of hematopoietic progenitor cell mobilization in rhesus monkeys by a single injection of SB-251353, a specific truncated form of the human CXC chemokine GROβ," Blood, (2001), vol. 97, No. 6, pp. 1534-1542.

Lack, et al., "A pharmacokinetic-pharmacodynamic model for the mobilization of CD34+ hematopoietic progenitor cells by AMD3100," Clinical Pharmacology & Therapeutics, (2005), pp. 427-436.

Larochelle, et al., "AMD3100 mobilizes hematopoietic stem cells with long-term repopulating capacity in nonhuman primates," Blood, (2006), vol. 107, No. 9, pp. 3772-3778.

Liles, et al., "Mobilization of hematopoietic progenitor cells in healthy volunteers by AMD3100, a CXCR4 antagonist," Blood, (2003),vol. 102, No. 8, pp. 2728-2730.

Pelus, et al., "Peripheral blood stem cell mobilization A role for CXC chemokines," Critical Reviews in Oncology Hematology, (2002), vol. 43, pp. 257-275.

Pelus, et al., "Neutrophil-derived MMP-9 mediates synergistic mobilization of hematopoietic stem and progenitor cells by the combination of G-CSF and chemokines GROβ/CXCL2 and GROβT/CXCL2Δ4," Blood, (2004), vol. 103, No. 1, pp. 110-119.

Pelus, et al., "Peripheral blood stem cell mobilization: new regimens, new cells, where do we stand," Curr Opin Hematol, (2008), vol. 15, No. 4, pp. 285-292.

Pelus et al., "The CXCR4 Antagonist AMD3100 and the CXCR2 Agonist Groβ Synergistically Mobilize Hematopoetic Stem Cells (HSC) with Short and Long Term Repopulating Activity," American Society of Hematology Annual Meeting (Dec. 9-12, 2006), PowerPoint Presentation accompanying oral presentation, 11 pages.

Pelus et al., "The Combination of AMD3100 plus GROβ Rapidly Mobilizes Hematopoietic Stem Cells with Enhanced Homing, Adhesion and Survival Properties," American Society of Hematology Annual Meeting (Dec. 6-9, 2008), PowerPoint Presentation accompanying oral presentation, 13 pages.

Hoggatt et al., "Hematopoietic Stem Cell Mobilization with Agents other than G-CSF," in Stem Cell Mobilization: Methods and Protocols, Methods in Molecular Biology, (2012), vol. 904, Chapter 4, pp. 49-67.

Shaughnessy, et al., "Plerixafor and G-CSF for autologous stem cell mobilization in patients with NHL, Hodgkin's lymphoma and multiple myeloma: results from the expanded access program," Bone Marrow Transplantation, (2013), vol. 48, pp. 777-781.

Tay, et al., "Cellular player of hematopoietic stem cell mobilization in the bone marrow niche," Int J Hematol, (2017), vol. 105, pp. 129-140.

Verda, et al., "Effect of hematopoietic growth factors on severity of experimental autoimmune encephalomyelitis," Bone Marrow Transplantation, (2006), vol. 38, pp. 453-460.

Winkler, et al., "Hematopoietic stem cell mobilizing agents G-CSF, cyclophosphamide or AMD3100 have distinct mechanisms of action on bone marrow HSC niches and bone formation," Leukemia, (2012), vol. 26, pp. 1594-1601.

Nair et al. (2016) "A simple practice guide for dose conversion between animals and human," *J Basic Clin Pharma* 7:27-31.

Okpala (2004) "The intriguing contribution of white blood cells to sickle cell disease—a red cell disorder," *Blood Reviews* 18:65-73.

Blau (2001) "Adverse effects of G-CSF in sickle cell syndromes," *Blood Journal* 97(12):3682.

Fitzhugh et al. (2009) "Granulocyte Colony-Stimulating Factor (G-CSF) Administration in Individuals with Sickle Cell Disease: Time for a Moratorium?" *Cytotherapy* 11(4):464-471.

(56) References Cited

OTHER PUBLICATIONS

Majeti et al. (2007) "Identification of a Hierarchy of Multipotent Hematopoietic Progenitors in Human Cord Blood," Cell Stem Cell 1(6):635-645.
Falahee et al. (2017) "The Combination of Groβ and AMD3100 Leads to Rapid and Robust Mobilization of Hematopoietic Stem Cells in Nonhuman Primates," *Blood* 130:1920. Available online Nov. 1, 2017.
International Search Report and Written Opinion dated Jun. 14, 2019 for International Application No. PCT/US2018/064335, 26 pages.
Pelus et al., "Suprasynergistic Peripheral Blood Stem Cell Mobilization in Normal and Fanconi Anemia Knockout Mice by the Combination of G-CSF Plus the CXCR4 Antagonist AMD3100 and the CXCR2 Agonist GROβ," American Society of Hematology Annual Meeting (Dec. 9-12, 2006), Poster presentation, 1 page.
International Search Report and the Written Opinion of the International Searching Authority, or the Declaration, Int'l Application No. PCT/US2020/058420, dated Mar. 3, 2021, 16 pages.

\* cited by examiner

FIG. 3B
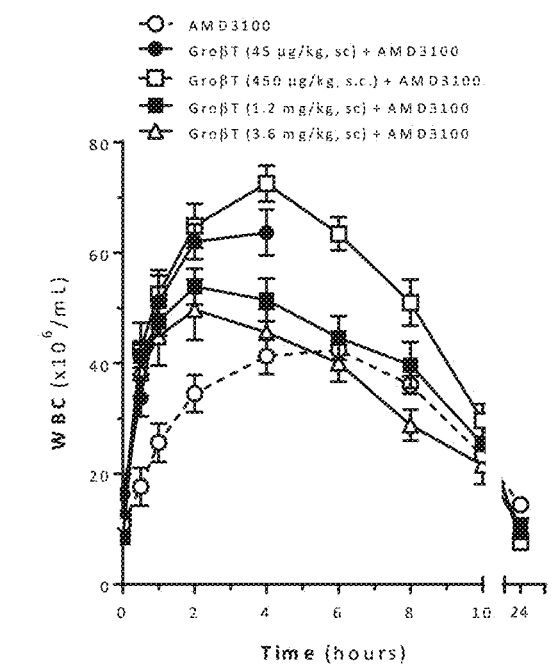
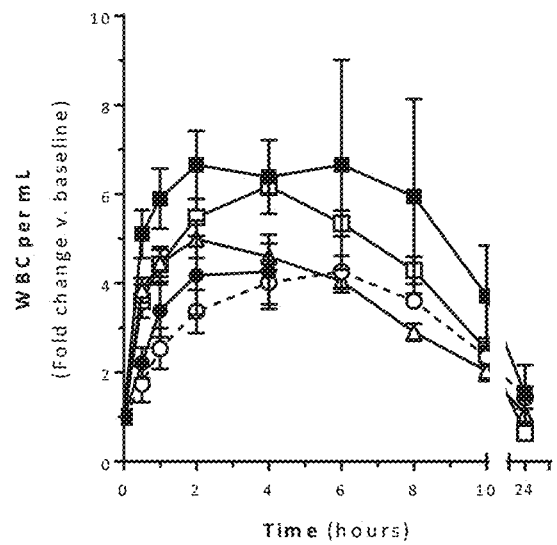

FIG. 4B
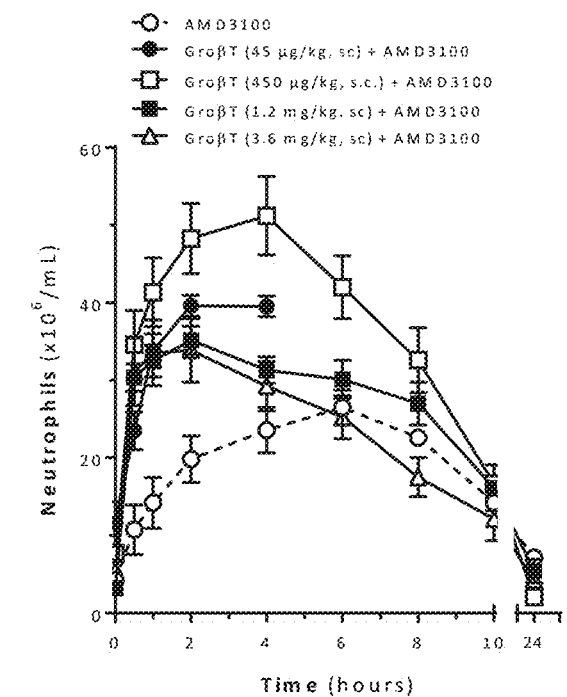
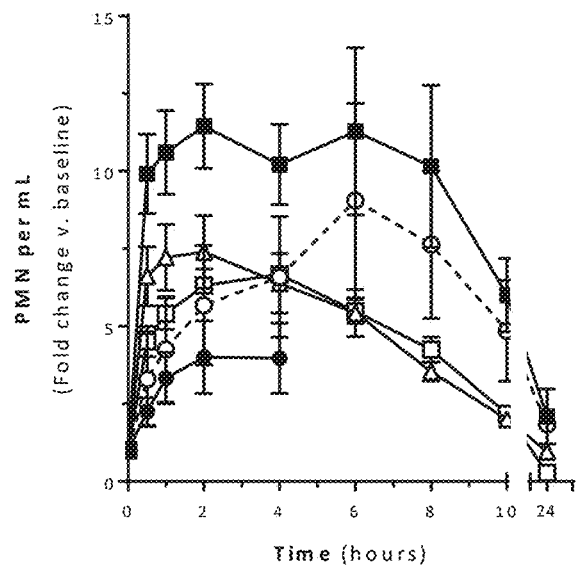

FIG. 5A
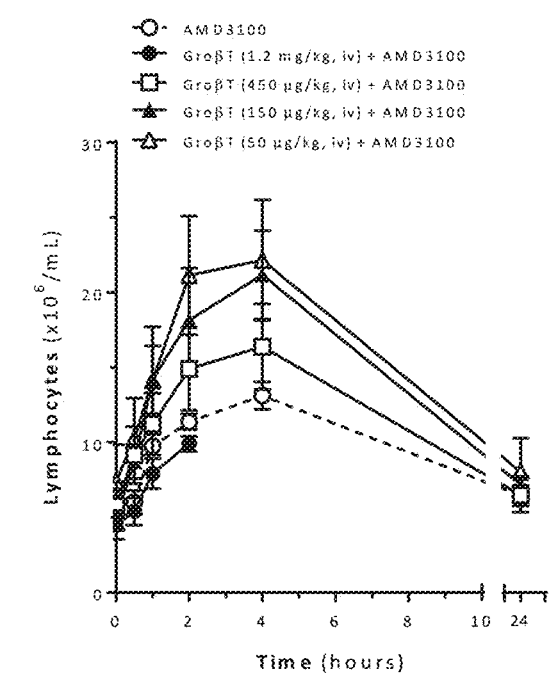
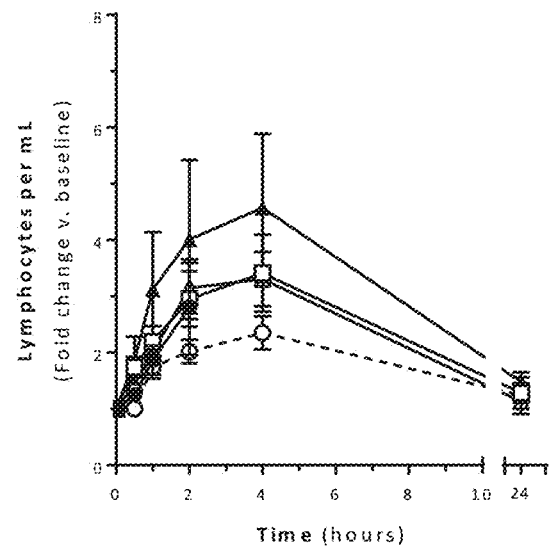

FIG. 5B
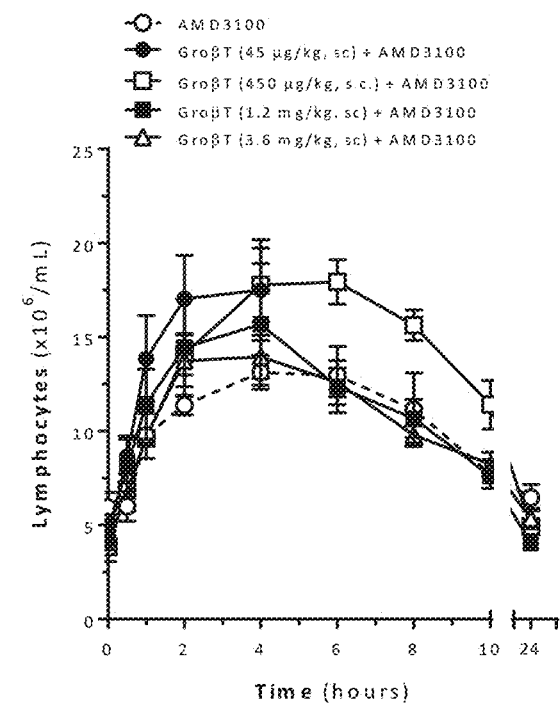
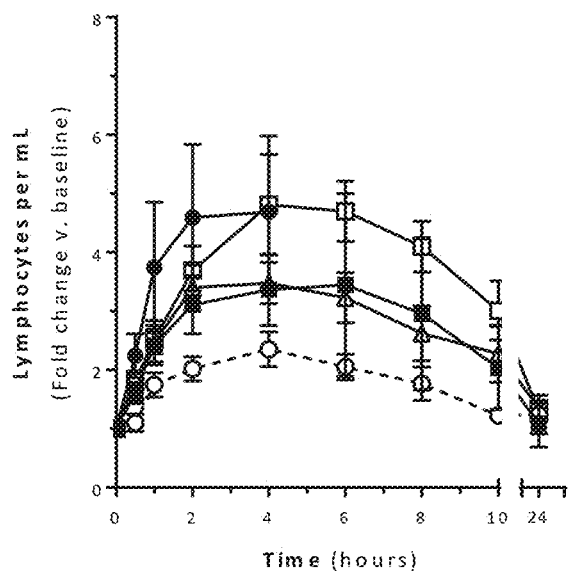

FIG. 6A
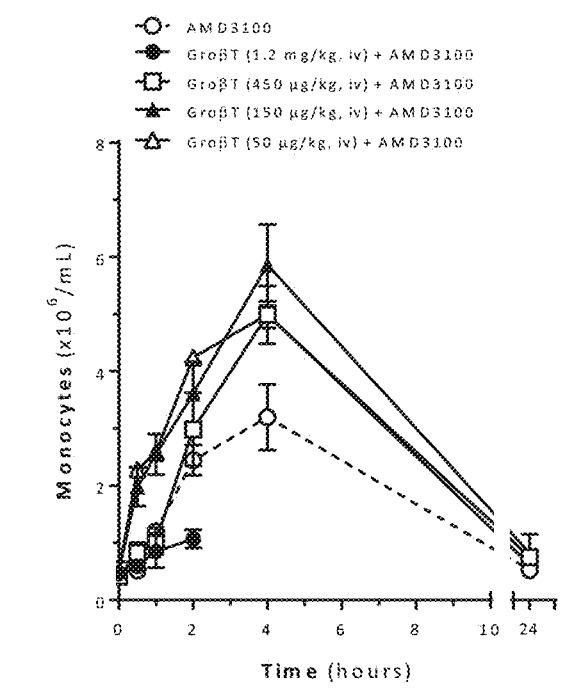
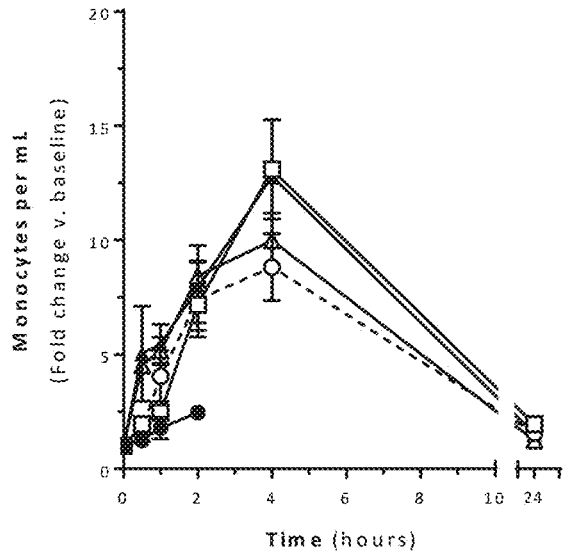

FIG. 6B
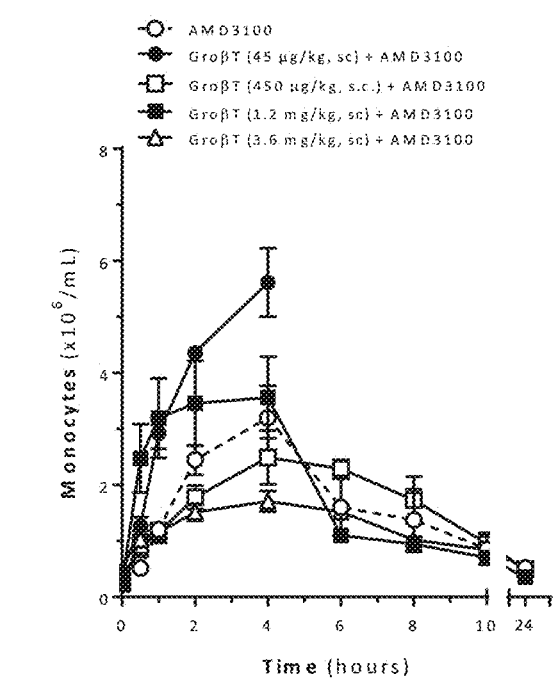
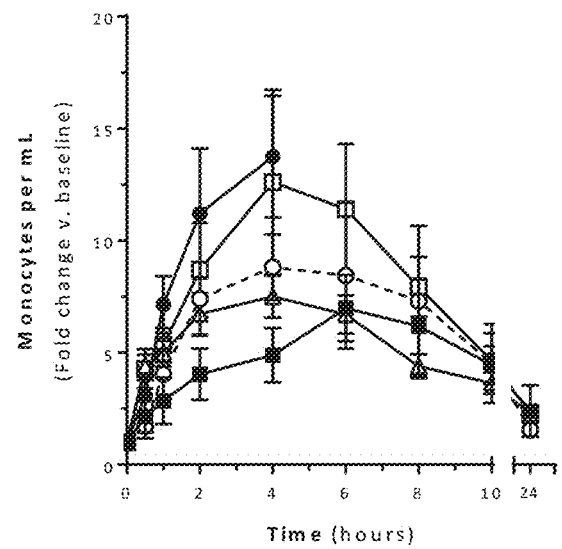

FIG. 7A
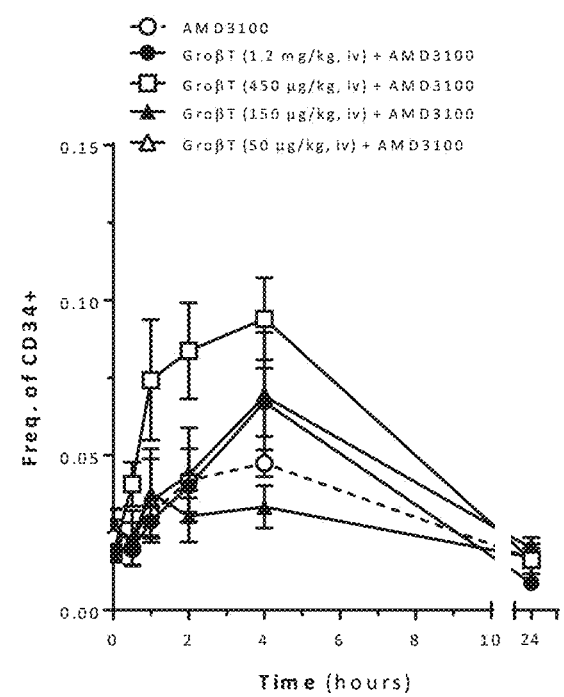
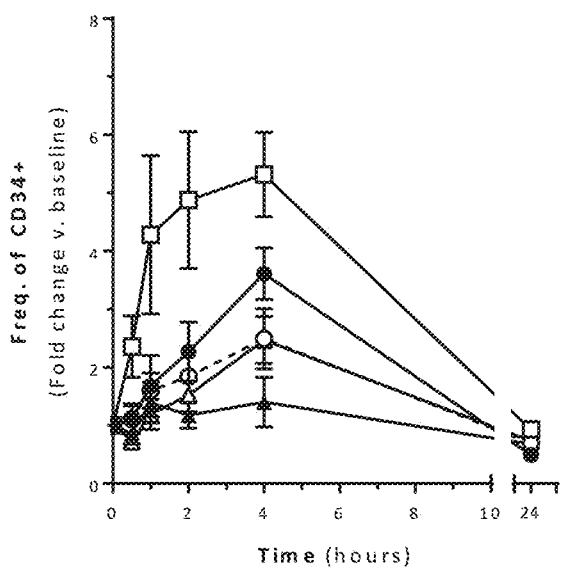

FIG. 8A
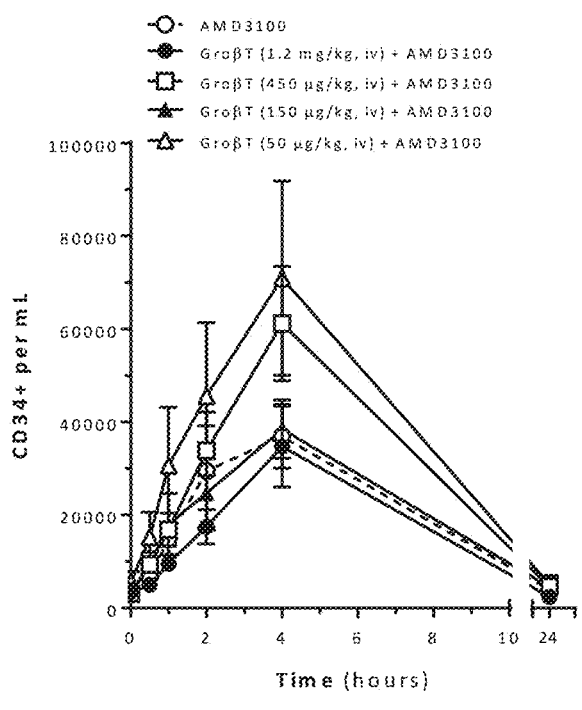
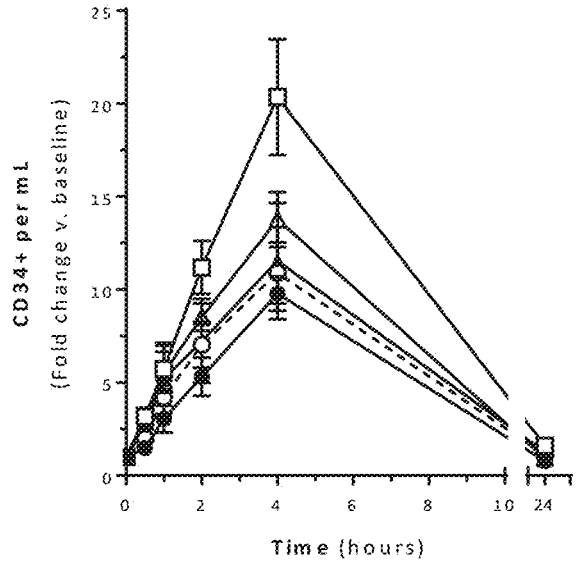

FIG. 8B
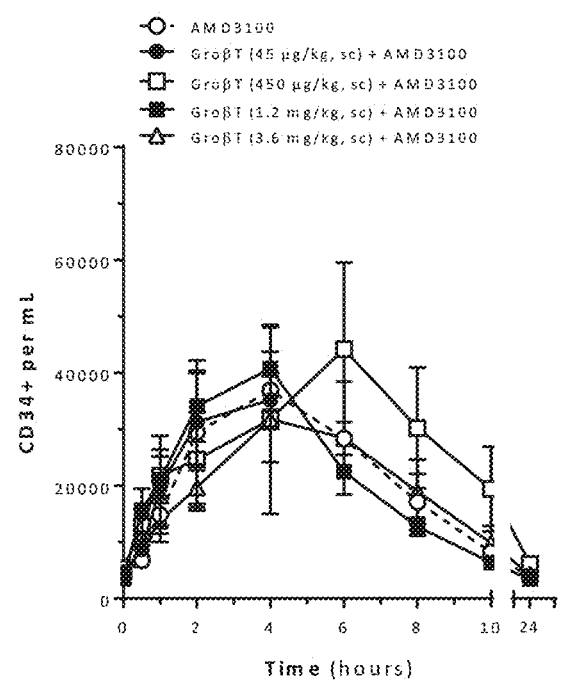
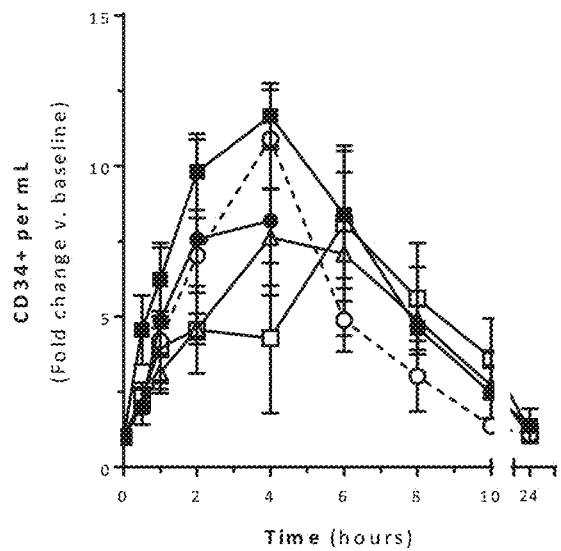

FIG. 9A
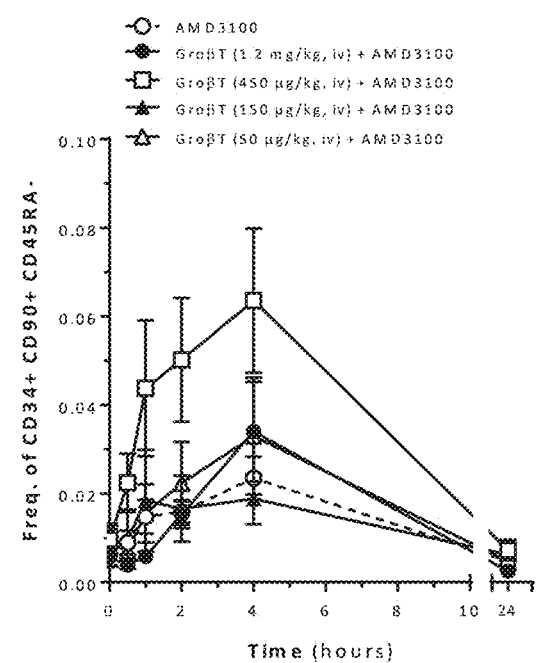
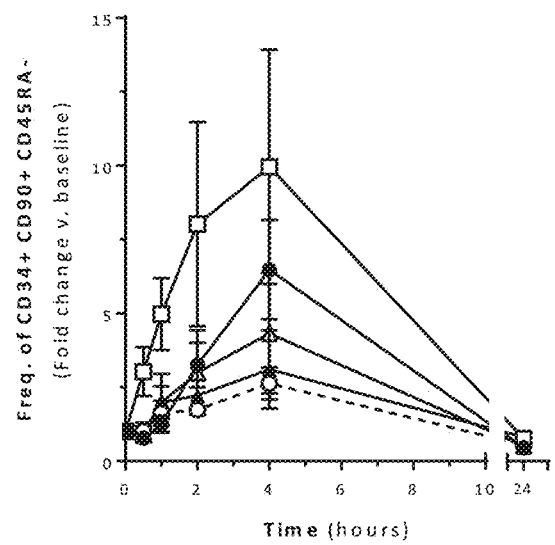

FIG. 11
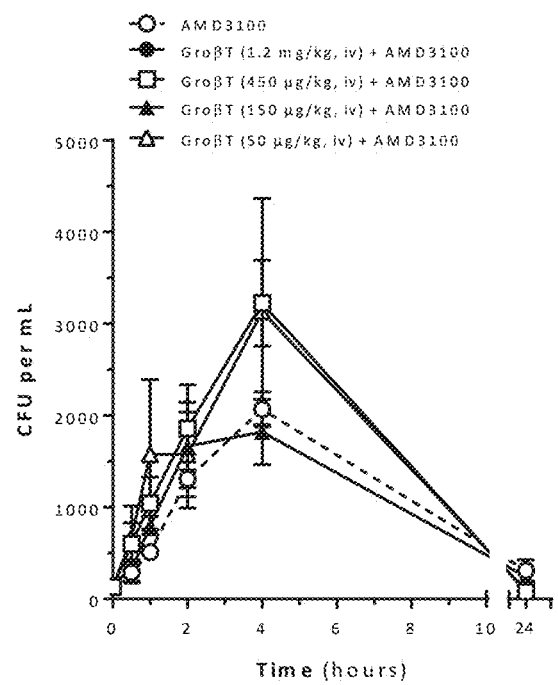
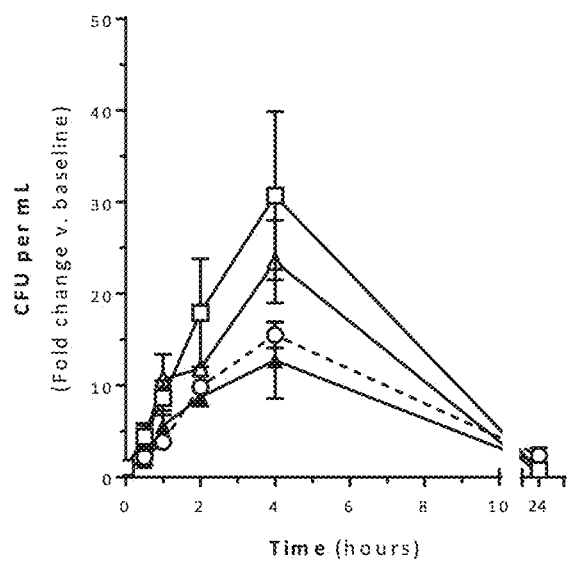

FIG. 13A
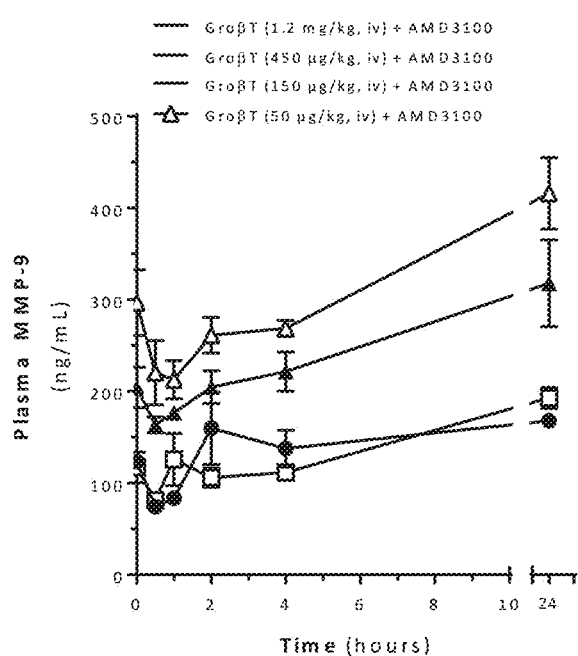
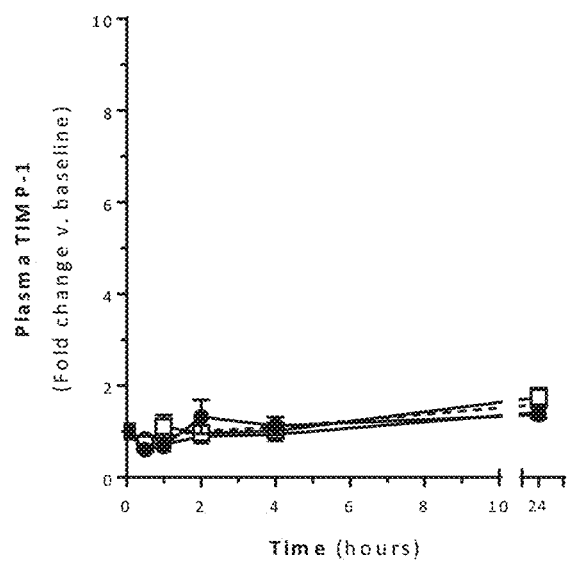

Fig. 16: Gro-βT + plerixafor mobilizes a population of CD34$^{dim}$ cells in rhesus macaques ID DOSING REGIMENS FOR THE MOBILIZATION OF HEMATOPOIETIC STEM AND PROGENITOR CELLS

CROSS REFERENCE TO RELATED APPLICATIONS

This application is a continuation of International Patent Application No. PCT/US2018/064335, filed on Dec. 6, 2018, which (1) claims the benefit of and priority to U.S. Provisional Patent Application No. 62/596,056, filed on Dec. 7, 2017, U.S. Provisional Patent Application No. 62/753,656, filed on Oct. 31, 2018, and U.S. Provisional Patent Application No. 62/773,954, filed on Nov. 30, 2018, and which (2) is a continuation-in-part of U.S. application Ser. No. 16/101,676, filed on Aug. 13, 2018, which is a continuation of U.S. application Ser. No. 15/834,017, filed on Dec. 6, 2017. The disclosure of each of the foregoing is hereby incorporated by reference in its entirety.

FIELD OF THE INVENTION

The invention relates to the mobilization of hematopoietic stem and progenitor cells from a donor, such as a human donor, and to the treatment of patients suffering from various pathologies, such as blood diseases, metabolic disorders, cancers, and autoimmune diseases, among others.

BACKGROUND OF THE INVENTION

Despite advances in the medicinal arts, there remains a demand for treating pathologies of the hematopoietic system, such as diseases of a particular blood cell, metabolic disorders, cancers, and autoimmune conditions, among others. While hematopoietic stem cells have significant therapeutic potential, a limitation that has hindered their use in the clinic has been the difficulty associated with releasing hematopoietic stem cells from the bone marrow into the peripheral blood of a donor, from which the hematopoietic stem cells may be isolated for infusion into a patient.

A further limitation is that up to 80% of mobilized peripheral blood (mPB) allogeneic recipients will experience graft-versus-host disease (GVHD). Despite the higher levels of CD3+ T cells in mPB grafts compared to bone marrow transplants, the level of acute GVHD observed following transplant of HLA-matched mPB is comparable to HLA-matched bone marrow. One explanation is that G-CSF mobilized grafts contain myeloid-derived suppressor cells (MDSCs) possessing potent immunosuppressive properties capable of inhibiting T cell proliferation in vitro. The percentage of MDSCs is variable in grafts mobilized with G-CSF, and clinical data suggest that patients transplanted with mPB grafts that contain higher numbers of MDSCs may have better outcomes including lower rates of acute GVHD (Vendramin et al., (2014) *BBMT* 20(12):2049-2055).

Accordingly, there is currently a need for compositions and methods for promoting the mobilization of hematopoietic stem and progenitor cells, and particularly for methods of identifying populations of mobilized cells that are suitable for therapeutic use. There is also a need for compositions and methods for promoting the mobilization of hematopoietic stem and progenitor cells that consistently produce higher numbers of MDSCs than do prior art methods.

SUMMARY OF THE INVENTION

The present invention provides compositions and methods for mobilizing hematopoietic stem and progenitor cells in a subject. For example, the subject may be a hematopoietic stem and progenitor cell donor (i.e., a donor), such as a mammalian donor, and particularly a human donor. The invention additionally provides compositions and methods for the treatment of disorders, such as stem cell disorders, in a patient, such as a human patient. Using the compositions and methods described herein, a C-X-C chemokine receptor type 2 (CXCR2) agonist, such as Gro-β or a variant thereof, such as a truncated form of Gro-β (e.g., Gro-β T), as described herein, optionally in combination with a C-X-C chemokine receptor type 4 (CXCR4) antagonist, such as 1,1'-[1,4-phenylenebis(methylene)]-bis-1,4,8,11-tetra-azacyclotetradecane or a variant thereof, may be administered to a subject in amounts sufficient to mobilize hematopoietic stem and progenitor cells. Significantly, the compositions and methods described herein may be used to mobilize hematopoietic stem and progenitor cells from a stem cell niche within a donor, such as a human donor, into the circulating peripheral blood of the donor while reducing the mobilization of other cells of the hematopoietic lineage, such as white blood cells, neutrophils, lymphocytes, and monocytes. The compositions and methods described herein thus enable the selective mobilization of hematopoietic stem and progenitor cells in a donor, which may then be isolated from a donor for therapeutic use.

In some embodiments, the hematopoietic stem or progenitor cells may be mobilized from the bone marrow of the donor to the peripheral blood, from which the hematopoietic stem or progenitor cells may be collected and/or isolated. Upon collection of the mobilized cells, the withdrawn hematopoietic stem or progenitor cells may then be infused into a patient, which may be the donor or another subject, such as a subject that is HLA-matched to the donor, for the treatment of one or more pathologies of the hematopoietic system. In some embodiments, the withdrawn hematopoietic stem or progenitor cells are first expanded ex vivo prior to infusion of these cells, and/or progeny thereof, into the patient. The compositions and methods described herein provide the important clinical benefit of enabling the production of populations of cells that are enriched in hematopoietic stem cells relative to other cell types, such as leukocytes, neutrophils, and monocytes. Thus, the populations of mobilized hematopoietic stem and progenitor cells produced using the compositions and methods described herein are particularly suitable for hematopoietic stem cell transplantation therapy, optionally preceded by ex vivo expansion in order to increase the quantity of hematopoietic stem and progenitor cells available for infusion into a patient.

Further, the methods described herein provide the advantage of inhibiting leukocytosis in the donor. Leukocytosis may lead to adverse effects such as splenic rupture, renal dysfunction, acute febrile noninfectious pneumonitis (i.e., pulmonary toxicity), cardiovascular toxicity (e.g., hypercoagulation, heart attack, dyspnea, angina, arrhythmia, atherosclerotic plaque rupture due to proinflammatory actions related o high neutrophil counts), neurological disturbances (e.g., blurred vision, headache, and retinal hemorrhage), and sickle cell crisis. See, e.g., D'Souza et al. (2008) *Transfusion Medicine Reviews* 22(4):280-290.

As described herein, hematopoietic stem cells are capable of differentiating into a multitude of cell types in the hematopoietic lineage and can thus be administered to a patient in order to populate or repopulate a cell type that is defective or deficient in the patient. The patient may be one, for example, that is suffering from one or more blood disorders, such as an autoimmune disease, cancer, hemoglobinopathy, or other hematopoietic pathology, and is therefore in need of hematopoietic stem cell transplantation. The invention thus provides methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, as well as cancers and autoimmune diseases, among others.

In a first aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of $CD34^+$ cells to leukocytes of from about 0.0008 to about 0.0021 in a sample of peripheral blood of the donor following administration of the CXCR2 agonist and CXCR4 antagonist. In some embodiments, the ratio of $CD34^+$ cells to leukocytes in the sample may be about 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, or 0.00225. In some embodiments, the ratio of $CD34^+$ cells to leukocytes in the sample is from about 0.0009 to about 0.002, about 0.001 to about 0.0019, about 0.0011 to about 0.0018, about 0.0012 to about 0.0017, about 0.0013 to about 0.0016, or about 0.0014 to about 0.0015. In some embodiments, the ratio of $CD34^+$ cells to leukocytes in the sample is from about 0.0010 to about 0.0018, such as a ratio of hematopoietic stem cells to leukocytes in the sample of about 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00178, 0.00179, or 0.00180. In some embodiments, the ratio of $CD34^+$ cells to leukocytes in the sample is from about 0.0012 to about 0.0016, such as a ratio of $CD34^+$ cells to leukocytes in the sample of about 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, or 0.00160. In some embodiments, the ratio of $CD34^+$ cells to leukocytes in the sample is about 0.0014.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with $CD34^+$ cells relative to leukocytes by a ratio of from about 3.40:1 to about 6.90:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with $CD34^+$ cells relative to leukocytes by a ratio of about 3.40:1, 3.45:1, 3.50:1, 3.55:1, 3.60:1, 3.65:1, 3.70:1, 3.75:1, 3.80:1, 3.85:1, 3.90:1, 3.95:1, 4.00:1, 4.05:1, 4.10:1, 4.15:1, 4.20:1, 4.25:1, 4.30:1, 4.35:1, 4.40:1, 4.45:1, 4.50:1, 4.55:1, 4.60:1, 4.65:1, 4.70:1, 4.75:1, 4.80:1, 4.85:1, 4.90:1, 4.95:1, 5.00:1, 5.05:1, 5.10:1, 5.15:1, 5.20:1, 5.25:1, 5.30:1, 5.35:1, 5.40:1, 5.45:1, 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, 6.50:1, 6.55:1, 6.60:1, 6.65:1, 6.70:1, 6.75:1, 6.80:1, 6.85:1, or 6.90:11. In some embodiments, the peripheral blood of the donor is enriched with CD34+ cells relative to leukocytes by a ratio of from about 3.5:1 to about 6.8:1, about 3.6:1 to about 6.7:1, about 3.8:1 to about 6.6:1, about 3.9:1 to about 6.5:1, about 4:1 to about 6.4:1, about 4.1:1 to about 6.3:1, about 4.2:1 to about 6.2:1, about 4.3:1 to about 6.1:1, about 4.4:1 to about 6:1, about 4.5:1 to about 6:1, about 4.6:1 to about 5.9:1, about 4.7:1 to about 5.8:1, or about 4.8:1 to about 5.7:1. In some embodiments, the peripheral blood of the donor is enriched with $CD34^+$ cells relative to leukocytes by a ratio of about from about 4.0:1 to about 6.0:1, such as a ratio of about 4.00:1, 4.05:1, 4.10:1, 4.15:1, 4.20:1, 4.25:1, 4.30:1, 4.35:1, 4.40:1, 4.45:1, 4.50:1, 4.55:1, 4.60:1, 4.65:1, 4.70:1, 4.75:1, 4.80:1, 4.85:1, 4.90:1, 4.95:1, 5.00:1, 5.05:1, 5.10:1, 5.15:1, 5.20:1, 5.25:1, 5.30:1, 5.35:1, 5.40:1, 5.45:1, 5.50:1, 5.55:1, 5.60:1, 5.65:1, 5.70:1, 5.75:1, 5.80:1, 5.85:1, 5.90:1, 5.95:1, or 6.00:1. In some embodiments, the peripheral blood of the donor is enriched with $CD34^+$ cells relative to leukocytes by a ratio of about from about 4.5:1 to about 5.5:1, such as a ratio of about 4.50:1, 4.55:1, 4.60:1, 4.65:1, 4.70:1, 4.75:1, 4.80:1, 4.85:1, 4.90:1, 4.95:1, 5.00:1, 5.05:1, 5.10:1, 5.15:1, 5.20:1, 5.25:1, 5.30:1, 5.35:1, 5.40:1, 5.45:1, or 5.50. In some embodiments, the peripheral blood of the donor is enriched with $CD34^+$ cells relative to leukocytes by a ratio of about 5.1:1.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a density of CD34+ cells of at least about 38,000 cells/ml, such as a density of CD34+ cells of from about 38,000 cells/ml to about 100,000 cells/ml, about 40,000 cells/ml to about 90,000 cells/nil, about 50,000 cells/ml to about 80,000 cells/ml, or about 60,000 cells/ml to about 70,000 cells/ml (e.g., about 38,00 cells/ml, 39,000 cells/ml, 40,000 cells/ml, 41,000 cells/ml, 42,000 cells/ml, 43,000 cells/ml, 44,000 cells/ml, 45,000 cells/nil, 46,000 cells/ml, 47,000 cells/ml, 48,000 cells/ml, 49,000 cells/ml, 50,000 cells/ml, 51,000 cells/ml, 52,000 cells/ml, 53,000 cells/ml, 54,000 cells/ml, 55,000 cells/ml, 56,000 cells/ml, 57,000 cells/ml, 58,000 cells/ml, 59,000 cells/ml, 60,000 cells/ml, 61,000 cells/ml, 62,000 cells/ml, 63,000 cells/ml, 64,000 cells/ml, 65,000 cells/ml, 66,000 cells/ml, 67,000 cells/ml, 68,000 cells/ml, 69,000 cells/ml, 70,000 cells/ml, 71,000 cells/ml, 72,000 cells/ml, 73,000 cells/ml, 74,000 cells/ml, 75,000 cells/ml, 76,000 cells/ml, 77,000 cells/ml, 78,000 cells/ml, 79,000 cells/ml, 80,000 cells/ml, 81,000 cells/ml, 82,000 cells/ml, 83,000 cells/ml, 84,000 cells/ml, 85,000 cells/ml, 86,000 cells/ml, 87,000 cells/ml, 88,000 cells/ml, 89,000 cells/ml, 90,000 cells/ml, 91,000 cells/ml, 92,000 cells/ml, 93,000 cells/ml, 94,000 cells/ml, 95,000 cells/ml, 96,000 cells/ml, 97,000 cells/ml, 98,000 cells/ml, 99,000 cells/ml, 100,000 cells/ml, or more), and having a density of leukocytes of no more than about $5.3\times10^7$ cells/ml, such as a density of leukocytes of about $2.3\times10^7$ cells/ml to about $5.3\times10^7$ cells/ml, about $2.5\times10^7$ cells/ml to about $5.1\times10^7$ cells/ml, $2.9\times10^7$ cells/ml to about $4.5\times10^7$ cells/ml, about $3\times10^7$ cells/ml to about $4\times10^7$ cells/ml (e.g., $5.3\times10^7$ cells/ml, $5.2\times10^7$ cells/ml, $5.1\times10^7$ cells/ml, $5\times10^7$ cells/ml, $4.9\times10^7$ cells/ml, $4.8\times10^7$ cells/ml, $4.7\times10^7$ cells/ml, $4.6\times10^7$ cells/ml, $4.5\times10^7$ cells/ml, $4.4\times10^7$ cells/ml, $4.3\times10^7$ cells/ml $4.2\times10^7$ cells/ml, $4.1\times10^7$ cells/ml $4\times10^7$ cells/ml, $3.9\times10^7$ cells/ml, $3.8\times10^7$ cells/ml, $3.7\times10^7$ cells/ml, $3.6\times10^7$ cells/ml, $3.5\times10^7$ cells/ml, $3.4\times10^7$ cells/ml, $3.3\times10^7$ cells/ml, $3.2\times10^7$ cells/ml, $3.1\times10^7$ cells/ml, $3\times10^7$ cells/ml, $2.9\times10^7$ cells/ml, $2.8\times10^7$ cells/ml, $2.7\times10^7$ cells/ml, $2.6\times10^7$ cells/ml, $2.5\times10^7$ cells/ml, $2.4\times10^7$ cells/ml, $2.3\times10^7$ cells/ml, or less). In some embodiments, the method includes administering to the donor a CXCR2 agonist and a CXCR4 antagonist in amounts sufficient to produce a population of cells having a density of CD34+ cells of from about 38,000 cells/ml to about 100,000 cells/ml, and having a density of leukocytes of from about $2.3\times10^7$ cells/ml to about $5.3\times10^7$ cells/ml. In some embodiments, the method includes administering to the donor a CXCR2 agonist and a CXCR4 antagonist in amounts sufficient to produce a population of cells having a density of CD34+ cells of from about 40,000 cells/ml to about 80,000 cells/ml, and having a density of leukocytes of from about $2.5\times10^7$ cells/ml to about $5\times10^7$ cells/ml. In some embodiments, the method includes administering to the donor a CXCR2 agonist and a CXCR4 antagonist in amounts sufficient to produce a population of cells having a density of CD34+ cells of from about 50,000 cells/ml to about 90,000 cells/ml, and having a density of leukocytes of from about $3\times10^7$ cells/ml to about $4\times10^7$ cells/ml.

In a further aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of CD34+ cells to neutrophils of from about 0.0018 to about 0.0058 in a sample of peripheral blood of the donor following administration of the CXCR2 agonist and CXCR4 antagonist. In some embodiments, the ratio of CD34+ cells to neutrophils in the sample may be about 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00377, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00400, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, 0.00460, 0.00461, 0.00462, 0.00463, 0.00464, 0.00465, 0.00466, 0.00467, 0.00468, 0.00469, 0.00470, 0.00471, 0.00472, 0.00473, 0.00474, 0.00475, 0.00476, 0.00477, 0.00478, 0.00479, 0.00480, 0.00481, 0.00482, 0.00483, 0.00484, 0.00485, 0.00486, 0.00487, 0.00488, 0.00489, 0.00490, 0.00491, 0.00492, 0.00493, 0.00494, 0.00495, 0.00496, 0.00497, 0.00498, 0.00499, 0.00500, 0.00501, 0.00502, 0.00503, 0.00504, 0.00505, 0.00506, 0.00507, 0.00508, 0.00509, 0.00510, 0.00511, 0.00512, 0.00513, 0.00514, 0.00515, 0.00516, 0.00517, 0.00518, 0.00519, 0.00520, 0.00521, 0.00522, 0.00523, 0.00524, 0.00525, 0.00526, 0.00527, 0.00528, 0.00529, 0.00530, 0.00531, 0.00532, 0.00533, 0.00534, 0.00535, 0.00536, 0.00537, 0.00538, 0.00539, 0.00540, 0.00541, 0.00542, 0.00543, 0.00544, 0.00545, 0.00546, 0.00547, 0.00548, 0.00549, 0.00550, 0.00551, 0.00552, 0.00553, 0.00554, 0.00555, 0.00556, 0.00557, 0.00558, 0.00559, 0.00560, 0.00561, 0.00562, 0.00563, 0.00564, 0.00565, 0.00566, 0.00567, 0.00568, 0.00569, 0.00570, 0.00571, 0.00572, 0.00573, 0.00574, 0.00575, 0.00576, 0.00577, 0.00578, 0.00579, or 0.00580. In some embodiments, the ratio of CD34+ cells to neutrophils in the sample is from about 0.002 to about 0.0056, about 0.0022 to about 0.0054, about 0.0024 to about 0.0052, about 0.0026 to about 0.005, about 0.0028 to about 0.0048, or about 0.003 to about 0.0046. In some embodiments, the ratio of CD34+ cells to neutrophils in the sample is from about 0.0026 to about 0.0046, such as a ratio of CD34+ cells to neutrophils in the sample of about 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00377, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00400, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, or 0.00460. In some embodiments, the ratio of CD34+ cells to neutrophils in the sample is about 0.0036.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with CD34+ cells relative to neutrophils by a ratio of from about 2.1:1 to about 8.1:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with CD34+ cells relative to neutrophils by a ratio of about 2.10:1, 2.15:1, 2.20:1, 2.25:1, 2.30:1, 2.35:1, 2.40:1, 2.45:1, 2.50:1, 2.55:1, 2.60:1, 2.65:1, 2.70:1, 2.75:1, 2.80:1, 2.85:1, 2.90:1, 2.95:1, 3.00:1, 3.05:1, 3.10:1, 3.15:1, 3.20:1, 3.25:1, 3.30:1, 3.35:1, 3.40:1, 3.45:1, 3.50:1, 3.55:1, 3.60:1, 3.65:1, 3.70:1, 3.75:1, 3.80:1, 3.85:1, 3.90:1, 3.95:1, 4.00:1, 4.05:1, 4.10:1, 4.15:1, 4.20:1, 4.25:1, 4.30:1, 4.35:1, 4.40:1, 4.45:1, 4.50:1, 4.55:1, 4.60:1, 4.65:1, 4.70:1, 4.75:1, 4.80:1, 4.85:1, 4.90:1, 4.95:1, 5.00:1, 5.05:1, 5.10:1, 5.15:1, 5.20:1, 5.25:1, 5.30:1, 5.35:1, 5.40:1, 5.45:1, 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, 6.50:1, 6.55:1, 6.60:1, 6.65:1, 6.70:1, 6.75:1, 6.80:1, 6.85:1, 6.90:1, 6.95:1, 7.00:1, 7.05:1, 7.10:1, 7.15:1, 7.20:1, 7.25:1, 7.30:1, 7.35:1, 7.40:1, 7.45:1, 7.50:1, 7.55:1, 7.60:1, 7.65:1, 7.70:1, 7.75:1, 7.80:1, 7.85:1, 7.90:1, 7.95:1, or 8.00:1. In some embodiments, the peripheral blood of the donor is enriched with CD34+ cells relative to neutrophils by a ratio of from about 2.5:1 to about 7:1, about 2.6:1 to about 6.9:1, about 2.7:1 to about 6.8:1, about 2.8:1 to about 6.7:1, about 2.9:1 to about 6.6:1, about 3:1 to about 6.5:1, about 3.2:1 to about 6.4:1, about 3.3:1 to about 6.3:1, about 3.4:1 to about 6.2:1, or about 3.5:1 to about 6.1:1 In some embodiments, the peripheral blood of the donor is enriched with CD34+ cells relative to neutrophils by a ratio of from about from about 5.4:1 to about 7.4:1, such as a ratio of about 5.40:1, 5.45:1, 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, 6.50:1, 6.55:1, 6.60:1, 6.65:1, 6.70:1, 6.75:1, 6.80:1, 6.85:1, 6.90:1, 6.95:1, 7.00:1, 7.05:1, 7.10:1, 7.15:1, 7.20:1, 7.25:1, 7.30:1, 7.35:1, or 7.40:1. In some embodiments, the peripheral blood of the donor is enriched with CD34+ cells relative to neutrophils by a ratio of about 6.4:1.

In yet another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of CD34+ cells to lymphocytes of from about 0.0021 to about 0.0094 in a sample of peripheral blood of the donor following administration of the CXCR2 agonist and CXCR4 antagonist. In some embodiments, the ratio of CD34+ cells to lymphocytes in the sample may be about 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00377, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00400, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, 0.00460, 0.00461, 0.00462, 0.00463, 0.00464, 0.00465, 0.00466, 0.00467, 0.00468, 0.00469, 0.00470, 0.00471, 0.00472, 0.00473, 0.00474, 0.00475, 0.00476, 0.00477, 0.00478, 0.00479, 0.00480, 0.00481, 0.00482, 0.00483, 0.00484, 0.00485, 0.00486, 0.00487, 0.00488, 0.00489, 0.00490, 0.00491, 0.00492, 0.00493, 0.00494, 0.00495, 0.00496, 0.00497, 0.00498, 0.00499, 0.00500, 0.00501, 0.00502, 0.00503, 0.00504, 0.00505, 0.00506, 0.00507, 0.00508, 0.00509, 0.00510, 0.00511, 0.00512, 0.00513, 0.00514, 0.00515, 0.00516, 0.00517, 0.00518, 0.00519, 0.00520, 0.00521, 0.00522, 0.00523, 0.00524, 0.00525, 0.00526, 0.00527, 0.00528, 0.00529, 0.00530, 0.00531, 0.00532, 0.00533, 0.00534, 0.00535, 0.00536, 0.00537, 0.00538, 0.00539, 0.00540, 0.00541, 0.00542, 0.00543, 0.00544, 0.00545, 0.00546, 0.00547, 0.00548, 0.00549, 0.00550, 0.00551, 0.00552, 0.00553, 0.00554, 0.00555, 0.00556, 0.00557, 0.00558, 0.00559, 0.00560, 0.00561, 0.00562, 0.00563, 0.00564, 0.00565, 0.00566, 0.00567, 0.00568, 0.00569, 0.00570, 0.00571, 0.00572, 0.00573, 0.00574, 0.00575, 0.00576, 0.00577, 0.00578, 0.00579, 0.00580, 0.00581, 0.00582, 0.00583, 0.00584, 0.00585, 0.00586, 0.00587, 0.00588, 0.00589, 0.00590, 0.00591, 0.00592, 0.00593, 0.00594, 0.00595, 0.00596, 0.00597, 0.00598, 0.00599, 0.00600, 0.00601, 0.00602, 0.00603, 0.00604, 0.00605, 0.00606, 0.00607, 0.00608, 0.00609, 0.00610, 0.00611, 0.00612, 0.00613, 0.00614, 0.00615, 0.00616, 0.00617, 0.00618, 0.00619, 0.00620, 0.00621, 0.00622, 0.00623, 0.00624, 0.00625, 0.00626, 0.00627, 0.00628, 0.00629, 0.00630, 0.00631, 0.00632, 0.00633, 0.00634, 0.00635, 0.00636, 0.00637, 0.00638, 0.00639, 0.00640, 0.00641, 0.00642, 0.00643, 0.00644, 0.00645, 0.00646, 0.00647, 0.00648, 0.00649, 0.00650, 0.00651, 0.00652, 0.00653, 0.00654, 0.00655, 0.00656, 0.00657, 0.00658, 0.00659, 0.00660, 0.00661, 0.00662, 0.00663, 0.00664, 0.00665, 0.00666, 0.00667, 0.00668, 0.00669, 0.00670, 0.00671, 0.00672, 0.00673, 0.00674, 0.00675, 0.00676, 0.00677, 0.00678, 0.00679, 0.00680, 0.00681, 0.00682, 0.00683, 0.00684, 0.00685, 0.00686, 0.00687, 0.00688, 0.00689, 0.00690, 0.00691, 0.00692, 0.00693, 0.00694, 0.00695, 0.00696, 0.00697, 0.00698, 0.00699, 0.00700, 0.00701, 0.00702, 0.00703, 0.00704, 0.00705, 0.00706, 0.00707, 0.00708, 0.00709, 0.00710, 0.00711, 0.00712, 0.00713, 0.00714, 0.00715, 0.00716, 0.00717, 0.00718, 0.00719, 0.00720, 0.00721, 0.00722, 0.00723, 0.00724, 0.00725, 0.00726, 0.00727, 0.00728, 0.00729, 0.00730, 0.00731, 0.00732, 0.00733, 0.00734, 0.00735, 0.00736, 0.00737, 0.00738, 0.00739, 0.00740, 0.00741, 0.00742, 0.00743, 0.00744, 0.00745, 0.00746, 0.00747, 0.00748, 0.00749, 0.00750, 0.00751, 0.00752, 0.00753, 0.00754, 0.00755, 0.00756, 0.00757, 0.00758, 0.00759, 0.00760, 0.00761, 0.00762, 0.00763, 0.00764, 0.00765, 0.00766, 0.00767, 0.00768, 0.00769, 0.00770, 0.00771, 0.00772, 0.00773, 0.00774, 0.00775, 0.00776, 0.00777, 0.00778, 0.00779, 0.00780, 0.00781, 0.00782, 0.00783, 0.00784, 0.00785, 0.00786, 0.00787, 0.00788, 0.00789, 0.00790, 0.00791, 0.00792, 0.00793, 0.00794, 0.00795, 0.00796, 0.00797, 0.00798, 0.00799, 0.00800, 0.00801, 0.00802, 0.00803, 0.00804, 0.00805, 0.00806, 0.00807, 0.00808, 0.00809, 0.00810, 0.00811, 0.00812, 0.00813, 0.00814, 0.00815, 0.00816, 0.00817, 0.00818, 0.00819, 0.00820, 0.00821, 0.00822, 0.00823, 0.00824, 0.00825, 0.00826, 0.00827, 0.00828, 0.00829, 0.00830, 0.00831, 0.00832, 0.00833, 0.00834, 0.00835, 0.00836, 0.00837, 0.00838, 0.00839, 0.00840, 0.00841, 0.00842, 0.00843, 0.00844, 0.00845, 0.00846, 0.00847, 0.00848, 0.00849, 0.00850, 0.00851, 0.00852, 0.00853, 0.00854, 0.00855, 0.00856, 0.00857, 0.00858, 0.00859, 0.00860, 0.00861, 0.00862, 0.00863, 0.00864, 0.00865, 0.00866, 0.00867, 0.00868, 0.00869, 0.00870, 0.00871, 0.00872, 0.00873, 0.00874, 0.00875, 0.00876, 0.00877, 0.00878, 0.00879, 0.00880, 0.00881, 0.00882, 0.00883, 0.00884, 0.00885, 0.00886, 0.00887, 0.00888, 0.00889, 0.00890, 0.00891, 0.00892, 0.00893, 0.00894, 0.00895, 0.00896, 0.00897, 0.00898, 0.00899, 0.00900, 0.00901, 0.00902, 0.00903, 0.00904, 0.00905, 0.00906, 0.00907, 0.00908, 0.00909, 0.00910, 0.00911, 0.00912, 0.00913, 0.00914, 0.00915, 0.00916, 0.00917, 0.00918, 0.00919, 0.00920, 0.00921, 0.00922, 0.00923, 0.00924, 0.00925, 0.00926, 0.00927, 0.00928, 0.00929, 0.00930, 0.00931, 0.00932, 0.00933, 0.00934, 0.00935, 0.00936, 0.00937, 0.00938, 0.00939, or 0.00940.

In some embodiments, the ratio of $CD34^+$ cells to lymphocytes in the sample is from about 0.0022 to about 0.0093, about 0.0023 to about 0.0092, about 0.0024 to about 0.0091, about 0.003 to about 0.0085, about 0.0035 to about 0.0075, or about 0.0045 to about 0.0065. In some embodiments, the ratio of $CD34^+$ cells to lymphocytes in the sample is from about 0.0025 to about 0.0035, such as a ratio of $CD34^+$ cells to lymphocytes in the sample of about 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, or 0.00350. In some embodiments, the ratio of $CD34^+$ cells to lymphocytes in the sample is about 0.0031.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with $CD34^+$ cells relative to lymphocytes by a ratio of from about 4.8:1 to about 8.4:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with $CD34^+$ cells relative to lymphocytes by a ratio of about 4.80:1, 4.85:1, 4.90:1, 4.95:1, 5.00:1, 5.05:1, 5.10:1, 5.15:1, 5.20:1, 5.25:1, 5.30:1, 5.35:1, 5.40:1, 5.45:1, 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, 6.50:1, 6.55:1, 6.60:1, 6.65:1, 6.70:1, 6.75:1, 6.80:1, 6.85:1, 6.90:1, 6.95:1, 7.00:1, 7.05:1, 7.10:1, 7.15:1, 7.20:1, 7.25:1, 7.30:1, 7.35:1, 7.40:1, 7.45:1, 7.50:1, 7.55:1, 7.60:1, 7.65:1, 7.70:1, 7.75:1, 7.80:1, 7.85:1, 7.90:1, 7.95:1, 8.00:1, 8.05:1, 8.10:1, 8.15:1, 8.20:1, 8.25:1, 8.30:1, 8.35:1, or 8.40:1. In some embodiments, the peripheral blood of the donor is enriched with $CD34^+$ cells relative to lymphocytes by a ratio of from about 5:1 to about 7:1, about 5.5:1 to about 6.5:1, or about 5.2:1 to about 5.7:1. In some embodiments, the peripheral blood of the donor is enriched with $CD34^+$ cells relative to lymphocytes by a ratio of from about 5.0:1 to about 6.5:1, such as a ratio of about 5.00:1, 5.05:1, 5.10:1, 5.15:1, 5.20:1, 5.25:1, 5.30:1, 5.35:1, 5.40:1, 5.45:1, 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, or 6.50:1. In some embodiments, the peripheral blood of the donor is enriched with $CD34^+$ cells relative to lymphocytes by a ratio of about 5.7:1.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a density of $CD34^+$ cells of at least about 38,000 cells/ml, such as a density of $CD34^+$ cells of from about 38,000 cells/ml to about 100,000 cells/ml, about 40,000 cells/ml to about 90,000 cells/ml, about 50,000 cells/ml to about 80,000 cells/ml, or about 60,000 cells/ml to about 70,000 cells/ml (e.g., about 38,00 cells/ml, 39,000 cells/ml, 40,000 cells/ml, 41,000 cells/ml, 42,000 cells/ml, 43,000 cells/ml, 44,000 cells/ml, 45,000 cells/ml, 46,000 cells/ml, 47,000 cells/ml, 48,000 cells/ml, 49,000 cells/ml, 50,000 cells/ml, 51,000 cells/ml, 52,000 cells/ml, 53,000 cells/ml, 54,000 cells/ml, 55,000 cells/ml, 56,000 cells/ml, 57,000 cells/ml, 58,000 cells/ml, 59,000 cells/ml, 60,000 cells/ml, 61,000 cells/ml, 62,000 cells/ml, 63,000 cells/ml, 64,000 cells/ml, 65,000 cells/ml, 66,000 cells/ml, 67,000 cells/ml, 68,000 cells/ml, 69,000 cells/ml, 70,000 cells/ml, 71,000 cells/ml, 72,000 cells/ml, 73,000 cells/ml, 74,000 cells/ml, 75,000 cells/ml, 76,000 cells/ml, 77,000 cells/ml, 78,000 cells/ml, 79,000 cells/ml, 80,000 cells/ml, 81,000 cells/ml, 82,000 cells/ml, 83,000 cells/ml, 84,000 cells/ml, 85,000 cells/ml, 86,000 cells/ml, 87,000 cells/ml, 88,000 cells/ml, 89,000 cells/ml, 90,000 cells/ml, 91,000 cells/ml, 92,000 cells/ml, 93,000 cells/ml, 94,000 cells/ml, 95,000 cells/ml, 96,000 cells/ml, 97,000 cells/ml, 98,000 cells/ml, 99,000 cells/ml, 100,000 cells/ml, or more), and having a density of lymphocytes of no more than about $2.4 \times 10^7$ cells/ml, such as a density of lymphocytes of about $1 \times 10^7$ cells/ml to about $2.3 \times 10^7$ cells/ml, about $1.3 \times 10^7$ cells/ml to about $2.1 \times 10^7$ cells/ml, or about $1.5 \times 10^7$ cells/ml to about $1.9 \times 10^7$ cells/ml (e.g., about $2.4 \times 10^7$ cells/ml, $2.3 \times 10^7$ cells/ml, $2.2 \times 10^7$ cells/ml, $2.1 \times 10^7$ cells/ml, $2 \times 10^7$ cells/ml, $1.9 \times 10^7$ cells/ml, $1.8 \times 10^7$ cells/ml, $1.7 \times 10^7$ cells/ml, $1.6 \times 10^7$ cells/ml, $1.5 \times 10^7$ cells/ml $1.4 \times 10^7$ cells/ml, $1.3 \times 10^7$ cells/ml, $1.2 \times 10^7$ cells/ml, $1.1 \times 10^7$ cells/ml, $1 \times 10^7$ cells/ml, or less, $0.9 \times 10^7$ cells/ml, $0.8 \times 10^7$ cells/ml, or less). In some embodiments, the method includes administering to the donor a CXCR2 agonist and a CXCR4 antagonist in amounts sufficient to produce a population of cells having a density of $CD34^+$ cells of from about 38,000 cells/ml to about 100,000 cells/ml, and having a density of lymphocytes of from about $1 \times 10^7$ cells/ml to about $2.3 \times 10^7$ cells/ml. In some embodiments, the method includes administering to the donor a CXCR2 agonist and a CXCR4 antagonist in amounts sufficient to produce a population of cells having a density of $CD34^+$ cells of from about 40,000 cells/ml to about 80,000 cells/ml, and having a density of lymphocytes of from about $1.3 \times 10^7$ cells/ml to about $2.3 \times 10^7$ cells/ml. In some embodiments, the method includes administering to the donor a CXCR2 agonist and a CXCR4 antagonist in amounts sufficient to produce a population of cells having a density of $CD34^+$ cells of from about 50,000 cells/ml to about 90,000 cells/ml, and having a density of lymphocytes of from about $1.5 \times 10^7$ cells/ml to about $2 \times 10^7$ cells/ml.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of $CD34^+$ cells to monocytes of from about 0.0071 to about 0.0174 in a sample of peripheral blood of the donor following administration of the CXCR2 agonist. In some embodiments, the ratio of $CD34^+$ cells to monocytes in the sample may be about 0.00710, 0.00711, 0.00712, 0.00713, 0.00714, 0.00715, 0.00716, 0.00717, 0.00718, 0.00719, 0.00720, 0.00721, 0.00722, 0.00723, 0.00724, 0.00725, 0.00726, 0.00727, 0.00728, 0.00729, 0.00730, 0.00731, 0.00732, 0.00733, 0.00734, 0.00735, 0.00736, 0.00737, 0.00738, 0.00739, 0.00740, 0.00741, 0.00742, 0.00743, 0.00744, 0.00745, 0.00746, 0.00747, 0.00748, 0.00749, 0.00750, 0.00751, 0.00752, 0.00753, 0.00754, 0.00755, 0.00756, 0.00757, 0.00758, 0.00759, 0.00760, 0.00761, 0.00762, 0.00763, 0.00764, 0.00765, 0.00766, 0.00767, 0.00768, 0.00769, 0.00770, 0.00771, 0.00772, 0.00773, 0.00774, 0.00775, 0.00776, 0.00777, 0.00778, 0.00779, 0.00780, 0.00781, 0.00782, 0.00783, 0.00784, 0.00785, 0.00786, 0.00787, 0.00788, 0.00789, 0.00790, 0.00791, 0.00792, 0.00793, 0.00794, 0.00795, 0.00796, 0.00797, 0.00798, 0.00799, 0.00800, 0.00801, 0.00802, 0.00803, 0.00804, 0.00805, 0.00806, 0.00807, 0.00808, 0.00809, 0.00810, 0.00811, 0.00812, 0.00813, 0.00814, 0.00815, 0.00816, 0.00817, 0.00818, 0.00819, 0.00820, 0.00821, 0.00822, 0.00823, 0.00824, 0.00825, 0.00826, 0.00827, 0.00828, 0.00829, 0.00830, 0.00831, 0.00832, 0.00833, 0.00834, 0.00835, 0.00836, 0.00837, 0.00838, 0.00839, 0.00840, 0.00841, 0.00842, 0.00843, 0.00844, 0.00845, 0.00846, 0.00847, 0.00848, 0.00849, 0.00850, 0.00851, 0.00852, 0.00853, 0.00854, 0.00855, 0.00856, 0.00857, 0.00858, 0.00859, 0.00860, 0.00861, 0.00862, 0.00863, 0.00864, 0.00865, 0.00866, 0.00867, 0.00868, 0.00869, 0.00870, 0.00871, 0.00872, 0.00873, 0.00874, 0.00875, 0.00876, 0.00877, 0.00878, 0.00879, 0.00880, 0.00881, 0.00882, 0.00883, 0.00884, 0.00885, 0.00886, 0.00887, 0.00888, 0.00889, 0.00890, 0.00891, 0.00892, 0.00893, 0.00894, 0.00895, 0.00896, 0.00897, 0.00898, 0.00899, 0.00900, 0.00901, 0.00902, 0.00903, 0.00904, 0.00905, 0.00906, 0.00907, 0.00908, 0.00909, 0.00910, 0.00911, 0.00912, 0.00913, 0.00914, 0.00915, 0.00916, 0.00917, 0.00918, 0.00919, 0.00920, 0.00921, 0.00922, 0.00923, 0.00924, 0.00925, 0.00926, 0.00927, 0.00928, 0.00929, 0.00930, 0.00931, 0.00932, 0.00933, 0.00934, 0.00935, 0.00936, 0.00937, 0.00938, 0.00939, 0.00940, 0.00941, 0.00942, 0.00943, 0.00944, 0.00945, 0.00946, 0.00947, 0.00948, 0.00949, 0.00950, 0.00951, 0.00952, 0.00953, 0.00954, 0.00955, 0.00956, 0.00957, 0.00958, 0.00959, 0.00960, 0.00961, 0.00962, 0.00963, 0.00964, 0.00965, 0.00966, 0.00967, 0.00968, 0.00969, 0.00970, 0.00971, 0.00972, 0.00973, 0.00974, 0.00975, 0.00976, 0.00977, 0.00978, 0.00979, 0.00980, 0.00981, 0.00982, 0.00983, 0.00984, 0.00985, 0.00986, 0.00987, 0.00988, 0.00989, 0.00990, 0.00991, 0.00992, 0.00993, 0.00994, 0.00995, 0.00996, 0.00997, 0.00998, 0.00999, 0.0100, 0.0101, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, 0.0150, 0.0151, 0.0152, 0.0153, 0.0154, 0.0155, 0.0156, 0.0157, 0.0158, 0.0159, 0.0160, 0.0161, 0.0162, 0.0163, 0.0164, 0.0165, 0.0166, 0.0167, 0.0168, 0.0169, 0.0170, 0.0171, 0.0172, 0.0173, or 0.0174. In some embodiments, the ratio of $CD34^+$ cells to monocytes in the sample is from 0.008 to about 0.016, about 0.009 to about 0.015, about 0.01 to about 0.014, or about 0.011 to about 0.013. In some embodiments, the ratio of $CD34^+$ cells to monocytes in the sample is from about 0.0100 to about 0.0140, such as a ratio of $CD34^+$ cells to monocytes in the sample of about 0.0100, 0.0101, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, or 0.0140. In some embodiments, the ratio of $CD34^+$ cells to monocytes in the sample is about 0.0118.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a density of $CD34^+$ cells of at least about 38,000 cells/ml, such as a density of $CD34^+$ cells of from about 38,000 cells/ml to about 100,000 cells/ml, about 40,000 cells/ml to about 90,000 cells/ml, about 50,000 cells/ml to about 80,000 cells/ml, or about 60,000 cells/ml to about 70,000 cells/ml (e.g., about 38,00 cells/ml, 39,000 cells/ml, 40,000 cells/ml, 41,000 cells/ml, 42,000 cells/ml, 43,000 cells/ml, 44,000 cells/ml, 45,000 cells/ml, 46,000 cells/ml, 47,000 cells/ml, 48,000 cells/ml, 49,000 cells/ml, 50,000 cells/ml, 51,000 cells/ml, 52,000 cells/ml, 53,000 cells/ml, 54,000 cells/ml, 55,000 cells/ml, 56,000 cells/ml, 57,000 cells/ml, 58,000 cells/ml, 59,000 cells/ml, 60,000 cells/ml, 61,000 cells/ml, 62,000 cells/ml, 63,000 cells/ml, 64,000 cells/ml, 65,000 cells/ml, 66,000 cells/ml, 67,000 cells/ml, 68,000 cells/ml, 69,000 cells/ml, 70,000 cells/ml, 71,000 cells/ml, 72,000 cells/ml, 73,000 cells/ml, 74,000 cells/ml, 75,000 cells/ml, 76,000 cells/ml, 77,000 cells/ml, 78,000 cells/ml, 79,000 cells/ml, 80,000 cells/ml, 81,000 cells/ml, 82,000 cells/ml, 83,000 cells/ml, 84,000 cells/ml, 85,000 cells/ml, 86,000 cells/ml, 87,000 cells/ml, 88,000 cells/ml, 89,000 cells/ml, 90,000 cells/ml, 91,000 cells/ml, 92,000 cells/ml, 93,000 cells/ml, 94,000 cells/ml, 95,000 cells/ml, 96,000 cells/ml, 97,000 cells/ml, 98,000 cells/ml, 99,000 cells/ml, 100,000 cells/ml, or more), and having a density of monocytes of no more than about $6 \times 10^6$ cells/ml, such as a density of monocytes of from $3.4 \times 10^6$ cells/ml to about $5.9 \times 10^6$ cells/ml, about $3.5 \times 10^6$ cells/ml to about $5.7 \times 10^6$ cells/ml, or about $4 \times 10^6$ cells/ml to about $5 \times 10^6$ cells/ml (e.g., $5.9 \times 10^6$ cells/ml, $5.8 \times 10^6$ cells/ml, $5.7 \times 10^6$ cells/ml, $5.6 \times 10^6$ cells/ml, $5.5 \times 10^6$ cells/ml, $5.4 \times 10^6$ cells/ml, $5.3 \times 10^6$ cells/ml, $5.2 \times 10^6$ cells/ml, $5.1 \times 10^6$ cells/ml, $5 \times 10^6$ cells/ml, $4.9 \times 10^6$ cells/ml, $4.8 \times 10^6$ cells/ml, $4.7 \times 10^6$ cells/ml, $4.6 \times 10^6$ cells/ml, $4.5 \times 10^6$ cells/ml, $4.4 \times 10^6$ cells/ml, $4.3 \times 10^6$ cells/ml, $4.2 \times 10^6$ cells/ml, $4.1 \times 10^6$ cells/ml, $4 \times 10^6$ cells/ml, $3.9 \times 10^6$ cells/ml, $3.8 \times 10^6$ cells/ml, $3.7 \times 10^6$ cells/ml, $3.6 \times 10^6$ cells/ml, $3.5 \times 10^6$ cells/ml, $3.4 \times 10^6$ cells/ml, or less). In some embodiments, the method includes administering to the donor a CXCR2 agonist and a CXCR4 antagonist in amounts sufficient to produce a population of cells having a density of $CD34^+$ cells of from about 38,000 cells/ml to about 100,000 cells/ml, and having a density of monocytes of from about $3.4 \times 10^6$ cells/ml to about $6 \times 10^6$ cells/ml. In some embodiments, the method includes administering to the donor a CXCR2 agonist and a CXCR4 antagonist in amounts sufficient to produce a population of cells having a density of $CD34^+$ cells of from about 40,000 cells/ml to about 80,000 cells/ml, and having a density of monocytes of from about $4 \times 10^6$ cells/ml to about $5.5 \times 10^6$ cells/ml. In some embodiments, the method includes administering to the donor a CXCR2 agonist and a CXCR4 antagonist in amounts sufficient to produce a population of cells having a density of $CD34^+$ cells of from about 50,000 cells/ml to about 90,000 cells/ml, and having a density of monocytes of from about $4 \times 10^6$ cells/ml to about $5 \times 10^6$ cells/ml.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with $CD34^+$ cells relative to monocytes by a ratio of from about 1.1:1 to about 2.3:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with $CD34^+$ cells relative to monocytes by a ratio of about 1.10:1, 1.15:1, 1.20:1, 1.25:1, 1.30:1, 1.35:1, 1.40:1, 1.45:1, 1.50:1, 1.55:1, 1.60:1, 1.65:1, 1.70:1, 1.75:1, 1.80:1, 1.85:1, 1.90:1, 1.95:1, 2.00:1, 2.05:1, 2.10:1, 2.15:1, 2.20:1, 2.25:1, or 2.30:1. In some embodiments, the peripheral blood of the donor is enriched with $CD34^+$ cells relative to monocytes by a ratio of about from about 1.3:1 to about 1.9:1, such as a ratio of about 1.30:1, 1.35:1, 1.40:1, 1.45:1, 1.50:1, 1.55:1, 1.60:1, 1.65:1, 1.70:1, 1.75:1, 1.80:1, 1.85:1, or 1.90:1.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a frequency of $CD34^+$ cells of from about 0.051% to about 0.140% in a sample of peripheral blood of the donor following administration of the CXCR2 agonist and CXCR4 antagonist. In some embodiments, the population of cells may have a frequency of $CD34^+$ cells of about 0.051%, 0.052%, 0.053%, 0.054%, 0.055%, 0.056%, 0.057%, 0.058%, 0.059%, 0.060%, 0.061%, 0.062%, 0.063%, 0.064%, 0.065%, 0.066%, 0.067%, 0.068%, 0.069%, 0.070%, 0.071%, 0.072%, 0.073%, 0.074%, 0.075%, 0.076%, 0.077%, 0.078%, 0.079%, 0.080%, 0.081%, 0.082%, 0.083%, 0.084%, 0.085%, 0.086%, 0.087%, 0.088%, 0.089%, 0.090%, 0.091%, 0.092%, 0.093%, 0.094%, 0.095%, 0.096%, 0.097%, 0.098%, 0.099%, 0.100%, 0.101%, 0.102%, 0.103%, 0.104%, 0.105%, 0.106%, 0.107%, 0.108%, 0.109%, 0.110%, 0.111%, 0.112%, 0.113%, 0.114%, 0.115%, 0.116%, 0.117%, 0.118%, 0.119%, 0.120%, 0.121%, 0.122%, 0.123%, 0.124%, 0.125%, 0.126%, 0.127%, 0.128%, 0.129%, 0.130%, 0.131%, 0.132%, 0.133%, 0.134%, 0.135%, 0.136%, 0.137%, 0.138%, 0.139%, or 0.140%. In some embodiments, the population of cells has a frequency of CD34$^+$ cells of from about 0.050% to about 0.120%, about 0.060% to about 0.110%, or about 0.080% to about 0.100%. In some embodiments, the population of cells has a frequency of CD34$^+$ cells of from about 0.080% to about 0.120%, such as a frequency of hematopoietic stem cells of about 0.080%, 0.081%, 0.082%, 0.083%, 0.084%, 0.085%, 0.086%, 0.087%, 0.088%, 0.089%, 0.090%, 0.091%, 0.092%, 0.093%, 0.094%, 0.095%, 0.096%, 0.097%, 0.098%, 0.099%, 0.100%, 0.101%, 0.102%, 0.103%, 0.104%, 0.105%, 0.106%, 0.107%, 0.108%, 0.109%, 0.110%, 0.111%, 0.112%, 0.113%, 0.114%, 0.115%, 0.116%, 0.117%, 0.118%, 0.119%, or 0.120%. In some embodiments, the population of cells has a frequency of CD34$^+$ cells of about 0.097%.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to induce an increase in the frequency of CD34$^+$ cells in the peripheral blood of the donor by at least 3-fold as assessed by comparing a sample of peripheral blood of the donor following administration of the CXCR2 agonist and CXCR4 antagonist to a sample of peripheral blood of the donor prior to administration of the CXCR2 agonist and CXCR4 antagonist (e.g., by from about 3.4-fold to about 7.1-fold, such as by about 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, 5.0-fold, 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold, 7.0-fold, or 7.1-fold. In some embodiments, the frequency of CD34$^+$ cells in the peripheral blood of the donor is increased by from about 4-fold to about 7-fold, about 4.5-fold to about 6.5-fold, or about 5-fold to about 6-fold following administration of the CXCR2 agonist and CXCR4 antagonist. In some embodiments, the frequency of CD34$^+$ cells in the peripheral blood of the donor is increased by from about 4.0-fold to about 6.0-fold following administration of the CXCR2 agonist and CXCR4 antagonist, such as by about 4.0-fold, 4.1-fold, 4.2-fold, 4.3-fold, 4.4-fold, 4.5-fold, 4.6-fold, 4.7-fold, 4.8-fold, 4.9-fold, 5.0-fold, 5.1-fold, 5.2-fold, 5.3-fold, 5.4-fold, 5.5-fold, 5.6-fold, 5.7-fold, 5.8-fold, 5.9-fold, or 6.0-fold. In some embodiments, the frequency of CD34$^+$ cells in the peripheral blood of the donor is increased by about 4.8-fold.

In a further aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of CD34$^+$ CD90$^+$ CD45RA$^-$ cells to leukocytes of from about 0.0003 to about 0.0016 in a sample of peripheral blood of the donor following administration of the CXCR2 agonist and CXCR4 antagonist. In some embodiments, the ratio of CD34$^+$ CD90$^+$ CD45RA$^-$ cells to leukocytes in the sample may be about 0.00030, 0.00031, 0.00032, 0.00033, 0.00034, 0.00035, 0.00036, 0.00037, 0.00038, 0.00039, 0.00040, 0.00041, 0.00042, 0.00043, 0.00044, 0.00045, 0.00046, 0.00047, 0.00048, 0.00049, 0.00050, 0.00051, 0.00052, 0.00053, 0.00054, 0.00055, 0.00056, 0.00057, 0.00058, 0.00059, 0.00060, 0.00061, 0.00062, 0.00063, 0.00064, 0.00065, 0.00066, 0.00067, 0.00068, 0.00069, 0.00070, 0.00071, 0.00072, 0.00073, 0.00074, 0.00075, 0.00076, 0.00077, 0.00078, 0.00079, 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, or 0.00160. In some embodiments, the ratio of CD34$^+$ CD90$^+$ CD45RA$^-$ cells to leukocytes in the sample is from about 0.0008 to about 0.0010. In some embodiments, the ratio of CD34$^+$ CD90$^+$ CD45RA$^-$ cells to leukocytes in the sample is from about 0.0006 to about 0.0012, such as a ratio of hematopoietic stem cells to leukocytes in the sample of about 0.00060, 0.00061, 0.00062, 0.00063, 0.00064, 0.00065, 0.00066, 0.00067, 0.00068, 0.00069, 0.00070, 0.00071, 0.00072, 0.00073, 0.00074, 0.00075, 0.00076, 0.00077, 0.00078, 0.00079, 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, or 0.00120. In some embodiments, the ratio of CD34$^+$ CD90$^+$ CD45RA$^-$ cells to leukocytes in the sample is about 0.0009.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with CD34$^+$ CD90$^+$ CD45RA$^-$ cells relative to leukocytes by a ratio of from about 5.5:1 to about 26.9:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with CD34$^+$ CD90$^+$ CD45RA$^-$ cells relative to leukocytes by a ratio of about 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, 6.50:1, 6.55:1, 6.60:1, 6.65:1, 6.70:1, 6.75:1, 6.80:1, 6.85:1, 6.90:1, 6.95:1, 7.00:1, 7.05:1, 7.10:1, 7.15:1, 7.20:1, 7.25:1, 7.30:1, 7.35:1, 7.40:1, 7.45:1, 7.50:1, 7.55:1, 7.60:1, 7.65:1, 7.70:1, 7.75:1, 7.80:1, 7.85:1, 7.90:1, 7.95:1, 8.00:1, 8.05:1, 8.10:1, 8.15:1, 8.20:1, 8.25:1, 8.30:1, 8.35:1, 8.40:1, 8.45:1, 8.50:1, 8.55:1, 8.60:1, 8.65:1, 8.70:1, 8.75:1, 8.80:1, 8.85:1, 8.90:1, 8.95:1, 9.00:1, 9.05:1, 9.10:1, 9.15:1, 9.20:1, 9.25:1, 9.30:1, 9.35:1, 9.40:1, 9.45:1, 9.50:1, 9.55:1, 9.60:1, 9.65:1, 9.70:1, 9.75:1, 9.80:1, 9.85:1, 9.90:1, 9.95:1, 10.00:1, 10.05:1, 10.10:1, 10.15:1, 10.20:1, 10.25:1, 10.30:1, 10.35:1, 10.40:1, 10.45:1, 10.50:1, 10.55:1, 10.60:1, 10.65:1, 10.70:1, 10.75:1, 10.80:1, 10.85:1, 10.90:1, 10.95:1, 11.00:1, 11.05:1, 11.10:1, 11.15:1, 11.20:1, 11.25:1, 11.30:1, 11.35:1, 11.40:1, 11.45:1, 11.50:1, 11.55:1, 11.60:1, 11.65:1, 11.70:1, 11.75:1, 11.80:1, 11.85:1, 11.90:1, 11.95:1, 12.00:1, 12.05:1, 12.10:1, 12.15:1, 12.20:1, 12.25:1, 12.30:1, 12.35:1, 12.40:1, 12.45:1, 12.50:1, 12.55:1, 12.60:1, 12.65:1, 12.70:1, 12.75:1, 12.80:1, 12.85:1, 12.90:1, 12.95:1, 13.00:1, 13.05:1, 13.10:1, 13.15:1, 13.20:1, 13.25:1, 13.30:1, 13.35:1, 13.40:1, 13.45:1, 13.50:1, 13.55:1, 13.60:1, 13.65:1, 13.70:1, 13.75:1, 13.80:1, 13.85:1, 13.90:1, 13.95:1, 14.00:1, 14.05:1, 14.10:1, 14.15:1, 14.20:1, 14.25:1, 14.30:1, 14.35:1, 14.40:1, 14.45:1, 14.50:1, 14.55:1, 14.60:1, 14.65:1, 14.70:1, 14.75:1, 14.80:1, 14.85:1, 14.90:1, 14.95:1, 15.00:1, 15.05:1, 15.10:1, 15.15:1, 15.20:1, 15.25:1, 15.30:1, 15.35:1, 15.40:1, 15.45:1, 15.50:1, 15.55:1, 15.60:1, 15.65:1, 15.70:1, 15.75:1, 15.80:1, 15.85:1, 15.90:1, 15.95:1, 16.00:1, 16.05:1, 16.10:1, 16.15:1, 16.20:1, 16.25:1, 16.30:1, 16.35:1, 16.40:1, 16.45:1, 16.50:1, 16.55:1, 16.60:1, 16.65:1, 16.70:1, 16.75:1, 16.80:1, 16.85:1, 16.90:1, 16.95:1, 17.00:1, 17.05:1, 17.10:1, 17.15:1, 17.20:1, 17.25:1, 17.30:1, 17.35:1, 17.40:1, 17.45:1, 17.50:1, 17.55:1, 17.60:1, 17.65:1, 17.70:1, 17.75:1, 17.80:1, 17.85:1, 17.90:1, 17.95:1, 18.00:1, 18.05:1, 18.10:1, 18.15:1, 18.20:1, 18.25:1, 18.30:1, 18.35:1, 18.40:1, 18.45:1, 18.50:1, 18.55:1, 18.60:1, 18.65:1, 18.70:1, 18.75:1, 18.80:1, 18.85:1, 18.90:1, 18.95:1, 19.00:1, 19.05:1, 19.10:1, 19.15:1, 19.20:1, 19.25:1, 19.30:1, 19.35:1, 19.40:1, 19.45:1, 19.50:1, 19.55:1, 19.60:1, 19.65:1, 19.70:1, 19.75:1, 19.80:1, 19.85:1, 19.90:1, 19.95:1, 20.00:1, 20.05:1, 20.10:1, 20.15:1, 20.20:1, 20.25:1, 20.30:1, 20.35:1, 20.40:1, 20.45:1, 20.50:1, 20.55:1, 20.60:1, 20.65:1, 20.70:1, 20.75:1, 20.80:1, 20.85:1, 20.90:1, 20.95:1, 21.00:1, 21.05:1, 21.10:1, 21.15:1, 21.20:1, 21.25:1, 21.30:1, 21.35:1, 21.40:1, 21.45:1, 21.50:1, 21.55:1, 21.60:1, 21.65:1, 21.70:1, 21.75:1, 21.80:1, 21.85:1, 21.90:1, 21.95:1, 22.00:1, 22.05:1, 22.10:1, 22.15:1, 22.20:1, 22.25:1, 22.30:1, 22.35:1, 22.40:1, 22.45:1, 22.50:1, 22.55:1, 22.60:1, 22.65:1, 22.70:1, 22.75:1, 22.80:1, 22.85:1, 22.90:1, 22.95:1, 23.00, 23.05:1, 23.10:1, 23.15:1, 23.20:1, 23.25:1, 23.30:1, 23.35:1, 23.40:1, 23.45:1, 23.50:1, 23.55:1, 23.60:1, 23.65:1, 23.70:1, 23.75:1, 23.80:1, 23.85:1, 23.90:1, 23.95:1, 24.00:1, 24.05:1, 24.10:1, 24.15:1, 24.20:1, 24.25:1, 24.30:1, 24.35:1, 24.40:1, 24.45:1, 24.50:1, 24.55:1, 24.60:1, 24.65:1, 24.70:1, 24.75:1, 24.80:1, 24.85:1, 24.90:1, 24.95:1, 25.05:1, 25.10:1, 25.15:1, 25.20:1, 25.25:1, 25.30:1, 25.35:1, 25.40:1, 25.45:1, 25.50:1, 25.55:1, 25.60:1, 25.65:1, 25.70:1, 25.75:1, 25.80:1, 25.85:1, 25.90:1, 25.95:1, 26.00:1, 26.05:1, 26.10:1, 26.15:1, 26.20:1, 26.25:1, 26.30:1, 26.35:1, 26.40:1, 26.45:1, 26.50:1, 26.55:1, 26.60:1, 26.65:1, 26.70:1, 26.75:1, 26.80:1, 26.85:1, 26.90:1, or 26.95:1. In some embodiments, the peripheral blood of the donor is enriched with $CD34^+$ $CD90^+$ $CD45RA^-$ cells relative to leukocytes by a ratio of about from about 5.5:1 to about 6.5:1, such as a ratio of about 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, or 6.50:1. In some embodiments, the peripheral blood of the donor is enriched with $CD34^+$ $CD90^+$ $CD45RA^-$ cells relative to leukocytes by a ratio of about 6.0:1.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a density of $CD34^+$ $CD90^+$ $CD45RA^-$ cells of at least about 16,000 cells/ml, such as a density of from about 20,000 cells/ml to about 75,000 cells/ml, about 25,000 cells/ml to about 70,000 cells/ml, about 30,000 cells/ml to about 65,000 cells/ml, about 35,000 cells/ml to about 60,000 cells/ml, about 40,000 cells/ml to about 55,000 cells/ml, or about 45,000 cells/ml to about 50,000 cells/ml (e.g., about 16,000 cells/ml, 17,000 cells/ml, 18,000 cells/ml, 19,000 cells/ml, 20,000 cells/ml, 21,000 cells/ml, 22,000 cells/ml, 23,000 cells/ml, 24,000 cells/ml, 25,000 cells/ml, 26,000 cells/ml, 27,000 cells/ml, 28,000 cells/ml, 29,000 cells/ml, 30,000 cells/ml, 31,000 cells/ml, 32,000 cells/ml, 33,000 cells/ml, 34,000 cells/ml, 35,000 cells/ml, 36,000 cells/ml, 37,000 cells/ml, 38,000 cells/ml, 39,000 cells/ml, 40,000 cells/ml, 41,000 cells/ml, 42,000 cells/ml, 43,000 cells/ml, 44,000 cells/ml, 45,000 cells/ml, 46,000 cells/ml, 47,000 cells/ml, 48,000 cells/ml, 49,000 cells/ml, 50,000 cells/ml, 51,000 cells/ml, 52,000 cells/ml, 53,000 cells/ml, 54,000 cells/ml, 55,000 cells/ml, 56,000 cells/ml, 57,000 cells/ml, 58,000 cells/ml, 59,000 cells/ml, 60,000 cells/ml, 61,000 cells/ml, 62,000 cells/ml, 63,000 cells/ml, 64,000 cells/ml, 65,000 cells/ml, 66,000 cells/ml, 67,000 cells/ml, 68,000 cells/ml, 69,000 cells/ml, 70,000 cells/ml, 71,000 cells/ml, 72,000 cells/ml, 73,000 cells/ml, 74,000 cells/ml, 75,000 cells/ml, 76,000 cells/ml, 77,000 cells/ml, or more), and having a density of leukocytes of no more than about $5.3 \times 10^7$ cells/ml, such as a density of leukocytes of about $2.3 \times 10^7$ cells/ml to about $5.3 \times 10^7$ cells/ml, about $2.5 \times 10^7$ cells/ml to about $5.1 \times 10^7$ cells/ml, $2.9 \times 10^7$ cells/ml to about $4.5 \times 10^7$ cells/ml, about $3 \times 10^7$ cells/ml to about $4 \times 10^7$ cells/ml (e.g., $5.3 \times 10^7$ cells/ml, $5.2 \times 10^7$ cells/ml, $5.1 \times 10^7$ cells/ml, $5 \times 10^7$ cells/ml, $4.9 \times 10^7$ cells/ml, $4.8 \times 10^7$ cells/ml, $4.7 \times 10^7$ cells/ml, $4.6 \times 10^7$ cells/ml, $4.5 \times 10^7$ cells/ml, $4.4 \times 10^7$ cells/ml, $4.3 \times 10^7$ cells/ml $4.2 \times 10^7$ cells/ml, $4.1 \times 10^7$ cells/ml $4 \times 10^7$ cells/ml, $3.9 \times 10^7$ cells/ml, $3.8 \times 10^7$ cells/ml, $3.7 \times 10^7$ cells/ml, $3.6 \times 10^7$ cells/ml, $3.5 \times 10^7$ cells/ml, $3.4 \times 10^7$ cells/ml, $3.3 \times 10^7$ cells/ml, $3.2 \times 10^7$ cells/ml, $3.1 \times 10^7$ cells/ml, $3 \times 10^7$ cells/ml, $2.9 \times 10^7$ cells/ml, $2.8 \times 10^7$ cells/ml, $2.7 \times 10^7$ cells/ml, $2.6 \times 10^7$ cells/ml, $2.5 \times 10^7$ cells/ml, $2.4 \times 10^7$ cells/ml, $2.3 \times 10^7$ cells/ml, or less). In some embodiments, the method includes administering to the donor a CXCR2 agonist and a CXCR4 antagonist in amounts sufficient to produce a population of cells having a density of $CD34^+$ $CD90^+$ $CD45RA^-$ cells of from about 20,000 cells/ml to about 75,000 cells/ml, and having a density of leukocytes of from about $2.3 \times 10^7$ cells/ml to about $5.3 \times 10^7$ cells/ml. In some embodiments, the method includes administering to the donor a CXCR2 agonist and a CXCR4 antagonist in amounts sufficient to produce a population of cells having a density of $CD34^+$ $CD90^+$ $CD45RA^-$ cells of from about 30,000 cells/ml to about 60,000 cells/ml, and having a density of leukocytes of from about $2.5 \times 10^7$ cells/ml to about $5 \times 10^7$ cells/ml. In some embodiments, the method includes administering to the donor a CXCR2 agonist and a CXCR4 antagonist in amounts sufficient to produce a population of cells having a density of $CD34^+$ $CD90^+$ $CD45RA^-$ cells of from about 40,000 cells/ml to about 50,000 cells/ml, and having a density of leukocytes of from about $3 \times 10^7$ cells/ml to about $4 \times 10^7$ cells/ml.

In a further aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of $CD34^+$ $CD90^+$ $CD45RA^-$ cells to neutrophils of from about 0.0007 to about 0.0043 in a sample of peripheral blood of the donor following administration of the CXCR2 agonist and CXCR4 antagonist. In some embodiments, the ratio of $CD34^+$ $CD90^+$ $CD45RA^-$ cells to neutrophils in the sample may be about 0.00070, 0.00071, 0.00072, 0.00073, 0.00074, 0.00075, 0.00076, 0.00077, 0.00078, 0.00079, 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00177, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00377, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00400, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, or 0.00430. In some embodiments, the ratio of CD34$^+$ CD90$^+$ CD45RA$^-$ cells to neutrophils in the sample is from about 0.002 to about 0.003. In some embodiments, the ratio of CD34$^+$ CD90$^+$ CD45RA$^-$ cells to neutrophils in the sample is from about 0.0014 to about 0.0034, such as a ratio of CD34$^+$ CD90$^+$ CD45RA$^-$ cells to neutrophils in the sample of about 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00177, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, or 0.00340. In some embodiments, the ratio of CD34$^+$ CD90$^+$ CD45RA$^-$ cells to neutrophils in the sample is about 0.0024.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with CD34$^+$ CD90$^+$ CD45RA$^-$ cells relative to neutrophils by a ratio of from about 3.5:1 to about 22.0:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with CD34$^+$ CD90$^+$ CD45RA$^-$ cells relative to neutrophils by a ratio of about 3.50:1, 3.55:1, 3.60:1, 3.65:1, 3.70:1, 3.75:1, 3.80:1, 3.85:1, 3.90:1, 3.95:1, 4.00:1, 4.05:1, 4.10:1, 4.15:1, 4.20:1, 4.25:1, 4.30:1, 4.35:1, 4.40:1, 4.45:1, 4.50:1, 4.55:1, 4.60:1, 4.65:1, 4.70:1, 4.75:1, 4.80:1, 4.85:1, 4.90:1, 4.95:1, 5.00:1, 5.05:1, 5.10:1, 5.15:1, 5.20:1, 5.25:1, 5.30:1, 5.35:1, 5.40:1, 5.45:1, 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, 6.50:1, 6.55:1, 6.60:1, 6.65:1, 6.70:1, 6.75:1, 6.80:1, 6.85:1, 6.90:1, 6.95:1, 7.00:1, 7.05:1, 7.10:1, 7.15:1, 7.20:1, 7.25:1, 7.30:1, 7.35:1, 7.40:1, 7.45:1, 7.50:1, 7.55:1, 7.60:1, 7.65:1, 7.70:1, 7.75:1, 7.80:1, 7.85:1, 7.90:1, 7.95:1, 8.00:1, 8.05:1, 8.10:1, 8.15:1, 8.20:1, 8.25:1, 8.30:1, 8.35:1, 8.40:1, 8.45:1, 8.50:1, 8.55:1, 8.60:1, 8.65:1, 8.70:1, 8.75:1, 8.80:1, 8.85:1, 8.90:1, 8.95:1, 9.00:1, 9.05:1, 9.10:1, 9.15:1, 9.20:1, 9.25:1, 9.30:1, 9.35:1, 9.40:1, 9.45:1, 9.50:1, 9.55:1, 9.60:1, 9.65:1, 9.70:1, 9.75:1, 9.80:1, 9.85:1, 9.90:1, 9.95:1, 10.00:1, 10.05:1, 10.10:1, 10.15:1, 10.20:1, 10.25:1, 10.30:1, 10.35:1, 10.40:1, 10.45:1, 10.50:1, 10.55:1, 10.60:1, 10.65:1, 10.70:1, 10.75:1, 10.80:1, 10.85:1, 10.90:1, 10.95:1, 11.00:1, 11.05:1, 11.10:1, 11.15:1, 11.20:1, 11.25:1, 11.30:1, 11.35:1, 11.40:1, 11.45:1, 11.50:1, 11.55:1, 11.60:1, 11.65:1, 11.70:1, 11.75:1, 11.80:1, 11.85:1, 11.90:1, 11.95:1, 12.00:1, 12.05:1, 12.10:1, 12.15:1, 12.20:1, 12.25:1, 12.30:1, 12.35:1, 12.40:1, 12.45:1, 12.50:1, 12.55:1, 12.60:1, 12.65:1, 12.70:1, 12.75:1, 12.80:1, 12.85:1, 12.90:1, 12.95:1, 13.00:1, 13.05:1, 13.10:1, 13.15:1, 13.20:1, 13.25:1, 13.30:1, 13.35:1, 13.40:1, 13.45:1, 13.50:1, 13.55:1, 13.60:1, 13.65:1, 13.70:1, 13.75:1, 13.80:1, 13.85:1, 13.90:1, 13.95:1, 14.00:1, 14.05:1, 14.10:1, 14.15:1, 14.20:1, 14.25:1, 14.30:1, 14.35:1, 14.40:1, 14.45:1, 14.50:1, 14.55:1, 14.60:1, 14.65:1, 14.70:1, 14.75:1, 14.80:1, 14.85:1, 14.90:1, 14.95:1, 15.00:1, 15.05:1, 15.10:1, 15.15:1, 15.20:1, 15.25:1, 15.30:1, 15.35:1, 15.40:1, 15.45:1, 15.50:1, 15.55:1, 15.60:1, 15.65:1, 15.70:1, 15.75:1, 15.80:1, 15.85:1, 15.90:1, 15.95:1, 16.00:1, 16.05:1, 16.10:1, 16.15:1, 16.20:1, 16.25:1, 16.30:1, 16.35:1, 16.40:1, 16.45:1, 16.50:1, 16.55:1, 16.60:1, 16.65:1, 16.70:1, 16.75:1, 16.80:1, 16.85:1, 16.90:1, 16.95:1, 17.00:1, 17.05:1, 17.10:1, 17.15:1, 17.20:1, 17.25:1, 17.30:1, 17.35:1, 17.40:1, 17.45:1, 17.50:1, 17.55:1, 17.60:1, 17.65:1, 17.70:1, 17.75:1, 17.80:1, 17.85:1, 17.90:1, 17.95:1, 18.00:1, 18.05:1, 18.10:1, 18.15:1, 18.20:1, 18.25:1, 18.30:1, 18.35:1, 18.40:1, 18.45:1, 18.50:1, 18.55:1, 18.60:1, 18.65:1, 18.70:1, 18.75:1, 18.80:1, 18.85:1, 18.90:1, 18.95:1, 19.00:1, 19.05:1, 19.10:1, 19.15:1, 19.20:1, 19.25:1, 19.30:1, 19.35:1, 19.40:1, 19.45:1, 19.50:1, 19.55:1, 19.60:1, 19.65:1, 19.70:1, 19.75:1, 19.80:1, 19.85:1, 19.90:1, 19.95:1, 20.00:1, 20.05:1, 20.10:1, 20.15:1, 20.20:1, 20.25:1, 20.30:1, 20.35:1, 20.40:1, 20.45:1, 20.50:1, 20.55:1, 20.60:1, 20.65:1, 20.70:1, 20.75:1, 20.80:1, 20.85:1, 20.90:1, 20.95:1, 21.00:1, 21.05:1, 21.10:1, 21.15:1, 21.20:1, 21.25:1, 21.30:1, 21.35:1, 21.40:1, 21.45:1, 21.50:1, 21.55:1, 21.60:1, 21.65:1, 21.70:1, 21.75:1, 21.80:1, 21.85:1, 21.90:1, 21.95:1, or 22.00:1. In some embodiments, the peripheral blood of the donor is enriched with CD34$^+$ CD90$^+$ CD45RA$^-$ cells relative to neutrophils by a ratio of about from about 7.0:1 to about 10:1. In some embodiments, the peripheral blood of the donor is enriched with CD34$^+$ CD90$^+$ CD45RA$^-$ cells relative to neutrophils by a ratio of from about 7.00:1 to about 9.00:1, such as a ratio of about 7.00:1, 7.05:1, 7.10:1, 7.15:1, 7.20:1, 7.25:1, 7.30:1, 7.35:1, 7.40:1, 7.45:1, 7.50:1, 7.55:1, 7.60:1, 7.65:1, 7.70:1, 7.75:1, 7.80:1, 7.85:1, 7.90:1, 7.95:1, 8.00:1, 8.05:1, 8.10:1, 8.15:1, 8.20:1, 8.25:1, 8.30:1, 8.35:1, 8.40:1, 8.45:1, 8.50:1, 8.55:1, 8.60:1, 8.65:1, 8.70:1, 8.75:1, 8.80:1, 8.85:1, 8.90:1, 8.95:1, or 9.00:1. In some embodiments, the peripheral blood of the donor is enriched with CD34$^+$ CD90$^+$ CD45RA$^-$ cells relative to neutrophils by a ratio of about 8.2:1.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a density of CD34$^+$ CD90$^+$ CD45RA$^-$ cells of at least about 16,000 cells/ml, such as a density of from about 20,000 cells/ml to about 75,000 cells/ml, about 25,000 cells/ml to about 70,000 cells/ml, about 30,000 cells/ml to about 65,000 cells/ml, about 35,000 cells/ml to about 60,000 cells/ml, about 40,000 cells/ml to about 55,000 cells/ml, or about 45,000 cells/ml to about 50,000 cells/ml (e.g., about 16,000 cells/ml, 17,000 cells/ml, 18,000 cells/ml, 19,000 cells/ml, 20,000 cells/ml, 21,000 cells/ml, 22,000 cells/ml, 23,000 cells/ml, 24,000 cells/ml, 25,000 cells/ml, 26,000 cells/ml, 27,000 cells/ml, 28,000 cells/ml, 29,000 cells/ml, 30,000 cells/ml, 31,000 cells/ml, 32,000 cells/ml, 33,000 cells/ml, 34,000 cells/ml, 35,000 cells/ml, 36,000 cells/ml, 37,000 cells/ml, 38,000 cells/ml, 39,000 cells/ml, 40,000 cells/ml, 41,000 cells/ml, 42,000 cells/ml, 43,000 cells/ml, 44,000 cells/ml, 45,000 cells/ml, 46,000 cells/ml, 47,000 cells/ml, 48,000 cells/ml, 49,000 cells/ml, 50,000 cells/ml, 51,000 cells/ml, 52,000 cells/ml, 53,000 cells/ml, 54,000 cells/ml, 55,000 cells/ml, 56,000 cells/ml, 57,000 cells/ml, 58,000 cells/ml, 59,000 cells/ml, 60,000 cells/ml, 61,000 cells/ml, 62,000 cells/ml, 63,000 cells/ml, 64,000 cells/ml, 65,000 cells/ml, 66,000 cells/ml, 67,000 cells/ml, 68,000 cells/ml, 69,000 cells/ml, 70,000 cells/nil, 71,000 cells/ml, 72,000 cells/ml, 73,000 cells/ml, 74,000 cells/ml, 75,000 cells/ml, 76,000 cells/ml, 77,000 cells/ml, or more), and having a density of neutrophils of no more than about $2.5 \times 10^7$ cells/ml, such as a density of neutrophils of about $1 \times 10^7$ cells/ml to about $2.5 \times 10^7$ cells/ml, about $1.3 \times 10^7$ cells/ml to about $2 \times 10^7$ cells/ml, or about $1.5 \times 10^7$ cells/ml to about $1.9 \times 10^7$ cells/ml (e.g., about $2.5 \times 10^7$ cells/ml, $2.4 \times 10^7$ cells/ml, $2.3 \times 10^7$ cells/ml, $2.2 \times 10^7$ cells/ml, $2.1 \times 10^7$ cells/ml, $2 \times 10^7$ cells/ml, $1.9 \times 10^7$ cells/ml, $1.8 \times 10^7$ cells/ml, $1.7 \times 10^7$ cells/ml, $1.6 \times 10^7$ cells/ml, $1.5 \times 10^7$ cells/ml $1.4 \times 10^7$ cells/ml, $1.3 \times 10^7$ cells/ml, $1.2 \times 10^7$ cells/ml, $1.1 \times 10^7$ cells/ml, $1 \times 10^7$ cells/ml, or less). In some embodiments, the method includes administering to the donor a CXCR2 agonist and a CXCR4 antagonist in amounts sufficient to produce a population of cells having a density of CD34$^+$ CD90$^+$ CD45RA$^-$ cells of from about 20,000 cells/ml to about 75,000 cells/ml, and having a density of neutrophils of from about $1 \times 10^7$ cells/ml to about $2.5 \times 10^7$ cells/ml. In some embodiments, the method includes administering to the donor a CXCR2 agonist and a CXCR4 antagonist in amounts sufficient to produce a population of cells having a density of CD34$^+$ CD90$^+$ CD45RA$^-$ cells of from about 30,000 cells/ml to about 60,000 cells/ml, and having a density of neutrophils of from about $1.3 \times 10^7$ cells/ml to about $2.3 \times 10^7$ cells/ml. In some embodiments, the method includes administering to the donor a CXCR2 agonist and a CXCR4 antagonist in amounts sufficient to produce a population of cells having a density of CD34$^+$ CD90$^+$ CD45RA$^-$ cells of from about 40,000 cells/ml to about 50,000 cells/ml, and having a density of neutrophils of from about $1.5 \times 10^7$ cells/ml to about $2 \times 10^7$ cells/ml.

In yet another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of CD34$^+$ CD90$^+$ CD45RA$^-$ cells to lymphocytes of from about 0.0008 to about 0.0069 in a sample of peripheral blood of the donor following administration of the CXCR2 agonist and CXCR4 antagonist. In some embodiments, the ratio of CD34$^+$ CD90$^+$ CD45RA$^-$ cells to lymphocytes in the sample may be about 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, 0.00460, 0.00461, 0.00462, 0.00463, 0.00464, 0.00465, 0.00466, 0.00467, 0.00468, 0.00469, 0.00470, 0.00471, 0.00472, 0.00473, 0.00474, 0.00475, 0.00476, 0.00478, 0.00479, 0.00480, 0.00481, 0.00482, 0.00483, 0.00484, 0.00485, 0.00486, 0.00487, 0.00488, 0.00489, 0.00490, 0.00491, 0.00492, 0.00493, 0.00494, 0.00495, 0.00496, 0.00497, 0.00498, 0.00499, 0.00500, 0.00501, 0.00502, 0.00503, 0.00504, 0.00505, 0.00506, 0.00507, 0.00508, 0.00509, 0.00510, 0.00511, 0.00512, 0.00513, 0.00514, 0.00515, 0.00516, 0.00517, 0.00518, 0.00519, 0.00520, 0.00521, 0.00522, 0.00523, 0.00524, 0.00525, 0.00526, 0.00527, 0.00528, 0.00529, 0.00530, 0.00531, 0.00532, 0.00533, 0.00534, 0.00535, 0.00536, 0.00537, 0.00538, 0.00539, 0.00540, 0.00541, 0.00542, 0.00543, 0.00544, 0.00545, 0.00546, 0.00547, 0.00548, 0.00549, 0.00550, 0.00551, 0.00552, 0.00553, 0.00554, 0.00555, 0.00556, 0.00557, 0.00558, 0.00559, 0.00560, 0.00561, 0.00562, 0.00563, 0.00564, 0.00565, 0.00566, 0.00567, 0.00568, 0.00569, 0.00570, 0.00571, 0.00572, 0.00573, 0.00574, 0.00575, 0.00576, 0.00578, 0.00579, 0.00580, 0.00581, 0.00582, 0.00583, 0.00584, 0.00585, 0.00586, 0.00587, 0.00588, 0.00589, 0.00590, 0.00591, 0.00592, 0.00593, 0.00594, 0.00595, 0.00596, 0.00597, 0.00598, 0.00599, 0.00600, 0.00601, 0.00602, 0.00603, 0.00604, 0.00605, 0.00606, 0.00607, 0.00608, 0.00609, 0.00610, 0.00611, 0.00612, 0.00613, 0.00614, 0.00615, 0.00616, 0.00617, 0.00618, 0.00619, 0.00620, 0.00621, 0.00622, 0.00623, 0.00624, 0.00625, 0.00626, 0.00627, 0.00628, 0.00629, 0.00630, 0.00631, 0.00632, 0.00633, 0.00634, 0.00635, 0.00636, 0.00637, 0.00638, 0.00639, 0.00640, 0.00641, 0.00642, 0.00643, 0.00644, 0.00645, 0.00646, 0.00647, 0.00648, 0.00649, 0.00650, 0.00651, 0.00652, 0.00653, 0.00654, 0.00655, 0.00656, 0.00657, 0.00658, 0.00659, 0.00660, 0.00661, 0.00662, 0.00663, 0.00664, 0.00665, 0.00666, 0.00667, 0.00668, 0.00669, 0.00670, 0.00671, 0.00672, 0.00673, 0.00674, 0.00675, 0.00676, 0.00678, 0.00679, 0.00680, 0.00681, 0.00682, 0.00683, 0.00684, 0.00685, 0.00686, 0.00687, 0.00688, 0.00689, or 0.00690. In some embodiments, the ratio of CD34$^+$ CD90$^+$ CD45RA$^-$ cells to lymphocytes in the sample is from about 0.0011 to about 0.0031, such as a ratio of CD34$^+$ CD90$^+$ CD45RA$^-$ cells to lymphocytes in the sample of about 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00301, 0.00302, 0.00303, 0.00304, 0.00305, 0.00306, 0.00307, 0.00308, 0.00309, or 0.00310. In some embodiments, the ratio of CD34$^+$ CD90$^+$ CD45RA$^-$ cells to lymphocytes in the sample is about 0.0021.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with CD34$^+$ CD90$^+$ CD45RA$^-$ cells relative to lymphocytes by a ratio of from about 5.6:1 to about 37.0:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with CD34$^+$ CD90$^+$ CD45RA$^-$ cells relative to lymphocytes by a ratio of about 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, 6.50:1, 6.55:1, 6.60:1, 6.65:1, 6.70:1, 6.75:1, 6.80:1, 6.85:1, 6.90:1, 6.95:1, 7.00:1, 7.05:1, 7.10:1, 7.15:1, 7.20:1, 7.25:1, 7.30:1, 7.35:1, 7.40:1, 7.45:1, 7.50:1, 7.55:1, 7.60:1, 7.65:1, 7.70:1, 7.75:1, 7.80:1, 7.85:1, 7.90:1, 7.95:1, 8.00:1, 8.05:1, 8.10:1, 8.15:1, 8.20:1, 8.25:1, 8.30:1, 8.35:1, 8.40:1, 8.45:1, 8.50:1, 8.55:1, 8.60:1, 8.65:1, 8.70:1, 8.75:1, 8.80:1, 8.85:1, 8.90:1, 8.95:1, 9.00:1, 9.05:1, 9.10:1, 9.15:1, 9.20:1, 9.25:1, 9.30:1, 9.35:1, 9.40:1, 9.45:1, 9.50:1, 9.55:1, 9.60:1, 9.65:1, 9.70:1, 9.75:1, 9.80:1, 9.85:1, 9.90:1, 9.95:1, 10.00:1, 10.05:1, 10.10:1, 10.15:1, 10.20:1, 10.25:1, 10.30:1, 10.35:1, 10.40:1, 10.45:1, 10.50:1, 10.55:1, 10.60:1, 10.65:1, 10.70:1, 10.75:1, 10.80:1, 10.85:1, 10.90:1, 10.95:1, 11.00:1, 11.05:1, 11.10:1, 11.15:1, 11.20:1, 11.25:1, 11.30:1, 11.35:1, 11.40:1, 11.45:1, 11.50:1, 11.55:1, 11.60:1, 11.65:1, 11.70:1, 11.75:1, 11.80:1, 11.85:1, 11.90:1, 11.95:1, 12.00:1, 12.05:1, 12.10:1, 12.15:1, 12.20:1, 12.25:1, 12.30:1, 12.35:1, 12.40:1, 12.45:1, 12.50:1, 12.55:1, 12.60:1, 12.65:1, 12.70:1, 12.75:1, 12.80:1, 12.85:1, 12.90:1, 12.95:1, 13.00:1, 13.05:1, 13.10:1, 13.15:1, 13.20:1, 13.25:1, 13.30:1, 13.35:1, 13.40:1, 13.45:1, 13.50:1, 13.55:1, 13.60:1, 13.65:1, 13.70:1, 13.75:1, 13.80:1, 13.85:1, 13.90:1, 13.95:1, 14.00:1, 14.05:1, 14.10:1, 14.15:1, 14.20:1, 14.25:1, 14.30:1, 14.35:1, 14.40:1, 14.45:1, 14.50:1, 14.55:1, 14.60:1, 14.65:1, 14.70:1, 14.75:1, 14.80:1, 14.85:1, 14.90:1, 14.95:1, 15.00:1, 15.05:1, 15.10:1, 15.15:1, 15.20:1, 15.25:1, 15.30:1, 15.35:1, 15.40:1, 15.45:1, 15.50:1, 15.55:1, 15.60:1, 15.65:1, 15.70:1, 15.75:1, 15.80:1, 15.85:1, 15.90:1, 15.95:1, 16.00:1, 16.05:1, 16.10:1, 16.15:1, 16.20:1, 16.25:1, 16.30:1, 16.35:1, 16.40:1, 16.45:1, 16.50:1, 16.55:1, 16.60:1, 16.65:1, 16.70:1, 16.75:1, 16.80:1, 16.85:1, 16.90:1, 16.95:1, 17.00:1, 17.05:1, 17.10:1, 17.15:1, 17.20:1, 17.25:1, 17.30:1, 17.35:1, 17.40:1, 17.45:1, 17.50:1, 17.55:1, 17.60:1, 17.65:1, 17.70:1, 17.75:1, 17.80:1, 17.85:1, 17.90:1, 17.95:1, 18.00:1, 18.05:1, 18.10:1, 18.15:1, 18.20:1, 18.25:1, 18.30:1, 18.35:1, 18.40:1, 18.45:1, 18.50:1, 18.55:1, 18.60:1, 18.65:1, 18.70:1, 18.75:1, 18.80:1, 18.85:1, 18.90:1, 18.95:1, 19.00:1, 19.05:1, 19.10:1, 19.15:1, 19.20:1, 19.25:1, 19.30:1, 19.35:1, 19.40:1, 19.45:1, 19.50:1, 19.55:1, 19.60:1, 19.65:1, 19.70:1, 19.75:1, 19.80:1, 19.85:1, 19.90:1, 19.95:1, 20.00:1, 20.05:1, 20.10:1, 20.15:1, 20.20:1, 20.25:1, 20.30:1, 20.35:1, 20.40:1, 20.45:1, 20.50:1, 20.55:1, 20.60:1, 20.65:1, 20.70:1, 20.75:1, 20.80:1, 20.85:1, 20.90:1, 20.95:1, 21.00:1, 21.05:1, 21.10:1, 21.15:1, 21.20:1, 21.25:1, 21.30:1, 21.35:1, 21.40:1, 21.45:1, 21.50:1, 21.55:1, 21.60:1, 21.65:1, 21.70:1, 21.75:1, 21.80:1, 21.85:1, 21.90:1, 21.95:1, 22.00:1, 22.05:1, 22.10:1, 22.15:1, 22.20:1, 22.25:1, 22.30:1, 22.35:1, 22.40:1, 22.45:1, 22.50:1, 22.55:1, 22.60:1, 22.65:1, 22.70:1, 22.75:1, 22.80:1, 22.85:1, 22.90:1, 22.95:1, 23.00, 23.05:1, 23.10:1, 23.15:1, 23.20:1, 23.25:1, 23.30:1, 23.35:1, 23.40:1, 23.45:1, 23.50:1, 23.55:1, 23.60:1, 23.65:1, 23.70:1, 23.75:1, 23.80:1, 23.85:1, 23.90:1, 23.95:1, 24.00:1, 24.05:1, 24.10:1, 24.15:1, 24.20:1, 24.25:1, 24.30:1, 24.35:1, 24.40:1, 24.45:1, 24.50:1, 24.55:1, 24.60:1, 24.65:1, 24.70:1, 24.75:1, 24.80:1, 24.85:1, 24.90:1, 24.95:1, 25.05:1, 25.10:1, 25.15:1, 25.20:1, 25.25:1, 25.30:1, 25.35:1, 25.40:1, 25.45:1, 25.50:1, 25.55:1, 25.60:1, 25.65:1, 25.70:1, 25.75:1, 25.80:1, 25.85:1, 25.90:1, 25.95:1, 26.00:1, 26.05:1, 26.10:1, 26.15:1, 26.20:1, 26.25:1, 26.30:1, 26.35:1, 26.40:1, 26.45:1, 26.50:1, 26.55:1, 26.60:1, 26.65:1, 26.70:1, 26.75:1, 26.80:1, 26.85:1, 26.90:1, 26.95:1, 27.00:1, 27.05:1, 27.10:1, 27.15:1, 27.20:1, 27.25:1, 27.30:1, 27.35:1, 27.40:1, 27.45:1, 27.50:1, 27.55:1, 27.60:1, 27.65:1, 27.70:1, 27.75:1, 27.80:1, 27.85:1, 27.90:1, 27.95:1, 28.00:1, 28.05:1, 28.10:1, 28.15:1, 28.20:1, 28.25:1, 28.30:1, 28.35:1, 28.40:1, 28.45:1, 28.50:1, 28.55:1, 28.60:1, 28.65:1, 28.70:1, 28.75:1, 28.80:1, 28.85:1, 28.90:1, 28.95:1, 29.00:1, 29.05:1, 29.10:1, 29.15:1, 29.20:1, 29.25:1, 29.30:1, 29.35:1, 29.40:1, 29.45:1, 29.50:1, 29.55:1, 29.60:1, 29.65:1, 29.70:1, 29.75:1, 29.80:1, 29.85:1, 29.90:1, 29.95:1, 30.00:1, 30.05:1, 30.10:1, 30.15:1, 30.20:1, 30.25:1, 30.30:1, 30.35:1, 30.40:1, 30.45:1, 30.50:1, 30.55:1, 30.60:1, 30.65:1, 30.70:1, 30.75:1, 30.80:1, 30.85:1, 30.90:1, 30.95:1, 31.00:1, 31.05:1, 31.10:1, 31.15:1, 31.20:1, 31.25:1, 31.30:1, 31.35:1, 31.40:1, 31.45:1, 31.50:1, 31.55:1, 31.60:1, 31.65:1, 31.70:1, 31.75:1, 31.80:1, 31.85:1, 31.90:1, 31.95:1, 32.00:1, 32.05:1, 32.10:1, 32.15:1, 32.20:1, 32.25:1, 32.30:1, 32.35:1, 32.40:1, 32.45:1, 32.50:1, 32.55:1, 32.60:1, 32.65:1, 32.70:1, 32.75:1, 32.80:1, 32.85:1, 32.90:1, 32.95:1, 33.00:1, 33.05:1, 33.10:1, 33.15:1, 33.20:1, 33.25:1, 33.30:1, 33.35:1, 33.40:1, 33.45:1, 33.50:1, 33.55:1, 33.60:1, 33.65:1, 33.70:1, 33.75:1, 33.80:1, 33.85:1, 33.90:1, 33.95:1, 34.00:1, 34.05:1, 34.10:1, 34.15:1, 34.20:1, 34.25:1, 34.30:1, 34.35:1, 34.40:1, 34.45:1, 34.50:1, 34.55:1, 34.60:1, 34.65:1, 34.70:1, 34.75:1, 34.80:1, 34.85:1, 34.90:1, 34.95:1, 35.00:1, 35.05:1, 35.10:1, 35.15:1, 35.20:1, 35.25:1, 35.30:1, 35.35:1, 35.40:1, 35.45:1, 35.50:1, 35.55:1, 35.60:1, 35.65:1, 35.70:1, 35.75:1, 35.80:1, 35.85:1, 35.90:1, 35.95:1, 36.00:1, 36.05:1, 36.10:1, 36.15:1, 36.20:1, 36.25:1, 36.30:1, 36.35:1, 36.40:1, 36.45:1, 36.50:1, 36.55:1, 36.60:1, 36.65:1, 36.70:1, 36.75:1, 36.80:1, 36.85:1, 36.90:1, 36.95:1, or 37.00. In some embodiments, the peripheral blood of the donor is enriched with CD34$^+$ CD90$^+$ CD45RA$^-$ cells relative to lymphocytes by a ratio of about from about 8.0:1 to about 10.0:1, such as a ratio of about 8.00:1, 8.05:1, 8.10:1, 8.15:1, 8.20:1, 8.25:1, 8.30:1, 8.35:1, 8.40:1, 8.45:1, 8.50:1, 8.55:1, 8.60:1, 8.65:1, 8.70:1, 8.75:1, 8.80:1, 8.85:1, 8.90:1, 8.95:1, 9.00:1, 9.05:1, 9.10:1, 9.15:1, 9.20:1, 9.25:1, 9.30:1, 9.35:1, 9.40:1, 9.45:1, 9.50:1, 9.55:1, 9.60:1, 9.65:1, 9.70:1, 9.75:1, 9.80:1, 9.85:1, 9.90:1, 9.95:1, or 10.00:1. In some embodiments, the peripheral blood of the donor is enriched with CD34$^+$ CD90$^+$ CD45RA$^-$ cells relative to lymphocytes by a ratio of about 9.3:1.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a density of CD34$^+$ CD90$^+$ CD45RA$^-$ cells of at least about 16,000 cells/ml, such as a density of from about 20,000 cells/ml to about 75,000 cells/ml, about 25,000 cells/ml to about 70,000 cells/ml, about 30,000 cells/ml to about 65,000 cells/ml, about 35,000 cells/ml to about 60,000 cells/ml, about 40,000 cells/ml to about 55,000 cells/ml, or about 45,000 cells/ml to about 50,000 cells/ml (e.g., about 16,000 cells/ml, 17,000 cells/ml, 18,000 cells/ml, 19,000 cells/ml, 20,000 cells/ml, 21,000 cells/ml, 22,000 cells/ml, 23,000 cells/ml, 24,000 cells/ml, 25,000 cells/ml, 26,000 cells/ml, 27,000 cells/ml, 28,000 cells/ml, 29,000 cells/ml, 30,000 cells/ml, 31,000 cells/ml, 32,000 cells/ml, 33,000 cells/ml, 34,000 cells/ml, 35,000 cells/ml, 36,000 cells/ml, 37,000 cells/ml, 38,000 cells/ml, 39,000 cells/ml, 40,000 cells/ml, 41,000 cells/ml, 42,000 cells/ml, 43,000 cells/ml, 44,000 cells/ml, 45,000 cells/ml, 46,000 cells/ml, 47,000 cells/ml, 48,000 cells/ml, 49,000 cells/ml, 50,000 cells/ml, 51,000 cells/ml, 52,000 cells/ml, 53,000 cells/ml, 54,000 cells/ml, 55,000 cells/ml, 56,000 cells/ml, 57,000 cells/ml, 58,000 cells/ml, 59,000 cells/ml, 60,000 cells/ml, 61,000 cells/ml, 62,000 cells/ml, 63,000 cells/ml, 64,000 cells/ml, 65,000 cells/ml, 66,000 cells/ml, 67,000 cells/ml, 68,000 cells/ml, 69,000 cells/ml, 70,000 cells/ml, 71,000 cells/ml, 72,000 cells/ml, 73,000 cells/ml, 74,000 cells/ml, 75,000 cells/ml, 76,000 cells/ml, 77,000 cells/ml, or more), and having a density of lymphocytes of no more than about $2.4 \times 10^7$ cells/ml, such as a density of lymphocytes of about $1 \times 10^7$ cells/ml to about $2.3 \times 10^7$ cells/ml, about $1.3 \times 10^7$ cells/ml to about $2.1 \times 10^7$ cells/ml, or about $1.5 \times 10^7$ cells/ml to about $1.9 \times 10^7$ cells/ml (e.g., about $2.4 \times 10^7$ cells/ml, $2.3 \times 10^7$ cells/ml, $2.2 \times 10^7$ cells/ml, $2.1 \times 10^7$ cells/ml, $2 \times 10^7$ cells/ml, $1.9 \times 10^7$ cells/ml, $1.8 \times 10^7$ cells/ml, $1.7 \times 10^7$ cells/ml, $1.6 \times 10^7$ cells/ml, $1.5 \times 10^7$ cells/ml $1.4 \times 10^7$ cells/ml, $1.3 \times 10^7$ cells/ml, $1.2 \times 10^7$ cells/ml, $1.1 \times 10^7$ cells/ml, $1 \times 10^7$ cells/ml, or less, $0.9 \times 10^7$ cells/ml, $0.8 \times 10^7$ cells/ml, or less). In some embodiments, the method includes administering to the donor a CXCR2 agonist and a CXCR4 antagonist in amounts sufficient to produce a population of cells having a density of CD34$^+$ CD90$^+$ CD45RA$^-$ cells of from about 20,000 cells/ml to about 75,000 cells/ml, and having a density of lymphocytes of from about $1 \times 10^7$ cells/ml to about $2.3 \times 10^7$ cells/ml. In some embodiments, the method includes administering to the donor a CXCR2 agonist and a CXCR4 antagonist in amounts sufficient to produce a population of cells having a density of CD34$^+$ CD90$^+$ CD45RA$^-$ cells of from about 30,000 cells/ml to about 60,000 cells/ml, and having a density of lymphocytes of from about $1.3 \times 10^7$ cells/ml to about $2.3 \times 10^7$ cells/ml. In some embodiments, the method includes administering to the donor a CXCR2 agonist and a CXCR4 antagonist in amounts sufficient to produce a population of cells having a density of CD34$^+$ CD90$^+$ CD45RA$^-$ cells of from about 40,000 cells/ml to about 50,000 cells/ml, and having a density of lymphocytes of from about $1.5 \times 10^7$ cells/ml to about $2 \times 10^7$ cells/ml.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of CD34$^+$ CD90$^+$ CD45RA$^-$ cells to monocytes of from about 0.0028 to about 0.0130 in a sample of peripheral blood of the donor following administration of the CXCR2 agonist. In some embodiments, the ratio of CD34$^+$ CD90$^+$ CD45RA$^-$ cells to monocytes in the sample may be about 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, 0.00460, 0.00461, 0.00462, 0.00463, 0.00464, 0.00465, 0.00466, 0.00467, 0.00468, 0.00469, 0.00470, 0.00471, 0.00472, 0.00473, 0.00474, 0.00475, 0.00476, 0.00478, 0.00479, 0.00480, 0.00481, 0.00482, 0.00483, 0.00484, 0.00485, 0.00486, 0.00487, 0.00488, 0.00489, 0.00490, 0.00491, 0.00492, 0.00493, 0.00494, 0.00495, 0.00496, 0.00497, 0.00498, 0.00499, 0.00500, 0.00501, 0.00502, 0.00503, 0.00504, 0.00505, 0.00506, 0.00507, 0.00508, 0.00509, 0.00510, 0.00511, 0.00512, 0.00513, 0.00514, 0.00515, 0.00516, 0.00517, 0.00518, 0.00519, 0.00520, 0.00521, 0.00522, 0.00523, 0.00524, 0.00525, 0.00526, 0.00527, 0.00528, 0.00529, 0.00530, 0.00531, 0.00532, 0.00533, 0.00534, 0.00535, 0.00536, 0.00537, 0.00538, 0.00539, 0.00540, 0.00541, 0.00542, 0.00543, 0.00544, 0.00545, 0.00546, 0.00547, 0.00548, 0.00549, 0.00550, 0.00551, 0.00552, 0.00553, 0.00554, 0.00555, 0.00556, 0.00557, 0.00558, 0.00559, 0.00560, 0.00561, 0.00562, 0.00563, 0.00564, 0.00565, 0.00566, 0.00567, 0.00568, 0.00569, 0.00570, 0.00571, 0.00572, 0.00573, 0.00574, 0.00575, 0.00576, 0.00578, 0.00579, 0.00580, 0.00581, 0.00582, 0.00583, 0.00584, 0.00585, 0.00586, 0.00587, 0.00588, 0.00589, 0.00590, 0.00591, 0.00592, 0.00593, 0.00594, 0.00595, 0.00596, 0.00597, 0.00598, 0.00599, 0.00600, 0.00601, 0.00602, 0.00603, 0.00604, 0.00605, 0.00606, 0.00607, 0.00608, 0.00609, 0.00610, 0.00611, 0.00612, 0.00613, 0.00614, 0.00615, 0.00616, 0.00617, 0.00618, 0.00619, 0.00620, 0.00621, 0.00622, 0.00623, 0.00624, 0.00625, 0.00626, 0.00627, 0.00628, 0.00629, 0.00630, 0.00631, 0.00632, 0.00633, 0.00634, 0.00635, 0.00636, 0.00637, 0.00638, 0.00639, 0.00640, 0.00641, 0.00642, 0.00643, 0.00644, 0.00645, 0.00646, 0.00647, 0.00648, 0.00649, 0.00650, 0.00651, 0.00652, 0.00653, 0.00654, 0.00655, 0.00656, 0.00657, 0.00658, 0.00659, 0.00660, 0.00661, 0.00662, 0.00663, 0.00664, 0.00665, 0.00666, 0.00667, 0.00668, 0.00669, 0.00670, 0.00671, 0.00672, 0.00673, 0.00674, 0.00675, 0.00676, 0.00678, 0.00679, 0.00680, 0.00681, 0.00682, 0.00683, 0.00684, 0.00685, 0.00686, 0.00687, 0.00688, 0.00689, 0.00690, 0.00691, 0.00692, 0.00693, 0.00694, 0.00695, 0.00696, 0.00697, 0.00698, 0.00699, 0.00700, 0.00701, 0.00702, 0.00703, 0.00704, 0.00705, 0.00706, 0.00707, 0.00708, 0.00709, 0.00710, 0.00711, 0.00712, 0.00713, 0.00714, 0.00715, 0.00716, 0.00717, 0.00718, 0.00719, 0.00720, 0.00721, 0.00722, 0.00723, 0.00724, 0.00725, 0.00726, 0.00727, 0.00728, 0.00729, 0.00730, 0.00731, 0.00732, 0.00733, 0.00734, 0.00735, 0.00736, 0.00737, 0.00738, 0.00739, 0.00740, 0.00741, 0.00742, 0.00743, 0.00744, 0.00745, 0.00746, 0.00747, 0.00748, 0.00749, 0.00750, 0.00751, 0.00752, 0.00753, 0.00754, 0.00755, 0.00756, 0.00757, 0.00758, 0.00759, 0.00760, 0.00761, 0.00762, 0.00763, 0.00764, 0.00765, 0.00766, 0.00767, 0.00768, 0.00769, 0.00770, 0.00771, 0.00772, 0.00773, 0.00774, 0.00775, 0.00776, 0.00777, 0.00778, 0.00779, 0.00780, 0.00781, 0.00782, 0.00783, 0.00784, 0.00785, 0.00786, 0.00787, 0.00788, 0.00789, 0.00790, 0.00791, 0.00792, 0.00793, 0.00794, 0.00795, 0.00796, 0.00797, 0.00798, 0.00799, 0.00800, 0.00801, 0.00802, 0.00803, 0.00804, 0.00805, 0.00806, 0.00807, 0.00808, 0.00809, 0.00810, 0.00811, 0.00812, 0.00813, 0.00814, 0.00815, 0.00816, 0.00817, 0.00818, 0.00819, 0.00820, 0.00821, 0.00822, 0.00823, 0.00824, 0.00825, 0.00826, 0.00827, 0.00828, 0.00829, 0.00830, 0.00831, 0.00832, 0.00833, 0.00834, 0.00835, 0.00836, 0.00837, 0.00838, 0.00839, 0.00840, 0.00841, 0.00842, 0.00843, 0.00844, 0.00845, 0.00846, 0.00847, 0.00848, 0.00849, 0.00850, 0.00851, 0.00852, 0.00853, 0.00854, 0.00855, 0.00856, 0.00857, 0.00858, 0.00859, 0.00860, 0.00861, 0.00862, 0.00863, 0.00864, 0.00865, 0.00866, 0.00867, 0.00868, 0.00869, 0.00870, 0.00871, 0.00872, 0.00873, 0.00874, 0.00875, 0.00876, 0.00877, 0.00878, 0.00879, 0.00880, 0.00881, 0.00882, 0.00883, 0.00884, 0.00885, 0.00886, 0.00887, 0.00888, 0.00889, 0.00890, 0.00891, 0.00892, 0.00893, 0.00894, 0.00895, 0.00896, 0.00897, 0.00898, 0.00899, 0.00900, 0.00901, 0.00902, 0.00903, 0.00904, 0.00905, 0.00906, 0.00907, 0.00908, 0.00909, 0.00910, 0.00911, 0.00912, 0.00913, 0.00914, 0.00915, 0.00916, 0.00917, 0.00918, 0.00919, 0.00920, 0.00921, 0.00922, 0.00923, 0.00924, 0.00925, 0.00926, 0.00927, 0.00928, 0.00929, 0.00930, 0.00931, 0.00932, 0.00933, 0.00934, 0.00935, 0.00936, 0.00937, 0.00938, 0.00939, 0.00940, 0.00941, 0.00942, 0.00943, 0.00944, 0.00945, 0.00946, 0.00947, 0.00948, 0.00949, 0.00950, 0.00951, 0.00952, 0.00953, 0.00954, 0.00955, 0.00956, 0.00957, 0.00958, 0.00959, 0.00960, 0.00961, 0.00962, 0.00963, 0.00964, 0.00965, 0.00966, 0.00967, 0.00968, 0.00969, 0.00970, 0.00971, 0.00972, 0.00973, 0.00974, 0.00975, 0.00976, 0.00977, 0.00978, 0.00979, 0.00980, 0.00981, 0.00982, 0.00983, 0.00984, 0.00985, 0.00986, 0.00987, 0.00988, 0.00989, 0.00990, 0.00991, 0.00992, 0.00993, 0.00994, 0.00995, 0.00996, 0.00997, 0.00998, 0.00999, 0.0100, 0.0101, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, or 0.0130. In some embodiments, the ratio of CD34$^+$ CD90$^+$ CD45RA$^-$ cells to monocytes in the sample is from about 0.0063 to about 0.0083, such as a ratio of CD34$^+$ CD90$^+$ CD45RA$^-$ cells to monocytes in the sample of about 0.00630, 0.00631, 0.00632, 0.00633, 0.00634, 0.00635, 0.00636, 0.00637, 0.00638, 0.00639, 0.00640, 0.00641, 0.00642, 0.00643, 0.00644, 0.00645, 0.00646, 0.00647, 0.00648, 0.00649, 0.00650, 0.00651, 0.00652, 0.00653, 0.00654, 0.00655, 0.00656, 0.00657, 0.00658, 0.00659, 0.00660, 0.00661, 0.00662, 0.00663, 0.00664, 0.00665, 0.00666, 0.00667, 0.00668, 0.00669, 0.00670, 0.00671, 0.00672, 0.00673, 0.00674, 0.00675, 0.00676, 0.00678, 0.00679, 0.00680, 0.00681, 0.00682, 0.00683, 0.00684, 0.00685, 0.00686, 0.00687, 0.00688, 0.00689, 0.00690, 0.00691, 0.00692, 0.00693, 0.00694, 0.00695, 0.00696, 0.00697, 0.00698, 0.00699, 0.00700, 0.00701, 0.00702, 0.00703, 0.00704, 0.00705, 0.00706, 0.00707, 0.00708, 0.00709, 0.00710, 0.00711, 0.00712, 0.00713, 0.00714, 0.00715, 0.00716, 0.00717, 0.00718, 0.00719, 0.00720, 0.00721, 0.00722, 0.00723, 0.00724, 0.00725, 0.00726, 0.00727, 0.00728, 0.00729, 0.00730, 0.00731, 0.00732, 0.00733, 0.00734, 0.00735, 0.00736, 0.00737, 0.00738, 0.00739, 0.00740, 0.00741, 0.00742, 0.00743, 0.00744, 0.00745, 0.00746, 0.00747, 0.00748, 0.00749, 0.00750, 0.00751, 0.00752, 0.00753, 0.00754, 0.00755, 0.00756, 0.00757, 0.00758, 0.00759, 0.00760, 0.00761, 0.00762, 0.00763, 0.00764, 0.00765, 0.00766, 0.00767, 0.00768, 0.00769, 0.00770, 0.00771, 0.00772, 0.00773, 0.00774, 0.00775, 0.00776, 0.00777, 0.00778, 0.00779, 0.00780, 0.00781, 0.00782, 0.00783, 0.00784, 0.00785, 0.00786, 0.00787, 0.00788, 0.00789, 0.00790, 0.00791, 0.00792, 0.00793, 0.00794, 0.00795, 0.00796, 0.00797, 0.00798, 0.00799, 0.00800, 0.00801, 0.00802, 0.00803, 0.00804, 0.00805, 0.00806, 0.00807, 0.00808, 0.00809, 0.00810, 0.00811, 0.00812, 0.00813, 0.00814, 0.00815, 0.00816, 0.00817, 0.00818, 0.00819, 0.00820, 0.00821, 0.00822, 0.00823, 0.00824, 0.00825, 0.00826, 0.00827, 0.00828, 0.00829, 0.00830. In some embodiments, the ratio of CD34$^+$ CD90$^+$ CD45RA$^-$ cells to monocytes in the sample is about 0.0073.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with CD34$^+$ CD90$^+$ CD45RA$^-$ cells relative to monocytes by a ratio of from about 1.5:1 to about 8.5:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with CD34$^+$ CD90$^+$ CD45RA$^-$ cells relative to monocytes by a ratio of about 1.50:1, 1.55:1, 1.60:1, 1.65:1, 1.70:1, 1.75:1, 1.80:1, 1.85:1, 1.90:1, 1.95:1, 2.00:1, 2.05:1, 2.10:1, 2.15:1, 2.20:1, 2.25:1, 2.30:1, 2.35:1, 2.40:1, 2.45:1, 2.50:1, 2.55:1, 2.60:1, 2.65:1, 2.70:1, 2.75:1, 2.80:1, 2.85:1, 2.90:1, 2.95:1, 3.00:1, 3.05:1, 3.10:1, 3.15:1, 3.20:1, 3.25:1, 3.30:1, 3.35:1, 3.40:1, 3.45:1, 3.50:1, 3.55:1, 3.60:1, 3.65:1, 3.70:1, 3.75:1, 3.80:1, 3.85:1, 3.90:1, 3.95:1, 4.00:1, 4.05:1, 4.10:1, 4.15:1, 4.20:1, 4.25:1, 4.30:1, 4.35:1, 4.40:1, 4.45:1, 4.50:1, 4.55:1, 4.60:1, 4.65:1, 4.70:1, 4.75:1, 4.80:1, 4.85:1, 4.90:1, 4.95:1, 5.00:1, 5.05:1, 5.10:1, 5.15:1, 5.20:1, 5.25:1, 5.30:1, 5.35:1, 5.40:1, 5.45:1, 5.50:1, 5.55:1, 5.60:1, 5.65:1, 5.70:1, 5.75:1, 5.80:1, 5.85:1, 5.90:1, 5.95:1, 6.00:1, 6.05:1, 6.10:1, 6.15:1, 6.20:1, 6.25:1, 6.30:1, 6.35:1, 6.40:1, 6.45:1, 6.50:1, 6.55:1, 6.60:1, 6.65:1, 6.70:1, 6.75:1, 6.80:1, 6.85:1, 6.90:1, 6.95:1, 7.00:1, 7.05:1, 7.10:1, 7.15:1, 7.20:1, 7.25:1, 7.30:1, 7.35:1, 7.40:1, 7.45:1, 7.50:1, 7.55:1, 7.60:1, 7.65:1, 7.70:1, 7.75:1, 7.80:1, 7.85:1, 7.90:1, 7.95:1, 8.00:1, 8.05:1, 8.10:1, 8.15:1, 8.20:1, 8.25:1, 8.30:1, 8.35:1, 8.40:1, 8.45:1, or 8.50:1. In some embodiments, the peripheral blood of the donor is enriched with CD34$^+$ CD90$^+$ CD45RA$^-$ cells relative to monocytes by a ratio of about 1.9:1.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a density of CD34$^+$ CD90$^+$ CD45RA$^-$ cells of at least about 16,000 cells/ml, such as a density of from about 20,000 cells/ml to about 75,000 cells/ml, about 25,000 cells/ml to about 70,000 cells/ml, about 30,000 cells/ml to about 65,000 cells/ml, about 35,000 cells/ml to about 60,000 cells/ml, about 40,000 cells/ml to about 55,000 cells/ml, or about 45,000 cells/ml to about 50,000 cells/ml (e.g., about 16,000 cells/ml, 17,000 cells/ml, 18,000 cells/ml, 19,000 cells/ml, 20,000 cells/ml, 21,000 cells/ml, 22,000 cells/ml, 23,000 cells/ml, 24,000 cells/ml, 25,000 cells/ml, 26,000 cells/ml, 27,000 cells/ml, 28,000 cells/ml, 29,000 cells/ml, 30,000 cells/ml, 31,000 cells/ml, 32,000 cells/ml, 33,000 cells/ml, 34,000 cells/ml, 35,000 cells/ml, 36,000 cells/ml, 37,000 cells/ml, 38,000 cells/ml, 39,000 cells/ml, 40,000 cells/ml, 41,000 cells/nil, 42,000 cells/ml, 43,000 cells/ml, 44,000 cells/ml, 45,000 cells/ml, 46,000 cells/ml, 47,000 cells/ml, 48,000 cells/ml, 49,000 cells/ml, 50,000 cells/ml, 51,000 cells/ml, 52,000 cells/ml, 53,000 cells/ml, 54,000 cells/ml, 55,000 cells/ml, 56,000 cells/ml, 57,000 cells/ml, 58,000 cells/ml, 59,000 cells/ml, 60,000 cells/ml, 61,000 cells/ml, 62,000 cells/ml, 63,000 cells/ml, 64,000 cells/ml, 65,000 cells/ml, 66,000 cells/ml, 67,000 cells/ml, 68,000 cells/ml, 69,000 cells/ml, 70,000 cells/ml, 71,000 cells/ml, 72,000 cells/ml, 73,000 cells/ml, 74,000 cells/ml, 75,000 cells/ml, 76,000 cells/ml, 77,000 cells/ml, or more), and having a density of monocytes of no more than about $6 \times 10^6$ cells/ml, such as a density of monocytes of from $3.4 \times 10^6$ cells/ml to about $5.9 \times 10^6$ cells/ml, about $3.5 \times 10^6$ cells/ml to about $5.7 \times 10^6$ cells/ml, or about $4 \times 10^6$ cells/ml to about $5 \times 10^6$ cells/ml (e.g., $5.9 \times 10^6$ cells/ml, $5.8 \times 10^6$ cells/ml, $5.7 \times 10^6$ cells/ml, $5.6 \times 10^6$ cells/ml, $5.5 \times 10^6$ cells/ml, $5.4 \times 10^6$ cells/ml, $5.3 \times 10^6$ cells/ml, $5.2 \times 10^6$ cells/ml, $5.1 \times 10^6$ cells/ml, $5 \times 10^6$ cells/ml, $4.9 \times 10^6$ cells/ml, $4.8 \times 10^6$ cells/ml, $4.7 \times 10^6$ cells/ml, $4.6 \times 10^6$ cells/ml, $4.5 \times 10^6$ cells/ml, $4.4 \times 10^6$ cells/ml, $4.3 \times 10^6$ cells/ml, $4.2 \times 10^6$ cells/ml, $4.1 \times 10^6$ cells/ml, $4 \times 10^6$ cells/ml, $3.9 \times 10^6$ cells/ml, $3.8 \times 10^6$ cells/ml, $3.7 \times 10^6$ cells/ml, $3.6 \times 10^6$ cells/ml, $3.5 \times 10^6$ cells/ml, $3.4 \times 10^6$ cells/ml, or less). In some embodiments, the method includes administering to the donor a CXCR2 agonist and a CXCR4 antagonist in amounts sufficient to produce a population of cells having a density of $CD34^+$ $CD90^+$ $CD45RA^-$ cells of from about 20,000 cells/ml to about 75,000 cells/ml, and having a density of monocytes of from about $3.4 \times 10^6$ cells/ml to about $6 \times 10^6$ cells/ml. In some embodiments, the method includes administering to the donor a CXCR2 agonist and a CXCR4 antagonist in amounts sufficient to produce a population of cells having a density of $CD34^+$ $CD90^+$ $CD45RA^-$ cells of from about 30,000 cells/ml to about 60,000 cells/ml, and having a density of monocytes of from about $4 \times 10^6$ cells/ml to about $5.5 \times 10^6$ cells/ml. In some embodiments, the method includes administering to the donor a CXCR2 agonist and a CXCR4 antagonist in amounts sufficient to produce a population of cells having a density of $CD34^+$ $CD90^+$ $CD45RA^-$ cells of from about 40,000 cells/ml to about 50,000 cells/ml, and having a density of monocytes of from about $4 \times 10^6$ cells/ml to about $5 \times 10^6$ cells/ml.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a ratio of $CD34^+$ $CD90^+$ $CD45RA^-$ cells to $CD34^+$ cells of from about 0.393 to about 0.745 in a sample of peripheral blood of the donor following administration of the CXCR2 agonist. In some embodiments, the ratio of $CD34^+$ $CD90^+$ $CD45RA^-$ cells to $CD34^+$ cells in the sample may be about 0.393, 0.394, 0.395, 0.396, 0.397, 0.398, 0.399, 0.401, 0.402, 0.403, 0.404, 0.405, 0.406, 0.407, 0.408, 0.409, 0.410, 0.411, 0.412, 0.413, 0.414, 0.415, 0.416, 0.417, 0.418, 0.419, 0.420, 0.421, 0.422, 0.423, 0.424, 0.425, 0.426, 0.427, 0.428, 0.429, 0.430, 0.431, 0.432, 0.433, 0.434, 0.435, 0.436, 0.437, 0.438, 0.439, 0.440, 0.441, 0.442, 0.443, 0.444, 0.445, 0.446, 0.447, 0.448, 0.449, 0.450, 0.451, 0.452, 0.453, 0.454, 0.455, 0.456, 0.457, 0.458, 0.459, 0.460, 0.461, 0.462, 0.463, 0.464, 0.465, 0.466, 0.467, 0.468, 0.469, 0.470, 0.471, 0.472, 0.473, 0.474, 0.475, 0.476, 0.478, 0.479, 0.480, 0.481, 0.482, 0.483, 0.484, 0.485, 0.486, 0.487, 0.488, 0.489, 0.490, 0.491, 0.492, 0.493, 0.494, 0.495, 0.496, 0.497, 0.498, 0.499, 0.500, 0.501, 0.502, 0.503, 0.504, 0.505, 0.506, 0.507, 0.508, 0.509, 0.510, 0.511, 0.512, 0.513, 0.514, 0.515, 0.516, 0.517, 0.518, 0.519, 0.520, 0.521, 0.522, 0.523, 0.524, 0.525, 0.526, 0.527, 0.528, 0.529, 0.530, 0.531, 0.532, 0.533, 0.534, 0.535, 0.536, 0.537, 0.538, 0.539, 0.540, 0.541, 0.542, 0.543, 0.544, 0.545, 0.546, 0.547, 0.548, 0.549, 0.550, 0.551, 0.552, 0.553, 0.554, 0.555, 0.556, 0.557, 0.558, 0.559, 0.560, 0.561, 0.562, 0.563, 0.564, 0.565, 0.566, 0.567, 0.568, 0.569, 0.570, 0.571, 0.572, 0.573, 0.574, 0.575, 0.576, 0.578, 0.579, 0.580, 0.581, 0.582, 0.583, 0.584, 0.585, 0.586, 0.587, 0.588, 0.589, 0.590, 0.591, 0.592, 0.593, 0.594, 0.595, 0.596, 0.597, 0.598, 0.599, 0.600, 0.601, 0.602, 0.603, 0.604, 0.605, 0.606, 0.607, 0.608, 0.609, 0.610, 0.611, 0.612, 0.613, 0.614, 0.615, 0.616, 0.617, 0.618, 0.619, 0.620, 0.621, 0.622, 0.623, 0.624, 0.625, 0.626, 0.627, 0.628, 0.629, 0.630, 0.631, 0.632, 0.633, 0.634, 0.635, 0.636, 0.637, 0.638, 0.639, 0.640, 0.641, 0.642, 0.643, 0.644, 0.645, 0.646, 0.647, 0.648, 0.649, 0.650, 0.651, 0.652, 0.653, 0.654, 0.655, 0.656, 0.657, 0.658, 0.659, 0.660, 0.661, 0.662, 0.663, 0.664, 0.665, 0.666, 0.667, 0.668, 0.669, 0.670, 0.671, 0.672, 0.673, 0.674, 0.675, 0.676, 0.678, 0.679, 0.680, 0.681, 0.682, 0.683, 0.684, 0.685, 0.686, 0.687, 0.688, 0.689, 0.690, 0.691, 0.692, 0.693, 0.694, 0.695, 0.696, 0.697, 0.698, 0.699, 0.700, 0.701, 0.702, 0.703, 0.704, 0.705, 0.706, 0.707, 0.708, 0.709, 0.710, 0.711, 0.712, 0.713, 0.714, 0.715, 0.716, 0.717, 0.718, 0.719, 0.720, 0.721, 0.722, 0.723, 0.724, 0.725, 0.726, 0.727, 0.728, 0.729, 0.730, 0.731, 0.732, 0.733, 0.734, 0.735, 0.736, 0.737, 0.738, 0.739, 0.740, 0.741, 0.742, 0.743, 0.744, or 0.745. In some embodiments, the ratio of $CD34^+$ $CD90^+$ $CD45RA^-$ cells to $CD34^+$ cells in the sample is from about 0.625 to about 0.725, such as a ratio of $CD34^+$ $CD90^+$ $CD45RA^-$ cells to $CD34^+$ cells in the sample of about 0.625, 0.626, 0.627, 0.628, 0.629, 0.630, 0.631, 0.632, 0.633, 0.634, 0.635, 0.636, 0.637, 0.638, 0.639, 0.640, 0.641, 0.642, 0.643, 0.644, 0.645, 0.646, 0.647, 0.648, 0.649, 0.650, 0.651, 0.652, 0.653, 0.654, 0.655, 0.656, 0.657, 0.658, 0.659, 0.660, 0.661, 0.662, 0.663, 0.664, 0.665, 0.666, 0.667, 0.668, 0.669, 0.670, 0.671, 0.672, 0.673, 0.674, 0.675, 0.676, 0.678, 0.679, 0.680, 0.681, 0.682, 0.683, 0.684, 0.685, 0.686, 0.687, 0.688, 0.689, 0.690, 0.691, 0.692, 0.693, 0.694, 0.695, 0.696, 0.697, 0.698, 0.699, 0.700, 0.701, 0.702, 0.703, 0.704, 0.705, 0.706, 0.707, 0.708, 0.709, 0.710, 0.711, 0.712, 0.713, 0.714, 0.715, 0.716, 0.717, 0.718, 0.719, 0.720, 0.721, 0.722, 0.723, 0.724, or 0.725. In some embodiments, the ratio of $CD34^+$ $CD90^+$ $CD45RA^-$ cells to $CD34^+$ cells in the sample is about 0.676.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to enrich the peripheral blood of the donor with $CD34^+$ $CD90^+$ $CD45RA^-$ cells relative to $CD34^+$ cells by a ratio of from about 1.1:1 to about 4.8:1 as assessed by comparing a sample of peripheral blood of the donor following administration of the CXCR2 agonist and CXCR4 antagonist to a sample of peripheral blood of the donor prior to administration of the CXCR2 agonist and CXCR4 antagonist. In some embodiments, the peripheral blood of the donor may be enriched with $CD34^+$ CD90⁺ CD45RA⁻ cells relative to monocytes by a ratio of about 1.10:1, 1.15:1, 1.20:1, 1.25:1, 1.30:1, 1.35:1, 1.40:1, 1.45:1, 1.50:1, 1.55:1, 1.60:1, 1.65:1, 1.70:1, 1.75:1, 1.80:1, 1.85:1, 1.90:1, 1.95:1, 2.00:1, 2.05:1, 2.10:1, 2.15:1, 2.20:1, 2.25:1, 2.30:1, 2.35:1, 2.40:1, 2.45:1, 2.50:1, 2.55:1, 2.60:1, 2.65:1, 2.70:1, 2.75:1, 2.80:1, 2.85:1, 2.90:1, 2.95:1, 3.00:1, 3.05:1, 3.10:1, 3.15:1, 3.20:1, 3.25:1, 3.30:1, 3.35:1, 3.40:1, 3.45:1, 3.50:1, 3.55:1, 3.60:1, 3.65:1, 3.70:1, 3.75:1, 3.80:1, 3.85:1, 3.90:1, 3.95:1, 4.00:1, 4.05:1, 4.10:1, 4.15:1, 4.20:1, 4.25:1, 4.30:1, 4.35:1, 4.40:1, 4.45:1, 4.50:1, 4.55:1, 4.60:1, 4.65:1, 4.70:1, 4.75:1, or 4.80:1. In some embodiments, the peripheral blood of the donor is enriched with CD34⁺ CD90⁺ CD45RA⁻ cells relative to CD34⁺ cells by a ratio of about 1.2:1.

In another aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to produce a population of cells having a frequency of CD34⁺ CD90⁺ CD45RA⁻ cells of from about 0.020% to about 0.110% in a sample of peripheral blood of the donor following administration of the CXCR2 agonist and CXCR4 antagonist. In some embodiments, the population of cells may have a frequency of CD34⁺ CD90⁺ CD45RA⁻ cells of about 0.020%, 0.021%, 0.022%, 0.023%, 0.024%, 0.025%, 0.026%, 0.027%, 0.028%, 0.029%, 0.030%, 0.031%, 0.032%, 0.033%, 0.034%, 0.035%, 0.036%, 0.037%, 0.038%, 0.039%, 0.040%, 0.041%, 0.042%, 0.043%, 0.044%, 0.045%, 0.046%, 0.047%, 0.048%, 0.049%, 0.050%, 0.051%, 0.052%, 0.053%, 0.054%, 0.055%, 0.056%, 0.057%, 0.058%, 0.059%, 0.060%, 0.061%, 0.062%, 0.063%, 0.064%, 0.065%, 0.066%, 0.067%, 0.068%, 0.069%, 0.070%, 0.071%, 0.072%, 0.073%, 0.074%, 0.075%, 0.076%, 0.077%, 0.078%, 0.079%, 0.080%, 0.081%, 0.082%, 0.083%, 0.084%, 0.085%, 0.086%, 0.087%, 0.088%, 0.089%, 0.090%, 0.091%, 0.092%, 0.093%, 0.094%, 0.095%, 0.096%, 0.097%, 0.098%, 0.099%, 0.100%, 0.101%, 0.102%, 0.103%, 0.104%, 0.105%, 0.106%, 0.107%, 0.108%, 0.109%, or 0.110%. In some embodiments, the population of cells has a frequency of CD34⁺ CD90⁺ CD45RA⁻ cells of from about 0.046% to about 0.086%, such as a frequency of hematopoietic stem cells of about 0.046%, 0.047%, 0.048%, 0.049%, 0.050%, 0.051%, 0.052%, 0.053%, 0.054%, 0.055%, 0.056%, 0.057%, 0.058%, 0.059%, 0.060%, 0.061%, 0.062%, 0.063%, 0.064%, 0.065%, 0.066%, 0.067%, 0.068%, 0.069%, 0.070%, 0.071%, 0.072%, 0.073%, 0.074%, 0.075%, 0.076%, 0.077%, 0.078%, 0.079%, 0.080%, 0.081%, 0.082%, 0.083%, 0.084%, 0.085%, or 0.086%. In some embodiments, the population of cells has a frequency of CD34⁺ CD90⁺ CD45RA⁻ cells of about 0.066%.

In an additional aspect, the invention features a method of mobilizing a population of hematopoietic stem cells from the bone marrow of a mammalian donor (e.g., a human donor) into peripheral blood, the method including administering to the donor a CXCR2 agonist and a CXCR4 antagonist in amounts sufficient to induce an increase in the frequency of CD34⁺ CD90⁺ CD45RA⁻ cells in the peripheral blood of the donor by at least 3-fold as assessed by comparing a sample of peripheral blood of the donor following administration of the CXCR2 agonist and CXCR4 antagonist to a sample of peripheral blood of the donor prior to administration of the CXCR2 agonist and CXCR4 antagonist (e.g., by from about 5.1-fold to about 25.7-fold, such as by about 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold, 7.0-fold, 7.1-fold, 7.2-fold, 7.3-fold, 7.4-fold, 7.5-fold, 7.6-fold, 7.7-fold, 7.8-fold, 7.9-fold, 8.0-fold, 8.1-fold, 8.2-fold, 8.3-fold, 8.4-fold, 8.5-fold, 8.6-fold, 8.7-fold, 8.8-fold, 8.9-fold, 9.0-fold, 9.1-fold, 9.2-fold, 9.3-fold, 9.4-fold, 9.5-fold, 9.6-fold, 9.7-fold, 9.8-fold, 9.9-fold, 10.0-fold, 10.1-fold, 10.2-fold, 10.3-fold, 10.4-fold, 10.5-fold, 10.6-fold, 10.7-fold, 10.8-fold, 10.9-fold, 11.0-fold, 11.1-fold, 11.2-fold, 11.3-fold, 11.4-fold, 11.5-fold, 11.6-fold, 11.7-fold, 11.8-fold, 11.9-fold, 12.0-fold, 12.1-fold, 12.2-fold, 12.3-fold, 12.4-fold, 12.5-fold, 12.6-fold, 12.7-fold, 12.8-fold, 12.9-fold, 13.0-fold, 13.1-fold, 13.2-fold, 13.3-fold, 13.4-fold, 13.5-fold, 13.6-fold, 13.7-fold, 13.8-fold, 13.9-fold, 14.0-fold, 14.1-fold, 14.2-fold, 14.3-fold, 14.4-fold, 14.5-fold, 14.6-fold, 14.7-fold, 14.8-fold, 14.9-fold, 15.0-fold, 15.1-fold, 15.2-fold, 15.3-fold, 15.4-fold, 15.5-fold, 15.6-fold, 15.7-fold, 15.8-fold, 15.9-fold, 16.0-fold, 16.1-fold, 16.2-fold, 16.3-fold, 16.4-fold, 16.5-fold, 16.6-fold, 16.7-fold, 16.8-fold, 16.9-fold, 17.0-fold, 17.1-fold, 17.2-fold, 17.3-fold, 17.4-fold, 17.5-fold, 17.6-fold, 17.7-fold, 17.8-fold, 17.9-fold, 18.0-fold, 18.1-fold, 18.2-fold, 18.3-fold, 18.4-fold, 18.5-fold, 18.6-fold, 18.7-fold, 18.8-fold, 18.9-fold, 19.0-fold, 19.1-fold, 19.2-fold, 19.3-fold, 19.4-fold, 19.5-fold, 19.6-fold, 19.7-fold, 19.8-fold, 19.9-fold, 20.0-fold, 20.1-fold, 20.2-fold, 20.3-fold, 20.4-fold, 20.5-fold, 20.6-fold, 20.7-fold, 20.8-fold, 20.9-fold, 21.0-fold, 21.1-fold, 21.2-fold, 21.3-fold, 21.4-fold, 21.5-fold, 21.6-fold, 21.7-fold, 21.8-fold, 21.9-fold, 22.0-fold, 22.1-fold, 22.2-fold, 22.3-fold, 22.4-fold, 22.5-fold, 22.6-fold, 22.7-fold, 22.8-fold, 22.9-fold, 23.0-fold, 23.1-fold, 23.2-fold, 23.3-fold, 23.4-fold, 23.5-fold, 23.6-fold, 23.7-fold, 23.8-fold, 23.9-fold, 24.0-fold, 24.1-fold, 24.2-fold, 24.3-fold, 24.4-fold, 24.5-fold, 24.6-fold, 24.7-fold, 24.8-fold, 24.9-fold, 25.0-fold, 25.1-fold, 25.2-fold, 25.3-fold, 25.4-fold, 25.5-fold, 25.6-fold, or 25.7-fold. In some embodiments, the frequency of CD34⁺ CD90⁺ CD45RA⁻ cells in the peripheral blood of the donor is increased by from about 5.1-fold to about 7.1-fold following administration of the CXCR2 agonist and CXCR4 antagonist, such as by about 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold, 7.0-fold, or 7.1-fold. In some embodiments, the frequency of CD34⁺ CD90⁺ CD45RA⁻ cells in the peripheral blood of the donor is increased by about 5.8-fold.

In another aspect, the invention features a method of mobilizing a population of hematopoietic stem cells, from the bone marrow of a mammalian donor into peripheral blood, the method comprising administering to the donor mobilizing amounts of a CXCR2 agonist and a CXCR4 antagonist; acquiring an input value for each of one or more parameters in TABLE 2 characterizing a sample of peripheral blood of the donor, and releasing the sample for ex vivo expansion of the hematopoietic stem cells or for use in the treatment of one or more stem cell disorders in a mammalian patient if the input value for each of the one or more parameters meets the corresponding reference criterion for each of the one or more parameters. In some embodiments, the one or more reference parameters are a set of parameters listed in any one of TABLES 3-6 herein.

In some embodiments of any of the above aspects of the invention, the sample is isolated from the donor at from about 3 hours to about 5 hours following administration of the CXCR2 agonist and CXCR4 antagonist (e.g., at about 3 hours, 3.1 hours, 3.2 hours, 3.3 hours, 3.4 hours, 3.5 hours, 3.6 hours, 3.7 hours, 3.8 hours, 3.9 hours, 4.0 hours, 4.1 hours, 4.2 hours, 4.3 hours, 4.4 hours, 4.5 hours, 4.6 hours, 4.7 hours, 4.8 hours, 4.9 hours, or 5.0 hours following administration of the CXCR2 agonist and CXCR4 antagonist. In some embodiments, the sample is isolated from the donor at about 4 hours following administration of the CXCR2 agonist and CXCR4 antagonist.

In some embodiments of any of the above aspects of the invention, the CXCR2 agonist is Gro-β T or a variant thereof. In some embodiments, the CXCR2 agonist may be a peptide having at least about 85% (e.g., at least about 85%, 90%, 95%, 96%, 97%, 98%, 99%, or more) sequence identity to the amino acid sequence of SEQ ID NO: 2. In some embodiments, the CXCR2 agonist is a peptide having from about 85% to 100% sequence identity to the amino acid sequence of SEQ ID NO: 2, such as a peptide having from about 86% to about 100%, from about 87% to about 99%, about 88% to about 98%, about 89%, to about 97%, about 90% to about 96%, or about 91% to about 95% sequence identity to the amino acid sequence of SEQ ID NO: 2. In some embodiments, the CXCR2 agonist is a peptide having an amino acid sequence that differs from that of SEQ ID NO: 2 only by way of one or more conservative amino acid substitutions (e.g., only by way of from 1 to 10 conservative amino acid substitutions, from 1 to 5 conservative amino acid substitutions, or from 1 to 3 conservative amino acid substitutions, such as 1, 2, 3, 4, 5, 6, 7, 8, 9, or 10 conservative amino acid substitutions). In some embodiments, the CXCR2 agonist is Gro-β T. In some embodiments, the Gro-β T is not covalently modified. In some embodiments, the Gro-β T is not covalently modified with a polyalkylene glycol moiety, such as a polyethylene glycol moiety.

In some embodiments of any of the above aspects of the invention, the CXCR2 agonist is Gro-β or a variant thereof. In some embodiments, the CXCR2 agonist may be a peptide having at least about 85% (e.g., about 85%, 90%, 95%, 96%, 97%, 98%, 99%, or more) sequence identity to the amino acid sequence of SEQ ID NO: 1. In some embodiments, the CXCR2 agonist is a peptide having from about 85% to 100% sequence identity to the amino acid sequence of SEQ ID NO: 1, such as a peptide having from about 86% to about 100%, from about 87% to about 99%, about 88% to about 98%, about 89%, to about 97%, about 90% to about 96%, or about 91% to about 95% sequence identity to the amino acid sequence of SEQ ID NO: 1. In some embodiments, the CXCR2 agonist is a peptide having an amino acid sequence that differs from that of SEQ ID NO: 1 only by way of one or more conservative amino acid substitutions (e.g., only by way of from 1 to 10 conservative amino acid substitutions, from 1 to 5 conservative amino acid substitutions, or from 1 to 3 conservative amino acid substitutions, such as 1, 2, 3, 4, 5, 6, 7, 8, 9, or 10 conservative amino acid substitutions). In some embodiments, the CXCR2 agonist is Gro-β. In some embodiments, the Gro-β T is not covalently modified. In some embodiments, the Gro-β is not covalently modified with a polyalkylene glycol moiety, such as a polyethylene glycol moiety.

In some embodiments, the CXCR2 agonist (e.g., Gro-β or Gro-β T, such as unmodified Gro-β or Gro-β T) is administered to the donor at a dose of from about 50 µg/kg to about 1 mg/kg, such as a dose of about 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 105 µg/kg, 110 µg/kg, 115 µg/kg, 120 µg/kg, 125 µg/kg, 130 µg/kg, 135 µg/kg, 140 µg/kg, 145 µg/kg, 150 µg/kg, 155 µg/kg, 160 µg/kg, 165 µg/kg, 170 µg/kg, 175 µg/kg, 180 µg/kg, 185 µg/kg, 190 µg/kg, 195 µg/kg, 200 µg/kg, 205 µg/kg, 210 µg/kg, 215 µg/kg, 220 µg/kg, 225 µg/kg, 230 µg/kg, 235 µg/kg, 240 µg/kg, 245 µg/kg, 250 µg/kg, 255 µg/kg, 260 µg/kg, 265 µg/kg, 270 µg/kg, 275 µg/kg, 280 µg/kg, 285 µg/kg, 290 µg/kg, 295 µg/kg, 300 µg/kg, 305 µg/kg, 310 µg/kg, 315 µg/kg, 320 µg/kg, 325 µg/kg, 330 µg/kg, 335 µg/kg, 340 µg/kg, 345 µg/kg, 350 µg/kg, 355 µg/kg, 360 µg/kg, 365 µg/kg, 370 µg/kg, 375 µg/kg, 380 µg/kg, 400 µg/kg, 405 µg/kg, 410 µg/kg, 415 µg/kg, 425 µg/kg, 430 µg/kg, 435 µg/kg, 440 µg/kg, 445 µg/kg, 450 µg/kg, 210 µg/kg, 300 µg/kg, 400 µg/kg, 405 µg/kg, 410 µg/kg, 415 µg/kg, 420 µg/kg, 425 µg/kg, 430 µg/kg, 435 µg/kg, 440 µg/kg, 445 µg/kg, 450 µg/kg, 455 µg/kg, 460 µg/kg, 465 µg/kg, 470 µg/kg, 475 µg/kg, 480 µg/kg, 485 µg/kg, 490 µg/kg, 495 µg/kg, 500 µg/kg, 505 µg/kg, 510 µg/kg, 505 µg/kg, 515 µg/kg, 520 µg/kg, 525 µg/kg, 530 µg/kg, 545 µg/kg, 550 µg/kg, 555 µg/kg, 560 µg/kg, 565 µg/kg, 570 µg/kg, 575 µg/kg, 580 µg/kg, 585 µg/kg, 590 µg/kg, 595 µg/kg, 600 µg/kg, 605 µg/kg, 610 µg/kg, 615 µg/kg, 620 µg/kg, 625 µg/kg, 630 µg/kg, 635 µg/kg, 640 µg/kg, 645 µg/kg, 650 µg/kg, 655 µg/kg, 660 µg/kg, 665 µg/kg, 670 µg/kg, 675 µg/kg, 680 µg/kg, 685 µg/kg, 690 µg/kg, 695 µg/kg, 700 µg/kg, 705 µg/kg, 710 µg/kg, 715 µg/kg, 720 µg/kg, 725 µg/kg, 730 µg/kg, 735 µg/kg, 740 µg/kg, 745 µg/kg, 750 µg/kg, 755 µg/kg, 760 µg/kg, 765 µg/kg, 770 µg/kg, 775 µg/kg, 780 µg/kg, 785 µg/kg, 790 µg/kg, 795 µg/kg, 800 µg/kg, 805 µg/kg, 810 µg/kg, 815 µg/kg, 820 µg/kg, 825 µg/kg, 830 µg/kg, 835 µg/kg, 840 µg/kg, 845 µg/kg, 850 µg/kg, 855 µg/kg, 860 µg/kg, 865 µg/kg, 870 µg/Kg, 875 µg/kg, 880 µg/kg, 885 µg/kg, 890 µg/kg, 895 µg/kg, 900 µg/kg, 905 µg/kg, 910 µg/kg, 915 µg/kg, 920 µg/kg, 925 µg/kg, 930 µg/kg, 935 µg/kg, 940 µg/kg, 945 µg/kg, 950 µg/kg, 955 µg/kg, 960 µg/kg, 965 µg/kg, 970 µg/kg, 975 µg/kg, 980 µg/kg, 985 µg/kg, 990 µg/kg, 995 µg/kg, or 1,000 µg/kg. In some embodiments, the CXCR2 agonist (e.g., Gro-β or Gro-β T, such as unmodified Gro-β or Gro-β T) is administered to the donor at a dose of from about 50 µg/kg to about 300 µg/kg, such as a dose of from about 100 µg/kg to about 250 µg/kg, or from about 125 µg/kg to about 225 µg/kg. In some embodiments, the CXCR2 agonist (e.g., Gro-β or Gro-β T, such as unmodified Gro-β or Gro-β T) is administered to the donor at a dose of about 150 µg/kg.

In another aspect, the invention features a method of mobilizing a population of hematopoietic stem cells from the bone marrow of a mammalian donor (e.g., a human donor) into peripheral blood, the method including administering to the donor a CXCR2 agonist selected from the group consisting of Gro-β, Gro-β T, and variants thereof at a dose of from about 50 µg/kg to about 1 mg/kg (e.g., a dose of 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 105 µg/kg, 110 µg/kg, 115 µg/kg, 120 µg/kg, 125 µg/kg, 130 µg/kg, 135 µg/kg, 140 µg/kg, 145 µg/kg, 150 µg/kg, 155 µg/kg, 160 µg/kg, 165 µg/kg, 170 µg/kg, 175 µg/kg, 180 µg/kg, 185 µg/kg, 190 µg/kg, 195 µg/kg, 200 µg/kg, 205 µg/kg, 210 µg/kg, 215 µg/kg, 220 µg/kg, 225 µg/kg, 230 µg/kg, 235 µg/kg, 240 µg/kg, 245 µg/kg, 250 µg/kg, 255 µg/kg, 260 µg/kg, 265 µg/kg, 270 µg/kg, 275 µg/kg, 280 µg/kg, 285 µg/kg, 290 µg/kg, 295 µg/kg, 300 µg/kg, 305 µg/kg, 310 µg/kg, 315 µg/kg, 320 µg/kg, 325 µg/kg, 330 µg/kg, 335 µg/kg, 340 µg/kg, 345 µg/kg, 350 µg/kg, 355 µg/kg, 360 µg/kg, 365 µg/kg, 370 µg/kg, 375 µg/kg, 380 µg/kg, 400 µg/kg, 405 µg/kg, 410 µg/kg, 415 µg/kg, 425 µg/kg, 430 µg/kg, 435 µg/kg, 440 µg/kg, 445 µg/kg, 450 µg/kg, 210 µg/kg, 300 µg/kg, 400 µg/kg, 405 µg/kg, 410 µg/kg, 415 µg/kg, 420 µg/kg, 425 µg/kg, 430 µg/kg, 435 µg/kg, 440 µg/kg, 445 µg/kg, 450 µg/kg, 455 µg/kg, 460 µg/kg, 465 µg/kg, 470 µg/kg, 475 µg/kg, 480 µg/kg, 485

µg/kg, 490 µg/kg, 495 µg/kg, 500 µg/kg, 505 µg/kg, 510 µg/kg, 505 µg/kg, 515 µg/kg, 520 µg/kg, 525 µg/kg, 530 µg/kg, 545 µg/kg, 550 µg/kg, 555 µg/kg, 560 µg/kg, 565 µg/kg, 570 µg/kg, 575 µg/kg, 580 µg/kg, 585 µg/kg, 590 µg/kg, 595 µg/kg, 600 µg/kg, 605 µg/kg, 610 µg/kg, 615 µg/kg, 620 µg/kg, 625 µg/kg, 630 µg/kg, 635 µg/kg, 640 µg/kg, 645 µg/kg, 650 µg/kg, 655 µg/kg, 660 µg/kg, 665 µg/kg, 670 µg/kg, 675 µg/kg, 680 µg/kg, 685 µg/kg, 690 µg/kg, 695 µg/kg, 700 µg/kg, 705 µg/kg, 710 µg/kg, 715 µg/kg, 720 µg/kg, 725 µg/kg, 730 µg/kg, 735 µg/kg, 740 µg/kg, 745 µg/kg, 750 µg/kg, 755 µg/kg, 760 µg/kg, 765 µg/kg, 770 µg/kg, 775 µg/kg, 780 µg/kg, 785 µg/kg, 790 µg/kg, 795 µg/kg, 800 µg/kg, 805 µg/kg, 810 µg/kg, 815 µg/kg, 820 µg/kg, 825 µg/kg, 830 µg/kg, 835 µg/kg, 840 µg/kg, 845 µg/kg, 850 µg/kg, 855 µg/kg, 860 µg/kg, 865 µg/kg, 870 µg/Kg, 875 µg/kg, 880 µg/kg, 885 µg/kg, 890 µg/kg, 895 µg/kg, 900 µg/kg, 905 µg/kg, 910 µg/kg, 915 µg/kg, 920 µg/kg, 925 µg/kg, 930 µg/kg, 935 µg/kg, 940 µg/kg, 945 µg/kg, 950 µg/kg, 955 µg/kg, 960 µg/kg, 965 µg/kg, 970 µg/kg, 975 µg/kg, 980 µg/kg, 985 µg/kg, 990 µs/kg, 995 µg/kg, or 1,000 µg/kg). In some embodiments, the method further includes administering a CXCR4 antagonist to the donor.

In some embodiments of any of the above aspects of the invention, the CXCR2 agonist (e.g., Gro-β or Gro-β T, such as unmodified Gro-β or Gro-β T) is administered to the donor at a dose of from about 50 µg/kg to about 300 µg/kg, such as a dose of about 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 105 µg/kg, 110 µg/kg, 115 µg/kg, 120 µg/kg, 125 µg/kg, 130 µg/kg, 135 µg/kg, 140 µg/kg, 145 µg/kg, 150 µg/kg, 155 µg/kg, 160 µg/kg, 165 µg/kg, 170 µg/kg, 175 µg/kg, 180 µg/kg, 185 µg/kg, 190 µg/kg, 195 µg/kg, 200 µg/kg, 205 µg/kg, 210 µg/kg, 215 µg/kg, 220 µg/kg, 225 µg/kg, 230 µg/kg, 235 µg/kg, 240 µg/kg, 245 µg/kg, 250 µg/kg, 255 µg/kg, 260 µg/kg, 265 µg/kg, 270 µg/kg, 275 µg/kg, 280 µg/kg, 285 µg/kg, 290 µg/kg, 295 µg/kg, or 300 µg/kg.

In some embodiments of any of the above aspects of the invention, the CXCR2 agonist (e.g., Gro-β or Gro-β T, such as unmodified Gro-β or Gro-β T) is administered to the donor at a dose of from about 100 µg/kg to about 250 µg/kg, such as a dose of about 100 pig/kg, 105 µg/kg, 110 µg/kg, 115 µg/kg, 120 µg/kg, 125 µg/kg, 130 µg/kg, 135 µg/kg, 140 µg/kg, 145 µg/kg, 150 µg/kg, 155 µg/kg, 160 µg/kg, 165 µg/kg, 170 µg/kg, 175 µg/kg, 180 µg/kg, 185 µg/kg, 190 µg/kg, 195 µg/kg, 200 µg/kg, 205 µg/kg, 210 µg/kg, 215 µg/kg, 220 µg/kg, 225 µg/kg, 230 µg/kg, 235 µg/kg, 240 µg/kg, 245 µg/kg, or 250 µg/kg.

In some embodiments of any of the above aspects of the invention, the CXCR2 agonist (e.g., Gro-β or Gro-β T, such as unmodified Gro-β or Gro-β T) is administered to the donor at a dose of about 150 µg/kg. For example, in some embodiments, the CXCR2 agonist (e.g., Gro-β or Gro-β T, such as unmodified Gro-β or Gro-β T) is administered to the donor at a dose of from about 50 µg/kg per day to about 1 mg/kg per day, such as a dose of about 50 µg/kg per day, 55 µg/kg per day, 60 µg/kg per day, 65 µg/kg per day, 70 µg/kg per day, 75 µg/kg per day, 80 µg/kg per day, 85 µg/kg per day, 90 µg/kg per day, 95 µg/kg per day, 100 pig/kg per day, 105 µg/kg per day, 110 µg/kg per day, 115 µg/kg per day, 120 µg/kg per day, 125 µg/kg per day, 130 µg/kg per day, 135 µg/kg per day, 140 µg/kg per day, 145 µg/kg per day, 150 µg/kg per day, 155 µg/kg per day, 160 µg/kg per day, 165 µg/kg per day, 170 µg/kg per day, 175 µg/kg per day, 180 µg/kg per day, 185 µg/kg per day, 190 µg/kg per day, 195 pig/kg per day, 200 µg/kg per day, 205 µg/kg per day, 210 µg/kg per day, 215 µg/kg per day, 220 µg/kg per day, 225 µg/kg per day, 230 µg/kg per day, 235 µg/kg per day, 240 µg/kg per day, 245 µg/kg per day, 250 µg/kg per day, 255 µg/kg per day, 260 µg/kg per day, 265 µg/kg per day, 270 µg/kg per day, 275 µg/kg per day, 280 µg/kg per day, 285 µg/kg per day, 290 pig/kg per day, 295 µg/kg per day, 300 µg/kg per day, 305 µg/kg per day, 310 µg/kg per day, 315 µg/kg per day, 320 µg/kg per day, 325 µg/kg per day, 330 µg/kg per day, 335 µg/kg per day, 340 µg/kg per day, 345 µg/kg per day, 350 µg/kg per day, 355 µg/kg per day, 360 µg/kg per day, 365 µg/kg per day, 370 µg/kg per day, 375 µg/kg per day, 380 µg/kg per day, 400 µg/kg per day, 405 µg/kg per day, 410 µg/kg per day, 415 µg/kg per day, 425 µg/kg per day, 430 µg/kg per day, 435 µg/kg per day, 440 µg/kg per day, 445 µg/kg per day, 450 µg/kg per day, 210 µg/kg per day, 300 µg/kg per day, 400 µg/kg per day, 405 µg/kg per day, 410 µg/kg per day, 415 µg/kg per day, 420 µg/kg per day, 425 µg/kg per day, 430 µg/kg per day, 435 µg/kg per day, 440 µg/kg per day, 445 µg/kg per day, 450 µg/kg per day, 455 µg/kg per day, 460 µg/kg per day, 465 µg/kg per day, 470 µg/kg per day, 475 µg/kg per day, 480 µg/kg per day, 485 µg/kg per day, 490 µg/kg per day, 495 µg/kg per day, 500 µg/kg per day, 505 µg/kg per day, 510 µg/kg per day, 505 µg/kg per day, 515 µg/kg per day, 520 µg/kg per day, 525 Kg/kg per day, 530 µg/kg per day, 545 µg/kg per day, 550 µg/kg per day, 555 µg/kg per day, 560 µg/kg per day, 565 µg/kg per day, 570 µg/kg per day, 575 µg/kg per day, 580 µg/kg per day, 585 µg/kg per day, 590 µg/kg per day, 595 µg/kg per day, 600 µg/kg per day, 605 µg/kg per day, 610 µg/kg per day, 615 µg/kg per day, 620 µg/kg per day, 625 µg/kg per day, 630 µg/kg per day, 635 µg/kg per day, 640 µg/kg per day, 645 µg/kg per day, 650 µg/kg per day, 655 µg/kg per day, 660 µg/kg per day, 665 µg/kg per day, 670 µg/kg per day, 675 µg/kg per day, 680 µg/kg per day, 685 µg/kg per day, 690 µg/kg per day, 695 µg/kg per day, 700 µg/kg per day, 705 µg/kg per day, 710 µg/kg per day, 715 µg/kg per day, 720 µg/kg per day, 725 µg/kg per day, 730 µg/kg per day, 735 µg/kg per day, 740 µg/kg per day, 745 µg/kg per day, 750 µg/kg per day, 755 µg/kg per day, 760 µg/kg per day, 765 µg/kg per day, 770 µg/kg per day, 775 µg/kg per day, 780 µg/kg per day, 785 µg/kg per day, 790 µg/kg per day, 795 µg/kg per day, 800 µg/kg per day, 805 µg/kg per day, 810 µg/kg per day, 815 µg/kg per day, 820 pig/kg per day, 825 µg/kg per day, 830 µg/kg per day, 835 µg/kg per day, 840 µg/kg per day, 845 µg/kg per day, 850 µg/kg per day, 855 µg/kg per day, 860 µg/kg per day, 865 µg/kg per day, 870 µg/kg per day, 875 µg/kg per day, 880 µg/kg per day, 885 µg/kg per day, 890 µg/kg per day, 895 µg/kg per day, 900 µg/kg per day, 905 µg/kg per day, 910 µg/kg per day, 915 pig/kg per day, 920 µg/kg per day, 925 µg/kg per day, 930 µg/kg per day, 935 µg/kg per day, 940 µg/kg per day, 945 µg/kg per day, 950 µg/kg per day, 955 µg/kg per day, 960 µg/kg per day, 965 µg/kg per day, 970 µg/kg per day, 975 µg/kg per day, 980 µg/kg per day, 985 µg/kg per day, 990 µg/kg per day, 995 µg/kg per day, or 1,000 µg/kg per day. In some embodiments, the CXCR2 agonist (e.g., Gro-β or Gro-β T, such as unmodified Gro-β or Gro-β T) is administered to the donor at a dose of from about 50 µg/kg per day to about 300 µg/kg per day, such as a dose of from about 100 µg/kg per day to about 250 µg/kg per day, or from about 125 µg/kg per day to about 225 µg/kg per day, or from about 125 µg/kg per day to about 175 µg/kg per day. In some embodiments, the CXCR2 agonist (e.g., Gro-β or Gro-β T, such as unmodified Gro-β or Gro-β T) is administered to the donor at a dose of about 150 µg/kg per day. In some embodiments, the CXCR2 agonist may be administered as a single dose. In other embodiments, the CXCR2 agonist may be administered as two or more doses.

In some embodiments, a human equivalent dose (HED) may be derived from animal dosage data using a conversion factor. For example, Nair and Jacob, *J. Basic Clin. Pharma.* (2016) 7:27-31 disclose methods extrapolation of dose between species. For instance, in one non-limiting example, HED may be derived from rhesus monkey dose by multiplying the rhesus monkey dose by about 0.324.

In some embodiments of any of the above aspects of the invention, the CXCR2 agonist (e.g., Gro-β or Gro-β T, such as unmodified Gro-β or Gro-β T) is administered intravenously to the donor.

In some embodiments of any of the above aspects of the invention, the CXCR4 antagonist is a compound represented by formula (I)

Z-linker-Z'           (I)

or a pharmaceutically acceptable salt thereof, wherein Z is:
(i) a cyclic polyamine containing from 9 to 32 ring members, wherein from 2 to 8 of the ring members are nitrogen atoms separated from one another by 2 or more carbon atoms; or
(ii) an amine represented by formula (IA)

(IA)

wherein A includes a monocyclic or bicyclic fused ring system including at least one nitrogen atom and B is H or a substituent of from 1 to 20 atoms;
and wherein Z' is:
(i) a cyclic polyamine containing from 9 to 32 ring members, wherein from 2 to 8 of the ring members are nitrogen atoms separated from one another by 2 or more carbon atoms;
(ii) an amine represented by formula (IB)

(IB)

wherein A' includes a monocyclic or bicyclic fused ring system including at least one nitrogen atom and B' is H or a substituent of from 1 to 20 atoms; or
(iii) a substituent represented by formula (IC)

—N(R)—(CR$_2$)$_n$—X         (IC)

wherein each R is independently H or $C_1$-$C_6$ alkyl, n is 1 or 2, and X is an aryl or heteroaryl group or a mercaptan;
wherein the linker is a bond, optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene.

In some embodiments, Z and Z' are each independently a cyclic polyamine containing from 9 to 32 ring members, of which from 2 to 8 are nitrogen atoms separated from one another by 2 or more carbon atoms. Z and Z' may be identical substituents. In some embodiments, Z and/or Z' is a cyclic polyamine including from 10 to 24 ring members, such as a cyclic polyamine including 14 ring members. In some embodiments, Z includes 4 nitrogen atoms. Z and/or Z' may be, for example, 1,4,8,11-tetraazocyclotetradecane.

In some embodiments, the linker is represented by formula (ID)

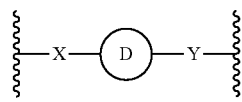

(ID)

wherein ring D is an optionally substituted aryl group, an optionally substituted heteroaryl group, an optionally substituted cycloalkyl group, or an optionally substituted heterocycloalkyl group; and
X and Y are each independently optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, or optionally substituted $C_2$-$C_6$ heteroalkynylene.

In some embodiments, the linker is represented by formula (IE)

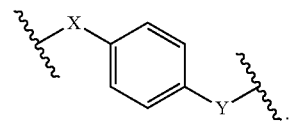

(IE)

wherein ring D is an optionally substituted aryl group, an optionally substituted heteroaryl group, an optionally substituted cycloalkyl group, or an optionally substituted heterocycloalkyl group; and
X and Y are each independently optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, or optionally substituted $C_2$-$C_6$ heteroalkynylene.

In some embodiments, X and Y are each independently optionally substituted $C_1$-$C_6$ alkylene. In some embodiments, X and Y are identical substituents, such as identical alkylene substituents (e.g., methylene, ethylene, propylene, or butylene substituents).

In some embodiments, the CXCR4 antagonist is plerixafor or a pharmaceutically acceptable salt thereof. In some embodiments, the CXCR4 antagonist (e.g., plerixafor or a pharmaceutically acceptable salt thereof) is administered subcutaneously to the donor. In some embodiments, the CXCR4 antagonist (e.g., plerixafor or a pharmaceutically acceptable salt thereof) is administered to the donor at a dose of from about 50 µg/kg to about 500 µg/kg, such as a dose of about 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 105 µg/kg, 110 µg/kg, 115 µg/kg, 120 µg/kg, 125 µg/kg, 130 µg/kg, 135 µg/kg, 140 µg/kg, 145 µg/kg, 150

μg/kg, 155 μg/kg, 160 μg/kg, 165 μg/kg, 170 μg/kg, 175 μg/kg, 180 μg/kg, 185 μg/kg, 190 μg/kg, 195 μg/kg, 200 μg/kg, 205 μg/kg, 210 μg/kg, 215 μg/kg, 220 μg/kg, 225 μg/kg, 230 μg/kg, 235 μg/kg, 240 μg/kg, 245 μg/kg, 250 μg/kg, 255 μg/kg, 260 μg/kg, 265 μg/kg, 270 μg/kg, 275 μg/kg, 280 μg/kg, 285 μg/kg, 290 μg/kg, 295 μg/kg, 300 μg/kg, 305 μg/kg, 310 μg/kg, 315 μg/kg, 320 μg/kg, 325 μg/kg, 330 μg/kg, 335 μg/kg, 340 μg/kg, 345 μg/kg, 350 μg/kg, 355 μg/kg, 360 μg/kg, 365 μg/kg, 370 μg/kg, 375 μg/kg, 380 μg/kg, 385 μg/kg, 390 μg/kg, 395 μg/kg, 400 μg/kg, 405 μg/kg, 410 μg/kg, 415 μg/kg, 420 μg/kg, 425 μg/kg, 430 μg/kg, 435 μg/kg, 440 μg/kg, 445 μg/kg, 450 μg/kg, 455 μg/kg, 460 μg/kg, 465 μg/kg, 470 μg/kg, 475 μg/kg, 480 μg/kg, 485 μg/kg, 490 μg/kg, 495 μg/kg, or 500 μg/kg. In some embodiments, the CXCR4 antagonist (e.g., plerixafor or a pharmaceutically acceptable salt thereof) is administered to the donor at a dose of from about 200 μg/kg to about 300 μg/kg, such as a dose of about 240 μg/kg.

For example, in some embodiments, the CXCR4 antagonist (e.g., plerixafor or a pharmaceutically acceptable salt thereof) is administered to the donor at a dose of from about 50 μg/kg per day to about 500 μg/kg per day, such as a dose of about 50 μg/kg per day, 55 μg/kg per day, 60 μg/kg per day, 65 μg/kg per day, 70 μg/kg per day, 75 μg/kg per day, 80 μg/kg per day, 85 μg/kg per day, 90 μg/kg per day, 95 μg/kg per day, 100 μg/kg per day, 105 μg/kg per day, 110 μg/kg per day, 115 μg/kg per day, 120 μg/kg per day, 125 μg/kg per day, 130 μg/kg per day, 135 μg/kg per day, 140 μg/kg per day, 145 μg/kg per day, 150 μg/kg per day, 155 μg/kg per day, 160 μg/kg per day, 165 μg/kg per day, 170 μg/kg per day, 175 μg/kg per day, 180 μg/kg per day, 185 μg/kg per day, 190 μg/kg per day, 195 μg/kg per day, 200 μg/kg per day, 205 μg/kg per day, 210 μg/kg per day, 215 μg/kg per day, 220 μg/kg per day, 225 μg/kg per day, 230 μg/kg per day, 235 μg/kg per day, 240 μg/kg per day, 245 μg/kg per day, 250 μg/kg per day, 255 μg/kg per day, 260 μg/kg per day, 265 μg/kg per day, 270 μg/kg per day, 275 μg/kg per day, 280 μg/kg per day, 285 μg/kg per day, 290 μg/kg per day, 295 μg/kg per day, 300 μg/kg per day, 305 μg/kg per day, 310 μg/kg per day, 315 μg/kg per day, 320 μg/kg per day, 325 μg/kg per day, 330 μg/kg per day, 335 μg/kg per day, 340 μg/kg per day, 345 μg/kg per day, 350 μg/kg per day, 355 μg/kg per day, 360 μg/kg per day, 365 μg/kg per day, 370 μg/kg per day, 375 μg/kg per day, 380 μg/kg per day, 385 μg/kg per day, 390 μg/kg per day, 395 μg/kg per day, 400 μs/kg per day, 405 μg/kg per day, 410 μg/kg per day, 415 μg/kg per day, 420 μg/kg per day, 425 μg/kg per day, 430 μg/kg per day, 435 μg/kg per day, 440 μg/kg per day, 445 μg/kg per day, 450 μg/kg per day, 455 μg/kg per day, 460 μg/kg per day, 465 μg/kg per day, 470 μg/kg per day, 475 μg/kg per day, 480 μg/kg per day, 485 μg/kg per day, 490 μg/kg per day, 495 μg/kg per day, or 500 μg/kg per day. In some embodiments, the CXCR4 antagonist (e.g., plerixafor or a pharmaceutically acceptable salt thereof) is administered to the donor at a dose of from about 200 μg/kg per day to about 300 μg/kg per day, such as a dose of about 240 μg/kg per day. In some embodiments, the CXCR4 antagonist may be administered as a single dose. In other embodiments, the CXCR4 antagonist may be administered as two or more doses.

In some embodiments of any of the above aspects of the invention, the CXCR2 agonist and the CXCR4 antagonist are administered to the donor concurrently. In some embodiments, the CXCR4 antagonist is administered to the donor prior to administration of the CXCR2 agonist. In some embodiments, the CXCR4 antagonist may be administered to the donor from about 1 minute to about 180 minutes prior to administration of the CXCR2 agonist, such as from about 15 minutes to about 180 minutes, about 30 minutes to about 180 minutes, about 40 minutes to about 160 minutes, about 50 minutes to about 150 minutes, about 60 minutes to about 140 minutes, about 70 minutes to about 130 minutes, about 60 minutes to about 120 minutes, about 70 minutes to about 110 minutes, or about 80 minutes to about 100 minutes (e.g., about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, or about 180 minutes prior to administration of the CXCR2 agonist). In some embodiments, the CXCR4 antagonist is administered to the donor from about 30 minutes to about 60 minutes prior to administration of the CXCR2 agonist (e.g., about 30 minutes, about 35 minutes, about 40 minutes, about 45 minutes, about 50 minutes, about 55 minutes, or about 60 minutes prior to administration of the CXCR2 agonist). In some embodiments, the CXCR4 antagonist may be administered to the donor about 45 minutes prior to administration of the CXCR2 agonist.

In a further aspect, the invention features a pharmaceutical composition including a population of hematopoietic stem cells or progeny thereof isolated from a mammalian donor (e.g., a human donor), wherein the ratio of $CD34^+$ cells to leukocytes in the population is from about 0.0008 to about 0.0021. In some embodiments, the ratio of $CD34^+$ cells to leukocytes may be about 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, or 0.00225. In some embodiments, the ratio of $CD34^+$ cells to leukocytes is from about 0.0010 to about 0.0018, such as a ratio of $CD34^+$ cells to leukocytes of about 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00178, 0.00179, or 0.00180. In some embodiments, the ratio of $CD34^+$ cells to leukocytes is about 0.0014.

In an additional aspect, the invention features a pharmaceutical composition including a population of hematopoietic stem cells or progeny thereof isolated from a mammalian donor (e.g., a human donor), wherein the ratio of $CD34^+$ cells to neutrophils in the population is from about 0.0018 to about 0.0058. In some embodiments, the ratio of $CD34^+$ cells to neutrophils may be about 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00377, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00400, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, 0.00460, 0.00461, 0.00462, 0.00463, 0.00464, 0.00465, 0.00466, 0.00467, 0.00468, 0.00469, 0.00470, 0.00471, 0.00472, 0.00473, 0.00474, 0.00475, 0.00476, 0.00477, 0.00478, 0.00479, 0.00480, 0.00481, 0.00482, 0.00483, 0.00484, 0.00485, 0.00486, 0.00487, 0.00488, 0.00489, 0.00490, 0.00491, 0.00492, 0.00493, 0.00494, 0.00495, 0.00496, 0.00497, 0.00498, 0.00499, 0.00500, 0.00501, 0.00502, 0.00503, 0.00504, 0.00505, 0.00506, 0.00507, 0.00508, 0.00509, 0.00510, 0.00511, 0.00512, 0.00513, 0.00514, 0.00515, 0.00516, 0.00517, 0.00518, 0.00519, 0.00520, 0.00521, 0.00522, 0.00523, 0.00524, 0.00525, 0.00526, 0.00527, 0.00528, 0.00529, 0.00530, 0.00531, 0.00532, 0.00533, 0.00534, 0.00535, 0.00536, 0.00537, 0.00538, 0.00539, 0.00540, 0.00541, 0.00542, 0.00543, 0.00544, 0.00545, 0.00546, 0.00547, 0.00548, 0.00549, 0.00550, 0.00551, 0.00552, 0.00553, 0.00554, 0.00555, 0.00556, 0.00557, 0.00558, 0.00559, 0.00560, 0.00561, 0.00562, 0.00563, 0.00564, 0.00565, 0.00566, 0.00567, 0.00568, 0.00569, 0.00570, 0.00571, 0.00572, 0.00573, 0.00574, 0.00575, 0.00576, 0.00577, 0.00578, 0.00579, or 0.00580. In some embodiments, the ratio of $CD34^+$ cells to neutrophils is from about 0.0026 to about 0.0046, such as a ratio of $CD34^+$ cells to neutrophils of about 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00377, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00400, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, or 0.00460. In some embodiments, the ratio of $CD34^+$ cells to neutrophils is about 0.0036.

In another aspect, the invention features a pharmaceutical composition including a population of hematopoietic stem cells or progeny thereof isolated from a mammalian donor (e.g., a human donor), wherein the ratio of $CD34^+$ cells to lymphocytes in the population is from about 0.0021 to about 0.0094. In some embodiments, the ratio of $CD34^+$ cells to lymphocytes may be about 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00377, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00400, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, 0.00460, 0.00461, 0.00462, 0.00463, 0.00464, 0.00465, 0.00466, 0.00467, 0.00468, 0.00469, 0.00470, 0.00471, 0.00472, 0.00473, 0.00474, 0.00475, 0.00476, 0.00477, 0.00478, 0.00479, 0.00480, 0.00481, 0.00482, 0.00483, 0.00484, 0.00485, 0.00486, 0.00487, 0.00488, 0.00489, 0.00490, 0.00491, 0.00492, 0.00493, 0.00494, 0.00495, 0.00496, 0.00497, 0.00498, 0.00499, 0.00500, 0.00501, 0.00502, 0.00503, 0.00504, 0.00505, 0.00506, 0.00507, 0.00508, 0.00509, 0.00510, 0.00511, 0.00512, 0.00513, 0.00514, 0.00515, 0.00516, 0.00517, 0.00518, 0.00519, 0.00520, 0.00521, 0.00522, 0.00523, 0.00524, 0.00525, 0.00526, 0.00527, 0.00528, 0.00529, 0.00530, 0.00531, 0.00532, 0.00533, 0.00534, 0.00535, 0.00536, 0.00537, 0.00538, 0.00539, 0.00540, 0.00541, 0.00542, 0.00543, 0.00544, 0.00545, 0.00546, 0.00547, 0.00548, 0.00549, 0.00550, 0.00551, 0.00552, 0.00553, 0.00554, 0.00555, 0.00556, 0.00557, 0.00558, 0.00559, 0.00560, 0.00561, 0.00562, 0.00563, 0.00564, 0.00565, 0.00566, 0.00567, 0.00568, 0.00569, 0.00570, 0.00571, 0.00572, 0.00573, 0.00574, 0.00575, 0.00576, 0.00577, 0.00578, 0.00579, 0.00580, 0.00581, 0.00582, 0.00583, 0.00584, 0.00585, 0.00586, 0.00587, 0.00588, 0.00589, 0.00590, 0.00591, 0.00592, 0.00593, 0.00594, 0.00595, 0.00596, 0.00597, 0.00598, 0.00599, 0.00600, 0.00601, 0.00602, 0.00603, 0.00604, 0.00605, 0.00606, 0.00607, 0.00608, 0.00609, 0.00610, 0.00611, 0.00612, 0.00613, 0.00614, 0.00615, 0.00616, 0.00617, 0.00618, 0.00619, 0.00620, 0.00621, 0.00622, 0.00623, 0.00624, 0.00625, 0.00626, 0.00627, 0.00628, 0.00629, 0.00630, 0.00631, 0.00632, 0.00633, 0.00634, 0.00635, 0.00636, 0.00637, 0.00638, 0.00639, 0.00640, 0.00641, 0.00642, 0.00643, 0.00644, 0.00645, 0.00646, 0.00647, 0.00648, 0.00649, 0.00650, 0.00651, 0.00652, 0.00653, 0.00654, 0.00655, 0.00656, 0.00657, 0.00658, 0.00659, 0.00660, 0.00661, 0.00662, 0.00663, 0.00664, 0.00665, 0.00666, 0.00667, 0.00668, 0.00669, 0.00670, 0.00671, 0.00672, 0.00673, 0.00674, 0.00675, 0.00676, 0.00677, 0.00678, 0.00679, 0.00680, 0.00681, 0.00682, 0.00683, 0.00684, 0.00685, 0.00686, 0.00687, 0.00688, 0.00689, 0.00690, 0.00691, 0.00692, 0.00693, 0.00694, 0.00695, 0.00696, 0.00697, 0.00698, 0.00699, 0.00700, 0.00701, 0.00702, 0.00703, 0.00704, 0.00705, 0.00706, 0.00707, 0.00708, 0.00709, 0.00710, 0.00711, 0.00712, 0.00713, 0.00714, 0.00715, 0.00716, 0.00717, 0.00718, 0.00719, 0.00720, 0.00721, 0.00722, 0.00723, 0.00724, 0.00725, 0.00726, 0.00727, 0.00728, 0.00729, 0.00730, 0.00731, 0.00732, 0.00733, 0.00734, 0.00735, 0.00736, 0.00737, 0.00738, 0.00739, 0.00740, 0.00741, 0.00742, 0.00743, 0.00744, 0.00745, 0.00746, 0.00747, 0.00748, 0.00749, 0.00750, 0.00751, 0.00752, 0.00753, 0.00754, 0.00755, 0.00756, 0.00757, 0.00758, 0.00759, 0.00760, 0.00761, 0.00762, 0.00763, 0.00764, 0.00765, 0.00766, 0.00767, 0.00768, 0.00769, 0.00770, 0.00771, 0.00772, 0.00773, 0.00774, 0.00775, 0.00776, 0.00777, 0.00778, 0.00779, 0.00780, 0.00781, 0.00782, 0.00783, 0.00784, 0.00785, 0.00786, 0.00787, 0.00788, 0.00789, 0.00790, 0.00791, 0.00792, 0.00793, 0.00794, 0.00795, 0.00796, 0.00797, 0.00798, 0.00799, 0.00800, 0.00801, 0.00802, 0.00803, 0.00804, 0.00805, 0.00806, 0.00807, 0.00808, 0.00809, 0.00810, 0.00811, 0.00812, 0.00813, 0.00814, 0.00815, 0.00816, 0.00817, 0.00818, 0.00819, 0.00820, 0.00821, 0.00822, 0.00823, 0.00824, 0.00825, 0.00826, 0.00827, 0.00828, 0.00829, 0.00830, 0.00831, 0.00832, 0.00833, 0.00834, 0.00835, 0.00836, 0.00837, 0.00838, 0.00839, 0.00840, 0.00841, 0.00842, 0.00843, 0.00844, 0.00845, 0.00846, 0.00847, 0.00848, 0.00849, 0.00850, 0.00851, 0.00852, 0.00853, 0.00854, 0.00855, 0.00856, 0.00857, 0.00858, 0.00859, 0.00860, 0.00861, 0.00862, 0.00863, 0.00864, 0.00865, 0.00866, 0.00867, 0.00868, 0.00869, 0.00870, 0.00871, 0.00872, 0.00873, 0.00874, 0.00875, 0.00876, 0.00877, 0.00878, 0.00879, 0.00880, 0.00881, 0.00882, 0.00883, 0.00884, 0.00885, 0.00886, 0.00887, 0.00888, 0.00889, 0.00890, 0.00891, 0.00892, 0.00893, 0.00894, 0.00895, 0.00896, 0.00897, 0.00898, 0.00899, 0.00900, 0.00901, 0.00902, 0.00903, 0.00904, 0.00905, 0.00906, 0.00907, 0.00908, 0.00909, 0.00910, 0.00911, 0.00912, 0.00913, 0.00914, 0.00915, 0.00916, 0.00917, 0.00918, 0.00919, 0.00920, 0.00921, 0.00922, 0.00923, 0.00924, 0.00925, 0.00926, 0.00927, 0.00928, 0.00929, 0.00930, 0.00931, 0.00932, 0.00933, 0.00934, 0.00935, 0.00936, 0.00937, 0.00938, 0.00939, or 0.00940. In some embodiments, the ratio of CD34$^+$ cells to lymphocytes is from about 0.0025 to about 0.0035, such as a ratio of CD34$^+$ cells to lymphocytes of about 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, or 0.00350. In some embodiments, the ratio of CD34$^+$ cells to lymphocytes is about 0.0031.

In a further aspect, the invention features a pharmaceutical composition including a population of hematopoietic stem cells or progeny thereof isolated from a mammalian donor (e.g., a human donor), wherein the ratio of CD34$^+$ cells to monocytes in the population is from about 0.0071 to about 0.0174. In some embodiments, the ratio of CD34$^+$ cells to monocytes may be about 0.00710, 0.00711, 0.00712, 0.00713, 0.00714, 0.00715, 0.00716, 0.00717, 0.00718, 0.00719, 0.00720, 0.00721, 0.00722, 0.00723, 0.00724, 0.00725, 0.00726, 0.00727, 0.00728, 0.00729, 0.00730, 0.00731, 0.00732, 0.00733, 0.00734, 0.00735, 0.00736, 0.00737, 0.00738, 0.00739, 0.00740, 0.00741, 0.00742, 0.00743, 0.00744, 0.00745, 0.00746, 0.00747, 0.00748, 0.00749, 0.00750, 0.00751, 0.00752, 0.00753, 0.00754, 0.00755, 0.00756, 0.00757, 0.00758, 0.00759, 0.00760, 0.00761, 0.00762, 0.00763, 0.00764, 0.00765, 0.00766, 0.00767, 0.00768, 0.00769, 0.00770, 0.00771, 0.00772, 0.00773, 0.00774, 0.00775, 0.00776, 0.00777, 0.00778, 0.00779, 0.00780, 0.00781, 0.00782, 0.00783, 0.00784, 0.00785, 0.00786, 0.00787, 0.00788, 0.00789, 0.00790, 0.00791, 0.00792, 0.00793, 0.00794, 0.00795, 0.00796, 0.00797, 0.00798, 0.00799, 0.00800, 0.00801, 0.00802, 0.00803, 0.00804, 0.00805, 0.00806, 0.00807, 0.00808, 0.00809, 0.00810, 0.00811, 0.00812, 0.00813, 0.00814, 0.00815, 0.00816, 0.00817, 0.00818, 0.00819, 0.00820, 0.00821, 0.00822, 0.00823, 0.00824, 0.00825, 0.00826, 0.00827, 0.00828, 0.00829, 0.00830, 0.00831, 0.00832, 0.00833, 0.00834, 0.00835, 0.00836, 0.00837, 0.00838, 0.00839, 0.00840, 0.00841, 0.00842, 0.00843, 0.00844, 0.00845, 0.00846, 0.00847, 0.00848, 0.00849, 0.00850, 0.00851, 0.00852, 0.00853, 0.00854, 0.00855, 0.00856, 0.00857, 0.00858, 0.00859, 0.00860, 0.00861, 0.00862, 0.00863, 0.00864, 0.00865, 0.00866, 0.00867, 0.00868, 0.00869, 0.00870, 0.00871, 0.00872, 0.00873, 0.00874, 0.00875, 0.00876, 0.00877, 0.00878, 0.00879, 0.00880, 0.00881, 0.00882, 0.00883, 0.00884, 0.00885, 0.00886, 0.00887, 0.00888, 0.00889, 0.00890, 0.00891, 0.00892, 0.00893, 0.00894, 0.00895, 0.00896, 0.00897, 0.00898, 0.00899, 0.00900, 0.00901, 0.00902, 0.00903, 0.00904, 0.00905, 0.00906, 0.00907, 0.00908, 0.00909, 0.00910, 0.00911, 0.00912, 0.00913, 0.00914, 0.00915, 0.00916, 0.00917, 0.00918, 0.00919, 0.00920, 0.00921, 0.00922, 0.00923, 0.00924, 0.00925, 0.00926, 0.00927, 0.00928, 0.00929, 0.00930, 0.00931, 0.00932, 0.00933, 0.00934, 0.00935, 0.00936, 0.00937, 0.00938, 0.00939, 0.00940, 0.00941, 0.00942, 0.00943, 0.00944, 0.00945, 0.00946, 0.00947, 0.00948, 0.00949, 0.00950, 0.00951, 0.00952, 0.00953, 0.00954, 0.00955, 0.00956, 0.00957, 0.00958, 0.00959, 0.00960, 0.00961, 0.00962, 0.00963, 0.00964, 0.00965, 0.00966, 0.00967, 0.00968, 0.00969, 0.00970, 0.00971, 0.00972, 0.00973, 0.00974, 0.00975, 0.00976, 0.00977, 0.00978, 0.00979, 0.00980, 0.00981, 0.00982, 0.00983, 0.00984, 0.00985, 0.00986, 0.00987, 0.00988, 0.00989, 0.00990, 0.00991, 0.00992, 0.00993, 0.00994, 0.00995, 0.00996, 0.00997, 0.00998, 0.00999, 0.0100, 0.0101, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, 0.0150, 0.0151, 0.0152, 0.0153, 0.0154, 0.0155, 0.0156, 0.0157, 0.0158, 0.0159, 0.0160, 0.0161, 0.0162, 0.0163, 0.0164, 0.0165, 0.0166, 0.0167, 0.0168, 0.0169, 0.0170, 0.0171, 0.0172, 0.0173, or 0.0174. In some embodiments, the ratio of CD34$^+$ cells to monocytes is from about 0.0100 to about 0.0140, such as a ratio of CD34$^+$ cells to monocytes of about 0.0100, 0.0101, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, or 0.0140. In some embodiments, the ratio of CD34$^+$ cells to monocytes is about 0.0118.

In a further aspect, the invention features a pharmaceutical composition including a population of hematopoietic stem cells or progeny thereof isolated from a mammalian donor (e.g., a human donor), wherein the frequency of CD34$^+$ cells in the population is from about 0.051% to about 0.140%. In some embodiments, the population of cells may have a frequency of CD34$^+$ cells of about 0.051%, 0.052%, 0.053%, 0.054%, 0.055%, 0.056%, 0.057%, 0.058%, 0.059%, 0.060%, 0.061%, 0.062%, 0.063%, 0.064%, 0.065%, 0.066%, 0.067%, 0.068%, 0.069%, 0.070%, 0.071%, 0.072%, 0.073%, 0.074%, 0.075%, 0.076%, 0.077%, 0.078%, 0.079%, 0.080%, 0.081%, 0.082%, 0.083%, 0.084%, 0.085%, 0.086%, 0.087%, 0.088%, 0.089%, 0.090%, 0.091%, 0.092%, 0.093%, 0.094%, 0.095%, 0.096%, 0.097%, 0.098%, 0.099%, 0.100%, 0.101%, 0.102%, 0.103%, 0.104%, 0.105%, 0.106%, 0.107%, 0.108%, 0.109%, 0.110%, 0.111%, 0.112%, 0.113%, 0.114%, 0.115%, 0.116%, 0.117%, 0.118%, 0.119%, 0.120%, 0.121%, 0.122%, 0.123%, 0.124%, 0.125%, 0.126%, 0.127%, 0.128%, 0.129%, 0.130%, 0.131%, 0.132%, 0.133%, 0.134%, 0.135%, 0.136%, 0.137%, 0.138%, 0.139%, or 0.140%. In some embodiments, the population of cells has a frequency of CD34$^+$ cells of from about 0.080% to about 0.120%, such as a frequency of CD34$^+$ cells of about 0.080%, 0.081%, 0.082%, 0.083%, 0.084%, 0.085%, 0.086%, 0.087%, 0.088%, 0.089%, 0.090%, 0.091%, 0.092%, 0.093%, 0.094%, 0.095%, 0.096%, 0.097%, 0.098%, 0.099%, 0.100%, 0.101%, 0.102%, 0.103%, 0.104%, 0.105%, 0.106%, 0.107%, 0.108%, 0.109%, 0.110%, 0.111%, 0.112%, 0.113%, 0.114%, 0.115%, 0.116%, 0.117%, 0.118%, 0.119%, or 0.120%. In some embodiments, the population of cells has a frequency of CD34$^+$ cells of about 0.097%.

In a further aspect, the invention features a pharmaceutical composition including a population of hematopoietic stem cells or progeny thereof isolated from a mammalian donor (e.g., a human donor), wherein the ratio of CD34$^+$ CD90$^+$ CD45RA$^-$ cells to leukocytes in the population is from about 0.0003 to about 0.0016. In some embodiments, the ratio of CD34$^+$ CD90$^+$ CD45RA$^-$ cells to leukocytes may be about 0.00030, 0.00031, 0.00032, 0.00033, 0.00034, 0.00035, 0.00036, 0.00037, 0.00038, 0.00039, 0.00040, 0.00041, 0.00042, 0.00043, 0.00044, 0.00045, 0.00046, 0.00047, 0.00048, 0.00049, 0.00050, 0.00051, 0.00052, 0.00053, 0.00054, 0.00055, 0.00056, 0.00057, 0.00058, 0.00059, 0.00060, 0.00061, 0.00062, 0.00063, 0.00064, 0.00065, 0.00066, 0.00067, 0.00068, 0.00069, 0.00070, 0.00071, 0.00072, 0.00073, 0.00074, 0.00075, 0.00076, 0.00077, 0.00078, 0.00079, 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, or 0.00160. In some embodiments, the ratio of $CD34^+$ $CD90^+$ $CD45RA^-$ cells to leukocytes is from about 0.0006 to about 0.0012, such as a ratio of $CD34^+$ $CD90^+$ $CD45RA^-$ cells to leukocytes of about 0.00060, 0.00061, 0.00062, 0.00063, 0.00064, 0.00065, 0.00066, 0.00067, 0.00068, 0.00069, 0.00070, 0.00071, 0.00072, 0.00073, 0.00074, 0.00075, 0.00076, 0.00077, 0.00078, 0.00079, 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, or 0.00120. In some embodiments, the ratio of $CD34^+$ $CD90^+$ $CD45RA^-$ cells to leukocytes is about 0.0009.

In an additional aspect, the invention features a pharmaceutical composition including a population of hematopoietic stem cells or progeny thereof isolated from a mammalian donor (e.g., a human donor), wherein the ratio of $CD34^+$ $CD90^+$ $CD45RA^-$ cells to neutrophils in the population is from about 0.0007 to about 0.0043. In some embodiments, the ratio of $CD34^+$ $CD90^+$ $CD45RA^-$ cells to neutrophils may be about 0.00070, 0.00071, 0.00072, 0.00073, 0.00074, 0.00075, 0.00076, 0.00077, 0.00078, 0.00079, 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00177, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00377, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00400, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, or 0.00430. In some embodiments, the ratio of $CD34^+$ $CD90^+$ $CD45RA^-$ cells to neutrophils is from about 0.0014 to about 0.0034, such as a ratio of $CD34^+$ $CD90^+$ $CD45RA^-$ cells to neutrophils of about 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00177, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00277, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, or 0.00340. In some embodiments, the ratio of $CD34^+$ $CD90^+$ $CD45RA^-$ cells to neutrophils is about 0.0024.

In another aspect, the invention features a pharmaceutical composition including a population of hematopoietic stem cells or progeny thereof isolated from a mammalian donor (e.g., a human donor), wherein the ratio of CD34⁺ CD90⁺ CD45RA⁻ cells to lymphocytes in the population is from about 0.0008 to about 0.0069. In some embodiments, the ratio of CD34⁺ CD90⁺ CD45RA⁻ cells to lymphocytes may be about 0.00080, 0.00081, 0.00082, 0.00083, 0.00084, 0.00085, 0.00086, 0.00087, 0.00088, 0.00089, 0.00090, 0.00091, 0.00092, 0.00093, 0.00094, 0.00095, 0.00096, 0.00097, 0.00098, 0.00099, 0.00100, 0.00101, 0.00102, 0.00103, 0.00104, 0.00105, 0.00106, 0.00107, 0.00108, 0.00109, 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00444, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, 0.00460, 0.00461, 0.00462, 0.00463, 0.00464, 0.00465, 0.00466, 0.00467, 0.00468, 0.00469, 0.00470, 0.00471, 0.00472, 0.00473, 0.00474, 0.00475, 0.00476, 0.00478, 0.00479, 0.00480, 0.00481, 0.00482, 0.00483, 0.00484, 0.00485, 0.00486, 0.00487, 0.00488, 0.00489, 0.00490, 0.00491, 0.00492, 0.00493, 0.00494, 0.00495, 0.00496, 0.00497, 0.00498, 0.00499, 0.00500, 0.00501, 0.00502, 0.00503, 0.00504, 0.00505, 0.00506, 0.00507, 0.00508, 0.00509, 0.00510, 0.00511, 0.00512, 0.00513, 0.00514, 0.00515, 0.00516, 0.00517, 0.00518, 0.00519, 0.00520, 0.00521, 0.00522, 0.00523, 0.00524, 0.00525, 0.00526, 0.00527, 0.00528, 0.00529, 0.00530, 0.00531, 0.00532, 0.00533, 0.00534, 0.00535, 0.00536, 0.00537, 0.00538, 0.00539, 0.00540, 0.00541, 0.00542, 0.00543, 0.00544, 0.00545, 0.00546, 0.00547, 0.00548, 0.00549, 0.00550, 0.00551, 0.00552, 0.00553, 0.00554, 0.00555, 0.00556, 0.00557, 0.00558, 0.00559, 0.00560, 0.00561, 0.00562, 0.00563, 0.00564, 0.00565, 0.00566, 0.00567, 0.00568, 0.00569, 0.00570, 0.00571, 0.00572, 0.00573, 0.00574, 0.00575, 0.00576, 0.00578, 0.00579, 0.00580, 0.00581, 0.00582, 0.00583, 0.00584, 0.00585, 0.00586, 0.00587, 0.00588, 0.00589, 0.00590, 0.00591, 0.00592, 0.00593, 0.00594, 0.00595, 0.00596, 0.00597, 0.00598, 0.00599, 0.00600, 0.00601, 0.00602, 0.00603, 0.00604, 0.00605, 0.00606, 0.00607, 0.00608, 0.00609, 0.00610, 0.00611, 0.00612, 0.00613, 0.00614, 0.00615, 0.00616, 0.00617, 0.00618, 0.00619, 0.00620, 0.00621, 0.00622, 0.00623, 0.00624, 0.00625, 0.00626, 0.00627, 0.00628, 0.00629, 0.00630, 0.00631, 0.00632, 0.00633, 0.00634, 0.00635, 0.00636, 0.00637, 0.00638, 0.00639, 0.00640, 0.00641, 0.00642, 0.00643, 0.00644, 0.00645, 0.00646, 0.00647, 0.00648, 0.00649, 0.00650, 0.00651, 0.00652, 0.00653, 0.00654, 0.00655, 0.00656, 0.00657, 0.00658, 0.00659, 0.00660, 0.00661, 0.00662, 0.00663, 0.00664, 0.00665, 0.00666, 0.00667, 0.00668, 0.00669, 0.00670, 0.00671, 0.00672, 0.00673, 0.00674, 0.00675, 0.00676, 0.00678, 0.00679, 0.00680, 0.00681, 0.00682, 0.00683, 0.00684, 0.00685, 0.00686, 0.00687, 0.00688, 0.00689, or 0.00690. In some embodiments, the ratio of CD34⁺ CD90⁺ CD45RA⁻ cells to lymphocytes is from about 0.0011 to about 0.0031, such as a ratio of CD34⁺ CD90⁺ CD45RA⁻ cells to lymphocytes of about 0.00110, 0.00111, 0.00112, 0.00113, 0.00114, 0.00115, 0.00116, 0.00117, 0.00118, 0.00119, 0.00120, 0.00121, 0.00122, 0.00123, 0.00124, 0.00125, 0.00126, 0.00127, 0.00128, 0.00129, 0.00130, 0.00131, 0.00132, 0.00133, 0.00134, 0.00135, 0.00136, 0.00137, 0.00138, 0.00139, 0.00140, 0.00141, 0.00142, 0.00143, 0.00144, 0.00145, 0.00146, 0.00147, 0.00148, 0.00149, 0.00150, 0.00151, 0.00152, 0.00153, 0.00154, 0.00155, 0.00156, 0.00157, 0.00158, 0.00159, 0.00160, 0.00161, 0.00162, 0.00163, 0.00164, 0.00165, 0.00166, 0.00167, 0.00168, 0.00169, 0.00170, 0.00171, 0.00172, 0.00173, 0.00174, 0.00175, 0.00176, 0.00178, 0.00179, 0.00180, 0.00181, 0.00182, 0.00183, 0.00184, 0.00185, 0.00186, 0.00187, 0.00188, 0.00189, 0.00190, 0.00191, 0.00192, 0.00193, 0.00194, 0.00195, 0.00196, 0.00197, 0.00198, 0.00199, 0.00200, 0.00201, 0.00202, 0.00203, 0.00204, 0.00205, 0.00206, 0.00207, 0.00208, 0.00209, 0.00210, 0.00211, 0.00212, 0.00213, 0.00214, 0.00215, 0.00216, 0.00217, 0.00218, 0.00219, 0.00220, 0.00221, 0.00222, 0.00223, 0.00224, 0.00225, 0.00226, 0.00227, 0.00228, 0.00229, 0.00230, 0.00231, 0.00232, 0.00233, 0.00234, 0.00235, 0.00236, 0.00237, 0.00238, 0.00239, 0.00240, 0.00241, 0.00242, 0.00243, 0.00244, 0.00245, 0.00246, 0.00247, 0.00248, 0.00249, 0.00250, 0.00251, 0.00252, 0.00253, 0.00254, 0.00255, 0.00256, 0.00257, 0.00258, 0.00259, 0.00260, 0.00261, 0.00262, 0.00263, 0.00264, 0.00265, 0.00266, 0.00267, 0.00268, 0.00269, 0.00270, 0.00271, 0.00272, 0.00273, 0.00274, 0.00275, 0.00276, 0.00278, 0.00279, 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00301, 0.00302, 0.00303, 0.00304, 0.00305, 0.00306, 0.00307, 0.00308, 0.00309, or 0.00310. In some embodiments, the ratio of $CD34^+$ $CD90^+$ $CD45RA^-$-cells to lymphocytes is about 0.0021.

In a further aspect, the invention features a pharmaceutical composition including a population of hematopoietic stem cells or progeny thereof isolated from a mammalian donor (e.g., a human donor), wherein the ratio of $CD34^+$ $CD90^+$ $CD45RA^-$ cells to monocytes in the population is from about 0.0028 to about 0.0130. In some embodiments, the ratio of $CD34^+$ $CD90^+$ $CD45RA^-$ cells to monocytes may be about 0.00280, 0.00281, 0.00282, 0.00283, 0.00284, 0.00285, 0.00286, 0.00287, 0.00288, 0.00289, 0.00290, 0.00291, 0.00292, 0.00293, 0.00294, 0.00295, 0.00296, 0.00297, 0.00298, 0.00299, 0.00300, 0.00301, 0.00302, 0.00303, 0.00304, 0.00305, 0.00306, 0.00307, 0.00308, 0.00309, 0.00310, 0.00311, 0.00312, 0.00313, 0.00314, 0.00315, 0.00316, 0.00317, 0.00318, 0.00319, 0.00320, 0.00321, 0.00322, 0.00323, 0.00324, 0.00325, 0.00326, 0.00327, 0.00328, 0.00329, 0.00330, 0.00331, 0.00332, 0.00333, 0.00334, 0.00335, 0.00336, 0.00337, 0.00338, 0.00339, 0.00340, 0.00341, 0.00342, 0.00343, 0.00344, 0.00345, 0.00346, 0.00347, 0.00348, 0.00349, 0.00350, 0.00351, 0.00352, 0.00353, 0.00354, 0.00355, 0.00356, 0.00357, 0.00358, 0.00359, 0.00360, 0.00361, 0.00362, 0.00363, 0.00364, 0.00365, 0.00366, 0.00367, 0.00368, 0.00369, 0.00370, 0.00371, 0.00372, 0.00373, 0.00374, 0.00375, 0.00376, 0.00378, 0.00379, 0.00380, 0.00381, 0.00382, 0.00383, 0.00384, 0.00385, 0.00386, 0.00387, 0.00388, 0.00389, 0.00390, 0.00391, 0.00392, 0.00393, 0.00394, 0.00395, 0.00396, 0.00397, 0.00398, 0.00399, 0.00401, 0.00402, 0.00403, 0.00404, 0.00405, 0.00406, 0.00407, 0.00408, 0.00409, 0.00410, 0.00411, 0.00412, 0.00413, 0.00414, 0.00415, 0.00416, 0.00417, 0.00418, 0.00419, 0.00420, 0.00421, 0.00422, 0.00423, 0.00424, 0.00425, 0.00426, 0.00427, 0.00428, 0.00429, 0.00430, 0.00431, 0.00432, 0.00433, 0.00434, 0.00435, 0.00436, 0.00437, 0.00438, 0.00439, 0.00440, 0.00441, 0.00442, 0.00443, 0.00414, 0.00445, 0.00446, 0.00447, 0.00448, 0.00449, 0.00450, 0.00451, 0.00452, 0.00453, 0.00454, 0.00455, 0.00456, 0.00457, 0.00458, 0.00459, 0.00460, 0.00461, 0.00462, 0.00463, 0.00464, 0.00465, 0.00466, 0.00467, 0.00468, 0.00469, 0.00470, 0.00471, 0.00472, 0.00473, 0.00474, 0.00475, 0.00476, 0.00478, 0.00479, 0.00480, 0.00481, 0.00482, 0.00483, 0.00484, 0.00485, 0.00486, 0.00487, 0.00488, 0.00489, 0.00490, 0.00491, 0.00492, 0.00493, 0.00494, 0.00495, 0.00496, 0.00497, 0.00498, 0.00499, 0.00500, 0.00501, 0.00502, 0.00503, 0.00504, 0.00505, 0.00506, 0.00507, 0.00508, 0.00509, 0.00510, 0.00511, 0.00512, 0.00513, 0.00514, 0.00515, 0.00516, 0.00517, 0.00518, 0.00519, 0.00520, 0.00521, 0.00522, 0.00523, 0.00524, 0.00525, 0.00526, 0.00527, 0.00528, 0.00529, 0.00530, 0.00531, 0.00532, 0.00533, 0.00534, 0.00535, 0.00536, 0.00537, 0.00538, 0.00539, 0.00540, 0.00541, 0.00542, 0.00543, 0.00544, 0.00545, 0.00546, 0.00547, 0.00548, 0.00549, 0.00550, 0.00551, 0.00552, 0.00553, 0.00554, 0.00555, 0.00556, 0.00557, 0.00558, 0.00559, 0.00560, 0.00561, 0.00562, 0.00563, 0.00564, 0.00565, 0.00566, 0.00567, 0.00568, 0.00569, 0.00570, 0.00571, 0.00572, 0.00573, 0.00574, 0.00575, 0.00576, 0.00578, 0.00579, 0.00580, 0.00581, 0.00582, 0.00583, 0.00584, 0.00585, 0.00586, 0.00587, 0.00588, 0.00589, 0.00590, 0.00591, 0.00592, 0.00593, 0.00594, 0.00595, 0.00596, 0.00597, 0.00598, 0.00599, 0.00600, 0.00601, 0.00602, 0.00603, 0.00604, 0.00605, 0.00606, 0.00607, 0.00608, 0.00609, 0.00610, 0.00611, 0.00612, 0.00613, 0.00614, 0.00615, 0.00616, 0.00617, 0.00618, 0.00619, 0.00620, 0.00621, 0.00622, 0.00623, 0.00624, 0.00625, 0.00626, 0.00627, 0.00628, 0.00629, 0.00630, 0.00631, 0.00632, 0.00633, 0.00634, 0.00635, 0.00636, 0.00637, 0.00638, 0.00639, 0.00640, 0.00641, 0.00642, 0.00643, 0.00644, 0.00645, 0.00646, 0.00647, 0.00648, 0.00649, 0.00650, 0.00651, 0.00652, 0.00653, 0.00654, 0.00655, 0.00656, 0.00657, 0.00658, 0.00659, 0.00660, 0.00661, 0.00662, 0.00663, 0.00664, 0.00665, 0.00666, 0.00667, 0.00668, 0.00669, 0.00670, 0.00671, 0.00672, 0.00673, 0.00674, 0.00675, 0.00676, 0.00678, 0.00679, 0.00680, 0.00681, 0.00682, 0.00683, 0.00684, 0.00685, 0.00686, 0.00687, 0.00688, 0.00689, 0.00690, 0.00691, 0.00692, 0.00693, 0.00694, 0.00695, 0.00696, 0.00697, 0.00698, 0.00699, 0.00700, 0.00701, 0.00702, 0.00703, 0.00704, 0.00705, 0.00706, 0.00707, 0.00708, 0.00709, 0.00710, 0.00711, 0.00712, 0.00713, 0.00714, 0.00715, 0.00716, 0.00717, 0.00718, 0.00719, 0.00720, 0.00721, 0.00722, 0.00723, 0.00724, 0.00725, 0.00726, 0.00727, 0.00728, 0.00729, 0.00730, 0.00731, 0.00732, 0.00733, 0.00734, 0.00735, 0.00736, 0.00737, 0.00738, 0.00739, 0.00740, 0.00741, 0.00742, 0.00743, 0.00744, 0.00745, 0.00746, 0.00747, 0.00748, 0.00749, 0.00750, 0.00751, 0.00752, 0.00753, 0.00754, 0.00755, 0.00756, 0.00757, 0.00758, 0.00759, 0.00760, 0.00761, 0.00762, 0.00763, 0.00764, 0.00765, 0.00766, 0.00767, 0.00768, 0.00769, 0.00770, 0.00771, 0.00772, 0.00773, 0.00774, 0.00775, 0.00776, 0.00777, 0.00778, 0.00779, 0.00780, 0.00781, 0.00782, 0.00783, 0.00784, 0.00785, 0.00786, 0.00787, 0.00788, 0.00789, 0.00790, 0.00791, 0.00792, 0.00793, 0.00794, 0.00795, 0.00796, 0.00797, 0.00798, 0.00799, 0.00800, 0.00801, 0.00802, 0.00803, 0.00804, 0.00805, 0.00806, 0.00807, 0.00808, 0.00809, 0.00810, 0.00811, 0.00812, 0.00813, 0.00814, 0.00815, 0.00816, 0.00817, 0.00818, 0.00819, 0.00820, 0.00821, 0.00822, 0.00823, 0.00824, 0.00825, 0.00826, 0.00827, 0.00828, 0.00829, 0.00830, 0.00831, 0.00832, 0.00833, 0.00834, 0.00835, 0.00836, 0.00837, 0.00838, 0.00839, 0.00840, 0.00841, 0.00842, 0.00843, 0.00844, 0.00845, 0.00846, 0.00847, 0.00848, 0.00849, 0.00850, 0.00851, 0.00852, 0.00853, 0.00854, 0.00855, 0.00856, 0.00857, 0.00858, 0.00859, 0.00860, 0.00861, 0.00862, 0.00863, 0.00864, 0.00865, 0.00866, 0.00867, 0.00868, 0.00869, 0.00870, 0.00871, 0.00872, 0.00873, 0.00874, 0.00875, 0.00876, 0.00877, 0.00878, 0.00879, 0.00880, 0.00881, 0.00882, 0.00883, 0.00884, 0.00885, 0.00886, 0.00887, 0.00888, 0.00889, 0.00890, 0.00891, 0.00892, 0.00893, 0.00894, 0.00895, 0.00896, 0.00897, 0.00898, 0.00899, 0.00900, 0.00901, 0.00902, 0.00903, 0.00904, 0.00905, 0.00906, 0.00907, 0.00908, 0.00909, 0.00910, 0.00911, 0.00912, 0.00913, 0.00914, 0.00915, 0.00916, 0.00917, 0.00918, 0.00919, 0.00920, 0.00921, 0.00922, 0.00923, 0.00924, 0.00925, 0.00926, 0.00927, 0.00928, 0.00929, 0.00930, 0.00931, 0.00932, 0.00933, 0.00934, 0.00935, 0.00936, 0.00937, 0.00938, 0.00939, 0.00940, 0.00941, 0.00942, 0.00943, 0.00944, 0.00945, 0.00946, 0.00947, 0.00948, 0.00949, 0.00950, 0.00951, 0.00952, 0.00953, 0.00954, 0.00955, 0.00956, 0.00957, 0.00958, 0.00959, 0.00960, 0.00961, 0.00962, 0.00963, 0.00964, 0.00965, 0.00966, 0.00967, 0.00968, 0.00969, 0.00970, 0.00971, 0.00972, 0.00973, 0.00974, 0.00975, 0.00976, 0.00977, 0.00978, 0.00979, 0.00980, 0.00981, 0.00982, 0.00983, 0.00984, 0.00985, 0.00986, 0.00987, 0.00988, 0.00989, 0.00990, 0.00991, 0.00992, 0.00993, 0.00994, 0.00995, 0.00996, 0.00997, 0.00998, 0.00999, 0.0100, 0.0101, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, or 0.0130. In some embodiments, the ratio of CD34$^+$ CD90$^+$ CD45RA$^-$ cells to monocytes is from about 0.0063 to about 0.0083, such as a ratio of CD34$^+$ CD90$^+$ CD45RA$^-$ cells to monocytes of about 0.00630, 0.00631, 0.00632, 0.00633, 0.00634, 0.00635, 0.00636, 0.00637, 0.00638, 0.00639, 0.00640, 0.00641, 0.00642, 0.00643, 0.00644, 0.00645, 0.00646, 0.00647, 0.00648, 0.00649, 0.00650, 0.00651, 0.00652, 0.00653, 0.00654, 0.00655, 0.00656, 0.00657, 0.00658, 0.00659, 0.00660, 0.00661, 0.00662, 0.00663, 0.00664, 0.00665, 0.00666, 0.00667, 0.00668, 0.00669, 0.00670, 0.00671, 0.00672, 0.00673, 0.00674, 0.00675, 0.00676, 0.00678, 0.00679, 0.00680, 0.00681, 0.00682, 0.00683, 0.00684, 0.00685, 0.00686, 0.00687, 0.00688, 0.00689, 0.00690, 0.00691, 0.00692, 0.00693, 0.00694, 0.00695, 0.00696, 0.00697, 0.00698, 0.00699, 0.00700, 0.00701, 0.00702, 0.00703, 0.00704, 0.00705, 0.00706, 0.00707, 0.00708, 0.00709, 0.00710, 0.00711, 0.00712, 0.00713, 0.00714, 0.00715, 0.00716, 0.00717, 0.00718, 0.00719, 0.00720, 0.00721, 0.00722, 0.00723, 0.00724, 0.00725, 0.00726, 0.00727, 0.00728, 0.00729, 0.00730, 0.00731, 0.00732, 0.00733, 0.00734, 0.00735, 0.00736, 0.00737, 0.00738, 0.00739, 0.00740, 0.00741, 0.00742, 0.00743, 0.00744, 0.00745, 0.00746, 0.00747, 0.00748, 0.00749, 0.00750, 0.00751, 0.00752, 0.00753, 0.00754, 0.00755, 0.00756, 0.00757, 0.00758, 0.00759, 0.00760, 0.00761, 0.00762, 0.00763, 0.00764, 0.00765, 0.00766, 0.00767, 0.00768, 0.00769, 0.00770, 0.00771, 0.00772, 0.00773, 0.00774, 0.00775, 0.00776, 0.00777, 0.00778, 0.00779, 0.00780, 0.00781, 0.00782, 0.00783, 0.00784, 0.00785, 0.00786, 0.00787, 0.00788, 0.00789, 0.00790, 0.00791, 0.00792, 0.00793, 0.00794, 0.00795, 0.00796, 0.00797, 0.00798, 0.00799, 0.00800, 0.00801, 0.00802, 0.00803, 0.00804, 0.00805, 0.00806, 0.00807, 0.00808, 0.00809, 0.00810, 0.00811, 0.00812, 0.00813, 0.00814, 0.00815, 0.00816, 0.00817, 0.00818, 0.00819, 0.00820, 0.00821, 0.00822, 0.00823, 0.00824, 0.00825, 0.00826, 0.00827, 0.00828, 0.00829, or 0.00830. In some embodiments, the ratio of CD34$^+$ CD90$^+$ CD45RA$^-$ cells to monocytes is about 0.0073.

In a further aspect, the invention features a pharmaceutical composition including a population of hematopoietic stem cells or progeny thereof isolated from a mammalian donor (e.g., a human donor), wherein the ratio of CD34$^+$ CD90$^+$ CD45RA$^-$ cells to CD34$^+$ cells in the population is from about 0.393 to about 0.745. In some embodiments, the ratio of CD34$^+$ CD90$^+$ CD45RA$^-$ cells to CD34$^+$ cells may be about 0.393, 0.394, 0.395, 0.396, 0.397, 0.398, 0.399, 0.401, 0.402, 0.403, 0.404, 0.405, 0.406, 0.407, 0.408, 0.409, 0.410, 0.411, 0.412, 0.413, 0.414, 0.415, 0.416, 0.417, 0.418, 0.419, 0.420, 0.421, 0.422, 0.423, 0.424, 0.425, 0.426, 0.427, 0.428, 0.429, 0.430, 0.431, 0.432, 0.433, 0.434, 0.435, 0.436, 0.437, 0.438, 0.439, 0.440, 0.441, 0.442, 0.443, 0.444, 0.445, 0.446, 0.447, 0.448, 0.449, 0.450, 0.451, 0.452, 0.453, 0.454, 0.455, 0.456, 0.457, 0.458, 0.459, 0.460, 0.461, 0.462, 0.463, 0.464, 0.465, 0.466, 0.467, 0.468, 0.469, 0.470, 0.471, 0.472, 0.473, 0.474, 0.475, 0.476, 0.478, 0.479, 0.480, 0.481, 0.482, 0.483, 0.484, 0.485, 0.486, 0.487, 0.488, 0.489, 0.490, 0.491, 0.492, 0.493, 0.494, 0.495, 0.496, 0.497, 0.498, 0.499, 0.500, 0.501, 0.502, 0.503, 0.504, 0.505, 0.506, 0.507, 0.508, 0.509, 0.510, 0.511, 0.512, 0.513, 0.514, 0.515, 0.516, 0.517, 0.518, 0.519, 0.520, 0.521, 0.522, 0.523, 0.524, 0.525, 0.526, 0.527, 0.528, 0.529, 0.530, 0.531, 0.532, 0.533, 0.534, 0.535, 0.536, 0.537, 0.538, 0.539, 0.540, 0.541, 0.542, 0.543, 0.544, 0.545, 0.546, 0.547, 0.548, 0.549, 0.550, 0.551, 0.552, 0.553, 0.554, 0.555, 0.556, 0.557, 0.558, 0.559, 0.560, 0.561, 0.562, 0.563, 0.564, 0.565, 0.566, 0.567, 0.568, 0.569, 0.570, 0.571, 0.572, 0.573, 0.574, 0.575, 0.576, 0.578, 0.579, 0.580, 0.581, 0.582, 0.583, 0.584, 0.585, 0.586, 0.587, 0.588, 0.589, 0.590, 0.591, 0.592, 0.593, 0.594, 0.595, 0.596, 0.597, 0.598, 0.599, 0.600, 0.601, 0.602, 0.603, 0.604, 0.605, 0.606, 0.607, 0.608, 0.609, 0.610, 0.611, 0.612, 0.613, 0.614, 0.615, 0.616, 0.617, 0.618, 0.619, 0.620, 0.621, 0.622, 0.623, 0.624, 0.625, 0.626, 0.627, 0.628, 0.629, 0.630, 0.631, 0.632, 0.633, 0.634, 0.635, 0.636, 0.637, 0.638, 0.639, 0.640, 0.641, 0.642, 0.643, 0.644, 0.645, 0.646, 0.647, 0.648, 0.649, 0.650, 0.651, 0.652, 0.653, 0.654, 0.655, 0.656, 0.657, 0.658, 0.659, 0.660, 0.661, 0.662, 0.663, 0.664, 0.665, 0.666, 0.667, 0.668, 0.669, 0.670, 0.671, 0.672, 0.673, 0.674, 0.675, 0.676, 0.678, 0.679, 0.680, 0.681, 0.682, 0.683, 0.684, 0.685, 0.686, 0.687, 0.688, 0.689, 0.690, 0.691, 0.692, 0.693, 0.694, 0.695, 0.696, 0.697, 0.698, 0.699, 0.700, 0.701, 0.702, 0.703, 0.704, 0.705, 0.706, 0.707, 0.708, 0.709, 0.710, 0.711, 0.712, 0.713, 0.714, 0.715, 0.716, 0.717, 0.718, 0.719, 0.720, 0.721, 0.722, 0.723, 0.724, 0.725, 0.726, 0.727, 0.728, 0.729, 0.730, 0.731, 0.732, 0.733, 0.734, 0.735, 0.736, 0.737, 0.738, 0.739, 0.740, 0.741, 0.742, 0.743, 0.744, or 0.745. In some embodiments, the ratio of CD34$^+$ CD90$^+$ CD45RA$^-$ cells to CD34$^+$ cells is from about 0.625 to about 0.725, such as a ratio of CD34$^+$ CD90$^+$ CD45RA$^-$ cells to CD34$^+$ cells of about 0.625, 0.626, 0.627, 0.628, 0.629, 0.630, 0.631, 0.632, 0.633, 0.634, 0.635, 0.636, 0.637, 0.638, 0.639, 0.640, 0.641, 0.642, 0.643, 0.644, 0.645, 0.646, 0.647, 0.648, 0.649, 0.650, 0.651, 0.652, 0.653, 0.654, 0.655, 0.656, 0.657, 0.658, 0.659, 0.660, 0.661, 0.662, 0.663, 0.664, 0.665, 0.666, 0.667, 0.668, 0.669, 0.670, 0.671, 0.672, 0.673, 0.674, 0.675, 0.676, 0.678, 0.679, 0.680, 0.681, 0.682, 0.683, 0.684, 0.685, 0.686, 0.687, 0.688, 0.689, 0.690, 0.691, 0.692, 0.693, 0.694, 0.695, 0.696, 0.697, 0.698, 0.699, 0.700, 0.701, 0.702, 0.703, 0.704, 0.705, 0.706, 0.707, 0.708, 0.709, 0.710, 0.711, 0.712, 0.713, 0.714, 0.715, 0.716, 0.717, 0.718, 0.719, 0.720, 0.721, 0.722, 0.723, 0.724, or 0.725. In some embodiments, the ratio of CD34$^+$ CD90$^+$ CD45RA$^-$ cells to CD34$^+$ cells is about 0.676.

In a further aspect, the invention features a pharmaceutical composition including a population of hematopoietic stem cells or progeny thereof isolated from a mammalian donor (e.g., a human donor), wherein the frequency of CD34$^+$ CD90$^+$ CD45RA$^-$ cells in the population is from about 0.020% to about 0.110%. In some embodiments, the population of cells may have a frequency of CD34$^+$ CD90$^+$ CD45RA$^-$ cells of about 0.020%, 0.021%, 0.022%, 0.023%, 0.024%, 0.025%, 0.026%, 0.027%, 0.028%, 0.029%, 0.030%, 0.031%, 0.032%, 0.033%, 0.034%, 0.035%, 0.036%, 0.037%, 0.038%, 0.039%, 0.040%, 0.041%, 0.042%, 0.043%, 0.044%, 0.045%, 0.046%, 0.047%, 0.048%, 0.049%, 0.050%, 0.051%, 0.052%, 0.053%, 0.054%, 0.055%, 0.056%, 0.057%, 0.058%, 0.059%, 0.060%, 0.061%, 0.062%, 0.063%, 0.064%, 0.065%, 0.066%, 0.067%, 0.068%, 0.069%, 0.070%, 0.071%, 0.072%, 0.073%, 0.074%, 0.075%, 0.076%, 0.077%, 0.078%, 0.079%, 0.080%, 0.081%, 0.082%, 0.083%, 0.084%, 0.085%, 0.086%, 0.087%, 0.088%, 0.089%, 0.090%, 0.091%, 0.092%, 0.093%, 0.094%, 0.095%, 0.096%, 0.097%, 0.098%, 0.099%, 0.100%, 0.101%, 0.102%, 0.103%, 0.104%, 0.105%, 0.106%, 0.107%, 0.108%, 0.109%, or 0.110%. In some embodiments, the population of cells has a frequency of CD34$^+$ CD90$^+$ CD45RA$^-$-cells of from about 0.046% to about 0.086%, such as a frequency of hematopoietic stem cells of about 0.046%, 0.047%, 0.048%, 0.049%, 0.050%, 0.051%, 0.052%, 0.053%, 0.054%, 0.055%, 0.056%, 0.057%, 0.058%, 0.059%, 0.060%, 0.061%, 0.062%, 0.063%, 0.064%, 0.065%, 0.066%, 0.067%, 0.068%, 0.069%, 0.070%, 0.071%, 0.072%, 0.073%, 0.074%, 0.075%, 0.076%, 0.077%, 0.078%, 0.079%, 0.080%, 0.081%, 0.082%, 0.083%, 0.084%, 0.085%, or 0.086%. In some embodiments, the population of cells has a frequency of CD34$^+$ CD90$^+$ CD45RA$^-$ cells of about 0.066%.

In another aspect, the invention features a method of treating a stem cell disorder in a mammalian patient (e.g., a human patient), the method including mobilizing a population of hematopoietic stem cells in a mammalian donor (e.g., a human donor) in accordance with any of the above-described methods, and infusing a therapeutically effective amount of the hematopoietic stem cells, or progeny thereof, into the patient.

In a further aspect, the invention features a method of treating a stem cell disorder in a mammalian patient (e.g., a human patient), the method including infusing into the patient a therapeutically effective amount of the hematopoietic stem cells mobilized by any of the above-described methods, or progeny thereof.

In another aspect, the invention features a method of treating a stem cell disorder in a mammalian patient (e.g., a human patient), the method including administering to the patient any one or more of the above-described pharmaceutical compositions.

In some embodiments of any of the three preceding aspects, the stem cell disorder is a hemoglobinopathy disorder, such as sickle cell anemia, thalassemia, Fanconi anemia, aplastic anemia, and Wiskott-Aldrich syndrome. In some embodiments, the stem cell disorder is a myelodysplastic disorder. The stem cell disorder may be an immunodeficiency disorder, such as a congenital immunodeficiency or an acquired immunodeficiency, for example, human immunodeficiency virus or acquired immune deficiency syndrome. In some embodiments, the stem cell disorder is a metabolic disorder, such as a metabolic disorder selected from glycogen storage diseases, mucopolysaccharidoses, Gaucher's Disease, Hurlers Disease, sphingolipidoses, and metachromatic leukodystrophy.

In some embodiments, the stem cell disorder is cancer. The cancer may be, for example, leukemia, lymphoma, multiple myeloma, and neuroblastoma. In some embodiments, the cancer is a hematological cancer. In some embodiments, the cancer is acute myeloid leukemia, acute lymphoid leukemia, chronic myeloid leukemia, chronic lymphoid leukemia, multiple myeloma, diffuse large B-cell lymphoma, or non-Hodgkin's lymphoma.

In some embodiments, the stem cell disorder is a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

In some embodiments, the stem cell disorder is an autoimmune disorder, such as an autoimmune disorder selected from multiple sclerosis, human systemic lupus, rheumatoid arthritis, inflammatory bowel disease, treating psoriasis, Type 1 diabetes mellitus, acute disseminated encephalomyelitis, Addison's disease, alopecia universalis, ankylosing spondylitis, antiphospholipid antibody syndrome, aplastic anemia, autoimmune hemolytic anemia, autoimmune hepatitis, autoimmune inner ear disease, autoimmune lymphoproliferative syndrome, autoimmune oophoritis, Balo disease, Behcet's disease, bullous pemphigoid, cardiomyopathy, Chagas' disease, chronic fatigue immune dysfunction syndrome, chronic inflammatory demyelinating polyneuropathy, Crohn's disease, cicatricial pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome, Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease, myasthenia gravis, neuromyotonia, opsoclonus myoclonus syndrome, optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis, ulcerative colitis, uveitis, vasculitis, vitiligo, vulvodynia, and Wegener's granulomatosis.

In some embodiments, the hematopoietic stem cells are autologous with respect to the patient. In some embodiments, the hematopoietic stem cells are allogeneic with respect to the patient, and may be, for example, HLA-matched with respect to the patient.

In some embodiments, the hematopoietic stem cells have been genetically modified to disrupt an endogenous gene, such as a gene encoding a major histocompatibility complex protein. The hematopoietic stem cells may be genetically modified to disrupt an endogenous by way of, for example, a CRISPR-associated protein, such as caspase 9, or another nuclease described herein, such as a transcription activator-like effector nuclease, a meganuclease, or a zinc finger nuclease.

In some embodiments, the hematopoietic stem cells, or progeny thereof, maintain hematopoietic stem cell functional potential after two or more days following infusion of the hematopoietic stem cells, or progeny thereof, into the patient. In some embodiments, the hematopoietic stem cells, or progeny thereof, localize to hematopoietic tissue and/or reestablish hematopoiesis following infusion of the hematopoietic stem cells, or progeny thereof, into the patient. In some embodiments, upon infusion into the patient, the hematopoietic stem cells, or progeny thereof, give rise to recovery of a population of cells selected from the group consisting of megakaryocytes, thrombocytes, platelets, erythrocytes, mast cells, myeoblasts, basophils, neutrophils, eosinophils, microglia, granulocytes, monocytes, osteoclasts, antigen-presenting cells.

In another aspect, the disclosure relates to a method of mobilizing CD34$^{dim}$ cells from the bone marrow of a human donor into peripheral blood, the method comprising administering to the donor (i) a CXCR2 agonist selected from the group consisting of Gro-β, Gro-β T, and variants thereof at a dose of from about 50 μg/kg to about 1,000 μg/kg and (ii) a CXCR4 antagonist.

In another aspect, the disclosure relates to a method of performing an allogeneic hematopoietic stem cell transplant in a patient in need thereof, the method comprising infusing into the patient a therapeutically effective amount of allogeneic hematopoietic stem cells, wherein the hematopoietic stem cells were mobilized from bone marrow of a human donor into peripheral blood of the human donor by a method comprising administering to the donor (i) a CXCR2 agonist selected from the group consisting of Gro-β, Gro-β T, and variants thereof at a dose of from about 50 µg/kg to about 1,000 µg/kg and (ii) a CXCR4 antagonist.

In another aspect, the disclosure relates to a method of preventing, reducing the risk of developing, or reducing the severity of a post-transplant infection in a patient in need thereof, the method comprising infusing into the patient a therapeutically effective amount of hematopoietic stem cells, wherein the hematopoietic stem cells were mobilized from bone marrow of a human donor into peripheral blood of the human donor by a method comprising administering to the human donor (i) a CXCR2 agonist selected from the group consisting of Gro-β, Gro-β T, and variants thereof at a dose of from about 50 µg/kg to about 1,000 µg/kg and (ii) a CXCR4 antagonist.

In another aspect, the disclosure relates to a method of preventing, reducing the risk of developing, or reducing the severity of graft versus host disease (GVHD) in a patient in need thereof, the method comprising infusing into the patient a therapeutically effective amount of hematopoietic stem cells, wherein the hematopoietic stem cells were mobilized from bone marrow of a human donor into peripheral blood of the human donor by a method comprising administering to the human donor (i) a CXCR2 agonist selected from the group consisting of Gro-β, Gro-β T, and variants thereof at a dose of from about 50 µg/kg to about 1,000 µg/kg and (ii) a CXCR4 antagonist.

In certain embodiments, the $CD34^{dim}$ cells are present in a higher amount in the peripheral blood than if the hematopoietic stem cells were mobilized using the CXCR4 antagonist alone. In certain embodiments, the $CD34^{dim}$ cells are capable of suppressing alloreactive T lymphocyte proliferation when administered to a recipient.

In certain embodiments, the CXCR2 agonist is Gro-β T. In certain embodiments, the CXCR2 agonist is administered to the donor at a dose of from about 100 µg/kg to about 250 µg/kg. In certain embodiments, the CXCR2 agonist is administered to the donor at a dose of from about 125 µg/kg to about 225 µg/kg. In certain embodiments, the CXCR2 agonist is administered to the donor at a dose of about 150 µg/kg. In certain embodiments, the CXCR2 agonist is administered intravenously to the donor.

In certain embodiments, the CXCR4 antagonist is administered subcutaneously to the donor. In certain embodiments, the CXCR4 antagonist is plerixafor or a pharmaceutically acceptable salt thereof. In certain embodiments, the plerixafor or pharmaceutically acceptable salt thereof is administered to the donor at a dose of from about 50 µg/kg to about 500 µg/kg. In certain embodiments, the plerixafor or pharmaceutically acceptable salt thereof is administered to the donor at a dose of from about 200 µg/kg to about 300 µg/kg. In certain embodiments, the plerixafor or pharmaceutically acceptable salt thereof is administered to the donor at a dose of about 240 µg/kg.

In certain embodiments, the method further includes testing a sample of peripheral blood for the presence of $CD34^{dim}$ cells and releasing the sample for ex vivo expansion of the $CD34^{dim}$ cells.

In certain embodiments, the disclosure relates to the population of $CD34^{dim}$ cells derived from any of the above methods, or a composition comprising the same.

BRIEF DESCRIPTION OF THE FIGURES

FIG. 3B shows a series of graphs demonstrating the mobilization response of leukocytes (white blood cells, "WBCs") to various dosages of Gro-β T upon subcutaneous administration to Rhesus monkeys. Leukocyte response is shown both in terms of the quantity of cells mobilized (top) and the fold change in leukocyte density relative to baseline leukocyte density prior to administration (bottom). In all experiments, Gro-β T was administered to subjects concurrently with plerixafor.

FIG. 4B shows a series of graphs demonstrating the mobilization response of neutrophils to various dosages of Gro-β T upon subcutaneous administration to Rhesus monkeys. Neutrophil response is shown both in terms of the quantity of cells mobilized (top) and the fold change in neutrophil density relative to baseline neutrophil density prior to administration (bottom). In all experiments, Gro-β T was administered to subjects concurrently with plerixafor.

FIG. 5A shows a series of graphs demonstrating the mobilization response of lymphocytes to various dosages of Gro-β T upon intravenous administration to Rhesus monkeys. Lymphocyte response is shown both in terms of the quantity of cells mobilized (top) and the fold change in lymphocyte density relative to baseline lymphocyte density prior to administration (bottom). FIG. 5B shows a series of graphs demonstrating the mobilization response of lymphocytes to various dosages of Gro-β T upon subcutaneous administration to Rhesus monkeys. Lymphocyte response is shown both in terms of the quantity of cells mobilized (top) and the fold change in lymphocyte density relative to baseline lymphocyte density prior to administration (bottom). In all experiments, Gro-β T was administered to subjects concurrently with plerixafor.

FIG. 6A shows a series of graphs demonstrating the mobilization response of monocytes to various dosages of Gro-β T upon intravenous administration to Rhesus monkeys. Monocyte response is shown both in terms of the quantity of cells mobilized (top) and the fold change in monocyte density relative to baseline monocyte density prior to administration (bottom). FIG. 6B shows a series of graphs demonstrating the mobilization response of monocytes to various dosages of Gro-β T upon subcutaneous administration to Rhesus monkeys. Monocyte response is shown both in terms of the quantity of cells mobilized (top) and the fold change in monocyte density relative to baseline monocyte density prior to administration (bottom). In all experiments, Gro-β T was administered to subjects concurrently with plerixafor.

FIG. 7A shows a series of graphs demonstrating the mobilization response of $CD34^+$ cells to various dosages of Gro-β T upon intravenous administration to Rhesus monkeys. $CD34^+$ cell response is shown both in terms of the frequency of $CD34^+$ cells in the sample obtained from peripheral blood of the subjects (top) and the fold change in $CD34^+$ cell frequency relative to baseline $CD34^+$ cell frequency prior to administration (bottom).

FIG. 8A shows a series of graphs demonstrating the mobilization response of $CD34^+$ cells to various dosages of Gro-β T upon intravenous administration to Rhesus monkeys. $CD34^+$ cell response is shown both in terms of the quantity of cells mobilized (top) and the fold change in $CD34^+$ cell density relative to baseline $CD34^+$ cell density prior to administration (bottom). FIG. 8B shows a series of graphs demonstrating the mobilization response of $CD34^+$ cells to various dosages of Gro-β T upon subcutaneous administration to Rhesus monkeys. $CD34^+$ cell response is shown both in terms of the quantity of cells mobilized (top) and the fold change in $CD34^+$ cell density relative to baseline $CD34^+$ cell density prior to administration (bottom). In all experiments, Gro-β T was administered to subjects concurrently with plerixafor.

FIG. 9A shows a series of graphs demonstrating the mobilization response of hematopoietic stem cells ($CD34^+$ $CD90^+$ $CD45RA^-$ cells) to various dosages of Gro-β T upon intravenous administration to Rhesus monkeys. $CD34^+$ $CD90^+$ $CD45RA^-$ cell response is shown both in terms of the frequency of $CD34^+$ $CD90^+$ $CD45RA^-$ cells in the sample obtained from peripheral blood of the subjects (top) and the fold change in $CD34^+$ $CD90^+$ $CD45RA^-$ cell frequency relative to baseline $CD34^+$ $CD90^+$ $CD45RA^-$ cell frequency prior to administration (bottom).

FIG. 11 shows a series of graphs demonstrating the increase in the quantity of colony-forming units (CFU) of hematopoietic stem cells achieved by the intravenous administration of various dosages of Gro-β T to Rhesus monkeys. CFR response is shown both in terms of the concentration of CFUs (top) and the fold change in CFU concentration relative to baseline CFU concentration prior to administration (bottom). In all experiments, Gro-β T was administered to subjects concurrently with plerixafor.

FIG. 13A shows a series of graphs demonstrating the response of plasma tissue inhibitor of matrix metalloproteinase 1 (TIMP-1) to various dosages of Gro-β T upon intravenous administration to Rhesus monkeys. Plasma TIMP-1 response is shown both in terms of absolute concentration (top) and the fold change in plasma TIMP-1 concentration relative to baseline TIMP-1 concentration prior to administration (bottom).

DETAILED DESCRIPTION

Figure 1A:
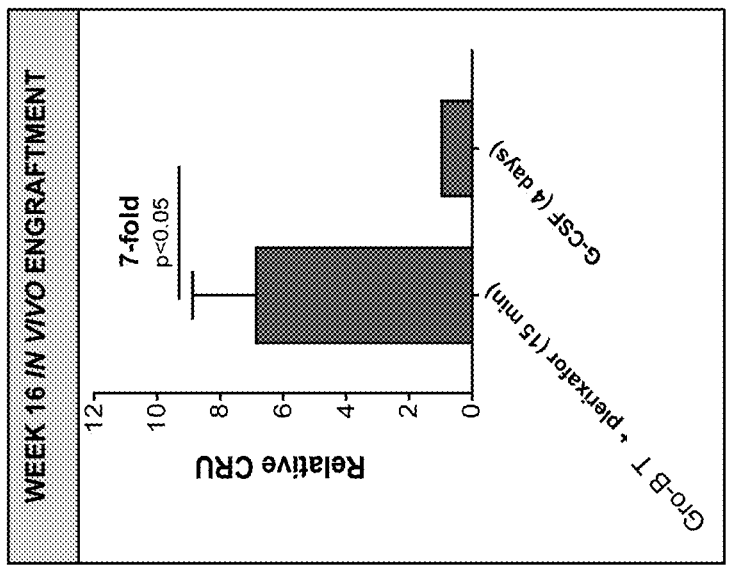
FIG. 1A provides a graph showing that, when Gro-β T is co-administered with plerixafor (AMD3100) in mice, a synergistic increase in mobilization results, and grafts are enriched in highly engraftable, long-term hematopoietic stem cells (LT-HSC=Lin-c-kit$^+$ Sca-1$^+$ CD150$^+$ CD48$^+$).

The present invention provides compositions and methods for mobilizing hematopoietic stem and progenitor cells in a subject. For example, the subject may be a hematopoietic stem and progenitor cell donor (i.e., a donor), such as a mammalian donor (e.g., a human donor). The compositions and methods described herein can additionally be used for the treatment of one or more stem cell disorders in a patient, such as a human patient. Using the compositions and methods described herein, a C-X-C chemokine receptor type 2 (CXCR2) agonist, such as Gro-β or a variant thereof, such as a truncated form of Gro-β (e.g., Gro-β T), as described herein, optionally in combination with a C-X-C chemokine receptor type 4 (CXCR4) antagonist, such as 1,1'-[1,4-phenylenebis(methylene)]-bis-1,4,8,11-tetra-azacyclotetradecane or a variant thereof, may be administered to a donor, as described herein, in amounts sufficient to mobilize hematopoietic stem and progenitor cells. The compositions and methods described herein are capable of mobilizing hematopoietic stem and progenitor cells from a stem cell niche within a donor into circulating peripheral blood while reducing the mobilization of other cells of the hematopoietic lineage, such as leukocytes, neutrophils, lymphocytes, and monocytes. The compositions and methods described herein thus enable the selective mobilization of hematopoietic stem and progenitor cells in a donor, which may then be isolated from a donor for therapeutic use.

The invention is based, in part, on the discovery that administration of a CXCR2 agonist, such as Gro-β, Gro-β T, or a variant thereof, optionally in combination with a CXCR4 antagonist, such as plerixafor or a pharmaceutically acceptable salt thereof, at particular doses can provide the important clinical benefit of mobilizing populations of cells that are enriched in hematopoietic stem cells relative to other cell types, such as leukocytes, neutrophils, and monocytes. This ability is advantageous, as these other cell types may be undesirable for administration to a human patient undergoing hematopoietic stem cell transplant therapy. Thus, the populations of mobilized hematopoietic stem and progenitor cells produced using the compositions and methods described herein are particularly suitable for hematopoietic stem cell transplantation therapy.

Following mobilization, the hematopoietic stem or progenitor cells may be isolated for ex vivo expansion and/or for therapeutic use. In some embodiments, upon collection of the mobilized hematopoietic stem and/or progenitor cells, the withdrawn cells may be infused into a patient, such as the donor or another subject (e.g., a subject that is HLA-matched to the donor) for the treatment of one or more pathologies of the hematopoietic system. Additionally or alternatively, the mobilized cells may be withdrawn and then expanded ex vivo, such as by contacting the cells with an aryl hydrocarbon receptor antagonist, so as to produce a population of hematopoietic stem cells having a sufficient quantity of cells for transplantation.

As described herein, hematopoietic stem cells are capable of differentiating into a multitude of cell types in the hematopoietic lineage, and can thus be administered to a patient in order to populate or repopulate a cell type that is defective or deficient in the patient. The patient may be one, for example, that is suffering from one or more blood disorders, such as an autoimmune disease, cancer, hemoglobinopathy, or other hematopoietic pathology, and is therefore in need of hematopoietic stem cell transplantation. The invention thus provides methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, as well as cancers and autoimmune diseases, among others.

The sections that follow provide a description of CXCR4 antagonists and CXCR2 agonists that can be administered to a donor so as to induce mobilization of a population of hematopoietic stem or progenitor cells from a stem cell niche into peripheral blood, from which the cells may subsequently be isolated and infused into a patient for the treatment, for example, of one or more stem cell disorders, such as a cancer, autoimmune disease, of metabolic disorder described herein. The following sections additionally describe methods of determining whether populations of cells mobilized with a CXCR2 agonist and/or a CXCR antagonist are suitable for release for ex vivo expansion and/or for therapeutic applications.

Definitions

As used herein, the term "about" refers to a value that is within 10% above or below the value being described. For example, the term "about 5 nM" indicates a range of from 4.5 nM to 5.5 nM.

As used herein, the terms "acquire" and "acquiring" means obtaining possession of a physical entity, or a value, such as a numerical value, directly acquiring or indirectly acquiring the physical entity or value. "Directly acquiring" means performing a process (e.g., performing an assay or test on a sample or analyzing a sample) to obtain the physical entity or value. "Indirectly acquiring" refers to receiving the physical entity or value from another party or source (e.g., a third party laboratory that directly acquired the physical entity or value). Directly acquiring a physical entity includes performing a process, e.g., analyzing a sample, such as a sample of hematopoietic cells isolated from a donor that has undergone or is undergoing a hematopoietic stem cell mobilization regimen described herein. Directly acquiring a value includes performing a process, such as an assay, on a sample or another substance, e.g., performing an analytical process which includes determining the quantity of hematopoietic stem cells in a sample, the ratio of hematopoietic stem cells to cells of another type within the hematopoietic lineage, or the frequency of hematopoietic stem cells among the total quantity of cells in a sample.

As used herein, the term "affinity" refers to the strength of the non-covalent interaction between two or more molecules, such as two or more proteins (e.g., a metalloproteinase and an endogenous inhibitor thereof as described herein). Affinity can be expressed quantitatively, for example, as an equilibrium dissociation constant ($K_d$) or, in cases in which one of the binding partners is an enzyme, as an inhibition constant ($K_i$). Binding affinity can be determined using standard techniques, such as enzyme-linked immunosorbent assays (ELISA), surface plasmon resonance assays, and isothermal titration calorimetry assays, among others.

As used herein, the term "antibody" refers to an immunoglobulin molecule that specifically binds to, or is immunologically reactive with, a particular antigen, and includes polyclonal, monoclonal, genetically engineered, and otherwise modified forms of antibodies, including but not limited to chimeric antibodies, humanized antibodies, heteroconjugate antibodies (e.g., bi- tri- and quad-specific antibodies, diabodies, triabodies, and tetrabodies), and antigen binding fragments of antibodies, including, for example, Fab', $F(ab')_2$, Fab, Fv, rlgG, and scFv fragments. Unless otherwise indicated, the term "monoclonal antibody" (mAb) is meant to include both intact molecules, as well as antibody fragments (including, for example, Fab and $F(ab')_2$ fragments) that are capable of specifically binding to a target protein. As used herein, the Fab and $F(ab')_2$ fragments refer to antibody fragments that lack the Fc fragment of an intact antibody. Examples of these antibody fragments are described herein.

The term "antigen-binding fragment," as used herein, refers to one or more fragments of an antibody that retain the ability to specifically bind to a target antigen. The antigen-binding function of an antibody can be performed by fragments of a full-length antibody.

The antibody fragments can be, for example, a Fab, $F(ab')_2$, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a $F(ab')_2$ fragment, a bivalent fragment containing two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment that consists of a $V_H$ domain (see, e.g., Ward et al. (1989) *Nature* 341:544-546); (vii) a dAb which consists of a $V_H$ or a $V_L$ domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv); see, for example, Bird et al. (1988) *Science* 242:423-426 and Huston et al. (1988) *Proc. Natl. Acad. Sci. USA* 85:5879-5883). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "bispecific antibody" refers to, for example, a monoclonal, often a human or humanized antibody that is capable of binding at least two different antigens.

As used herein the term "$CD34^{dim}$ cells" refers to a population of cells, of which at least a portion of the population expresses the markers CD34, CD11b, and CD45 and does not substantially express the markers CD3, CD8, or CD20, wherein CD34 and CD45 are expressed at a relatively low level. This cell population exhibits characteristics of monocytes, for example, the ability to suppress alloreactive T lymphocyte proliferation. (D'Aveni et al. (2015) *Science Translational Medicine* 7(281):1-12. In some embodiments, a population of $CD34^{dim}$ cells may be CD14+.

The person of skill can readily recognize a $CD34^{dim}$ cell population when viewing a flow cytometry plot as a population of cells that is $CD34^+$ but has a brightness between the base level of fluorescence (e.g., autofluorescence) in the cell population being examined and the brightness of a CD34+ bright cell (e.g., a hematopoietic stem cell and/or a CD34+ CD90+ cell) population. For example, in certain embodiments, a CD34$^{dim}$ cell population exhibits between 5% and 95% of the brightness of a CD34+ bright cell (e.g., a hematopoietic stem cell) population, but is brighter than a CD34− cell population.

In certain embodiments, CD34$^{dim}$ cells exhibit between 10% and 90%, 10% and 80%, 10% and 70%, 10% and 60%, 10% and 50%, 10% and 40%, 10% and 30%, 10% and 20%, 20% and 90%, 20% and 80%, 20% and 70%, 20% and 60%, 20% and 50%, 20% and 40%, 20% and 30%, 30% and 90%, 30% and 80%, 30% and 70%, 30% and 60%, 30% and 50%, 30% and 40%, 40% and 90%, 40% and 80%, 40% and 70%, 40% and 60%, 40% and 50%, 50% and 90%, 50% and 80%, 50% and 70%, 50% and 60%, 60% and 90%, 60% and 80%, 60% and 70%, 70% and 90%, 70% and 80%, or 80% and 90%, of the brightness of CD34+ bright cells (e.g., hematopoietic stem cells), but is brighter than CD34− cells. In certain embodiments, the CD34$^{dim}$ cells are at least 5% brighter, at least 10% brighter, at least 20% brighter or at least 30% brighter than CD34− cells, but is less bright than CD34+ bright cells (e.g., a hematopoietic stem cell).

In certain embodiments, CD34$^{dim}$ cells are identified in a cell sample by using flow cytometry with magnetic beads instead of fluorescence. The magnetic beads will selectively pull down CD34+ bright cells, leaving CD34$^{dim}$ cells in the cell sample.

In certain embodiments, CD34$^{dim}$ cells are identified by measuring the number of copies of CD34 expressed by the cells. For example, CD34$^{dim}$ cells can exhibit between 5% and 95% of the number of copies of CD34 as compared to CD34+ bright cells (e.g., hematopoietic stem cells), or between 10% and 90%, 10% and 80%, 10% and 70%, 10% and 60%, 10% and 50%, 10% and 40%, 10% and 30%, 10% and 20%, 20% and 90%, 20% and 80%, 20% and 70%, 20% and 60%, 20% and 50%, 20% and 40%, 20% and 30%, 30% and 90%, 30% and 80%, 30% and 70%, 30% and 60%, 30% and 50%, 30% and 40%, 40% and 90%, 40% and 80%, 40% and 70%, 40% and 60%, 40% and 50%, 50% and 90%, 50% and 80%, 50% and 70%, 50% and 60%, 60% and 90%, 60% and 80%, 60% and 70%, 70% and 90%, 70% and 80%, or 80% and 90% of the number of copies of CD34 as compared to CD34+ bright cells (e.g., hematopoietic stem cells).

As used herein, the term "complementarity determining region" (CDR) refers to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each contain four framework regions that primarily adopt a n-sheet configuration, connected by three CDRs, which form loops that connect, and in some cases form part of, the β-sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (see Kabat et al., Sequences of Proteins of Immunological Interest, National Institute of Health, Bethesda, Md., 1987). As used herein, numbering of immunoglobulin amino acid residues is performed according to the immunoglobulin amino acid residue numbering system of Kabat et al., unless otherwise indicated.

As used herein in the context of the administration of one or more agents to a subject, the term "completion of administration" refers to the point in time by which the one or more agents have been administered to the subject in their entirety. In some embodiments, an agent as described herein, such as a CXCR4 antagonist (e.g., plerixafor or a variant thereof) and/or a CXCR2 agonist (e.g., Gro-β or a variant or truncation thereof, such as Gro-β T) can be administered to a subject over a period of time, for example, by intravenous or subcutaneous injection. An agent is considered to have "completed administration" once the prescribed dosage of the agent has been administered to the subject in its entirety. In the case of the administration of multiple agents to a subject, such as both a CXCR4 antagonist (e.g., plerixafor or a variant thereof) and a CXCR2 agonist (e.g., Gro-β or a variant or truncation thereof, such as Gro-β T), the agents are considered to have "completed administration" once the prescribed dosages of all agents in a particular regimen have been administered to the subject in their entirety.

As used herein, the terms "conservative mutation," "conservative substitution," or "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in TABLE 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume† |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |

TABLE 1-continued

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

[†]based on volume in A3: 50-100 is small, 100-500 is intermediate, 150-200 is large and >200 is bulky From this table it is appreciated that the conservative amino acid families include, e.g., (i) G, A, V, L, I, P, and M; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, "CRU (competitive repopulating unit)" refers to a unit of measure of long-term engrafting stem cells, which can be detected after in-vivo transplantation.

As used herein, the term "donor" refers to a subject, such as a mammalian subject (e.g., a human subject) from which one or more cells are isolated prior to administration of the cells, or progeny thereof, into a recipient. The one or more cells may be, for example, a population of hematopoietic stem or progenitor cells.

As used herein, the term "diabody" refers to a bivalent antibody containing two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabody" refers to trivalent antibodies containing three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structures, peptides configured in this way typically trimerize so as to position the $V_H$ and $V_L$ domains of neighboring peptide chains spatially proximal to one another (see, for example, Holliger et al. (1993) Proc. Natl. Acad. Sci. USA 90:6444-48).

As used herein, the term "disrupt" with respect to a gene refers to preventing the formation of a functional gene product. A gene product is functional only if it fulfills its normal (wild-type) functions. Disruption of the gene prevents expression of a functional factor encoded by the gene and comprises an insertion, deletion, or substitution of one or more bases in a sequence encoded by the gene and/or a promoter and/or an operator that is necessary for expression of the gene in the animal. The disrupted gene may be disrupted by, e.g., removal of at least a portion of the gene from a genome of the animal, alteration of the gene to prevent expression of a functional factor encoded by the gene, an interfering RNA, or expression of a dominant negative factor by an exogenous gene. Materials and methods of genetically modifying hematopoietic stem/progenitor cells are detailed in U.S. Pat. No. 8,518,701; US 2010/0251395; and US 2012/0222143, the disclosures of each of which are incorporated herein by reference in their entirety (in case of conflict, the instant specification is controlling).

Various techniques known in the art can be used to inactivate genes to make knockout animals and/or to introduce nucleic acid constructs into animals to produce founder animals and to make animal lines, in which the knockout or nucleic acid construct is integrated into the genome. Such techniques include, without limitation, pronuclear microinjection (U.S. Pat. No. 4,873,191), retrovirus mediated gene transfer into germ lines (Van der Putten et al. (1985) Proc. Natl. Acad. Sci. USA, 82:6148-6152), gene targeting into embryonic stem cells (Thompson et al. (1989) Cell, 56:313-321), electroporation of embryos (Lo (1983) Mol. Cell. Biol., 3:1803-1814), sperm-mediated gene transfer (Lavitrano et al. (2002) Proc. Natl. Acad. Sci. USA, 99:14230-14235; Lavitrano et al. (2006) Reprod. Fert. Develop., 18:19-23), and in vitro transformation of somatic cells, such as cumulus or mammary cells, or adult, fetal, or embryonic stem cells, followed by nuclear transplantation (Wilmut et al. (1997) Nature, 385:810-813; and Wakayama et al. (1998) Nature, 394:369-374). Pronuclear microinjection, sperm mediated gene transfer, and somatic cell nuclear transfer are particularly useful techniques. An animal that is genomically modified is an animal wherein all of its cells have the genetic modification, including its germ line cells. When methods are used that produce an animal that is mosaic in its genetic modification, the animals may be inbred and progeny that are genomically modified may be selected. Cloning, for example, may be used to make a mosaic animal if its cells are modified at the blastocyst state, or genomic modification can take place when a single-cell is modified. Animals that are modified so they do not sexually mature can be homozygous or heterozygous for the modification, depending on the specific approach that is used. If a particular gene is inactivated by a knock out modification, homozygosity would normally be required. If a particular gene is inactivated by an RNA interference or dominant negative strategy, then heterozygosity is often adequate.

As used herein, a "dual variable domain immunoglobulin" ("DVD-Ig") refers to an antibody that combines the target-binding variable domains of two monoclonal antibodies via linkers to create a tetravalent, dual-targeting single agent (see, for example, Gu et al. (2012) Meth. Enzymol., 502:25-41).

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is found naturally in a particular organism, such as a human patient.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "exogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is not found naturally in a particular organism, such as a human patient. Exogenous substances include those that are provided from an external source to an organism or to cultured matter extracted therefrom.

As used herein, the term "framework region" or "FW region" includes amino acid residues that are adjacent to the CDRs of an antibody or antigen-binding fragment thereof. FW region residues may be present in, for example, human antibodies, humanized antibodies, monoclonal antibodies, antibody fragments, Fab fragments, single chain antibody fragments, scFv fragments, antibody domains, and bispecific antibodies, among others.

As used herein, the term "hematopoietic progenitor cells" includes pluripotent cells capable of differentiating into several cell types of the hematopoietic system, including, without limitation, granulocytes, monocytes, erythrocytes, megakaryocytes, B-cells and T-cells, among others. Hematopoietic progenitor cells are committed to the hematopoietic cell lineage and generally do not self-renew. Hematopoietic progenitor cells can be identified, for example, by expression patterns of cell surface antigens, and include cells having the following immunophenotype: $Lin^-$ $KLS^+$ $Flk2^-$ $CD34^+$. Hematopoietic progenitor cells include short-term hematopoietic stem cells, multi-potent progenitor cells, common myeloid progenitor cells, granulocyte-monocyte progenitor cells, and megakaryocyte-erythrocyte progenitor cells. The presence of hematopoietic progenitor cells can be determined functionally, for example, by detecting colony-forming unit cells, e.g., in complete methylcellulose assays, or phenotypically through the detection of cell surface markers using flow cytometry and cell sorting assays described herein and known in the art.

As used herein, the term "hematopoietic stem cells" ("HSCs") refers to immature blood cells having the capacity to self-renew and to differentiate into mature blood cells containing diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Such cells may include $CD34^+$ cells. $CD34^+$ cells are immature cells that express the CD34 cell surface marker. In humans, $CD34^+$ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are $CD34^+$, $CD38^-$, $CD45RA^-$, $CD90^+$, $CD49F^+$, and $lin^-$ (negative for mature lineage markers including CD2, CD3, CD4, CD7, CD8, CD10, CD11B, CD19, CD20, CD56, CD235A). In mice, bone marrow LT-HSCs are CD34-, SCA-1+, C-kit+, CD135−, Slamf1/CD150+, CD48−, and lin− (negative for mature lineage markers including Ter119, CD11b, Gr1, CD3, CD4, CD8, B220, IL7ra), whereas ST-HSCs are $CD34^+$, $SCA-1^+$, $C-kit^+$, $CD135^-$, $Slamf1/CD150^+$, and $lin^-$ (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self-renewal potential (i.e., they survive throughout adulthood, and can be serially transplanted through successive recipients), whereas ST-HSCs have limited self-renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the terms "Major histocompatibility complex antigens" ("MHC", also referred to as "human leukocyte antigens" ("HLA") in the context of humans) refer to proteins expressed on the cell surface that confer a unique antigenic identity to a cell. MHC/HLA antigens are target molecules that are recognized by T cells and NK cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells. Both have been implicated in the rejection of transplanted organs. An important aspect of the HLA gene system is its polymorphism. Each gene, MHC class I (A, B and C) and MEC class II (DP, DQ and DR) exists in different alleles. For example, two unrelated individuals may carry class I HLA-B, genes B5, and Bw41, respectively. Allelic gene products differ in one or more amino acids in the α and/or β domain(s). Large panels of specific antibodies or nucleic acid reagents are used to type HLA haplotypes of individuals, using leukocytes that express class I and class II molecules. The genes commonly used for HLA typing are the six MHC Class I and Class II proteins, two alleles for each of HLA-A; HLA-B and HLA-DR. The HLA genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

As used herein, the term "HLA-matched" refers to a donor-recipient pair in which none of the HLA antigens are mismatched between the donor and recipient, such as a donor providing a hematopoietic stem cell graft to a recipient in need of hematopoietic stem cell transplant therapy. HLA-matched (i.e., where all of the 6 alleles are matched) donor-recipient pairs have a decreased risk of graft rejection, as endogenous T cells and NK cells are less likely to recognize the incoming graft as foreign, and are thus less likely to mount an immune response against the transplant.

As used herein, the term "HLA-mismatched" refers to a donor-recipient pair in which at least one HLA antigen, in particular with respect to HLA-A, HLA-B and HLA-DR, is mismatched between the donor and recipient, such as a donor providing a hematopoietic stem cell graft to a recipient in need of hematopoietic stem cell transplant therapy. In some embodiments, one haplotype is matched and the other is mismatched. HLA-mismatched donor-recipient pairs may have an increased risk of graft rejection relative to HLA-matched donor-recipient pairs, as endogenous T cells and NK cells are more likely to recognize the incoming graft as foreign in the case of an HLA-mismatched donor-recipient pair, and such T cells and NK cells are thus more likely to mount an immune response against the transplant.

As used herein, the term "human antibody" refers to an antibody in which substantially every part of the protein (for example, all CDRs, framework regions, $C_L$, $C_H$ domains (e.g., $C_H1$, $C_H2$, $C_H3$), hinge, and $V_L$ and $V_H$ domains) is substantially non-immunogenic in humans, with only minor sequence changes or variations. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625,126; 5,633,425; 5,569,825; 5,661,016; 5,545,896; 5,814,318; 5,885,793; 5,916,771; and 5,939,598).

As used herein, the term "humanized" antibody refers to a non-human antibody that contains minimal sequences derived from non-human immunoglobulin. In general, a humanized antibody contains substantially all of at least one, and typically two, variable domains, in which all or substantially all of the CDR regions correspond to those of a non-human immunoglobulin. All or substantially all of the FW regions may also be those of a human immunoglobulin sequence. The humanized antibody can also contain at least a portion of an immunoglobulin constant region (Fc), typically that of a human immunoglobulin consensus sequence. Methods of antibody humanization are known in the art and have been described, for example, in Riechmann et al. (1988) *Nature* 332:323-7; U.S. Pat. Nos. 5,530,101; 5,585,089; 5,693,761; 5,693,762; and 6,180,370.

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis.

Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a hemoglobinopathy (e.g., a non-malignant hemoglobinopathy), such as sickle cell anemia, thalassemia, Fanconi anemia, aplastic anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as neuroblastoma or a hematologic cancer. In some embodiments, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the subject has myelodysplastic syndrome. In some embodiments, the subject has an autoimmune disease, such as scleroderma, multiple sclerosis, ulcerative colitis, Crohn's disease, Type 1 diabetes, or another autoimmune pathology described herein. In some embodiments, the subject is in need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for example, by way of flow cytometry and fluorescence activated cell sorting (FACS) methods, among other procedures, known in the art.

As used herein, the term "leukocyte" refers to a heterogeneous group of nucleated blood cell types, and excludes erythrocytes and platelets. Leukocytes can be divided into two general groups: polymorphonucleocytes, which include neutrophils, eosinophils, and basophils, and mononucleocytes, which include lymphocytes and monocytes. Polymorphonucleocytes contain many cytoplasmic granules and a multilobed nucleus and include the following: neutrophils, which are generally amoeboid in shape, phagocytic, and stain with both basic and acidic dyes, and eosinophils and basophils, which contain cytoplasmic granules that stain with acidic dyes and with basic dyes, respectively.

As used herein, the term "lymphocyte" refers to a mononuclear leukocyte that is involved in the mounting of an immune response. In general, lymphocytes include B lymphocytes, T lymphocytes, and NK cells.

As used herein, the terms "mobilize" and "mobilization" refer to processes by which a population of hematopoietic stem or progenitor cells is released from a stem cell niche, such as the bone marrow of a subject, into circulation in the peripheral blood. Mobilization of hematopoietic stem and progenitor cells can be monitored, for example, by assessing the quantity or concentration of hematopoietic stem or progenitor cells in a peripheral blood sample isolated from a subject. For example, the peripheral blood sample may be withdrawn from the subject, and the quantity or concentration of hematopoietic stem or progenitor cells in the peripheral blood sample may subsequently be assessed, following the administration of a hematopoietic stem or progenitor cell mobilization regimen to the subject. The mobilization regimen may include, for example, a CXCR4 antagonist, such as a CXCR4 antagonist described herein (e.g., plerixafor or a variant thereof), and a CXCR2 agonist, such as a CXCR2 agonist described herein (e.g., Gro-β or a variant thereof, such as a truncation of Gro-β, for example, Gro-β T). The quantity or concentration of hematopoietic stem or progenitor cells in the peripheral blood sample isolated from the subject following administration of the mobilization regimen may be compared to the quantity or concentration of hematopoietic stem or progenitor cells in a peripheral blood sample isolated from the subject prior to administration of the mobilization regimen. An observation that the quantity or concentration of hematopoietic stem or progenitor cells has increased in the peripheral blood of the subject following administration of the mobilization regimen is an indication that the subject is responding to the mobilization regimen, and that hematopoietic stem and progenitor cells have been released from one or more stem cell niches, such as the bone marrow, into peripheral blood circulation. In some embodiments, an observation that the quantity or concentration of hematopoietic stem or progenitor cells has increased in the peripheral blood of the subject by 1%, 100%, 1,000%, or more (e.g., by 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1,000%, or more) following administration of the mobilization regimen is an indication that the subject is responding to the mobilization regimen, and that hematopoietic stem and progenitor cells have been released from one or more stem cell niches, such as the bone marrow, into peripheral blood circulation. Methods for determining the quantity or concentration of hematopoietic stem or progenitor cells are described herein and known in the art, and include, for example, flow cytometry techniques that quantify hematopoietic stem or progenitor cells on the basis of the antigen expression profile of such cells, which is described herein. For example, human HSCs are $CD34^+$, $CD38^-$, $CD45RA^-$, $CD90^+$, $CD49F^+$, and lin– (negative for mature lineage markers including CD2, CD3, CD4, CD7, CD8, CD10, CD11B, CD19, CD20, CD56, CD235A). Additional methods for determining the quantity or concentration of hematopoietic stem or progenitor cells in a peripheral blood sample isolated from a subject include assays that quantify the number of colony-forming units (CFUs) in the sample, which is a measure of the quantity of viable hematopoietic stem or progenitor cells that, upon incubation with an appropriate culture medium, give rise to an individual population of hematopoietic stem or progenitor cells.

As used herein, the term "mobilizing amount" refers to a quantity of one or more agents, such as a quantity of a CXCR4 antagonist and/or a CXCR2 agonist described herein (In some embodiments, a quantity of plerixafor, or a variant thereof, and/or Gro-β, or a variant thereof, such as a truncation of Gro-β, for example, Gro-β T) that mobilizes a population of hematopoietic stem or progenitor cells upon administration to a subject, such as a mammalian subject (e.g., a human subject). Exemplary mobilizing amounts of these agents include amounts sufficient to effectuate the release of a population of, for example, from about 20 to about 40 $CD34^+$ cells/μL of peripheral blood, such as from about 21 to about 39 $CD34^+$ cells/μL of peripheral blood, about 22 to about 38 $CD34^+$ cells/4 of peripheral blood, about 23 to about 37 $CD34^+$ cells/4 of peripheral blood, about 24 to about 36 $CD34^+$ cells/μL of peripheral blood, about 25 to about 35 $CD34^+$ cells/4 of peripheral blood, about 26 to about 34 $CD34^+$ cells/4 of peripheral blood, about 27 to about 33 $CD34^+$ cells/4 of peripheral blood, about 28 to about 32 $CD34^+$ cells/4 of peripheral blood, or about 29 to about 31 $CD34^+$ cells/4 of peripheral blood (e.g., about 20 $CD34^+$ cells/4 of peripheral blood, 21 $CD34^+$ cells/4 of peripheral blood, 22 $CD34^+$ cells/4 of peripheral blood, 23 $CD34^+$ cells/4 of peripheral blood, 24, $CD34^+$ cells/μL of peripheral blood, 25 $CD34^+$ cells/4 of peripheral blood, 26 $CD34^+$ cells/4 of peripheral blood, 27 $CD34^+$ cells/4 of peripheral blood, 28 $CD34^+$ cells/4 of peripheral blood, 29 $CD34^+$ cells/μL of peripheral blood, 30 $CD34^+$ cells/4 of peripheral blood, 31 $CD34^+$ cells/4 of peripheral blood, 32 $CD34^+$ cells/4 of peripheral blood 33 $CD34^+$ cells/4 of peripheral blood, 34 $CD34^+$ cells/4 of peripheral blood, 35 $CD34^+$ cells/4 of peripheral blood, 36 $CD34^+$ cells/4 of peripheral blood, 37 $CD34^+$ cells/4 of peripheral blood, 38 $CD34^+$ cells/4 of peripheral blood, 39 $CD34^+$ cells/4 of peripheral blood, 40 $CD34^+$ cells/μL of peripheral blood, or more. For instance, mobilizing amounts of a CXCR2 agonist, such as Gro-β T, include from about 50 μg/kg of recipient to about 1 mg/kg of recipient, such as from about 50 μg/kg to about 300 μg/kg, 100 μg/kg to about 250 μg/kg, or about 150 μg/kg. Mobilizing amounts of a CXCR4 antagonist, such as plerixafor or a pharmaceutically acceptable salt thereof, include from about 50 μg/kg of recipient to about 500 μg/kg of recipient, such as from about 200 μg/kg to about 300 μg/kg, or about 240 μg/kg.

As used herein, the term "monoclonal antibody" refers to an antibody that is derived from a single clone, including any eukaryotic, prokaryotic, or phage clone, and not the method by which it is produced.

As used herein, the term "monocyte" refers to a $CD14^+$ and CD34– peripheral blood mononuclear cell (PBMC), which is generally capable of differentiating into a macrophage and/or dendritic cell upon activation by one or more foreign substances, such as, a microbial product. In particular, a monocyte may express elevated levels of the CD14 surface antigen marker, and may express at least one biomarker selected from CD64, CD93, CD180, CD328 (also known as sialic acid-binding Ig-like lectin 7 or Siglec7), and CD329 (sialic acid-binding Ig-like lectin 9 or Siglec9), as well as the peanut agglutinin protein (PNA).

As used herein, a "peptide" refers to a single-chain polyamide containing a plurality of amino acid residues, such as naturally-occurring and/or non-natural amino acid residues, that are consecutively bound by amide bonds. Examples of peptides include shorter fragments of full-length proteins, such as full-length naturally-occurring proteins.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject. A sample may be, for example, withdrawn peripheral blood from a donor that is undergoing or has undergone a hematopoietic stem or progenitor cell mobilization regimen described herein.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain ($V_L$) (e.g., CDR-L1, CDR-L2, and/or CDR-L3) and the variable region of an antibody heavy chain ($V_H$) (e.g., CDR-H1, CDR-H2, and/or CDR-H3) separated by a linker. The linker that joins the $V_L$ and $V_H$ regions of a scFv fragment can be a peptide linker composed of proteinogenic amino acids. Alternative linkers can be used to so as to increase the resistance of the scFv fragment to proteolytic degradation (for example, linkers containing D-amino acids), in order to enhance the solubility of the scFv fragment (for example, hydrophilic linkers such as polyethylene glycol-containing linkers or polypeptides containing repeating glycine and serine residues), to improve the biophysical stability of the molecule (for example, a linker containing cysteine residues that form intramolecular or intermolecular disulfide bonds), or to attenuate the immunogenicity of the scFv fragment (for example, linkers containing glycosylation sites). It will also be understood by one of ordinary skill in the art that the variable regions of the scFv molecules described herein can be modified such that they vary in amino acid sequence from the antibody molecule from which they were derived. For example, nucleotide or amino acid substitutions leading to conservative substitutions or changes at amino acid residues can be made (e.g., in CDR and/or framework residues) so as to preserve or enhance the ability of the scFv to bind to the antigen recognized by the corresponding antibody.

As used herein, the phrase "stem cell disorder" broadly refers to any disease, disorder, or condition that may be treated or cured by engrafting or transplanting a population of hematopoietic stem or progenitor cells in a target tissue within a patient. For example, Type I diabetes has been shown to be cured by hematopoietic stem cell transplant, along with various other disorders. Exemplary diseases that can be treated by infusion of hematopoietic stem or progenitor cells into a patient are sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome. Additional diseases that may be treated by transplantation of hematopoietic stem and progenitor cells as described herein include blood disorders (e.g., sickle cell anemia) and autoimmune disorders, such as scleroderma, multiple sclerosis, ulcerative colitis, and Crohn's disease. Additional diseases that may be treated using hematopoietic stem and progenitor cell transplant therapy include cancer, such as a cancer described herein. Exemplary stem cell disorders are malignancies, such as a neuroblastoma or a hematologic cancers, such as leukemia, lymphoma, and myeloma. In some embodiments, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Additional diseases treatable using hematopoietic stem or progenitor cell transplant therapy include myelodysplastic syndrome. In some embodiments, the patient has or is otherwise affected by a metabolic storage disorder. For example, the patient may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem or progenitor cell transplant therapy.

As used herein in the context of hematopoietic stem cell mobilization, the term "stem cell niche" refers to a microenvironment within a donor, such as a mammalian donor (e.g., a human donor) in which endogenous hematopoietic stem or progenitor cells reside. An exemplary stem cell niche is bone marrow tissue.

As used herein, the terms "subject" and "patient" refer to an organism, such as a human, that receives treatment for a particular disease or condition as described herein. In some embodiments, a patient, such as a human patient, that is in need of hematopoietic stem cell transplantation may receive treatment that includes a population of hematopoietic stem cells so as to treat a stem cell disorder, such as a cancer, autoimmune disease, or metabolic disorder described herein. The hematopoietic stem cells that are transplanted into the patient may be, for example, a population of hematopoietic stem cells that has been mobilized and withdrawn from a donor in accordance with the compositions and methods described herein. In some embodiments, the hematopoietic stem cells that are transplanted into the patient may be mobilized within a donor by administration of a CXCR4 antagonist and/or a CXCR2 agonist to the donor.

As used herein, the term "transfection" refers to any of a wide variety of techniques commonly used for the introduction of exogenous DNA into a prokaryotic or eukaryotic host cell, such as electroporation, lipofection, calcium-phosphate precipitation, DEAE-dextran transfection and the like.

As used herein, the terms "treat" or "treatment" refer to therapeutic treatment, in which the object is to prevent or slow down (lessen) an undesired physiological change or disorder or to promote a beneficial phenotype in the patient being treated. Beneficial or desired clinical results include, but are not limited to, promoting the engraftment of exogenous hematopoietic cells in a patient following hematopoietic stem or progenitor cell transplant therapy. In certain embodiments, the benefits include a more rapid engraftment of transplanted cells, e.g., neutrophils and platelets. For example, in certain embodiments, using the methods described herein, neutrophil recovery occurs within about 5-20 days post-transplant, about 5-15 days post-transplant, about 5-10 days post-transplant, about 7-12 days post-transplant, about 8-12 days post transplant, about 9-15 days post-transplant, about 10-15 days post-transplant, or about 10 days post-transplant. In certain embodiments, using the methods described herein, platelet recovery occurs within about 10-20 days post-transplant, about 10-15 days post-transplant, about 15-20 days post-transplant, about 12-18 days post-transplant, about 12-17 days post transplant, about 13-18 days post-transplant, about 12-17 days post-transplant, or about 15 days post-transplant. Additional beneficial results include an increase in the cell count or relative concentration of hematopoietic stem cells in a patient in need of a hematopoietic stem or progenitor cell transplant following administration of an exogenous hematopoietic stem or progenitor cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following and subsequent hematopoietic stem cell transplant therapy. Additional beneficial results may include the reduction in quantity of a disease-causing cell population, such as a population of cancer cells or autoimmune cells.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of peptides and proteins, such as those described herein, include plasmids that contain regulatory sequences, such as promoter and enhancer regions, which direct gene transcription. Other useful vectors for expression of peptides and proteins described herein contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "alkyl" refers to a straight- or branched-chain alkyl group having, for example, from 1 to 20 carbon atoms in the chain. Examples of alkyl groups include methyl, ethyl, n-propyl, isopropyl, butyl, isobutyl, sec-butyl, tert-butyl, pentyl, isopentyl, tert-pentyl, hexyl, isohexyl, and the like.

As used herein, the term "alkylene" refers to a straight- or branched-chain divalent alkyl group. The divalent positions may be on the same or different atoms within the alkyl chain. Examples of alkylene include methylene, ethylene, propylene, isopropylene, and the like.

As used herein, the term "heteroalkyl" refers to a straight or branched-chain alkyl group having, for example, from 1 to 20 carbon atoms in the chain, and further containing one or more heteroatoms (e.g., oxygen, nitrogen, or sulfur, among others) in the chain.

As used herein, the term "heteroalkylene" refers to a straight- or branched-chain divalent heteroalkyl group. The divalent positions may be on the same or different atoms within the heteroalkyl chain. The divalent positions may be one or more heteroatoms.

As used herein, the term "alkenyl" refers to a straight- or branched-chain alkenyl group having, for example, from 2 to 20 carbon atoms in the chain. Examples of alkenyl groups include vinyl, propenyl, isopropenyl, butenyl, tert-butylenyl, hexenyl, and the like.

As used herein, the term "alkenylene" refers to a straight- or branched-chain divalent alkenyl group. The divalent positions may be on the same or different atoms within the alkenyl chain. Examples of alkenylene include ethenylene, propenylene, isopropenylene, butenylene, and the like.

As used herein, the term "heteroalkenyl" refers to a straight- or branched-chain alkenyl group having, for example, from 2 to 20 carbon atoms in the chain, and further containing one or more heteroatoms (e.g., oxygen, nitrogen, or sulfur, among others) in the chain.

As used herein, the term "heteroalkenylene" refers to a straight- or branched-chain divalent heteroalkenyl group. The divalent positions may be on the same or different atoms within the heteroalkenyl chain. The divalent positions may be one or more heteroatoms.

As used herein, the term "alkynyl" refers to a straight- or branched-chain alkynyl group having, for example, from 2 to 20 carbon atoms in the chain. Examples of alkynyl groups include propargyl, butynyl, pentynyl, hexynyl, and the like.

As used herein, the term "alkynylene" refers to a straight- or branched-chain divalent alkynyl group. The divalent positions may be on the same or different atoms within the alkynyl chain.

As used herein, the term "heteroalkynyl" refers to a straight- or branched-chain alkynyl group having, for example, from 2 to 20 carbon atoms in the chain, and further containing one or more heteroatoms (e.g., oxygen, nitrogen, or sulfur, among others) in the chain.

As used herein, the term "heteroalkynylene" refers to a straight- or branched-chain divalent heteroalkynyl group. The divalent positions may be on the same or different atoms within the heteroalkynyl chain. The divalent positions may be one or more heteroatoms.

As used herein, the term "cycloalkyl" refers to a monocyclic, or fused, bridged, or spiro polycyclic ring structure that is saturated and has, for example, from 3 to 12 carbon ring atoms. Examples of cycloalkyl groups include cyclopropyl, cyclobutyl, cyclopentyl, cyclohexyl, cycloheptyl, cyclooctyl, bicyclo[3.1.0]hexane, and the like.

As used herein, the term "cycloalkylene" refers to a divalent cycloalkyl group. The divalent positions may be on the same or different atoms within the ring structure. Examples of cycloalkylene include cyclopropylene, cyclobutylene, cyclopentylene, cyclohexylene, and the like.

As used herein, the term "heterocycloalkyl" refers to a monocyclic, or fused, bridged, or spiro polycyclic ring structure that is saturated and has, for example, from 3 to 12 ring atoms per ring structure selected from carbon atoms and heteroatoms selected from, e.g., nitrogen, oxygen, and sulfur, among others. The ring structure may contain, for example, one or more oxo groups on carbon, nitrogen, or sulfur ring members.

As used herein, the term "heterocycloalkylene" refers to a divalent heterocyclolalkyl group. The divalent positions may be on the same or different atoms within the ring structure.

As used herein, the term "aryl" refers to a monocyclic or multicyclic aromatic ring system containing, for example, from 6 to 19 carbon atoms. Aryl groups include, but are not limited to, phenyl, fluorenyl, naphthyl, and the like. The divalent positions may be one or more heteroatoms.

As used herein, the term "arylene" refers to a divalent aryl group. The divalent positions may be on the same or different atoms.

As used herein, the term "heteroaryl" refers to a monocyclic heteroaromatic, or a bicyclic or a tricyclic fused-ring heteroaromatic group. Heteroaryl groups include pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a] pyridyl, benzothiazolyl, benzoxazolyl, quinolizinyl, quinazolinyl, phthalazinyl, quinoxalinyl, cinnolinyl, napthyridinyl, pyrido[3,4-b]pyridyl, pyrido[3,2-b]pyridyl, pyrido [4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heteroarylene" refers to a divalent heteroaryl group. The divalent positions may be on the same or different atoms. The divalent positions may be one or more heteroatoms.

Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", heterocycloalkylene", "aryl," "arylene", "heteroaryl", and "heteroarylene" groups can optionally be substituted. As used herein, the term "optionally substituted" refers to a compound or moiety containing one or more (for example, 1, 2, 3, 4, 5, 6, 7, 8, 9, 10, or more) substituents, as permitted by the valence of the compound or moiety or a site thereof, such as a substituent selected from the group consisting of alkyl, alkenyl, alkynyl, cycloalkyl, heterocycloalkyl, alkyl aryl, alkyl heteroaryl, alkyl cycloalkyl, alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, nitro, and the like. The substitution may include situations in which neighboring substituents have undergone ring closure, such as ring closure of vicinal functional substituents, to form, for example, lactams, lactones, cyclic anhydrides, acetals, hemiacetals, thioacetals, aminals, and hemiaminals, formed by ring closure, for example, to furnish a protecting group.

Methods of Mobilizing Hematopoietic Stem and Progenitor Cells and Releasing Cells for Expansion and Therapeutic Use The present invention is based, in part, on the discovery that hematopoietic stem and progenitor cells can be mobilized by administering particular doses of a CXCR2 agonist, such as Gro-β, Gro-β T, or a variant thereof, optionally in combination with a CXCR4 antagonist to a mammalian donor (e.g., a human donor) while reducing the mobilization of other cell types, such as leukocytes, neutrophils, lymphocytes, and monocytes. This property is particularly beneficial in the context of hematopoietic stem cell transplant therapy, as hematopoietic stem cells that are mobilized and isolated from a donor using the compositions and method described herein have reduced quantities of cell types that are undesirable for administration to a human patient suffering from a stem cell disorder.

Particularly, it has been discovered that CXCR2 agonists, such as Gro-β, Gro-β T, or a variant thereof, when administered intravenously at a dose of from about 50 µg/kg to about 1 mg/kg, preferably from about 100 µg/kg to about 250 µg/kg, and even more preferably at a dose of about 150 µg/kg, exhibit the ability to rapidly mobilize hematopoietic stem and progenitor cells in a donor (e.g., a mammalian donor, such as a human donor) while reducing the mobilization of other cells of the hematopoietic lineage that may be undesirable for infusion into a patient (e.g., a mammalian patient, such as a human patient) that is undergoing hematopoietic stem cell transplant therapy. CXCR2 agonists, such as Gro-β, Gro-β T, or a variant thereof, when administered at the above doses to a donor exhibit the ability to selectively mobilize hematopoietic stem cells as described in detail in Example 1, below.

When determining whether hematopoietic stem cells mobilized in a donor by administration of a CXCR2 agonist, such as Gro-β, Gro-β T, or a variant thereof, and optionally, a CXCR4 antagonist, such as plerixafor or a pharmaceutically acceptable salt thereof, are suitable for release for ex vivo expansion and/or for therapeutic use, one may acquire an input value for each of one or more parameters set forth in TABLE 2 that characterize a sample of peripheral blood of the donor. The one or more parameters may be compared to the corresponding reference criterion for each parameter, and if the reference criterion is satisfied by the ample of hematopoietic stem cells, the cells isolated from the donor may be released for expansion ex vivo and/or for infusion into a patient for therapeutic use (e.g., for the treatment of one or more stem cell disorders described herein).

Exemplary hematopoietic stem cell parameters and corresponding reference criteria useful in conjunction with the compositions and methods described herein are set forth in TABLE 2, below.

TABLE 2

Hematopoietic stem cell population parameters and corresponding reference criteria

| Parameter Category | Parameter No. | Parameter | Reference Criterion |
| --- | --- | --- | --- |
| Ratio of CD34+ cells (e.g., CD34+ CD90+ CD45RA− cells) to other cells of the hematopoietic lineage within peripheral blood sample isolated from mammalian donor | 1 | Ratio of CD34+ cells to leukocytes | At least 0.0006 |
| | 2 | Ratio of CD34+ cells to leukocytes | At least 0.0009 |
| | 3 | Ratio of CD34+ CD90+ CD45RA− cells to leukocytes | At least 0.0002 |
| | 4 | Ratio of CD34+ CD90+ CD45RA− cells to leukocytes | At least 0.0003 |
| | 5 | Ratio of CD34+ CD90+ CD45RA− cells to leukocytes | At least 0.0004 |
| | 6 | Ratio of CD34+ cells to neutrophils | At least 0.0011 |
| | 7 | Ratio of CD34+ cells to neutrophils | At least 0.0004 |
| | 8 | Ratio of CD34+ CD90+ CD45RA− cells to neutrophils | At least 0.0006 |
| | 9 | Ratio of CD34+ CD90+ CD45RA− cells to neutrophils | At least 0.0007 |
| | 10 | Ratio of CD34+ cells to lymphocytes | At least 0.0020 |
| | 11 | Ratio of CD34+ cells to lymphocytes | At least 0.0025 |
| | 12 | Ratio of CD34+ CD90+ CD45RA− cells to lymphocytes | At least 0.0005 |
| | 13 | Ratio of CD34+ CD90+ CD45RA− cells to lymphocytes | At least 0.0011 |
| | 14 | Ratio of CD34+ cells to monocytes | At least 0.0047 |
| | 15 | Ratio of CD34+ cells to monocytes | At least 0.0111 |
| | 16 | Ratio of CD34+ CD90+ CD45RA− cells to monocytes | At least 0.0020 |
| | 17 | Ratio of CD34+ CD90+ CD45RA− cells to monocytes | At least 0.0039 |

TABLE 2-continued

Hematopoietic stem cell population parameters and corresponding reference criteria

| Parameter Category | Parameter No. | Parameter | Reference Criterion |
|---|---|---|---|
| Proportion of CD34$^+$ cells (e.g., CD34$^+$ CD90$^+$ CD45RA$^-$ cells) in peripheral blood sample isolated from donor | 18 | Frequency of CD34$^+$ cells relative to total quantity of cells in sample isolated from donor | At least 0.051% |
| | 19 | Frequency of CD34$^+$ cells relative to total quantity of cells in sample isolated from donor | At least 0.097% |
| | 20 | Frequency of CD34$^+$ CD90$^+$ CD45RA$^-$ cells relative to total quantity of cells in sample isolated from donor | At least 0.020% |
| | 21 | Frequency of CD34$^+$ CD90$^+$ CD45RA$^-$ cells relative to total quantity of cells in sample isolated from donor | At least 0.066% |

In selecting parameters for determining whether a population of hematopoietic stem cells obtained from a donor (e.g., a mammalian donor, such as a human donor) is suitable for release for ex vivo expansion or therapeutic use, one may select one or more input parameters listed in TABLE 2. In some embodiments, one may select an individual parameter from parameter numbers 1-21. Alternatively, one may select a combination of parameters, such as a CD34$^+$ cell ratio parameter (e.g., one or more of parameter numbers 1-17 in TABLE 2) and a frequency parameter (e.g., one or more of parameter numbers 18-21 listed in TABLE 2). In some embodiments, the parameters used for determining whether a population of hematopoietic stem cells obtained from a donor (e.g., a mammalian donor, such as a human donor) is suitable for release for ex vivo expansion or therapeutic use are a combination of parameters as set forth in any one of TABLES 3-6, below.

TABLE 3

Two-way combinations of hematopoietic stem cell population parameters for assessment

| First Parameter No. | Second Parameter No. |
|---|---|
| 1 | 6 |
| 1 | 7 |
| 1 | 8 |
| 1 | 9 |
| 2 | 6 |
| 2 | 7 |
| 2 | 8 |
| 2 | 9 |
| 3 | 6 |
| 3 | 7 |
| 3 | 8 |
| 3 | 9 |
| 4 | 6 |
| 4 | 7 |
| 4 | 8 |
| 4 | 9 |
| 5 | 6 |
| 5 | 7 |
| 5 | 8 |
| 5 | 9 |
| 1 | 10 |
| 1 | 11 |
| 1 | 12 |
| 1 | 13 |
| 2 | 10 |
| 2 | 11 |
| 2 | 12 |
| 2 | 13 |
| 3 | 10 |
| 3 | 11 |
| 3 | 12 |
| 3 | 13 |
| 4 | 10 |
| 4 | 11 |
| 4 | 12 |
| 4 | 13 |
| 5 | 10 |
| 5 | 11 |
| 5 | 12 |
| 5 | 13 |
| 1 | 14 |
| 1 | 15 |
| 1 | 16 |
| 1 | 17 |
| 2 | 14 |
| 2 | 15 |
| 2 | 16 |
| 2 | 17 |
| 3 | 14 |
| 3 | 15 |
| 3 | 16 |
| 3 | 17 |
| 4 | 14 |
| 4 | 15 |
| 4 | 16 |
| 4 | 17 |
| 5 | 14 |
| 5 | 15 |
| 5 | 16 |
| 5 | 17 |
| 1 | 18 |
| 1 | 19 |
| 1 | 20 |
| 1 | 21 |
| 2 | 18 |
| 2 | 19 |
| 2 | 20 |
| 2 | 21 |
| 3 | 18 |
| 3 | 19 |

TABLE 3-continued

Two-way combinations of hematopoietic stem cell population parameters for assessment

| First Parameter No. | Second Parameter No. |
|---|---|
| 3 | 20 |
| 3 | 21 |
| 4 | 18 |
| 4 | 19 |
| 4 | 20 |
| 4 | 21 |
| 5 | 18 |
| 5 | 19 |
| 5 | 20 |
| 5 | 21 |
| 6 | 10 |
| 6 | 11 |
| 6 | 12 |
| 6 | 13 |
| 7 | 10 |
| 7 | 11 |
| 7 | 12 |
| 7 | 13 |
| 8 | 10 |
| 8 | 11 |
| 8 | 12 |
| 8 | 13 |
| 9 | 10 |
| 9 | 11 |
| 9 | 12 |
| 9 | 13 |
| 6 | 14 |
| 6 | 15 |
| 6 | 16 |
| 6 | 17 |
| 7 | 14 |
| 7 | 15 |
| 7 | 16 |
| 7 | 17 |
| 8 | 14 |
| 8 | 15 |
| 8 | 16 |
| 8 | 17 |
| 9 | 14 |
| 9 | 15 |
| 9 | 16 |
| 9 | 17 |
| 6 | 18 |
| 6 | 19 |
| 6 | 20 |
| 6 | 21 |
| 7 | 18 |
| 7 | 19 |
| 7 | 20 |
| 7 | 21 |
| 8 | 18 |
| 8 | 19 |
| 8 | 20 |
| 8 | 21 |
| 9 | 18 |
| 9 | 19 |
| 9 | 20 |
| 9 | 21 |
| 10 | 14 |
| 10 | 15 |
| 10 | 16 |
| 10 | 17 |
| 11 | 14 |
| 11 | 15 |
| 11 | 16 |
| 11 | 17 |
| 12 | 14 |
| 12 | 15 |
| 12 | 16 |
| 12 | 17 |
| 13 | 14 |
| 13 | 15 |
| 13 | 16 |
| 13 | 17 |
| 10 | 18 |
| 10 | 19 |
| 10 | 20 |
| 10 | 21 |
| 11 | 18 |
| 11 | 19 |
| 11 | 20 |
| 11 | 21 |
| 12 | 18 |
| 12 | 19 |
| 12 | 20 |
| 12 | 21 |
| 13 | 18 |
| 13 | 19 |
| 13 | 20 |
| 13 | 21 |
| 14 | 18 |
| 14 | 19 |
| 14 | 20 |
| 14 | 21 |
| 15 | 18 |
| 15 | 19 |
| 15 | 20 |
| 15 | 21 |
| 16 | 18 |
| 16 | 19 |
| 16 | 20 |
| 16 | 21 |
| 17 | 18 |
| 17 | 19 |
| 17 | 20 |
| 17 | 21 |

TABLE 4

Three-way combinations of hematopoietic stem cell population parameters for assessment

| First Parameter No. | Second Parameter No. | Third Parameter No. |
|---|---|---|
| 1 | 6 | 10 |
| 1 | 7 | 10 |
| 1 | 8 | 10 |
| 1 | 9 | 10 |
| 2 | 6 | 10 |
| 2 | 7 | 10 |
| 2 | 8 | 10 |
| 2 | 9 | 10 |
| 3 | 6 | 10 |
| 3 | 7 | 10 |
| 3 | 8 | 10 |
| 3 | 9 | 10 |
| 4 | 6 | 10 |
| 4 | 7 | 10 |
| 4 | 8 | 10 |
| 4 | 9 | 10 |
| 5 | 6 | 10 |
| 5 | 7 | 10 |
| 5 | 8 | 10 |
| 5 | 9 | 10 |
| 1 | 6 | 11 |
| 1 | 7 | 11 |
| 1 | 8 | 11 |
| 1 | 9 | 11 |
| 2 | 6 | 11 |
| 2 | 7 | 11 |
| 2 | 8 | 11 |
| 2 | 9 | 11 |
| 3 | 6 | 11 |
| 3 | 7 | 11 |

TABLE 4-continued

Three-way combinations of hematopoietic stem cell population parameters for assessment

| First Parameter No. | Second Parameter No. | Third Parameter No. |
|---|---|---|
| 3 | 8 | 11 |
| 3 | 9 | 11 |
| 4 | 6 | 11 |
| 4 | 7 | 11 |
| 4 | 8 | 11 |
| 4 | 9 | 11 |
| 5 | 6 | 11 |
| 5 | 7 | 11 |
| 5 | 8 | 11 |
| 5 | 9 | 11 |
| 1 | 6 | 12 |
| 1 | 7 | 12 |
| 1 | 8 | 12 |
| 1 | 9 | 12 |
| 2 | 6 | 12 |
| 2 | 7 | 12 |
| 2 | 8 | 12 |
| 2 | 9 | 12 |
| 3 | 6 | 12 |
| 3 | 7 | 12 |
| 3 | 8 | 12 |
| 3 | 9 | 12 |
| 4 | 6 | 12 |
| 4 | 7 | 12 |
| 4 | 8 | 12 |
| 4 | 9 | 12 |
| 5 | 6 | 12 |
| 5 | 7 | 12 |
| 5 | 8 | 12 |
| 5 | 9 | 12 |
| 1 | 6 | 13 |
| 1 | 7 | 13 |
| 1 | 8 | 13 |
| 1 | 9 | 13 |
| 2 | 6 | 13 |
| 2 | 7 | 13 |
| 2 | 8 | 13 |
| 2 | 9 | 13 |
| 3 | 6 | 13 |
| 3 | 7 | 13 |
| 3 | 8 | 13 |
| 3 | 9 | 13 |
| 4 | 6 | 13 |
| 4 | 7 | 13 |
| 4 | 8 | 13 |
| 4 | 9 | 13 |
| 5 | 6 | 13 |
| 5 | 7 | 13 |
| 5 | 8 | 13 |
| 5 | 9 | 13 |
| 1 | 6 | 14 |
| 1 | 7 | 14 |
| 1 | 8 | 14 |
| 1 | 9 | 14 |
| 2 | 6 | 14 |
| 2 | 7 | 14 |
| 2 | 8 | 14 |
| 2 | 9 | 14 |
| 3 | 6 | 14 |
| 3 | 7 | 14 |
| 3 | 8 | 14 |
| 3 | 9 | 14 |
| 4 | 6 | 14 |
| 4 | 7 | 14 |
| 4 | 8 | 14 |
| 4 | 9 | 14 |
| 5 | 6 | 14 |
| 5 | 7 | 14 |
| 5 | 8 | 14 |
| 5 | 9 | 14 |
| 1 | 6 | 15 |
| 1 | 7 | 15 |
| 1 | 8 | 15 |
| 1 | 9 | 15 |
| 2 | 6 | 15 |
| 2 | 7 | 15 |
| 2 | 8 | 15 |
| 2 | 9 | 15 |
| 3 | 6 | 15 |
| 3 | 7 | 15 |
| 3 | 8 | 15 |
| 3 | 9 | 15 |
| 4 | 6 | 15 |
| 4 | 7 | 15 |
| 4 | 8 | 15 |
| 4 | 9 | 15 |
| 5 | 6 | 15 |
| 5 | 7 | 15 |
| 5 | 8 | 15 |
| 5 | 9 | 15 |
| 1 | 6 | 16 |
| 1 | 7 | 16 |
| 1 | 8 | 16 |
| 1 | 9 | 16 |
| 2 | 6 | 16 |
| 2 | 7 | 16 |
| 2 | 8 | 16 |
| 2 | 9 | 16 |
| 3 | 6 | 16 |
| 3 | 7 | 16 |
| 3 | 8 | 16 |
| 3 | 9 | 16 |
| 4 | 6 | 16 |
| 4 | 7 | 16 |
| 4 | 8 | 16 |
| 4 | 9 | 16 |
| 5 | 6 | 16 |
| 5 | 7 | 16 |
| 5 | 8 | 16 |
| 5 | 9 | 16 |
| 1 | 6 | 17 |
| 1 | 7 | 17 |
| 1 | 8 | 17 |
| 1 | 9 | 17 |
| 2 | 6 | 17 |
| 2 | 7 | 17 |
| 2 | 8 | 17 |
| 2 | 9 | 17 |
| 3 | 6 | 17 |
| 3 | 7 | 17 |
| 3 | 8 | 17 |
| 3 | 9 | 17 |
| 4 | 6 | 17 |
| 4 | 7 | 17 |
| 4 | 8 | 17 |
| 4 | 9 | 17 |
| 5 | 6 | 17 |
| 5 | 7 | 17 |
| 5 | 8 | 17 |
| 5 | 9 | 17 |
| 1 | 6 | 18 |
| 1 | 7 | 18 |
| 1 | 8 | 18 |
| 1 | 9 | 18 |
| 2 | 6 | 18 |
| 2 | 7 | 18 |
| 2 | 8 | 18 |
| 2 | 9 | 18 |
| 3 | 6 | 18 |
| 3 | 7 | 18 |
| 3 | 8 | 18 |
| 3 | 9 | 18 |
| 4 | 6 | 18 |
| 4 | 7 | 18 |
| 4 | 8 | 18 |
| 4 | 9 | 18 |
| 5 | 6 | 18 |
| 5 | 7 | 18 |

TABLE 4-continued

Three-way combinations of hematopoietic stem cell population parameters for assessment

| First Parameter No. | Second Parameter No. | Third Parameter No. |
|---|---|---|
| 5 | 8 | 18 |
| 5 | 9 | 18 |
| 1 | 6 | 19 |
| 1 | 7 | 19 |
| 1 | 8 | 19 |
| 1 | 9 | 19 |
| 2 | 6 | 19 |
| 2 | 7 | 19 |
| 2 | 8 | 19 |
| 2 | 9 | 19 |
| 3 | 6 | 19 |
| 3 | 7 | 19 |
| 3 | 8 | 19 |
| 3 | 9 | 19 |
| 4 | 6 | 19 |
| 4 | 7 | 19 |
| 4 | 8 | 19 |
| 4 | 9 | 19 |
| 5 | 6 | 19 |
| 5 | 7 | 19 |
| 5 | 8 | 19 |
| 5 | 9 | 19 |
| 1 | 6 | 20 |
| 1 | 7 | 20 |
| 1 | 8 | 20 |
| 1 | 9 | 20 |
| 2 | 6 | 20 |
| 2 | 7 | 20 |
| 2 | 8 | 20 |
| 2 | 9 | 20 |
| 3 | 6 | 20 |
| 3 | 7 | 20 |
| 3 | 8 | 20 |
| 3 | 9 | 20 |
| 4 | 6 | 20 |
| 4 | 7 | 20 |
| 4 | 8 | 20 |
| 4 | 9 | 20 |
| 5 | 6 | 20 |
| 5 | 7 | 20 |
| 5 | 8 | 20 |
| 5 | 9 | 20 |
| 1 | 6 | 21 |
| 1 | 7 | 21 |
| 1 | 8 | 21 |
| 1 | 9 | 21 |
| 2 | 6 | 21 |
| 2 | 7 | 21 |
| 2 | 8 | 21 |
| 2 | 9 | 21 |
| 3 | 6 | 21 |
| 3 | 7 | 21 |
| 3 | 8 | 21 |
| 3 | 9 | 21 |
| 4 | 6 | 21 |
| 4 | 7 | 21 |
| 4 | 8 | 21 |
| 4 | 9 | 21 |
| 5 | 6 | 21 |
| 5 | 7 | 21 |
| 5 | 8 | 21 |
| 5 | 9 | 21 |
| 1 | 10 | 14 |
| 1 | 11 | 14 |
| 1 | 12 | 14 |
| 1 | 13 | 14 |
| 2 | 10 | 14 |
| 2 | 11 | 14 |
| 2 | 12 | 14 |
| 2 | 13 | 14 |
| 3 | 10 | 14 |
| 3 | 11 | 14 |
| 3 | 12 | 14 |
| 3 | 13 | 14 |
| 4 | 10 | 14 |
| 4 | 11 | 14 |
| 4 | 12 | 14 |
| 4 | 13 | 14 |
| 5 | 10 | 14 |
| 5 | 11 | 14 |
| 5 | 12 | 14 |
| 5 | 13 | 14 |
| 1 | 10 | 15 |
| 1 | 11 | 15 |
| 1 | 12 | 15 |
| 1 | 13 | 15 |
| 2 | 10 | 15 |
| 2 | 11 | 15 |
| 2 | 12 | 15 |
| 2 | 13 | 15 |
| 3 | 10 | 15 |
| 3 | 11 | 15 |
| 3 | 12 | 15 |
| 3 | 13 | 15 |
| 4 | 10 | 15 |
| 4 | 11 | 15 |
| 4 | 12 | 15 |
| 4 | 13 | 15 |
| 5 | 10 | 15 |
| 5 | 11 | 15 |
| 5 | 12 | 15 |
| 5 | 13 | 15 |
| 1 | 10 | 16 |
| 1 | 11 | 16 |
| 1 | 12 | 16 |
| 1 | 13 | 16 |
| 2 | 10 | 16 |
| 2 | 11 | 16 |
| 2 | 12 | 16 |
| 2 | 13 | 16 |
| 3 | 10 | 16 |
| 3 | 11 | 16 |
| 3 | 12 | 16 |
| 3 | 13 | 16 |
| 4 | 10 | 16 |
| 4 | 11 | 16 |
| 4 | 12 | 16 |
| 4 | 13 | 16 |
| 5 | 10 | 16 |
| 5 | 11 | 16 |
| 5 | 12 | 16 |
| 5 | 13 | 16 |
| 1 | 10 | 17 |
| 1 | 11 | 17 |
| 1 | 12 | 17 |
| 1 | 13 | 17 |
| 2 | 10 | 17 |
| 2 | 11 | 17 |
| 2 | 12 | 17 |
| 2 | 13 | 17 |
| 3 | 10 | 17 |
| 3 | 11 | 17 |
| 3 | 12 | 17 |
| 3 | 13 | 17 |
| 4 | 10 | 17 |
| 4 | 11 | 17 |
| 4 | 12 | 17 |
| 4 | 13 | 17 |
| 5 | 10 | 17 |
| 5 | 11 | 17 |
| 5 | 12 | 17 |
| 5 | 13 | 17 |
| 1 | 10 | 18 |
| 1 | 11 | 18 |
| 1 | 12 | 18 |
| 1 | 13 | 18 |
| 2 | 10 | 18 |
| 2 | 11 | 18 |

TABLE 4-continued

Three-way combinations of hematopoietic stem cell population parameters for assessment

| First Parameter No. | Second Parameter No. | Third Parameter No. |
|---|---|---|
| 2 | 12 | 18 |
| 2 | 13 | 18 |
| 3 | 10 | 18 |
| 3 | 11 | 18 |
| 3 | 12 | 18 |
| 3 | 13 | 18 |
| 4 | 10 | 18 |
| 4 | 11 | 18 |
| 4 | 12 | 18 |
| 4 | 13 | 18 |
| 5 | 10 | 18 |
| 5 | 11 | 18 |
| 5 | 12 | 18 |
| 5 | 13 | 18 |
| 1 | 10 | 19 |
| 1 | 11 | 19 |
| 1 | 12 | 19 |
| 1 | 13 | 19 |
| 2 | 10 | 19 |
| 2 | 11 | 19 |
| 2 | 12 | 19 |
| 2 | 13 | 19 |
| 3 | 10 | 19 |
| 3 | 11 | 19 |
| 3 | 12 | 19 |
| 3 | 13 | 19 |
| 4 | 10 | 19 |
| 4 | 11 | 19 |
| 4 | 12 | 19 |
| 4 | 13 | 19 |
| 5 | 10 | 19 |
| 5 | 11 | 19 |
| 5 | 12 | 19 |
| 5 | 13 | 19 |
| 1 | 10 | 20 |
| 1 | 11 | 20 |
| 1 | 12 | 20 |
| 1 | 13 | 20 |
| 2 | 10 | 20 |
| 2 | 11 | 20 |
| 2 | 12 | 20 |
| 2 | 13 | 20 |
| 3 | 10 | 20 |
| 3 | 11 | 20 |
| 3 | 12 | 20 |
| 3 | 13 | 20 |
| 4 | 10 | 20 |
| 4 | 11 | 20 |
| 4 | 12 | 20 |
| 4 | 13 | 20 |
| 5 | 10 | 20 |
| 5 | 11 | 20 |
| 5 | 12 | 20 |
| 5 | 13 | 20 |
| 1 | 10 | 21 |
| 1 | 11 | 21 |
| 1 | 12 | 21 |
| 1 | 13 | 21 |
| 2 | 10 | 21 |
| 2 | 11 | 21 |
| 2 | 12 | 21 |
| 2 | 13 | 21 |
| 3 | 10 | 21 |
| 3 | 11 | 21 |
| 3 | 12 | 21 |
| 3 | 13 | 21 |
| 4 | 10 | 21 |
| 4 | 11 | 21 |
| 4 | 12 | 21 |
| 4 | 13 | 21 |
| 5 | 10 | 21 |
| 5 | 11 | 21 |
| 5 | 12 | 21 |
| 5 | 13 | 21 |
| 1 | 14 | 18 |
| 1 | 15 | 18 |
| 1 | 16 | 18 |
| 1 | 17 | 18 |
| 2 | 14 | 18 |
| 2 | 15 | 18 |
| 2 | 16 | 18 |
| 2 | 17 | 18 |
| 3 | 14 | 18 |
| 3 | 15 | 18 |
| 3 | 16 | 18 |
| 3 | 17 | 18 |
| 4 | 14 | 18 |
| 4 | 15 | 18 |
| 4 | 16 | 18 |
| 4 | 17 | 18 |
| 5 | 14 | 18 |
| 5 | 15 | 18 |
| 5 | 16 | 18 |
| 5 | 17 | 18 |
| 1 | 14 | 19 |
| 1 | 15 | 19 |
| 1 | 16 | 19 |
| 1 | 17 | 19 |
| 2 | 14 | 19 |
| 2 | 15 | 19 |
| 2 | 16 | 19 |
| 2 | 17 | 19 |
| 3 | 14 | 19 |
| 3 | 15 | 19 |
| 3 | 16 | 19 |
| 3 | 17 | 19 |
| 4 | 14 | 19 |
| 4 | 15 | 19 |
| 4 | 16 | 19 |
| 4 | 17 | 19 |
| 5 | 14 | 19 |
| 5 | 15 | 19 |
| 5 | 16 | 19 |
| 5 | 17 | 19 |
| 1 | 14 | 20 |
| 1 | 15 | 20 |
| 1 | 16 | 20 |
| 1 | 17 | 20 |
| 2 | 14 | 20 |
| 2 | 15 | 20 |
| 2 | 16 | 20 |
| 2 | 17 | 20 |
| 3 | 14 | 20 |
| 3 | 15 | 20 |
| 3 | 16 | 20 |
| 3 | 17 | 20 |
| 4 | 14 | 20 |
| 4 | 15 | 20 |
| 4 | 16 | 20 |
| 4 | 17 | 20 |
| 5 | 14 | 20 |
| 5 | 15 | 20 |
| 5 | 16 | 20 |
| 5 | 17 | 20 |
| 1 | 14 | 21 |
| 1 | 15 | 21 |
| 1 | 16 | 21 |
| 1 | 17 | 21 |
| 2 | 14 | 21 |
| 2 | 15 | 21 |
| 2 | 16 | 21 |
| 2 | 17 | 21 |
| 3 | 14 | 21 |
| 3 | 15 | 21 |
| 3 | 16 | 21 |
| 3 | 17 | 21 |
| 4 | 14 | 21 |
| 4 | 15 | 21 |

TABLE 4-continued

Three-way combinations of hematopoietic stem cell population parameters for assessment

| First Parameter No. | Second Parameter No. | Third Parameter No. |
|---|---|---|
| 4 | 16 | 21 |
| 4 | 17 | 21 |
| 5 | 14 | 21 |
| 5 | 15 | 21 |
| 5 | 16 | 21 |
| 5 | 17 | 21 |
| 6 | 10 | 14 |
| 6 | 11 | 14 |
| 6 | 12 | 14 |
| 6 | 13 | 14 |
| 7 | 10 | 14 |
| 7 | 11 | 14 |
| 7 | 12 | 14 |
| 7 | 13 | 14 |
| 8 | 10 | 14 |
| 8 | 11 | 14 |
| 8 | 12 | 14 |
| 8 | 13 | 14 |
| 9 | 10 | 14 |
| 9 | 11 | 14 |
| 9 | 12 | 14 |
| 9 | 13 | 14 |
| 6 | 10 | 15 |
| 6 | 11 | 15 |
| 6 | 12 | 15 |
| 6 | 13 | 15 |
| 7 | 10 | 15 |
| 7 | 11 | 15 |
| 7 | 12 | 15 |
| 7 | 13 | 15 |
| 8 | 10 | 15 |
| 8 | 11 | 15 |
| 8 | 12 | 15 |
| 8 | 13 | 15 |
| 9 | 10 | 15 |
| 9 | 11 | 15 |
| 9 | 12 | 15 |
| 9 | 13 | 15 |
| 6 | 10 | 16 |
| 6 | 11 | 16 |
| 6 | 12 | 16 |
| 6 | 13 | 16 |
| 7 | 10 | 16 |
| 7 | 11 | 16 |
| 7 | 12 | 16 |
| 7 | 13 | 16 |
| 8 | 10 | 16 |
| 8 | 11 | 16 |
| 8 | 12 | 16 |
| 8 | 13 | 16 |
| 9 | 10 | 16 |
| 9 | 11 | 16 |
| 9 | 12 | 16 |
| 9 | 13 | 16 |
| 6 | 10 | 17 |
| 6 | 11 | 17 |
| 6 | 12 | 17 |
| 6 | 13 | 17 |
| 7 | 10 | 17 |
| 7 | 11 | 17 |
| 7 | 12 | 17 |
| 7 | 13 | 17 |
| 8 | 10 | 17 |
| 8 | 11 | 17 |
| 8 | 12 | 17 |
| 8 | 13 | 17 |
| 9 | 10 | 17 |
| 9 | 11 | 17 |
| 9 | 12 | 17 |
| 9 | 13 | 17 |
| 6 | 10 | 18 |
| 6 | 11 | 18 |
| 6 | 12 | 18 |
| 6 | 13 | 18 |
| 7 | 10 | 18 |
| 7 | 11 | 18 |
| 7 | 12 | 18 |
| 7 | 13 | 18 |
| 8 | 10 | 18 |
| 8 | 11 | 18 |
| 8 | 12 | 18 |
| 8 | 13 | 18 |
| 9 | 10 | 18 |
| 9 | 11 | 18 |
| 9 | 12 | 18 |
| 9 | 13 | 18 |
| 6 | 10 | 19 |
| 6 | 11 | 19 |
| 6 | 12 | 19 |
| 6 | 13 | 19 |
| 7 | 10 | 19 |
| 7 | 11 | 19 |
| 7 | 12 | 19 |
| 7 | 13 | 19 |
| 8 | 10 | 19 |
| 8 | 11 | 19 |
| 8 | 12 | 19 |
| 8 | 13 | 19 |
| 9 | 10 | 19 |
| 9 | 11 | 19 |
| 9 | 12 | 19 |
| 9 | 13 | 19 |
| 6 | 10 | 20 |
| 6 | 11 | 20 |
| 6 | 12 | 20 |
| 6 | 13 | 20 |
| 7 | 10 | 20 |
| 7 | 11 | 20 |
| 7 | 12 | 20 |
| 7 | 13 | 20 |
| 8 | 10 | 20 |
| 8 | 11 | 20 |
| 8 | 12 | 20 |
| 8 | 13 | 20 |
| 9 | 10 | 20 |
| 9 | 11 | 20 |
| 9 | 12 | 20 |
| 9 | 13 | 20 |
| 6 | 10 | 21 |
| 6 | 11 | 21 |
| 6 | 12 | 21 |
| 6 | 13 | 21 |
| 7 | 10 | 21 |
| 7 | 11 | 21 |
| 7 | 12 | 21 |
| 7 | 13 | 21 |
| 8 | 10 | 21 |
| 8 | 11 | 21 |
| 8 | 12 | 21 |
| 8 | 13 | 21 |
| 9 | 10 | 21 |
| 9 | 11 | 21 |
| 9 | 12 | 21 |
| 9 | 13 | 21 |
| 6 | 14 | 18 |
| 6 | 15 | 18 |
| 6 | 16 | 18 |
| 6 | 17 | 18 |
| 7 | 14 | 18 |
| 7 | 15 | 18 |
| 7 | 16 | 18 |
| 7 | 17 | 18 |
| 8 | 14 | 18 |
| 8 | 15 | 18 |
| 8 | 16 | 18 |
| 8 | 17 | 18 |
| 9 | 14 | 18 |
| 9 | 15 | 18 |

TABLE 4-continued

Three-way combinations of hematopoietic stem cell population parameters for assessment

| First Parameter No. | Second Parameter No. | Third Parameter No. |
|---|---|---|
| 9 | 16 | 18 |
| 9 | 17 | 18 |
| 6 | 14 | 19 |
| 6 | 15 | 19 |
| 6 | 16 | 19 |
| 6 | 17 | 19 |
| 7 | 14 | 19 |
| 7 | 15 | 19 |
| 7 | 16 | 19 |
| 7 | 17 | 19 |
| 8 | 14 | 19 |
| 8 | 15 | 19 |
| 8 | 16 | 19 |
| 8 | 17 | 19 |
| 9 | 14 | 19 |
| 9 | 15 | 19 |
| 9 | 16 | 19 |
| 9 | 17 | 19 |
| 6 | 14 | 20 |
| 6 | 15 | 20 |
| 6 | 16 | 20 |
| 6 | 17 | 20 |
| 7 | 14 | 20 |
| 7 | 15 | 20 |
| 7 | 16 | 20 |
| 7 | 17 | 20 |
| 8 | 14 | 20 |
| 8 | 15 | 20 |
| 8 | 16 | 20 |
| 8 | 17 | 20 |
| 9 | 14 | 20 |
| 9 | 15 | 20 |
| 9 | 16 | 20 |
| 9 | 17 | 20 |
| 6 | 14 | 21 |
| 6 | 15 | 21 |
| 6 | 16 | 21 |
| 6 | 17 | 21 |
| 7 | 14 | 21 |
| 7 | 15 | 21 |
| 7 | 16 | 21 |
| 7 | 17 | 21 |
| 8 | 14 | 21 |
| 8 | 15 | 21 |
| 8 | 16 | 21 |
| 8 | 17 | 21 |
| 9 | 14 | 21 |
| 9 | 15 | 21 |
| 9 | 16 | 21 |
| 9 | 17 | 21 |
| 10 | 14 | 18 |
| 10 | 15 | 18 |
| 10 | 16 | 18 |
| 10 | 17 | 18 |
| 11 | 14 | 18 |
| 11 | 15 | 18 |
| 11 | 16 | 18 |
| 11 | 17 | 18 |
| 12 | 14 | 18 |
| 12 | 15 | 18 |
| 12 | 16 | 18 |
| 12 | 17 | 18 |
| 13 | 14 | 18 |
| 13 | 15 | 18 |
| 13 | 16 | 18 |
| 13 | 17 | 18 |
| 10 | 14 | 19 |
| 10 | 15 | 19 |
| 10 | 16 | 19 |
| 10 | 17 | 19 |
| 11 | 14 | 19 |
| 11 | 15 | 19 |
| 11 | 16 | 19 |
| 11 | 17 | 19 |
| 12 | 14 | 19 |
| 12 | 15 | 19 |
| 12 | 16 | 19 |
| 12 | 17 | 19 |
| 13 | 14 | 19 |
| 13 | 15 | 19 |
| 13 | 16 | 19 |
| 13 | 17 | 19 |
| 10 | 14 | 20 |
| 10 | 15 | 20 |
| 10 | 16 | 20 |
| 10 | 17 | 20 |
| 11 | 14 | 20 |
| 11 | 15 | 20 |
| 11 | 16 | 20 |
| 11 | 17 | 20 |
| 12 | 14 | 20 |
| 12 | 15 | 20 |
| 12 | 16 | 20 |
| 12 | 17 | 20 |
| 13 | 14 | 20 |
| 13 | 15 | 20 |
| 13 | 16 | 20 |
| 13 | 17 | 20 |
| 10 | 14 | 21 |
| 10 | 15 | 21 |
| 10 | 16 | 21 |
| 10 | 17 | 21 |
| 11 | 14 | 21 |
| 11 | 15 | 21 |
| 11 | 16 | 21 |
| 11 | 17 | 21 |
| 12 | 14 | 21 |
| 12 | 15 | 21 |
| 12 | 16 | 21 |
| 12 | 17 | 21 |
| 13 | 14 | 21 |
| 13 | 15 | 21 |
| 13 | 16 | 21 |
| 13 | 17 | 21 |

TABLE 5

Four-way combinations of hematopoietic stem cell population parameters for assessment

| First Parameter No. | Second Parameter No. | Third Parameter No. | Fourth Parameter No. |
|---|---|---|---|
| 1 | 6 | 10 | 14 |
| 1 | 7 | 10 | 14 |
| 1 | 8 | 10 | 14 |
| 1 | 9 | 10 | 14 |
| 2 | 6 | 10 | 14 |
| 2 | 7 | 10 | 14 |
| 2 | 8 | 10 | 14 |
| 2 | 9 | 10 | 14 |
| 3 | 6 | 10 | 14 |
| 3 | 7 | 10 | 14 |
| 3 | 8 | 10 | 14 |
| 3 | 9 | 10 | 14 |
| 4 | 6 | 10 | 14 |
| 4 | 7 | 10 | 14 |
| 4 | 8 | 10 | 14 |
| 4 | 9 | 10 | 14 |
| 5 | 6 | 10 | 14 |
| 5 | 7 | 10 | 14 |
| 5 | 8 | 10 | 14 |
| 5 | 9 | 10 | 14 |
| 1 | 6 | 11 | 14 |
| 1 | 7 | 11 | 14 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 1 | 8 | 11 | 14 |
| 1 | 9 | 11 | 14 |
| 2 | 6 | 11 | 14 |
| 2 | 7 | 11 | 14 |
| 2 | 8 | 11 | 14 |
| 2 | 9 | 11 | 14 |
| 3 | 6 | 11 | 14 |
| 3 | 7 | 11 | 14 |
| 3 | 8 | 11 | 14 |
| 3 | 9 | 11 | 14 |
| 4 | 6 | 11 | 14 |
| 4 | 7 | 11 | 14 |
| 4 | 8 | 11 | 14 |
| 4 | 9 | 11 | 14 |
| 5 | 6 | 11 | 14 |
| 5 | 7 | 11 | 14 |
| 5 | 8 | 11 | 14 |
| 5 | 9 | 11 | 14 |
| 1 | 6 | 12 | 14 |
| 1 | 7 | 12 | 14 |
| 1 | 8 | 12 | 14 |
| 1 | 9 | 12 | 14 |
| 2 | 6 | 12 | 14 |
| 2 | 7 | 12 | 14 |
| 2 | 8 | 12 | 14 |
| 2 | 9 | 12 | 14 |
| 3 | 6 | 12 | 14 |
| 3 | 7 | 12 | 14 |
| 3 | 8 | 12 | 14 |
| 3 | 9 | 12 | 14 |
| 4 | 6 | 12 | 14 |
| 4 | 7 | 12 | 14 |
| 4 | 8 | 12 | 14 |
| 4 | 9 | 12 | 14 |
| 5 | 6 | 12 | 14 |
| 5 | 7 | 12 | 14 |
| 5 | 8 | 12 | 14 |
| 5 | 9 | 12 | 14 |
| 1 | 6 | 13 | 14 |
| 1 | 7 | 13 | 14 |
| 1 | 8 | 13 | 14 |
| 1 | 9 | 13 | 14 |
| 2 | 6 | 13 | 14 |
| 2 | 7 | 13 | 14 |
| 2 | 8 | 13 | 14 |
| 2 | 9 | 13 | 14 |
| 3 | 6 | 13 | 14 |
| 3 | 7 | 13 | 14 |
| 3 | 8 | 13 | 14 |
| 3 | 9 | 13 | 14 |
| 4 | 6 | 13 | 14 |
| 4 | 7 | 13 | 14 |
| 4 | 8 | 13 | 14 |
| 4 | 9 | 13 | 14 |
| 5 | 6 | 13 | 14 |
| 5 | 7 | 13 | 14 |
| 5 | 8 | 13 | 14 |
| 5 | 9 | 13 | 14 |
| 1 | 6 | 10 | 15 |
| 1 | 7 | 10 | 15 |
| 1 | 8 | 10 | 15 |
| 1 | 9 | 10 | 15 |
| 2 | 6 | 10 | 15 |
| 2 | 7 | 10 | 15 |
| 2 | 8 | 10 | 15 |
| 2 | 9 | 10 | 15 |
| 3 | 6 | 10 | 15 |
| 3 | 7 | 10 | 15 |
| 3 | 8 | 10 | 15 |
| 3 | 9 | 10 | 15 |
| 4 | 6 | 10 | 15 |
| 4 | 7 | 10 | 15 |
| 4 | 8 | 10 | 15 |
| 4 | 9 | 10 | 15 |
| 5 | 6 | 10 | 15 |
| 5 | 7 | 10 | 15 |
| 5 | 8 | 10 | 15 |
| 5 | 9 | 10 | 15 |
| 1 | 6 | 11 | 15 |
| 1 | 7 | 11 | 15 |
| 1 | 8 | 11 | 15 |
| 1 | 9 | 11 | 15 |
| 2 | 6 | 11 | 15 |
| 2 | 7 | 11 | 15 |
| 2 | 8 | 11 | 15 |
| 2 | 9 | 11 | 15 |
| 3 | 6 | 11 | 15 |
| 3 | 7 | 11 | 15 |
| 3 | 8 | 11 | 15 |
| 3 | 9 | 11 | 15 |
| 4 | 6 | 11 | 15 |
| 4 | 7 | 11 | 15 |
| 4 | 8 | 11 | 15 |
| 4 | 9 | 11 | 15 |
| 5 | 6 | 11 | 15 |
| 5 | 7 | 11 | 15 |
| 5 | 8 | 11 | 15 |
| 5 | 9 | 11 | 15 |
| 1 | 6 | 12 | 15 |
| 1 | 7 | 12 | 15 |
| 1 | 8 | 12 | 15 |
| 1 | 9 | 12 | 15 |
| 2 | 6 | 12 | 15 |
| 2 | 7 | 12 | 15 |
| 2 | 8 | 12 | 15 |
| 2 | 9 | 12 | 15 |
| 3 | 6 | 12 | 15 |
| 3 | 7 | 12 | 15 |
| 3 | 8 | 12 | 15 |
| 3 | 9 | 12 | 15 |
| 4 | 6 | 12 | 15 |
| 4 | 7 | 12 | 15 |
| 4 | 8 | 12 | 15 |
| 4 | 9 | 12 | 15 |
| 5 | 6 | 12 | 15 |
| 5 | 7 | 12 | 15 |
| 5 | 8 | 12 | 15 |
| 5 | 9 | 12 | 15 |
| 1 | 6 | 13 | 15 |
| 1 | 7 | 13 | 15 |
| 1 | 8 | 13 | 15 |
| 1 | 9 | 13 | 15 |
| 2 | 6 | 13 | 15 |
| 2 | 7 | 13 | 15 |
| 2 | 8 | 13 | 15 |
| 2 | 9 | 13 | 15 |
| 3 | 6 | 13 | 15 |
| 3 | 7 | 13 | 15 |
| 3 | 8 | 13 | 15 |
| 3 | 9 | 13 | 15 |
| 4 | 6 | 13 | 15 |
| 4 | 7 | 13 | 15 |
| 4 | 8 | 13 | 15 |
| 4 | 9 | 13 | 15 |
| 5 | 6 | 13 | 15 |
| 5 | 7 | 13 | 15 |
| 5 | 8 | 13 | 15 |
| 5 | 9 | 13 | 15 |
| 1 | 6 | 10 | 16 |
| 1 | 7 | 10 | 16 |
| 1 | 8 | 10 | 16 |
| 1 | 9 | 10 | 16 |
| 2 | 6 | 10 | 16 |
| 2 | 7 | 10 | 16 |
| 2 | 8 | 10 | 16 |
| 2 | 9 | 10 | 16 |
| 3 | 6 | 10 | 16 |
| 3 | 7 | 10 | 16 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 3 | 8 | 10 | 16 |
| 3 | 9 | 10 | 16 |
| 4 | 6 | 10 | 16 |
| 4 | 7 | 10 | 16 |
| 4 | 8 | 10 | 16 |
| 4 | 9 | 10 | 16 |
| 5 | 6 | 10 | 16 |
| 5 | 7 | 10 | 16 |
| 5 | 8 | 10 | 16 |
| 5 | 9 | 10 | 16 |
| 1 | 6 | 11 | 16 |
| 1 | 7 | 11 | 16 |
| 1 | 8 | 11 | 16 |
| 1 | 9 | 11 | 16 |
| 2 | 6 | 11 | 16 |
| 2 | 7 | 11 | 16 |
| 2 | 8 | 11 | 16 |
| 2 | 9 | 11 | 16 |
| 3 | 6 | 11 | 16 |
| 3 | 7 | 11 | 16 |
| 3 | 8 | 11 | 16 |
| 3 | 9 | 11 | 16 |
| 4 | 6 | 11 | 16 |
| 4 | 7 | 11 | 16 |
| 4 | 8 | 11 | 16 |
| 4 | 9 | 11 | 16 |
| 5 | 6 | 11 | 16 |
| 5 | 7 | 11 | 16 |
| 5 | 8 | 11 | 16 |
| 5 | 9 | 11 | 16 |
| 1 | 6 | 12 | 16 |
| 1 | 7 | 12 | 16 |
| 1 | 8 | 12 | 16 |
| 1 | 9 | 12 | 16 |
| 2 | 6 | 12 | 16 |
| 2 | 7 | 12 | 16 |
| 2 | 8 | 12 | 16 |
| 2 | 9 | 12 | 16 |
| 3 | 6 | 12 | 16 |
| 3 | 7 | 12 | 16 |
| 3 | 8 | 12 | 16 |
| 3 | 9 | 12 | 16 |
| 4 | 6 | 12 | 16 |
| 4 | 7 | 12 | 16 |
| 4 | 8 | 12 | 16 |
| 4 | 9 | 12 | 16 |
| 5 | 6 | 12 | 16 |
| 5 | 7 | 12 | 16 |
| 5 | 8 | 12 | 16 |
| 5 | 9 | 12 | 16 |
| 1 | 6 | 13 | 16 |
| 1 | 7 | 13 | 16 |
| 1 | 8 | 13 | 16 |
| 1 | 9 | 13 | 16 |
| 2 | 6 | 13 | 16 |
| 2 | 7 | 13 | 16 |
| 2 | 8 | 13 | 16 |
| 2 | 9 | 13 | 16 |
| 3 | 6 | 13 | 16 |
| 3 | 7 | 13 | 16 |
| 3 | 8 | 13 | 16 |
| 3 | 9 | 13 | 16 |
| 4 | 6 | 13 | 16 |
| 4 | 7 | 13 | 16 |
| 4 | 8 | 13 | 16 |
| 4 | 9 | 13 | 16 |
| 5 | 6 | 13 | 16 |
| 5 | 7 | 13 | 16 |
| 5 | 8 | 13 | 16 |
| 5 | 9 | 13 | 16 |
| 1 | 6 | 10 | 17 |
| 1 | 7 | 10 | 17 |
| 1 | 8 | 10 | 17 |
| 1 | 9 | 10 | 17 |
| 2 | 6 | 10 | 17 |
| 2 | 7 | 10 | 17 |
| 2 | 8 | 10 | 17 |
| 2 | 9 | 10 | 17 |
| 3 | 6 | 10 | 17 |
| 3 | 7 | 10 | 17 |
| 3 | 8 | 10 | 17 |
| 3 | 9 | 10 | 17 |
| 4 | 6 | 10 | 17 |
| 4 | 7 | 10 | 17 |
| 4 | 8 | 10 | 17 |
| 4 | 9 | 10 | 17 |
| 5 | 6 | 10 | 17 |
| 5 | 7 | 10 | 17 |
| 5 | 8 | 10 | 17 |
| 5 | 9 | 10 | 17 |
| 1 | 6 | 11 | 17 |
| 1 | 7 | 11 | 17 |
| 1 | 8 | 11 | 17 |
| 1 | 9 | 11 | 17 |
| 2 | 6 | 11 | 17 |
| 2 | 7 | 11 | 17 |
| 2 | 8 | 11 | 17 |
| 2 | 9 | 11 | 17 |
| 3 | 6 | 11 | 17 |
| 3 | 7 | 11 | 17 |
| 3 | 8 | 11 | 17 |
| 3 | 9 | 11 | 17 |
| 4 | 6 | 11 | 17 |
| 4 | 7 | 11 | 17 |
| 4 | 8 | 11 | 17 |
| 4 | 9 | 11 | 17 |
| 5 | 6 | 11 | 17 |
| 5 | 7 | 11 | 17 |
| 5 | 8 | 11 | 17 |
| 5 | 9 | 11 | 17 |
| 1 | 6 | 12 | 17 |
| 1 | 7 | 12 | 17 |
| 1 | 8 | 12 | 17 |
| 1 | 9 | 12 | 17 |
| 2 | 6 | 12 | 17 |
| 2 | 7 | 12 | 17 |
| 2 | 8 | 12 | 17 |
| 2 | 9 | 12 | 17 |
| 3 | 6 | 12 | 17 |
| 3 | 7 | 12 | 17 |
| 3 | 8 | 12 | 17 |
| 3 | 9 | 12 | 17 |
| 4 | 6 | 12 | 17 |
| 4 | 7 | 12 | 17 |
| 4 | 8 | 12 | 17 |
| 4 | 9 | 12 | 17 |
| 5 | 6 | 12 | 17 |
| 5 | 7 | 12 | 17 |
| 5 | 8 | 12 | 17 |
| 5 | 9 | 12 | 17 |
| 1 | 6 | 13 | 17 |
| 1 | 7 | 13 | 17 |
| 1 | 8 | 13 | 17 |
| 1 | 9 | 13 | 17 |
| 2 | 6 | 13 | 17 |
| 2 | 7 | 13 | 17 |
| 2 | 8 | 13 | 17 |
| 2 | 9 | 13 | 17 |
| 3 | 6 | 13 | 17 |
| 3 | 7 | 13 | 17 |
| 3 | 8 | 13 | 17 |
| 3 | 9 | 13 | 17 |
| 4 | 6 | 13 | 17 |
| 4 | 7 | 13 | 17 |
| 4 | 8 | 13 | 17 |
| 4 | 9 | 13 | 17 |
| 5 | 6 | 13 | 17 |
| 5 | 7 | 13 | 17 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 5 | 8 | 13 | 17 |
| 5 | 9 | 13 | 17 |
| 1 | 6 | 10 | 18 |
| 1 | 7 | 10 | 18 |
| 1 | 8 | 10 | 18 |
| 1 | 9 | 10 | 18 |
| 2 | 6 | 10 | 18 |
| 2 | 7 | 10 | 18 |
| 2 | 8 | 10 | 18 |
| 2 | 9 | 10 | 18 |
| 3 | 6 | 10 | 18 |
| 3 | 7 | 10 | 18 |
| 3 | 8 | 10 | 18 |
| 3 | 9 | 10 | 18 |
| 4 | 6 | 10 | 18 |
| 4 | 7 | 10 | 18 |
| 4 | 8 | 10 | 18 |
| 4 | 9 | 10 | 18 |
| 5 | 6 | 10 | 18 |
| 5 | 7 | 10 | 18 |
| 5 | 8 | 10 | 18 |
| 5 | 9 | 10 | 18 |
| 1 | 6 | 11 | 18 |
| 1 | 7 | 11 | 18 |
| 1 | 8 | 11 | 18 |
| 1 | 9 | 11 | 18 |
| 2 | 6 | 11 | 18 |
| 2 | 7 | 11 | 18 |
| 2 | 8 | 11 | 18 |
| 2 | 9 | 11 | 18 |
| 3 | 6 | 11 | 18 |
| 3 | 7 | 11 | 18 |
| 3 | 8 | 11 | 18 |
| 3 | 9 | 11 | 18 |
| 4 | 6 | 11 | 18 |
| 4 | 7 | 11 | 18 |
| 4 | 8 | 11 | 18 |
| 4 | 9 | 11 | 18 |
| 5 | 6 | 11 | 18 |
| 5 | 7 | 11 | 18 |
| 5 | 8 | 11 | 18 |
| 5 | 9 | 11 | 18 |
| 1 | 6 | 12 | 18 |
| 1 | 7 | 12 | 18 |
| 1 | 8 | 12 | 18 |
| 1 | 9 | 12 | 18 |
| 2 | 6 | 12 | 18 |
| 2 | 7 | 12 | 18 |
| 2 | 8 | 12 | 18 |
| 2 | 9 | 12 | 18 |
| 3 | 6 | 12 | 18 |
| 3 | 7 | 12 | 18 |
| 3 | 8 | 12 | 18 |
| 3 | 9 | 12 | 18 |
| 4 | 6 | 12 | 18 |
| 4 | 7 | 12 | 18 |
| 4 | 8 | 12 | 18 |
| 4 | 9 | 12 | 18 |
| 5 | 6 | 12 | 18 |
| 5 | 7 | 12 | 18 |
| 5 | 8 | 12 | 18 |
| 5 | 9 | 12 | 18 |
| 1 | 6 | 13 | 18 |
| 1 | 7 | 13 | 18 |
| 1 | 8 | 13 | 18 |
| 1 | 9 | 13 | 18 |
| 2 | 6 | 13 | 18 |
| 2 | 7 | 13 | 18 |
| 2 | 8 | 13 | 18 |
| 2 | 9 | 13 | 18 |
| 3 | 6 | 13 | 18 |
| 3 | 7 | 13 | 18 |
| 3 | 8 | 13 | 18 |
| 3 | 9 | 13 | 18 |
| 4 | 6 | 13 | 18 |
| 4 | 7 | 13 | 18 |
| 4 | 8 | 13 | 18 |
| 4 | 9 | 13 | 18 |
| 5 | 6 | 13 | 18 |
| 5 | 7 | 13 | 18 |
| 5 | 8 | 13 | 18 |
| 5 | 9 | 13 | 18 |
| 1 | 6 | 10 | 19 |
| 1 | 7 | 10 | 19 |
| 1 | 8 | 10 | 19 |
| 1 | 9 | 10 | 19 |
| 2 | 6 | 10 | 19 |
| 2 | 7 | 10 | 19 |
| 2 | 8 | 10 | 19 |
| 2 | 9 | 10 | 19 |
| 3 | 6 | 10 | 19 |
| 3 | 7 | 10 | 19 |
| 3 | 8 | 10 | 19 |
| 3 | 9 | 10 | 19 |
| 4 | 6 | 10 | 19 |
| 4 | 7 | 10 | 19 |
| 4 | 8 | 10 | 19 |
| 4 | 9 | 10 | 19 |
| 5 | 6 | 10 | 19 |
| 5 | 7 | 10 | 19 |
| 5 | 8 | 10 | 19 |
| 5 | 9 | 10 | 19 |
| 1 | 6 | 11 | 19 |
| 1 | 7 | 11 | 19 |
| 1 | 8 | 11 | 19 |
| 1 | 9 | 11 | 19 |
| 2 | 6 | 11 | 19 |
| 2 | 7 | 11 | 19 |
| 2 | 8 | 11 | 19 |
| 2 | 9 | 11 | 19 |
| 3 | 6 | 11 | 19 |
| 3 | 7 | 11 | 19 |
| 3 | 8 | 11 | 19 |
| 3 | 9 | 11 | 19 |
| 4 | 6 | 11 | 19 |
| 4 | 7 | 11 | 19 |
| 4 | 8 | 11 | 19 |
| 4 | 9 | 11 | 19 |
| 5 | 6 | 11 | 19 |
| 5 | 7 | 11 | 19 |
| 5 | 8 | 11 | 19 |
| 5 | 9 | 11 | 19 |
| 1 | 6 | 12 | 19 |
| 1 | 7 | 12 | 19 |
| 1 | 8 | 12 | 19 |
| 1 | 9 | 12 | 19 |
| 2 | 6 | 12 | 19 |
| 2 | 7 | 12 | 19 |
| 2 | 8 | 12 | 19 |
| 2 | 9 | 12 | 19 |
| 3 | 6 | 12 | 19 |
| 3 | 7 | 12 | 19 |
| 3 | 8 | 12 | 19 |
| 3 | 9 | 12 | 19 |
| 4 | 6 | 12 | 19 |
| 4 | 7 | 12 | 19 |
| 4 | 8 | 12 | 19 |
| 4 | 9 | 12 | 19 |
| 5 | 6 | 12 | 19 |
| 5 | 7 | 12 | 19 |
| 5 | 8 | 12 | 19 |
| 5 | 9 | 12 | 19 |
| 1 | 6 | 13 | 19 |
| 1 | 7 | 13 | 19 |
| 1 | 8 | 13 | 19 |
| 1 | 9 | 13 | 19 |
| 2 | 6 | 13 | 19 |
| 2 | 7 | 13 | 19 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 2 | 8 | 13 | 19 |
| 2 | 9 | 13 | 19 |
| 3 | 6 | 13 | 19 |
| 3 | 7 | 13 | 19 |
| 3 | 8 | 13 | 19 |
| 3 | 9 | 13 | 19 |
| 4 | 6 | 13 | 19 |
| 4 | 7 | 13 | 19 |
| 4 | 8 | 13 | 19 |
| 4 | 9 | 13 | 19 |
| 5 | 6 | 13 | 19 |
| 5 | 7 | 13 | 19 |
| 5 | 8 | 13 | 19 |
| 5 | 9 | 13 | 19 |
| 1 | 6 | 10 | 20 |
| 1 | 7 | 10 | 20 |
| 1 | 8 | 10 | 20 |
| 1 | 9 | 10 | 20 |
| 2 | 6 | 10 | 20 |
| 2 | 7 | 10 | 20 |
| 2 | 8 | 10 | 20 |
| 2 | 9 | 10 | 20 |
| 3 | 6 | 10 | 20 |
| 3 | 7 | 10 | 20 |
| 3 | 8 | 10 | 20 |
| 3 | 9 | 10 | 20 |
| 4 | 6 | 10 | 20 |
| 4 | 7 | 10 | 20 |
| 4 | 8 | 10 | 20 |
| 4 | 9 | 10 | 20 |
| 5 | 6 | 10 | 20 |
| 5 | 7 | 10 | 20 |
| 5 | 8 | 10 | 20 |
| 5 | 9 | 10 | 20 |
| 1 | 6 | 11 | 20 |
| 1 | 7 | 11 | 20 |
| 1 | 8 | 11 | 20 |
| 1 | 9 | 11 | 20 |
| 2 | 6 | 11 | 20 |
| 2 | 7 | 11 | 20 |
| 2 | 8 | 11 | 20 |
| 2 | 9 | 11 | 20 |
| 3 | 6 | 11 | 20 |
| 3 | 7 | 11 | 20 |
| 3 | 8 | 11 | 20 |
| 3 | 9 | 11 | 20 |
| 4 | 6 | 11 | 20 |
| 4 | 7 | 11 | 20 |
| 4 | 8 | 11 | 20 |
| 4 | 9 | 11 | 20 |
| 5 | 6 | 11 | 20 |
| 5 | 7 | 11 | 20 |
| 5 | 8 | 11 | 20 |
| 5 | 9 | 11 | 20 |
| 1 | 6 | 12 | 20 |
| 1 | 7 | 12 | 20 |
| 1 | 8 | 12 | 20 |
| 1 | 9 | 12 | 20 |
| 2 | 6 | 12 | 20 |
| 2 | 7 | 12 | 20 |
| 2 | 8 | 12 | 20 |
| 2 | 9 | 12 | 20 |
| 3 | 6 | 12 | 20 |
| 3 | 7 | 12 | 20 |
| 3 | 8 | 12 | 20 |
| 3 | 9 | 12 | 20 |
| 4 | 6 | 12 | 20 |
| 4 | 7 | 12 | 20 |
| 4 | 8 | 12 | 20 |
| 4 | 9 | 12 | 20 |
| 5 | 6 | 12 | 20 |
| 5 | 7 | 12 | 20 |
| 5 | 8 | 12 | 20 |
| 5 | 9 | 12 | 20 |
| 1 | 6 | 13 | 20 |
| 1 | 7 | 13 | 20 |
| 1 | 8 | 13 | 20 |
| 1 | 9 | 13 | 20 |
| 2 | 6 | 13 | 20 |
| 2 | 7 | 13 | 20 |
| 2 | 8 | 13 | 20 |
| 2 | 9 | 13 | 20 |
| 3 | 6 | 13 | 20 |
| 3 | 7 | 13 | 20 |
| 3 | 8 | 13 | 20 |
| 3 | 9 | 13 | 20 |
| 4 | 6 | 13 | 20 |
| 4 | 7 | 13 | 20 |
| 4 | 8 | 13 | 20 |
| 4 | 9 | 13 | 20 |
| 5 | 6 | 13 | 20 |
| 5 | 7 | 13 | 20 |
| 5 | 8 | 13 | 20 |
| 5 | 9 | 13 | 20 |
| 1 | 6 | 10 | 21 |
| 1 | 7 | 10 | 21 |
| 1 | 8 | 10 | 21 |
| 1 | 9 | 10 | 21 |
| 2 | 6 | 10 | 21 |
| 2 | 7 | 10 | 21 |
| 2 | 8 | 10 | 21 |
| 2 | 9 | 10 | 21 |
| 3 | 6 | 10 | 21 |
| 3 | 7 | 10 | 21 |
| 3 | 8 | 10 | 21 |
| 3 | 9 | 10 | 21 |
| 4 | 6 | 10 | 21 |
| 4 | 7 | 10 | 21 |
| 4 | 8 | 10 | 21 |
| 4 | 9 | 10 | 21 |
| 5 | 6 | 10 | 21 |
| 5 | 7 | 10 | 21 |
| 5 | 8 | 10 | 21 |
| 5 | 9 | 10 | 21 |
| 1 | 6 | 11 | 21 |
| 1 | 7 | 11 | 21 |
| 1 | 8 | 11 | 21 |
| 1 | 9 | 11 | 21 |
| 2 | 6 | 11 | 21 |
| 2 | 7 | 11 | 21 |
| 2 | 8 | 11 | 21 |
| 2 | 9 | 11 | 21 |
| 3 | 6 | 11 | 21 |
| 3 | 7 | 11 | 21 |
| 3 | 8 | 11 | 21 |
| 3 | 9 | 11 | 21 |
| 4 | 6 | 11 | 21 |
| 4 | 7 | 11 | 21 |
| 4 | 8 | 11 | 21 |
| 4 | 9 | 11 | 21 |
| 5 | 6 | 11 | 21 |
| 5 | 7 | 11 | 21 |
| 5 | 8 | 11 | 21 |
| 5 | 9 | 11 | 21 |
| 1 | 6 | 12 | 21 |
| 1 | 7 | 12 | 21 |
| 1 | 8 | 12 | 21 |
| 1 | 9 | 12 | 21 |
| 2 | 6 | 12 | 21 |
| 2 | 7 | 12 | 21 |
| 2 | 8 | 12 | 21 |
| 2 | 9 | 12 | 21 |
| 3 | 6 | 12 | 21 |
| 3 | 7 | 12 | 21 |
| 3 | 8 | 12 | 21 |
| 3 | 9 | 12 | 21 |
| 4 | 6 | 12 | 21 |
| 4 | 7 | 12 | 21 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 4 | 8 | 12 | 21 |
| 4 | 9 | 12 | 21 |
| 5 | 6 | 12 | 21 |
| 5 | 7 | 12 | 21 |
| 5 | 8 | 12 | 21 |
| 5 | 9 | 12 | 21 |
| 1 | 6 | 13 | 21 |
| 1 | 7 | 13 | 21 |
| 1 | 8 | 13 | 21 |
| 1 | 9 | 13 | 21 |
| 2 | 6 | 13 | 21 |
| 2 | 7 | 13 | 21 |
| 2 | 8 | 13 | 21 |
| 2 | 9 | 13 | 21 |
| 3 | 6 | 13 | 21 |
| 3 | 7 | 13 | 21 |
| 3 | 8 | 13 | 21 |
| 3 | 9 | 13 | 21 |
| 4 | 6 | 13 | 21 |
| 4 | 7 | 13 | 21 |
| 4 | 8 | 13 | 21 |
| 4 | 9 | 13 | 21 |
| 5 | 6 | 13 | 21 |
| 5 | 7 | 13 | 21 |
| 5 | 8 | 13 | 21 |
| 5 | 9 | 13 | 21 |
| 1 | 6 | 14 | 18 |
| 1 | 7 | 14 | 18 |
| 1 | 8 | 14 | 18 |
| 1 | 9 | 14 | 18 |
| 2 | 6 | 14 | 18 |
| 2 | 7 | 14 | 18 |
| 2 | 8 | 14 | 18 |
| 2 | 9 | 14 | 18 |
| 3 | 6 | 14 | 18 |
| 3 | 7 | 14 | 18 |
| 3 | 8 | 14 | 18 |
| 3 | 9 | 14 | 18 |
| 4 | 6 | 14 | 18 |
| 4 | 7 | 14 | 18 |
| 4 | 8 | 14 | 18 |
| 4 | 9 | 14 | 18 |
| 5 | 6 | 14 | 18 |
| 5 | 7 | 14 | 18 |
| 5 | 8 | 14 | 18 |
| 5 | 9 | 14 | 18 |
| 1 | 6 | 15 | 18 |
| 1 | 7 | 15 | 18 |
| 1 | 8 | 15 | 18 |
| 1 | 9 | 15 | 18 |
| 2 | 6 | 15 | 18 |
| 2 | 7 | 15 | 18 |
| 2 | 8 | 15 | 18 |
| 2 | 9 | 15 | 18 |
| 3 | 6 | 15 | 18 |
| 3 | 7 | 15 | 18 |
| 3 | 8 | 15 | 18 |
| 3 | 9 | 15 | 18 |
| 4 | 6 | 15 | 18 |
| 4 | 7 | 15 | 18 |
| 4 | 8 | 15 | 18 |
| 4 | 9 | 15 | 18 |
| 5 | 6 | 15 | 18 |
| 5 | 7 | 15 | 18 |
| 5 | 8 | 15 | 18 |
| 5 | 9 | 15 | 18 |
| 1 | 6 | 16 | 18 |
| 1 | 7 | 16 | 18 |
| 1 | 8 | 16 | 18 |
| 1 | 9 | 16 | 18 |
| 2 | 6 | 16 | 18 |
| 2 | 7 | 16 | 18 |
| 2 | 8 | 16 | 18 |
| 2 | 9 | 16 | 18 |
| 3 | 6 | 16 | 18 |
| 3 | 7 | 16 | 18 |
| 3 | 8 | 16 | 18 |
| 3 | 9 | 16 | 18 |
| 4 | 6 | 16 | 18 |
| 4 | 7 | 16 | 18 |
| 4 | 8 | 16 | 18 |
| 4 | 9 | 16 | 18 |
| 5 | 6 | 16 | 18 |
| 5 | 7 | 16 | 18 |
| 5 | 8 | 16 | 18 |
| 5 | 9 | 16 | 18 |
| 1 | 6 | 17 | 18 |
| 1 | 7 | 17 | 18 |
| 1 | 8 | 17 | 18 |
| 1 | 9 | 17 | 18 |
| 2 | 6 | 17 | 18 |
| 2 | 7 | 17 | 18 |
| 2 | 8 | 17 | 18 |
| 2 | 9 | 17 | 18 |
| 3 | 6 | 17 | 18 |
| 3 | 7 | 17 | 18 |
| 3 | 8 | 17 | 18 |
| 3 | 9 | 17 | 18 |
| 4 | 6 | 17 | 18 |
| 4 | 7 | 17 | 18 |
| 4 | 8 | 17 | 18 |
| 4 | 9 | 17 | 18 |
| 5 | 6 | 17 | 18 |
| 5 | 7 | 17 | 18 |
| 5 | 8 | 17 | 18 |
| 5 | 9 | 17 | 18 |
| 1 | 6 | 14 | 19 |
| 1 | 7 | 14 | 19 |
| 1 | 8 | 14 | 19 |
| 1 | 9 | 14 | 19 |
| 2 | 6 | 14 | 19 |
| 2 | 7 | 14 | 19 |
| 2 | 8 | 14 | 19 |
| 2 | 9 | 14 | 19 |
| 3 | 6 | 14 | 19 |
| 3 | 7 | 14 | 19 |
| 3 | 8 | 14 | 19 |
| 3 | 9 | 14 | 19 |
| 4 | 6 | 14 | 19 |
| 4 | 7 | 14 | 19 |
| 4 | 8 | 14 | 19 |
| 4 | 9 | 14 | 19 |
| 5 | 6 | 14 | 19 |
| 5 | 7 | 14 | 19 |
| 5 | 8 | 14 | 19 |
| 5 | 9 | 14 | 19 |
| 1 | 6 | 15 | 19 |
| 1 | 7 | 15 | 19 |
| 1 | 8 | 15 | 19 |
| 1 | 9 | 15 | 19 |
| 2 | 6 | 15 | 19 |
| 2 | 7 | 15 | 19 |
| 2 | 8 | 15 | 19 |
| 2 | 9 | 15 | 19 |
| 3 | 6 | 15 | 19 |
| 3 | 7 | 15 | 19 |
| 3 | 8 | 15 | 19 |
| 3 | 9 | 15 | 19 |
| 4 | 6 | 15 | 19 |
| 4 | 7 | 15 | 19 |
| 4 | 8 | 15 | 19 |
| 4 | 9 | 15 | 19 |
| 5 | 6 | 15 | 19 |
| 5 | 7 | 15 | 19 |
| 5 | 8 | 15 | 19 |
| 5 | 9 | 15 | 19 |
| 1 | 6 | 16 | 19 |
| 1 | 7 | 16 | 19 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 1 | 8 | 16 | 19 |
| 1 | 9 | 16 | 19 |
| 2 | 6 | 16 | 19 |
| 2 | 7 | 16 | 19 |
| 2 | 8 | 16 | 19 |
| 2 | 9 | 16 | 19 |
| 3 | 6 | 16 | 19 |
| 3 | 7 | 16 | 19 |
| 3 | 8 | 16 | 19 |
| 3 | 9 | 16 | 19 |
| 4 | 6 | 16 | 19 |
| 4 | 7 | 16 | 19 |
| 4 | 8 | 16 | 19 |
| 4 | 9 | 16 | 19 |
| 5 | 6 | 16 | 19 |
| 5 | 7 | 16 | 19 |
| 5 | 8 | 16 | 19 |
| 5 | 9 | 16 | 19 |
| 1 | 6 | 17 | 19 |
| 1 | 7 | 17 | 19 |
| 1 | 8 | 17 | 19 |
| 1 | 9 | 17 | 19 |
| 2 | 6 | 17 | 19 |
| 2 | 7 | 17 | 19 |
| 2 | 8 | 17 | 19 |
| 2 | 9 | 17 | 19 |
| 3 | 6 | 17 | 19 |
| 3 | 7 | 17 | 19 |
| 3 | 8 | 17 | 19 |
| 3 | 9 | 17 | 19 |
| 4 | 6 | 17 | 19 |
| 4 | 7 | 17 | 19 |
| 4 | 8 | 17 | 19 |
| 4 | 9 | 17 | 19 |
| 5 | 6 | 17 | 19 |
| 5 | 7 | 17 | 19 |
| 5 | 8 | 17 | 19 |
| 5 | 9 | 17 | 19 |
| 1 | 6 | 14 | 20 |
| 1 | 7 | 14 | 20 |
| 1 | 8 | 14 | 20 |
| 1 | 9 | 14 | 20 |
| 2 | 6 | 14 | 20 |
| 2 | 7 | 14 | 20 |
| 2 | 8 | 14 | 20 |
| 2 | 9 | 14 | 20 |
| 3 | 6 | 14 | 20 |
| 3 | 7 | 14 | 20 |
| 3 | 8 | 14 | 20 |
| 3 | 9 | 14 | 20 |
| 4 | 6 | 14 | 20 |
| 4 | 7 | 14 | 20 |
| 4 | 8 | 14 | 20 |
| 4 | 9 | 14 | 20 |
| 5 | 6 | 14 | 20 |
| 5 | 7 | 14 | 20 |
| 5 | 8 | 14 | 20 |
| 5 | 9 | 14 | 20 |
| 1 | 6 | 15 | 20 |
| 1 | 7 | 15 | 20 |
| 1 | 8 | 15 | 20 |
| 1 | 9 | 15 | 20 |
| 2 | 6 | 15 | 20 |
| 2 | 7 | 15 | 20 |
| 2 | 8 | 15 | 20 |
| 2 | 9 | 15 | 20 |
| 3 | 6 | 15 | 20 |
| 3 | 7 | 15 | 20 |
| 3 | 8 | 15 | 20 |
| 3 | 9 | 15 | 20 |
| 4 | 6 | 15 | 20 |
| 4 | 7 | 15 | 20 |
| 4 | 8 | 15 | 20 |
| 4 | 9 | 15 | 20 |
| 5 | 6 | 15 | 20 |
| 5 | 7 | 15 | 20 |
| 5 | 8 | 15 | 20 |
| 5 | 9 | 15 | 20 |
| 1 | 6 | 16 | 20 |
| 1 | 7 | 16 | 20 |
| 1 | 8 | 16 | 20 |
| 1 | 9 | 16 | 20 |
| 2 | 6 | 16 | 20 |
| 2 | 7 | 16 | 20 |
| 2 | 8 | 16 | 20 |
| 2 | 9 | 16 | 20 |
| 3 | 6 | 16 | 20 |
| 3 | 7 | 16 | 20 |
| 3 | 8 | 16 | 20 |
| 3 | 9 | 16 | 20 |
| 4 | 6 | 16 | 20 |
| 4 | 7 | 16 | 20 |
| 4 | 8 | 16 | 20 |
| 4 | 9 | 16 | 20 |
| 5 | 6 | 16 | 20 |
| 5 | 7 | 16 | 20 |
| 5 | 8 | 16 | 20 |
| 5 | 9 | 16 | 20 |
| 1 | 6 | 17 | 20 |
| 1 | 7 | 17 | 20 |
| 1 | 8 | 17 | 20 |
| 1 | 9 | 17 | 20 |
| 2 | 6 | 17 | 20 |
| 2 | 7 | 17 | 20 |
| 2 | 8 | 17 | 20 |
| 2 | 9 | 17 | 20 |
| 3 | 6 | 17 | 20 |
| 3 | 7 | 17 | 20 |
| 3 | 8 | 17 | 20 |
| 3 | 9 | 17 | 20 |
| 4 | 6 | 17 | 20 |
| 4 | 7 | 17 | 20 |
| 4 | 8 | 17 | 20 |
| 4 | 9 | 17 | 20 |
| 5 | 6 | 17 | 20 |
| 5 | 7 | 17 | 20 |
| 5 | 8 | 17 | 20 |
| 5 | 9 | 17 | 20 |
| 1 | 6 | 14 | 21 |
| 1 | 7 | 14 | 21 |
| 1 | 8 | 14 | 21 |
| 1 | 9 | 14 | 21 |
| 2 | 6 | 14 | 21 |
| 2 | 7 | 14 | 21 |
| 2 | 8 | 14 | 21 |
| 2 | 9 | 14 | 21 |
| 3 | 6 | 14 | 21 |
| 3 | 7 | 14 | 21 |
| 3 | 8 | 14 | 21 |
| 3 | 9 | 14 | 21 |
| 4 | 6 | 14 | 21 |
| 4 | 7 | 14 | 21 |
| 4 | 8 | 14 | 21 |
| 4 | 9 | 14 | 21 |
| 5 | 6 | 14 | 21 |
| 5 | 7 | 14 | 21 |
| 5 | 8 | 14 | 21 |
| 5 | 9 | 14 | 21 |
| 1 | 6 | 15 | 21 |
| 1 | 7 | 15 | 21 |
| 1 | 8 | 15 | 21 |
| 1 | 9 | 15 | 21 |
| 2 | 6 | 15 | 21 |
| 2 | 7 | 15 | 21 |
| 2 | 8 | 15 | 21 |
| 2 | 9 | 15 | 21 |
| 3 | 6 | 15 | 21 |
| 3 | 7 | 15 | 21 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 3 | 8 | 15 | 21 |
| 3 | 9 | 15 | 21 |
| 4 | 6 | 15 | 21 |
| 4 | 7 | 15 | 21 |
| 4 | 8 | 15 | 21 |
| 4 | 9 | 15 | 21 |
| 5 | 6 | 15 | 21 |
| 5 | 7 | 15 | 21 |
| 5 | 8 | 15 | 21 |
| 5 | 9 | 15 | 21 |
| 1 | 6 | 16 | 21 |
| 1 | 7 | 16 | 21 |
| 1 | 8 | 16 | 21 |
| 1 | 9 | 16 | 21 |
| 2 | 6 | 16 | 21 |
| 2 | 7 | 16 | 21 |
| 2 | 8 | 16 | 21 |
| 2 | 9 | 16 | 21 |
| 3 | 6 | 16 | 21 |
| 3 | 7 | 16 | 21 |
| 3 | 8 | 16 | 21 |
| 3 | 9 | 16 | 21 |
| 4 | 6 | 16 | 21 |
| 4 | 7 | 16 | 21 |
| 4 | 8 | 16 | 21 |
| 4 | 9 | 16 | 21 |
| 5 | 6 | 16 | 21 |
| 5 | 7 | 16 | 21 |
| 5 | 8 | 16 | 21 |
| 5 | 9 | 16 | 21 |
| 1 | 6 | 17 | 21 |
| 1 | 7 | 17 | 21 |
| 1 | 8 | 17 | 21 |
| 1 | 9 | 17 | 21 |
| 2 | 6 | 17 | 21 |
| 2 | 7 | 17 | 21 |
| 2 | 8 | 17 | 21 |
| 2 | 9 | 17 | 21 |
| 3 | 6 | 17 | 21 |
| 3 | 7 | 17 | 21 |
| 3 | 8 | 17 | 21 |
| 3 | 9 | 17 | 21 |
| 4 | 6 | 17 | 21 |
| 4 | 7 | 17 | 21 |
| 4 | 8 | 17 | 21 |
| 4 | 9 | 17 | 21 |
| 5 | 6 | 17 | 21 |
| 5 | 7 | 17 | 21 |
| 5 | 8 | 17 | 21 |
| 5 | 9 | 17 | 21 |
| 1 | 10 | 14 | 18 |
| 1 | 11 | 14 | 18 |
| 1 | 12 | 14 | 18 |
| 1 | 13 | 14 | 18 |
| 2 | 10 | 14 | 18 |
| 2 | 11 | 14 | 18 |
| 2 | 12 | 14 | 18 |
| 2 | 13 | 14 | 18 |
| 3 | 10 | 14 | 18 |
| 3 | 11 | 14 | 18 |
| 3 | 12 | 14 | 18 |
| 3 | 13 | 14 | 18 |
| 4 | 10 | 14 | 18 |
| 4 | 11 | 14 | 18 |
| 4 | 12 | 14 | 18 |
| 4 | 13 | 14 | 18 |
| 5 | 10 | 14 | 18 |
| 5 | 11 | 14 | 18 |
| 5 | 12 | 14 | 18 |
| 5 | 13 | 14 | 18 |
| 1 | 10 | 15 | 18 |
| 1 | 11 | 15 | 18 |
| 1 | 12 | 15 | 18 |
| 1 | 13 | 15 | 18 |
| 2 | 10 | 15 | 18 |
| 2 | 11 | 15 | 18 |
| 2 | 12 | 15 | 18 |
| 2 | 13 | 15 | 18 |
| 3 | 10 | 15 | 18 |
| 3 | 11 | 15 | 18 |
| 3 | 12 | 15 | 18 |
| 3 | 13 | 15 | 18 |
| 4 | 10 | 15 | 18 |
| 4 | 11 | 15 | 18 |
| 4 | 12 | 15 | 18 |
| 4 | 13 | 15 | 18 |
| 5 | 10 | 15 | 18 |
| 5 | 11 | 15 | 18 |
| 5 | 12 | 15 | 18 |
| 5 | 13 | 15 | 18 |
| 1 | 10 | 16 | 18 |
| 1 | 11 | 16 | 18 |
| 1 | 12 | 16 | 18 |
| 1 | 13 | 16 | 18 |
| 2 | 10 | 16 | 18 |
| 2 | 11 | 16 | 18 |
| 2 | 12 | 16 | 18 |
| 2 | 13 | 16 | 18 |
| 3 | 10 | 16 | 18 |
| 3 | 11 | 16 | 18 |
| 3 | 12 | 16 | 18 |
| 3 | 13 | 16 | 18 |
| 4 | 10 | 16 | 18 |
| 4 | 11 | 16 | 18 |
| 4 | 12 | 16 | 18 |
| 4 | 13 | 16 | 18 |
| 5 | 10 | 16 | 18 |
| 5 | 11 | 16 | 18 |
| 5 | 12 | 16 | 18 |
| 5 | 13 | 16 | 18 |
| 1 | 10 | 17 | 18 |
| 1 | 11 | 17 | 18 |
| 1 | 12 | 17 | 18 |
| 1 | 13 | 17 | 18 |
| 2 | 10 | 17 | 18 |
| 2 | 11 | 17 | 18 |
| 2 | 12 | 17 | 18 |
| 2 | 13 | 17 | 18 |
| 3 | 10 | 17 | 18 |
| 3 | 11 | 17 | 18 |
| 3 | 12 | 17 | 18 |
| 3 | 13 | 17 | 18 |
| 4 | 10 | 17 | 18 |
| 4 | 11 | 17 | 18 |
| 4 | 12 | 17 | 18 |
| 4 | 13 | 17 | 18 |
| 5 | 10 | 17 | 18 |
| 5 | 11 | 17 | 18 |
| 5 | 12 | 17 | 18 |
| 5 | 13 | 17 | 18 |
| 1 | 10 | 14 | 19 |
| 1 | 11 | 14 | 19 |
| 1 | 12 | 14 | 19 |
| 1 | 13 | 14 | 19 |
| 2 | 10 | 14 | 19 |
| 2 | 11 | 14 | 19 |
| 2 | 12 | 14 | 19 |
| 2 | 13 | 14 | 19 |
| 3 | 10 | 14 | 19 |
| 3 | 11 | 14 | 19 |
| 3 | 12 | 14 | 19 |
| 3 | 13 | 14 | 19 |
| 4 | 10 | 14 | 19 |
| 4 | 11 | 14 | 19 |
| 4 | 12 | 14 | 19 |
| 4 | 13 | 14 | 19 |
| 5 | 10 | 14 | 19 |
| 5 | 11 | 14 | 19 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 5 | 12 | 14 | 19 |
| 5 | 13 | 14 | 19 |
| 1 | 10 | 15 | 19 |
| 1 | 11 | 15 | 19 |
| 1 | 12 | 15 | 19 |
| 1 | 13 | 15 | 19 |
| 2 | 10 | 15 | 19 |
| 2 | 11 | 15 | 19 |
| 2 | 12 | 15 | 19 |
| 2 | 13 | 15 | 19 |
| 3 | 10 | 15 | 19 |
| 3 | 11 | 15 | 19 |
| 3 | 12 | 15 | 19 |
| 3 | 13 | 15 | 19 |
| 4 | 10 | 15 | 19 |
| 4 | 11 | 15 | 19 |
| 4 | 12 | 15 | 19 |
| 4 | 13 | 15 | 19 |
| 5 | 10 | 15 | 19 |
| 5 | 11 | 15 | 19 |
| 5 | 12 | 15 | 19 |
| 5 | 13 | 15 | 19 |
| 1 | 10 | 16 | 19 |
| 1 | 11 | 16 | 19 |
| 1 | 12 | 16 | 19 |
| 1 | 13 | 16 | 19 |
| 2 | 10 | 16 | 19 |
| 2 | 11 | 16 | 19 |
| 2 | 12 | 16 | 19 |
| 2 | 13 | 16 | 19 |
| 3 | 10 | 16 | 19 |
| 3 | 11 | 16 | 19 |
| 3 | 12 | 16 | 19 |
| 3 | 13 | 16 | 19 |
| 4 | 10 | 16 | 19 |
| 4 | 11 | 16 | 19 |
| 4 | 12 | 16 | 19 |
| 4 | 13 | 16 | 19 |
| 5 | 10 | 16 | 19 |
| 5 | 11 | 16 | 19 |
| 5 | 12 | 16 | 19 |
| 5 | 13 | 16 | 19 |
| 1 | 10 | 17 | 19 |
| 1 | 11 | 17 | 19 |
| 1 | 12 | 17 | 19 |
| 1 | 13 | 17 | 19 |
| 2 | 10 | 17 | 19 |
| 2 | 11 | 17 | 19 |
| 2 | 12 | 17 | 19 |
| 2 | 13 | 17 | 19 |
| 3 | 10 | 17 | 19 |
| 3 | 11 | 17 | 19 |
| 3 | 12 | 17 | 19 |
| 3 | 13 | 17 | 19 |
| 4 | 10 | 17 | 19 |
| 4 | 11 | 17 | 19 |
| 4 | 12 | 17 | 19 |
| 4 | 13 | 17 | 19 |
| 5 | 10 | 17 | 19 |
| 5 | 11 | 17 | 19 |
| 5 | 12 | 17 | 19 |
| 5 | 13 | 17 | 19 |
| 1 | 10 | 14 | 20 |
| 1 | 11 | 14 | 20 |
| 1 | 12 | 14 | 20 |
| 1 | 13 | 14 | 20 |
| 2 | 10 | 14 | 20 |
| 2 | 11 | 14 | 20 |
| 2 | 12 | 14 | 20 |
| 2 | 13 | 14 | 20 |
| 3 | 10 | 14 | 20 |
| 3 | 11 | 14 | 20 |
| 3 | 12 | 14 | 20 |
| 3 | 13 | 14 | 20 |
| 4 | 10 | 14 | 20 |
| 4 | 11 | 14 | 20 |
| 4 | 12 | 14 | 20 |
| 4 | 13 | 14 | 20 |
| 5 | 10 | 14 | 20 |
| 5 | 11 | 14 | 20 |
| 5 | 12 | 14 | 20 |
| 5 | 13 | 14 | 20 |
| 1 | 10 | 15 | 20 |
| 1 | 11 | 15 | 20 |
| 1 | 12 | 15 | 20 |
| 1 | 13 | 15 | 20 |
| 2 | 10 | 15 | 20 |
| 2 | 11 | 15 | 20 |
| 2 | 12 | 15 | 20 |
| 2 | 13 | 15 | 20 |
| 3 | 10 | 15 | 20 |
| 3 | 11 | 15 | 20 |
| 3 | 12 | 15 | 20 |
| 3 | 13 | 15 | 20 |
| 4 | 10 | 15 | 20 |
| 4 | 11 | 15 | 20 |
| 4 | 12 | 15 | 20 |
| 4 | 13 | 15 | 20 |
| 5 | 10 | 15 | 20 |
| 5 | 11 | 15 | 20 |
| 5 | 12 | 15 | 20 |
| 5 | 13 | 15 | 20 |
| 1 | 10 | 16 | 20 |
| 1 | 11 | 16 | 20 |
| 1 | 12 | 16 | 20 |
| 1 | 13 | 16 | 20 |
| 2 | 10 | 16 | 20 |
| 2 | 11 | 16 | 20 |
| 2 | 12 | 16 | 20 |
| 2 | 13 | 16 | 20 |
| 3 | 10 | 16 | 20 |
| 3 | 11 | 16 | 20 |
| 3 | 12 | 16 | 20 |
| 3 | 13 | 16 | 20 |
| 4 | 10 | 16 | 20 |
| 4 | 11 | 16 | 20 |
| 4 | 12 | 16 | 20 |
| 4 | 13 | 16 | 20 |
| 5 | 10 | 16 | 20 |
| 5 | 11 | 16 | 20 |
| 5 | 12 | 16 | 20 |
| 5 | 13 | 16 | 20 |
| 1 | 10 | 17 | 20 |
| 1 | 11 | 17 | 20 |
| 1 | 12 | 17 | 20 |
| 1 | 13 | 17 | 20 |
| 2 | 10 | 17 | 20 |
| 2 | 11 | 17 | 20 |
| 2 | 12 | 17 | 20 |
| 2 | 13 | 17 | 20 |
| 3 | 10 | 17 | 20 |
| 3 | 11 | 17 | 20 |
| 3 | 12 | 17 | 20 |
| 3 | 13 | 17 | 20 |
| 4 | 10 | 17 | 20 |
| 4 | 11 | 17 | 20 |
| 4 | 12 | 17 | 20 |
| 4 | 13 | 17 | 20 |
| 5 | 10 | 17 | 20 |
| 5 | 11 | 17 | 20 |
| 5 | 12 | 17 | 20 |
| 5 | 13 | 17 | 20 |
| 1 | 10 | 14 | 21 |
| 1 | 11 | 14 | 21 |
| 1 | 12 | 14 | 21 |
| 1 | 13 | 14 | 21 |
| 2 | 10 | 14 | 21 |
| 2 | 11 | 14 | 21 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 2 | 12 | 14 | 21 |
| 2 | 13 | 14 | 21 |
| 3 | 10 | 14 | 21 |
| 3 | 11 | 14 | 21 |
| 3 | 12 | 14 | 21 |
| 3 | 13 | 14 | 21 |
| 4 | 10 | 14 | 21 |
| 4 | 11 | 14 | 21 |
| 4 | 12 | 14 | 21 |
| 4 | 13 | 14 | 21 |
| 5 | 10 | 14 | 21 |
| 5 | 11 | 14 | 21 |
| 5 | 12 | 14 | 21 |
| 5 | 13 | 14 | 21 |
| 1 | 10 | 15 | 21 |
| 1 | 11 | 15 | 21 |
| 1 | 12 | 15 | 21 |
| 1 | 13 | 15 | 21 |
| 2 | 10 | 15 | 21 |
| 2 | 11 | 15 | 21 |
| 2 | 12 | 15 | 21 |
| 2 | 13 | 15 | 21 |
| 3 | 10 | 15 | 21 |
| 3 | 11 | 15 | 21 |
| 3 | 12 | 15 | 21 |
| 3 | 13 | 15 | 21 |
| 4 | 10 | 15 | 21 |
| 4 | 11 | 15 | 21 |
| 4 | 12 | 15 | 21 |
| 4 | 13 | 15 | 21 |
| 5 | 10 | 15 | 21 |
| 5 | 11 | 15 | 21 |
| 5 | 12 | 15 | 21 |
| 5 | 13 | 15 | 21 |
| 1 | 10 | 16 | 21 |
| 1 | 11 | 16 | 21 |
| 1 | 12 | 16 | 21 |
| 1 | 13 | 16 | 21 |
| 2 | 10 | 16 | 21 |
| 2 | 11 | 16 | 21 |
| 2 | 12 | 16 | 21 |
| 2 | 13 | 16 | 21 |
| 3 | 10 | 16 | 21 |
| 3 | 11 | 16 | 21 |
| 3 | 12 | 16 | 21 |
| 3 | 13 | 16 | 21 |
| 4 | 10 | 16 | 21 |
| 4 | 11 | 16 | 21 |
| 4 | 12 | 16 | 21 |
| 4 | 13 | 16 | 21 |
| 5 | 10 | 16 | 21 |
| 5 | 11 | 16 | 21 |
| 5 | 12 | 16 | 21 |
| 5 | 13 | 16 | 21 |
| 1 | 10 | 17 | 21 |
| 1 | 11 | 17 | 21 |
| 1 | 12 | 17 | 21 |
| 1 | 13 | 17 | 21 |
| 2 | 10 | 17 | 21 |
| 2 | 11 | 17 | 21 |
| 2 | 12 | 17 | 21 |
| 2 | 13 | 17 | 21 |
| 3 | 10 | 17 | 21 |
| 3 | 11 | 17 | 21 |
| 3 | 12 | 17 | 21 |
| 3 | 13 | 17 | 21 |
| 4 | 10 | 17 | 21 |
| 4 | 11 | 17 | 21 |
| 4 | 12 | 17 | 21 |
| 4 | 13 | 17 | 21 |
| 5 | 10 | 17 | 21 |
| 5 | 11 | 17 | 21 |
| 5 | 12 | 17 | 21 |
| 5 | 13 | 17 | 21 |
| 6 | 10 | 14 | 18 |
| 6 | 11 | 14 | 18 |
| 6 | 12 | 14 | 18 |
| 6 | 13 | 14 | 18 |
| 7 | 10 | 14 | 18 |
| 7 | 11 | 14 | 18 |
| 7 | 12 | 14 | 18 |
| 7 | 13 | 14 | 18 |
| 8 | 10 | 14 | 18 |
| 8 | 11 | 14 | 18 |
| 8 | 12 | 14 | 18 |
| 8 | 13 | 14 | 18 |
| 9 | 10 | 14 | 18 |
| 9 | 11 | 14 | 18 |
| 9 | 12 | 14 | 18 |
| 9 | 13 | 14 | 18 |
| 6 | 10 | 15 | 18 |
| 6 | 11 | 15 | 18 |
| 6 | 12 | 15 | 18 |
| 6 | 13 | 15 | 18 |
| 7 | 10 | 15 | 18 |
| 7 | 11 | 15 | 18 |
| 7 | 12 | 15 | 18 |
| 7 | 13 | 15 | 18 |
| 8 | 10 | 15 | 18 |
| 8 | 11 | 15 | 18 |
| 8 | 12 | 15 | 18 |
| 8 | 13 | 15 | 18 |
| 9 | 10 | 15 | 18 |
| 9 | 11 | 15 | 18 |
| 9 | 12 | 15 | 18 |
| 9 | 13 | 15 | 18 |
| 6 | 10 | 16 | 18 |
| 6 | 11 | 16 | 18 |
| 6 | 12 | 16 | 18 |
| 6 | 13 | 16 | 18 |
| 7 | 10 | 16 | 18 |
| 7 | 11 | 16 | 18 |
| 7 | 12 | 16 | 18 |
| 7 | 13 | 16 | 18 |
| 8 | 10 | 16 | 18 |
| 8 | 11 | 16 | 18 |
| 8 | 12 | 16 | 18 |
| 8 | 13 | 16 | 18 |
| 9 | 10 | 16 | 18 |
| 9 | 11 | 16 | 18 |
| 9 | 12 | 16 | 18 |
| 9 | 13 | 16 | 18 |
| 6 | 10 | 17 | 18 |
| 6 | 11 | 17 | 18 |
| 6 | 12 | 17 | 18 |
| 6 | 13 | 17 | 18 |
| 7 | 10 | 17 | 18 |
| 7 | 11 | 17 | 18 |
| 7 | 12 | 17 | 18 |
| 7 | 13 | 17 | 18 |
| 8 | 10 | 17 | 18 |
| 8 | 11 | 17 | 18 |
| 8 | 12 | 17 | 18 |
| 8 | 13 | 17 | 18 |
| 9 | 10 | 17 | 18 |
| 9 | 11 | 17 | 18 |
| 9 | 12 | 17 | 18 |
| 9 | 13 | 17 | 18 |
| 6 | 10 | 14 | 19 |
| 6 | 11 | 14 | 19 |
| 6 | 12 | 14 | 19 |
| 6 | 13 | 14 | 19 |
| 7 | 10 | 14 | 19 |
| 7 | 11 | 14 | 19 |
| 7 | 12 | 14 | 19 |
| 7 | 13 | 14 | 19 |
| 8 | 10 | 14 | 19 |
| 8 | 11 | 14 | 19 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 8 | 12 | 14 | 19 |
| 8 | 13 | 14 | 19 |
| 9 | 10 | 14 | 19 |
| 9 | 11 | 14 | 19 |
| 9 | 12 | 14 | 19 |
| 9 | 13 | 14 | 19 |
| 6 | 10 | 15 | 19 |
| 6 | 11 | 15 | 19 |
| 6 | 12 | 15 | 19 |
| 6 | 13 | 15 | 19 |
| 7 | 10 | 15 | 19 |
| 7 | 11 | 15 | 19 |
| 7 | 12 | 15 | 19 |
| 7 | 13 | 15 | 19 |
| 8 | 10 | 15 | 19 |
| 8 | 11 | 15 | 19 |
| 8 | 12 | 15 | 19 |
| 8 | 13 | 15 | 19 |
| 9 | 10 | 15 | 19 |
| 9 | 11 | 15 | 19 |
| 9 | 12 | 15 | 19 |
| 9 | 13 | 15 | 19 |
| 6 | 10 | 16 | 19 |
| 6 | 11 | 16 | 19 |
| 6 | 12 | 16 | 19 |
| 6 | 13 | 16 | 19 |
| 7 | 10 | 16 | 19 |
| 7 | 11 | 16 | 19 |
| 7 | 12 | 16 | 19 |
| 7 | 13 | 16 | 19 |
| 8 | 10 | 16 | 19 |
| 8 | 11 | 16 | 19 |
| 8 | 12 | 16 | 19 |
| 8 | 13 | 16 | 19 |
| 9 | 10 | 16 | 19 |
| 9 | 11 | 16 | 19 |
| 9 | 12 | 16 | 19 |
| 9 | 13 | 16 | 19 |
| 6 | 10 | 17 | 19 |
| 6 | 11 | 17 | 19 |
| 6 | 12 | 17 | 19 |
| 6 | 13 | 17 | 19 |
| 7 | 10 | 17 | 19 |
| 7 | 11 | 17 | 19 |
| 7 | 12 | 17 | 19 |
| 7 | 13 | 17 | 19 |
| 8 | 10 | 17 | 19 |
| 8 | 11 | 17 | 19 |
| 8 | 12 | 17 | 19 |
| 8 | 13 | 17 | 19 |
| 9 | 10 | 17 | 19 |
| 9 | 11 | 17 | 19 |
| 9 | 12 | 17 | 19 |
| 9 | 13 | 17 | 19 |
| 6 | 10 | 14 | 20 |
| 6 | 11 | 14 | 20 |
| 6 | 12 | 14 | 20 |
| 6 | 13 | 14 | 20 |
| 7 | 10 | 14 | 20 |
| 7 | 11 | 14 | 20 |
| 7 | 12 | 14 | 20 |
| 7 | 13 | 14 | 20 |
| 8 | 10 | 14 | 20 |
| 8 | 11 | 14 | 20 |
| 8 | 12 | 14 | 20 |
| 8 | 13 | 14 | 20 |
| 9 | 10 | 14 | 20 |
| 9 | 11 | 14 | 20 |
| 9 | 12 | 14 | 20 |
| 9 | 13 | 14 | 20 |
| 6 | 10 | 15 | 20 |
| 6 | 11 | 15 | 20 |
| 6 | 12 | 15 | 20 |
| 6 | 13 | 15 | 20 |
| 7 | 10 | 15 | 20 |
| 7 | 11 | 15 | 20 |
| 7 | 12 | 15 | 20 |
| 7 | 13 | 15 | 20 |
| 8 | 10 | 15 | 20 |
| 8 | 11 | 15 | 20 |
| 8 | 12 | 15 | 20 |
| 8 | 13 | 15 | 20 |
| 9 | 10 | 15 | 20 |
| 9 | 11 | 15 | 20 |
| 9 | 12 | 15 | 20 |
| 9 | 13 | 15 | 20 |
| 6 | 10 | 16 | 20 |
| 6 | 11 | 16 | 20 |
| 6 | 12 | 16 | 20 |
| 6 | 13 | 16 | 20 |
| 7 | 10 | 16 | 20 |
| 7 | 11 | 16 | 20 |
| 7 | 12 | 16 | 20 |
| 7 | 13 | 16 | 20 |
| 8 | 10 | 16 | 20 |
| 8 | 11 | 16 | 20 |
| 8 | 12 | 16 | 20 |
| 8 | 13 | 16 | 20 |
| 9 | 10 | 16 | 20 |
| 9 | 11 | 16 | 20 |
| 9 | 12 | 16 | 20 |
| 9 | 13 | 16 | 20 |
| 6 | 10 | 17 | 20 |
| 6 | 11 | 17 | 20 |
| 6 | 12 | 17 | 20 |
| 6 | 13 | 17 | 20 |
| 7 | 10 | 17 | 20 |
| 7 | 11 | 17 | 20 |
| 7 | 12 | 17 | 20 |
| 7 | 13 | 17 | 20 |
| 8 | 10 | 17 | 20 |
| 8 | 11 | 17 | 20 |
| 8 | 12 | 17 | 20 |
| 8 | 13 | 17 | 20 |
| 9 | 10 | 17 | 20 |
| 9 | 11 | 17 | 20 |
| 9 | 12 | 17 | 20 |
| 9 | 13 | 17 | 20 |
| 6 | 10 | 14 | 21 |
| 6 | 11 | 14 | 21 |
| 6 | 12 | 14 | 21 |
| 6 | 13 | 14 | 21 |
| 7 | 10 | 14 | 21 |
| 7 | 11 | 14 | 21 |
| 7 | 12 | 14 | 21 |
| 7 | 13 | 14 | 21 |
| 8 | 10 | 14 | 21 |
| 8 | 11 | 14 | 21 |
| 8 | 12 | 14 | 21 |
| 8 | 13 | 14 | 21 |
| 9 | 10 | 14 | 21 |
| 9 | 11 | 14 | 21 |
| 9 | 12 | 14 | 21 |
| 9 | 13 | 14 | 21 |
| 6 | 10 | 15 | 21 |
| 6 | 11 | 15 | 21 |
| 6 | 12 | 15 | 21 |
| 6 | 13 | 15 | 21 |
| 7 | 10 | 15 | 21 |
| 7 | 11 | 15 | 21 |
| 7 | 12 | 15 | 21 |
| 7 | 13 | 15 | 21 |
| 8 | 10 | 15 | 21 |
| 8 | 11 | 15 | 21 |
| 8 | 12 | 15 | 21 |
| 8 | 13 | 15 | 21 |
| 9 | 10 | 15 | 21 |
| 9 | 11 | 15 | 21 |

TABLE 5-continued

Four-way combinations of hematopoietic stem cell population parameters for assessment

| First Parameter No. | Second Parameter No. | Third Parameter No. | Fourth Parameter No. |
|---|---|---|---|
| 9 | 12 | 15 | 21 |
| 9 | 13 | 15 | 21 |
| 6 | 10 | 16 | 21 |
| 6 | 11 | 16 | 21 |
| 6 | 12 | 16 | 21 |
| 6 | 13 | 16 | 21 |
| 7 | 10 | 16 | 21 |
| 7 | 11 | 16 | 21 |
| 7 | 12 | 16 | 21 |
| 7 | 13 | 16 | 21 |
| 8 | 10 | 16 | 21 |
| 8 | 11 | 16 | 21 |
| 8 | 12 | 16 | 21 |
| 8 | 13 | 16 | 21 |
| 9 | 10 | 16 | 21 |
| 9 | 11 | 16 | 21 |
| 9 | 12 | 16 | 21 |
| 9 | 13 | 16 | 21 |
| 6 | 10 | 17 | 21 |
| 6 | 11 | 17 | 21 |
| 6 | 12 | 17 | 21 |
| 6 | 13 | 17 | 21 |
| 7 | 10 | 17 | 21 |
| 7 | 11 | 17 | 21 |
| 7 | 12 | 17 | 21 |
| 7 | 13 | 17 | 21 |
| 8 | 10 | 17 | 21 |
| 8 | 11 | 17 | 21 |
| 8 | 12 | 17 | 21 |
| 8 | 13 | 17 | 21 |
| 9 | 10 | 17 | 21 |
| 9 | 11 | 17 | 21 |
| 9 | 12 | 17 | 21 |
| 9 | 13 | 17 | 21 |

TABLE 6

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 1 | 6 | 10 | 14 | 18 |
| 1 | 7 | 10 | 14 | 18 |
| 1 | 8 | 10 | 14 | 18 |
| 1 | 9 | 10 | 14 | 18 |
| 2 | 6 | 10 | 14 | 18 |
| 2 | 7 | 10 | 14 | 18 |
| 2 | 8 | 10 | 14 | 18 |
| 2 | 9 | 10 | 14 | 18 |
| 3 | 6 | 10 | 14 | 18 |
| 3 | 7 | 10 | 14 | 18 |
| 3 | 8 | 10 | 14 | 18 |
| 3 | 9 | 10 | 14 | 18 |
| 4 | 6 | 10 | 14 | 18 |
| 4 | 7 | 10 | 14 | 18 |
| 4 | 8 | 10 | 14 | 18 |
| 4 | 9 | 10 | 14 | 18 |
| 5 | 6 | 10 | 14 | 18 |
| 5 | 7 | 10 | 14 | 18 |
| 5 | 8 | 10 | 14 | 18 |
| 5 | 9 | 10 | 14 | 18 |
| 1 | 6 | 11 | 14 | 18 |
| 1 | 7 | 11 | 14 | 18 |
| 1 | 8 | 11 | 14 | 18 |
| 1 | 9 | 11 | 14 | 18 |
| 2 | 6 | 11 | 14 | 18 |
| 2 | 7 | 11 | 14 | 18 |
| 2 | 8 | 11 | 14 | 18 |
| 2 | 9 | 11 | 14 | 18 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 3 | 6 | 11 | 14 | 18 |
| 3 | 7 | 11 | 14 | 18 |
| 3 | 8 | 11 | 14 | 18 |
| 3 | 9 | 11 | 14 | 18 |
| 4 | 6 | 11 | 14 | 18 |
| 4 | 7 | 11 | 14 | 18 |
| 4 | 8 | 11 | 14 | 18 |
| 4 | 9 | 11 | 14 | 18 |
| 5 | 6 | 11 | 14 | 18 |
| 5 | 7 | 11 | 14 | 18 |
| 5 | 8 | 11 | 14 | 18 |
| 5 | 9 | 11 | 14 | 18 |
| 1 | 6 | 12 | 14 | 18 |
| 1 | 7 | 12 | 14 | 18 |
| 1 | 8 | 12 | 14 | 18 |
| 1 | 9 | 12 | 14 | 18 |
| 2 | 6 | 12 | 14 | 18 |
| 2 | 7 | 12 | 14 | 18 |
| 2 | 8 | 12 | 14 | 18 |
| 2 | 9 | 12 | 14 | 18 |
| 3 | 6 | 12 | 14 | 18 |
| 3 | 7 | 12 | 14 | 18 |
| 3 | 8 | 12 | 14 | 18 |
| 3 | 9 | 12 | 14 | 18 |
| 4 | 6 | 12 | 14 | 18 |
| 4 | 7 | 12 | 14 | 18 |
| 4 | 8 | 12 | 14 | 18 |
| 4 | 9 | 12 | 14 | 18 |
| 5 | 6 | 12 | 14 | 18 |
| 5 | 7 | 12 | 14 | 18 |
| 5 | 8 | 12 | 14 | 18 |
| 5 | 9 | 12 | 14 | 18 |
| 1 | 6 | 13 | 14 | 18 |
| 1 | 7 | 13 | 14 | 18 |
| 1 | 8 | 13 | 14 | 18 |
| 1 | 9 | 13 | 14 | 18 |
| 2 | 6 | 13 | 14 | 18 |
| 2 | 7 | 13 | 14 | 18 |
| 2 | 8 | 13 | 14 | 18 |
| 2 | 9 | 13 | 14 | 18 |
| 3 | 6 | 13 | 14 | 18 |
| 3 | 7 | 13 | 14 | 18 |
| 3 | 8 | 13 | 14 | 18 |
| 3 | 9 | 13 | 14 | 18 |
| 4 | 6 | 13 | 14 | 18 |
| 4 | 7 | 13 | 14 | 18 |
| 4 | 8 | 13 | 14 | 18 |
| 4 | 9 | 13 | 14 | 18 |
| 5 | 6 | 13 | 14 | 18 |
| 5 | 7 | 13 | 14 | 18 |
| 5 | 8 | 13 | 14 | 18 |
| 5 | 9 | 13 | 14 | 18 |
| 1 | 6 | 10 | 15 | 18 |
| 1 | 7 | 10 | 15 | 18 |
| 1 | 8 | 10 | 15 | 18 |
| 1 | 9 | 10 | 15 | 18 |
| 2 | 6 | 10 | 15 | 18 |
| 2 | 7 | 10 | 15 | 18 |
| 2 | 8 | 10 | 15 | 18 |
| 2 | 9 | 10 | 15 | 18 |
| 3 | 6 | 10 | 15 | 18 |
| 3 | 7 | 10 | 15 | 18 |
| 3 | 8 | 10 | 15 | 18 |
| 3 | 9 | 10 | 15 | 18 |
| 4 | 6 | 10 | 15 | 18 |
| 4 | 7 | 10 | 15 | 18 |
| 4 | 8 | 10 | 15 | 18 |
| 4 | 9 | 10 | 15 | 18 |
| 5 | 6 | 10 | 15 | 18 |
| 5 | 7 | 10 | 15 | 18 |
| 5 | 8 | 10 | 15 | 18 |
| 5 | 9 | 10 | 15 | 18 |
| 1 | 6 | 11 | 15 | 18 |
| 1 | 7 | 11 | 15 | 18 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 1 | 8 | 11 | 15 | 18 |
| 1 | 9 | 11 | 15 | 18 |
| 2 | 6 | 11 | 15 | 18 |
| 2 | 7 | 11 | 15 | 18 |
| 2 | 8 | 11 | 15 | 18 |
| 2 | 9 | 11 | 15 | 18 |
| 3 | 6 | 11 | 15 | 18 |
| 3 | 7 | 11 | 15 | 18 |
| 3 | 8 | 11 | 15 | 18 |
| 3 | 9 | 11 | 15 | 18 |
| 4 | 6 | 11 | 15 | 18 |
| 4 | 7 | 11 | 15 | 18 |
| 4 | 8 | 11 | 15 | 18 |
| 4 | 9 | 11 | 15 | 18 |
| 5 | 6 | 11 | 15 | 18 |
| 5 | 7 | 11 | 15 | 18 |
| 5 | 8 | 11 | 15 | 18 |
| 5 | 9 | 11 | 15 | 18 |
| 1 | 6 | 12 | 15 | 18 |
| 1 | 7 | 12 | 15 | 18 |
| 1 | 8 | 12 | 15 | 18 |
| 1 | 9 | 12 | 15 | 18 |
| 2 | 6 | 12 | 15 | 18 |
| 2 | 7 | 12 | 15 | 18 |
| 2 | 8 | 12 | 15 | 18 |
| 2 | 9 | 12 | 15 | 18 |
| 3 | 6 | 12 | 15 | 18 |
| 3 | 7 | 12 | 15 | 18 |
| 3 | 8 | 12 | 15 | 18 |
| 3 | 9 | 12 | 15 | 18 |
| 4 | 6 | 12 | 15 | 18 |
| 4 | 7 | 12 | 15 | 18 |
| 4 | 8 | 12 | 15 | 18 |
| 4 | 9 | 12 | 15 | 18 |
| 5 | 6 | 12 | 15 | 18 |
| 5 | 7 | 12 | 15 | 18 |
| 5 | 8 | 12 | 15 | 18 |
| 5 | 9 | 12 | 15 | 18 |
| 1 | 6 | 13 | 15 | 18 |
| 1 | 7 | 13 | 15 | 18 |
| 1 | 8 | 13 | 15 | 18 |
| 1 | 9 | 13 | 15 | 18 |
| 2 | 6 | 13 | 15 | 18 |
| 2 | 7 | 13 | 15 | 18 |
| 2 | 8 | 13 | 15 | 18 |
| 2 | 9 | 13 | 15 | 18 |
| 3 | 6 | 13 | 15 | 18 |
| 3 | 7 | 13 | 15 | 18 |
| 3 | 8 | 13 | 15 | 18 |
| 3 | 9 | 13 | 15 | 18 |
| 4 | 6 | 13 | 15 | 18 |
| 4 | 7 | 13 | 15 | 18 |
| 4 | 8 | 13 | 15 | 18 |
| 4 | 9 | 13 | 15 | 18 |
| 5 | 6 | 13 | 15 | 18 |
| 5 | 7 | 13 | 15 | 18 |
| 5 | 8 | 13 | 15 | 18 |
| 5 | 9 | 13 | 15 | 18 |
| 1 | 6 | 10 | 16 | 18 |
| 1 | 7 | 10 | 16 | 18 |
| 1 | 8 | 10 | 16 | 18 |
| 1 | 9 | 10 | 16 | 18 |
| 2 | 6 | 10 | 16 | 18 |
| 2 | 7 | 10 | 16 | 18 |
| 2 | 8 | 10 | 16 | 18 |
| 2 | 9 | 10 | 16 | 18 |
| 3 | 6 | 10 | 16 | 18 |
| 3 | 7 | 10 | 16 | 18 |
| 3 | 8 | 10 | 16 | 18 |
| 3 | 9 | 10 | 16 | 18 |
| 4 | 6 | 10 | 16 | 18 |
| 4 | 7 | 10 | 16 | 18 |
| 4 | 8 | 10 | 16 | 18 |
| 4 | 9 | 10 | 16 | 18 |
| 5 | 6 | 10 | 16 | 18 |
| 5 | 7 | 10 | 16 | 18 |
| 5 | 8 | 10 | 16 | 18 |
| 5 | 9 | 10 | 16 | 18 |
| 1 | 6 | 11 | 16 | 18 |
| 1 | 7 | 11 | 16 | 18 |
| 1 | 8 | 11 | 16 | 18 |
| 1 | 9 | 11 | 16 | 18 |
| 2 | 6 | 11 | 16 | 18 |
| 2 | 7 | 11 | 16 | 18 |
| 2 | 8 | 11 | 16 | 18 |
| 2 | 9 | 11 | 16 | 18 |
| 3 | 6 | 11 | 16 | 18 |
| 3 | 7 | 11 | 16 | 18 |
| 3 | 8 | 11 | 16 | 18 |
| 3 | 9 | 11 | 16 | 18 |
| 4 | 6 | 11 | 16 | 18 |
| 4 | 7 | 11 | 16 | 18 |
| 4 | 8 | 11 | 16 | 18 |
| 4 | 9 | 11 | 16 | 18 |
| 5 | 6 | 11 | 16 | 18 |
| 5 | 7 | 11 | 16 | 18 |
| 5 | 8 | 11 | 16 | 18 |
| 5 | 9 | 11 | 16 | 18 |
| 1 | 6 | 12 | 16 | 18 |
| 1 | 7 | 12 | 16 | 18 |
| 1 | 8 | 12 | 16 | 18 |
| 1 | 9 | 12 | 16 | 18 |
| 2 | 6 | 12 | 16 | 18 |
| 2 | 7 | 12 | 16 | 18 |
| 2 | 8 | 12 | 16 | 18 |
| 2 | 9 | 12 | 16 | 18 |
| 3 | 6 | 12 | 16 | 18 |
| 3 | 7 | 12 | 16 | 18 |
| 3 | 8 | 12 | 16 | 18 |
| 3 | 9 | 12 | 16 | 18 |
| 4 | 6 | 12 | 16 | 18 |
| 4 | 7 | 12 | 16 | 18 |
| 4 | 8 | 12 | 16 | 18 |
| 4 | 9 | 12 | 16 | 18 |
| 5 | 6 | 12 | 16 | 18 |
| 5 | 7 | 12 | 16 | 18 |
| 5 | 8 | 12 | 16 | 18 |
| 5 | 9 | 12 | 16 | 18 |
| 1 | 6 | 13 | 16 | 18 |
| 1 | 7 | 13 | 16 | 18 |
| 1 | 8 | 13 | 16 | 18 |
| 1 | 9 | 13 | 16 | 18 |
| 2 | 6 | 13 | 16 | 18 |
| 2 | 7 | 13 | 16 | 18 |
| 2 | 8 | 13 | 16 | 18 |
| 2 | 9 | 13 | 16 | 18 |
| 3 | 6 | 13 | 16 | 18 |
| 3 | 7 | 13 | 16 | 18 |
| 3 | 8 | 13 | 16 | 18 |
| 3 | 9 | 13 | 16 | 18 |
| 4 | 6 | 13 | 16 | 18 |
| 4 | 7 | 13 | 16 | 18 |
| 4 | 8 | 13 | 16 | 18 |
| 4 | 9 | 13 | 16 | 18 |
| 5 | 6 | 13 | 16 | 18 |
| 5 | 7 | 13 | 16 | 18 |
| 5 | 8 | 13 | 16 | 18 |
| 5 | 9 | 13 | 16 | 18 |
| 1 | 6 | 10 | 17 | 18 |
| 1 | 7 | 10 | 17 | 18 |
| 1 | 8 | 10 | 17 | 18 |
| 1 | 9 | 10 | 17 | 18 |
| 2 | 6 | 10 | 17 | 18 |
| 2 | 7 | 10 | 17 | 18 |
| 2 | 8 | 10 | 17 | 18 |
| 2 | 9 | 10 | 17 | 18 |
| 3 | 6 | 10 | 17 | 18 |
| 3 | 7 | 10 | 17 | 18 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 3 | 8 | 10 | 17 | 18 |
| 3 | 9 | 10 | 17 | 18 |
| 4 | 6 | 10 | 17 | 18 |
| 4 | 7 | 10 | 17 | 18 |
| 4 | 8 | 10 | 17 | 18 |
| 4 | 9 | 10 | 17 | 18 |
| 5 | 6 | 10 | 17 | 18 |
| 5 | 7 | 10 | 17 | 18 |
| 5 | 8 | 10 | 17 | 18 |
| 5 | 9 | 10 | 17 | 18 |
| 1 | 6 | 11 | 17 | 18 |
| 1 | 7 | 11 | 17 | 18 |
| 1 | 8 | 11 | 17 | 18 |
| 1 | 9 | 11 | 17 | 18 |
| 2 | 6 | 11 | 17 | 18 |
| 2 | 7 | 11 | 17 | 18 |
| 2 | 8 | 11 | 17 | 18 |
| 2 | 9 | 11 | 17 | 18 |
| 3 | 6 | 11 | 17 | 18 |
| 3 | 7 | 11 | 17 | 18 |
| 3 | 8 | 11 | 17 | 18 |
| 3 | 9 | 11 | 17 | 18 |
| 4 | 6 | 11 | 17 | 18 |
| 4 | 7 | 11 | 17 | 18 |
| 4 | 8 | 11 | 17 | 18 |
| 4 | 9 | 11 | 17 | 18 |
| 5 | 6 | 11 | 17 | 18 |
| 5 | 7 | 11 | 17 | 18 |
| 5 | 8 | 11 | 17 | 18 |
| 5 | 9 | 11 | 17 | 18 |
| 1 | 6 | 12 | 17 | 18 |
| 1 | 7 | 12 | 17 | 18 |
| 1 | 8 | 12 | 17 | 18 |
| 1 | 9 | 12 | 17 | 18 |
| 2 | 6 | 12 | 17 | 18 |
| 2 | 7 | 12 | 17 | 18 |
| 2 | 8 | 12 | 17 | 18 |
| 2 | 9 | 12 | 17 | 18 |
| 3 | 6 | 12 | 17 | 18 |
| 3 | 7 | 12 | 17 | 18 |
| 3 | 8 | 12 | 17 | 18 |
| 3 | 9 | 12 | 17 | 18 |
| 4 | 6 | 12 | 17 | 18 |
| 4 | 7 | 12 | 17 | 18 |
| 4 | 8 | 12 | 17 | 18 |
| 4 | 9 | 12 | 17 | 18 |
| 5 | 6 | 12 | 17 | 18 |
| 5 | 7 | 12 | 17 | 18 |
| 5 | 8 | 12 | 17 | 18 |
| 5 | 9 | 12 | 17 | 18 |
| 1 | 6 | 13 | 17 | 18 |
| 1 | 7 | 13 | 17 | 18 |
| 1 | 8 | 13 | 17 | 18 |
| 1 | 9 | 13 | 17 | 18 |
| 2 | 6 | 13 | 17 | 18 |
| 2 | 7 | 13 | 17 | 18 |
| 2 | 8 | 13 | 17 | 18 |
| 2 | 9 | 13 | 17 | 18 |
| 3 | 6 | 13 | 17 | 18 |
| 3 | 7 | 13 | 17 | 18 |
| 3 | 8 | 13 | 17 | 18 |
| 3 | 9 | 13 | 17 | 18 |
| 4 | 6 | 13 | 17 | 18 |
| 4 | 7 | 13 | 17 | 18 |
| 4 | 8 | 13 | 17 | 18 |
| 4 | 9 | 13 | 17 | 18 |
| 5 | 6 | 13 | 17 | 18 |
| 5 | 7 | 13 | 17 | 18 |
| 5 | 8 | 13 | 17 | 18 |
| 5 | 9 | 13 | 17 | 18 |
| 1 | 6 | 10 | 14 | 19 |
| 1 | 7 | 10 | 14 | 19 |
| 1 | 8 | 10 | 14 | 19 |
| 1 | 9 | 10 | 14 | 19 |
| 2 | 6 | 10 | 14 | 19 |
| 2 | 7 | 10 | 14 | 19 |
| 2 | 8 | 10 | 14 | 19 |
| 2 | 9 | 10 | 14 | 19 |
| 3 | 6 | 10 | 14 | 19 |
| 3 | 7 | 10 | 14 | 19 |
| 3 | 8 | 10 | 14 | 19 |
| 3 | 9 | 10 | 14 | 19 |
| 4 | 6 | 10 | 14 | 19 |
| 4 | 7 | 10 | 14 | 19 |
| 4 | 8 | 10 | 14 | 19 |
| 4 | 9 | 10 | 14 | 19 |
| 5 | 6 | 10 | 14 | 19 |
| 5 | 7 | 10 | 14 | 19 |
| 5 | 8 | 10 | 14 | 19 |
| 5 | 9 | 10 | 14 | 19 |
| 1 | 6 | 11 | 14 | 19 |
| 1 | 7 | 11 | 14 | 19 |
| 1 | 8 | 11 | 14 | 19 |
| 1 | 9 | 11 | 14 | 19 |
| 2 | 6 | 11 | 14 | 19 |
| 2 | 7 | 11 | 14 | 19 |
| 2 | 8 | 11 | 14 | 19 |
| 2 | 9 | 11 | 14 | 19 |
| 3 | 6 | 11 | 14 | 19 |
| 3 | 7 | 11 | 14 | 19 |
| 3 | 8 | 11 | 14 | 19 |
| 3 | 9 | 11 | 14 | 19 |
| 4 | 6 | 11 | 14 | 19 |
| 4 | 7 | 11 | 14 | 19 |
| 4 | 8 | 11 | 14 | 19 |
| 4 | 9 | 11 | 14 | 19 |
| 5 | 6 | 11 | 14 | 19 |
| 5 | 7 | 11 | 14 | 19 |
| 5 | 8 | 11 | 14 | 19 |
| 5 | 9 | 11 | 14 | 19 |
| 1 | 6 | 12 | 14 | 19 |
| 1 | 7 | 12 | 14 | 19 |
| 1 | 8 | 12 | 14 | 19 |
| 1 | 9 | 12 | 14 | 19 |
| 2 | 6 | 12 | 14 | 19 |
| 2 | 7 | 12 | 14 | 19 |
| 2 | 8 | 12 | 14 | 19 |
| 2 | 9 | 12 | 14 | 19 |
| 3 | 6 | 12 | 14 | 19 |
| 3 | 7 | 12 | 14 | 19 |
| 3 | 8 | 12 | 14 | 19 |
| 3 | 9 | 12 | 14 | 19 |
| 4 | 6 | 12 | 14 | 19 |
| 4 | 7 | 12 | 14 | 19 |
| 4 | 8 | 12 | 14 | 19 |
| 4 | 9 | 12 | 14 | 19 |
| 5 | 6 | 12 | 14 | 19 |
| 5 | 7 | 12 | 14 | 19 |
| 5 | 8 | 12 | 14 | 19 |
| 5 | 9 | 12 | 14 | 19 |
| 1 | 6 | 13 | 14 | 19 |
| 1 | 7 | 13 | 14 | 19 |
| 1 | 8 | 13 | 14 | 19 |
| 1 | 9 | 13 | 14 | 19 |
| 2 | 6 | 13 | 14 | 19 |
| 2 | 7 | 13 | 14 | 19 |
| 2 | 8 | 13 | 14 | 19 |
| 2 | 9 | 13 | 14 | 19 |
| 3 | 6 | 13 | 14 | 19 |
| 3 | 7 | 13 | 14 | 19 |
| 3 | 8 | 13 | 14 | 19 |
| 3 | 9 | 13 | 14 | 19 |
| 4 | 6 | 13 | 14 | 19 |
| 4 | 7 | 13 | 14 | 19 |
| 4 | 8 | 13 | 14 | 19 |
| 4 | 9 | 13 | 14 | 19 |
| 5 | 6 | 13 | 14 | 19 |
| 5 | 7 | 13 | 14 | 19 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 5 | 8 | 13 | 14 | 19 |
| 5 | 9 | 13 | 14 | 19 |
| 1 | 6 | 10 | 15 | 19 |
| 1 | 7 | 10 | 15 | 19 |
| 1 | 8 | 10 | 15 | 19 |
| 1 | 9 | 10 | 15 | 19 |
| 2 | 6 | 10 | 15 | 19 |
| 2 | 7 | 10 | 15 | 19 |
| 2 | 8 | 10 | 15 | 19 |
| 2 | 9 | 10 | 15 | 19 |
| 3 | 6 | 10 | 15 | 19 |
| 3 | 7 | 10 | 15 | 19 |
| 3 | 8 | 10 | 15 | 19 |
| 3 | 9 | 10 | 15 | 19 |
| 4 | 6 | 10 | 15 | 19 |
| 4 | 7 | 10 | 15 | 19 |
| 4 | 8 | 10 | 15 | 19 |
| 4 | 9 | 10 | 15 | 19 |
| 5 | 6 | 10 | 15 | 19 |
| 5 | 7 | 10 | 15 | 19 |
| 5 | 8 | 10 | 15 | 19 |
| 5 | 9 | 10 | 15 | 19 |
| 1 | 6 | 11 | 15 | 19 |
| 1 | 7 | 11 | 15 | 19 |
| 1 | 8 | 11 | 15 | 19 |
| 1 | 9 | 11 | 15 | 19 |
| 2 | 6 | 11 | 15 | 19 |
| 2 | 7 | 11 | 15 | 19 |
| 2 | 8 | 11 | 15 | 19 |
| 2 | 9 | 11 | 15 | 19 |
| 3 | 6 | 11 | 15 | 19 |
| 3 | 7 | 11 | 15 | 19 |
| 3 | 8 | 11 | 15 | 19 |
| 3 | 9 | 11 | 15 | 19 |
| 4 | 6 | 11 | 15 | 19 |
| 4 | 7 | 11 | 15 | 19 |
| 4 | 8 | 11 | 15 | 19 |
| 4 | 9 | 11 | 15 | 19 |
| 5 | 6 | 11 | 15 | 19 |
| 5 | 7 | 11 | 15 | 19 |
| 5 | 8 | 11 | 15 | 19 |
| 5 | 9 | 11 | 15 | 19 |
| 1 | 6 | 12 | 15 | 19 |
| 1 | 7 | 12 | 15 | 19 |
| 1 | 8 | 12 | 15 | 19 |
| 1 | 9 | 12 | 15 | 19 |
| 2 | 6 | 12 | 15 | 19 |
| 2 | 7 | 12 | 15 | 19 |
| 2 | 8 | 12 | 15 | 19 |
| 2 | 9 | 12 | 15 | 19 |
| 3 | 6 | 12 | 15 | 19 |
| 3 | 7 | 12 | 15 | 19 |
| 3 | 8 | 12 | 15 | 19 |
| 3 | 9 | 12 | 15 | 19 |
| 4 | 6 | 12 | 15 | 19 |
| 4 | 7 | 12 | 15 | 19 |
| 4 | 8 | 12 | 15 | 19 |
| 4 | 9 | 12 | 15 | 19 |
| 5 | 6 | 12 | 15 | 19 |
| 5 | 7 | 12 | 15 | 19 |
| 5 | 8 | 12 | 15 | 19 |
| 5 | 9 | 12 | 15 | 19 |
| 1 | 6 | 13 | 15 | 19 |
| 1 | 7 | 13 | 15 | 19 |
| 1 | 8 | 13 | 15 | 19 |
| 1 | 9 | 13 | 15 | 19 |
| 2 | 6 | 13 | 15 | 19 |
| 2 | 7 | 13 | 15 | 19 |
| 2 | 8 | 13 | 15 | 19 |
| 2 | 9 | 13 | 15 | 19 |
| 3 | 6 | 13 | 15 | 19 |
| 3 | 7 | 13 | 15 | 19 |
| 3 | 8 | 13 | 15 | 19 |
| 3 | 9 | 13 | 15 | 19 |
| 4 | 6 | 13 | 15 | 19 |
| 4 | 7 | 13 | 15 | 19 |
| 4 | 8 | 13 | 15 | 19 |
| 4 | 9 | 13 | 15 | 19 |
| 5 | 6 | 13 | 15 | 19 |
| 5 | 7 | 13 | 15 | 19 |
| 5 | 8 | 13 | 15 | 19 |
| 5 | 9 | 13 | 15 | 19 |
| 1 | 6 | 10 | 16 | 19 |
| 1 | 7 | 10 | 16 | 19 |
| 1 | 8 | 10 | 16 | 19 |
| 1 | 9 | 10 | 16 | 19 |
| 2 | 6 | 10 | 16 | 19 |
| 2 | 7 | 10 | 16 | 19 |
| 2 | 8 | 10 | 16 | 19 |
| 2 | 9 | 10 | 16 | 19 |
| 3 | 6 | 10 | 16 | 19 |
| 3 | 7 | 10 | 16 | 19 |
| 3 | 8 | 10 | 16 | 19 |
| 3 | 9 | 10 | 16 | 19 |
| 4 | 6 | 10 | 16 | 19 |
| 4 | 7 | 10 | 16 | 19 |
| 4 | 8 | 10 | 16 | 19 |
| 4 | 9 | 10 | 16 | 19 |
| 5 | 6 | 10 | 16 | 19 |
| 5 | 7 | 10 | 16 | 19 |
| 5 | 8 | 10 | 16 | 19 |
| 5 | 9 | 10 | 16 | 19 |
| 1 | 6 | 11 | 16 | 19 |
| 1 | 7 | 11 | 16 | 19 |
| 1 | 8 | 11 | 16 | 19 |
| 1 | 9 | 11 | 16 | 19 |
| 2 | 6 | 11 | 16 | 19 |
| 2 | 7 | 11 | 16 | 19 |
| 2 | 8 | 11 | 16 | 19 |
| 2 | 9 | 11 | 16 | 19 |
| 3 | 6 | 11 | 16 | 19 |
| 3 | 7 | 11 | 16 | 19 |
| 3 | 8 | 11 | 16 | 19 |
| 3 | 9 | 11 | 16 | 19 |
| 4 | 6 | 11 | 16 | 19 |
| 4 | 7 | 11 | 16 | 19 |
| 4 | 8 | 11 | 16 | 19 |
| 4 | 9 | 11 | 16 | 19 |
| 5 | 6 | 11 | 16 | 19 |
| 5 | 7 | 11 | 16 | 19 |
| 5 | 8 | 11 | 16 | 19 |
| 5 | 9 | 11 | 16 | 19 |
| 1 | 6 | 12 | 16 | 19 |
| 1 | 7 | 12 | 16 | 19 |
| 1 | 8 | 12 | 16 | 19 |
| 1 | 9 | 12 | 16 | 19 |
| 2 | 6 | 12 | 16 | 19 |
| 2 | 7 | 12 | 16 | 19 |
| 2 | 8 | 12 | 16 | 19 |
| 2 | 9 | 12 | 16 | 19 |
| 3 | 6 | 12 | 16 | 19 |
| 3 | 7 | 12 | 16 | 19 |
| 3 | 8 | 12 | 16 | 19 |
| 3 | 9 | 12 | 16 | 19 |
| 4 | 6 | 12 | 16 | 19 |
| 4 | 7 | 12 | 16 | 19 |
| 4 | 8 | 12 | 16 | 19 |
| 4 | 9 | 12 | 16 | 19 |
| 5 | 6 | 12 | 16 | 19 |
| 5 | 7 | 12 | 16 | 19 |
| 5 | 8 | 12 | 16 | 19 |
| 5 | 9 | 12 | 16 | 19 |
| 1 | 6 | 13 | 16 | 19 |
| 1 | 7 | 13 | 16 | 19 |
| 1 | 8 | 13 | 16 | 19 |
| 1 | 9 | 13 | 16 | 19 |
| 2 | 6 | 13 | 16 | 19 |
| 2 | 7 | 13 | 16 | 19 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 2 | 8 | 13 | 16 | 19 |
| 2 | 9 | 13 | 16 | 19 |
| 3 | 6 | 13 | 16 | 19 |
| 3 | 7 | 13 | 16 | 19 |
| 3 | 8 | 13 | 16 | 19 |
| 3 | 9 | 13 | 16 | 19 |
| 4 | 6 | 13 | 16 | 19 |
| 4 | 7 | 13 | 16 | 19 |
| 4 | 8 | 13 | 16 | 19 |
| 4 | 9 | 13 | 16 | 19 |
| 5 | 6 | 13 | 16 | 19 |
| 5 | 7 | 13 | 16 | 19 |
| 5 | 8 | 13 | 16 | 19 |
| 5 | 9 | 13 | 16 | 19 |
| 1 | 6 | 10 | 17 | 19 |
| 1 | 7 | 10 | 17 | 19 |
| 1 | 8 | 10 | 17 | 19 |
| 1 | 9 | 10 | 17 | 19 |
| 2 | 6 | 10 | 17 | 19 |
| 2 | 7 | 10 | 17 | 19 |
| 2 | 8 | 10 | 17 | 19 |
| 2 | 9 | 10 | 17 | 19 |
| 3 | 6 | 10 | 17 | 19 |
| 3 | 7 | 10 | 17 | 19 |
| 3 | 8 | 10 | 17 | 19 |
| 3 | 9 | 10 | 17 | 19 |
| 4 | 6 | 10 | 17 | 19 |
| 4 | 7 | 10 | 17 | 19 |
| 4 | 8 | 10 | 17 | 19 |
| 4 | 9 | 10 | 17 | 19 |
| 5 | 6 | 10 | 17 | 19 |
| 5 | 7 | 10 | 17 | 19 |
| 5 | 8 | 10 | 17 | 19 |
| 5 | 9 | 10 | 17 | 19 |
| 1 | 6 | 11 | 17 | 19 |
| 1 | 7 | 11 | 17 | 19 |
| 1 | 8 | 11 | 17 | 19 |
| 1 | 9 | 11 | 17 | 19 |
| 2 | 6 | 11 | 17 | 19 |
| 2 | 7 | 11 | 17 | 19 |
| 2 | 8 | 11 | 17 | 19 |
| 2 | 9 | 11 | 17 | 19 |
| 3 | 6 | 11 | 17 | 19 |
| 3 | 7 | 11 | 17 | 19 |
| 3 | 8 | 11 | 17 | 19 |
| 3 | 9 | 11 | 17 | 19 |
| 4 | 6 | 11 | 17 | 19 |
| 4 | 7 | 11 | 17 | 19 |
| 4 | 8 | 11 | 17 | 19 |
| 4 | 9 | 11 | 17 | 19 |
| 5 | 6 | 11 | 17 | 19 |
| 5 | 7 | 11 | 17 | 19 |
| 5 | 8 | 11 | 17 | 19 |
| 5 | 9 | 11 | 17 | 19 |
| 1 | 6 | 12 | 17 | 19 |
| 1 | 7 | 12 | 17 | 19 |
| 1 | 8 | 12 | 17 | 19 |
| 1 | 9 | 12 | 17 | 19 |
| 2 | 6 | 12 | 17 | 19 |
| 2 | 7 | 12 | 17 | 19 |
| 2 | 8 | 12 | 17 | 19 |
| 2 | 9 | 12 | 17 | 19 |
| 3 | 6 | 12 | 17 | 19 |
| 3 | 7 | 12 | 17 | 19 |
| 3 | 8 | 12 | 17 | 19 |
| 3 | 9 | 12 | 17 | 19 |
| 4 | 6 | 12 | 17 | 19 |
| 4 | 7 | 12 | 17 | 19 |
| 4 | 8 | 12 | 17 | 19 |
| 4 | 9 | 12 | 17 | 19 |
| 5 | 6 | 12 | 17 | 19 |
| 5 | 7 | 12 | 17 | 19 |
| 5 | 8 | 12 | 17 | 19 |
| 5 | 9 | 12 | 17 | 19 |
| 1 | 6 | 13 | 17 | 19 |
| 1 | 7 | 13 | 17 | 19 |
| 1 | 8 | 13 | 17 | 19 |
| 1 | 9 | 13 | 17 | 19 |
| 2 | 6 | 13 | 17 | 19 |
| 2 | 7 | 13 | 17 | 19 |
| 2 | 8 | 13 | 17 | 19 |
| 2 | 9 | 13 | 17 | 19 |
| 3 | 6 | 13 | 17 | 19 |
| 3 | 7 | 13 | 17 | 19 |
| 3 | 8 | 13 | 17 | 19 |
| 3 | 9 | 13 | 17 | 19 |
| 4 | 6 | 13 | 17 | 19 |
| 4 | 7 | 13 | 17 | 19 |
| 4 | 8 | 13 | 17 | 19 |
| 4 | 9 | 13 | 17 | 19 |
| 5 | 6 | 13 | 17 | 19 |
| 5 | 7 | 13 | 17 | 19 |
| 5 | 8 | 13 | 17 | 19 |
| 5 | 9 | 13 | 17 | 19 |
| 1 | 6 | 10 | 14 | 20 |
| 1 | 7 | 10 | 14 | 20 |
| 1 | 8 | 10 | 14 | 20 |
| 1 | 9 | 10 | 14 | 20 |
| 2 | 6 | 10 | 14 | 20 |
| 2 | 7 | 10 | 14 | 20 |
| 2 | 8 | 10 | 14 | 20 |
| 2 | 9 | 10 | 14 | 20 |
| 3 | 6 | 10 | 14 | 20 |
| 3 | 7 | 10 | 14 | 20 |
| 3 | 8 | 10 | 14 | 20 |
| 3 | 9 | 10 | 14 | 20 |
| 4 | 6 | 10 | 14 | 20 |
| 4 | 7 | 10 | 14 | 20 |
| 4 | 8 | 10 | 14 | 20 |
| 4 | 9 | 10 | 14 | 20 |
| 5 | 6 | 10 | 14 | 20 |
| 5 | 7 | 10 | 14 | 20 |
| 5 | 8 | 10 | 14 | 20 |
| 5 | 9 | 10 | 14 | 20 |
| 1 | 6 | 11 | 14 | 20 |
| 1 | 7 | 11 | 14 | 20 |
| 1 | 8 | 11 | 14 | 20 |
| 1 | 9 | 11 | 14 | 20 |
| 2 | 6 | 11 | 14 | 20 |
| 2 | 7 | 11 | 14 | 20 |
| 2 | 8 | 11 | 14 | 20 |
| 2 | 9 | 11 | 14 | 20 |
| 3 | 6 | 11 | 14 | 20 |
| 3 | 7 | 11 | 14 | 20 |
| 3 | 8 | 11 | 14 | 20 |
| 3 | 9 | 11 | 14 | 20 |
| 4 | 6 | 11 | 14 | 20 |
| 4 | 7 | 11 | 14 | 20 |
| 4 | 8 | 11 | 14 | 20 |
| 4 | 9 | 11 | 14 | 20 |
| 5 | 6 | 11 | 14 | 20 |
| 5 | 7 | 11 | 14 | 20 |
| 5 | 8 | 11 | 14 | 20 |
| 5 | 9 | 11 | 14 | 20 |
| 1 | 6 | 12 | 14 | 20 |
| 1 | 7 | 12 | 14 | 20 |
| 1 | 8 | 12 | 14 | 20 |
| 1 | 9 | 12 | 14 | 20 |
| 2 | 6 | 12 | 14 | 20 |
| 2 | 7 | 12 | 14 | 20 |
| 2 | 8 | 12 | 14 | 20 |
| 2 | 9 | 12 | 14 | 20 |
| 3 | 6 | 12 | 14 | 20 |
| 3 | 7 | 12 | 14 | 20 |
| 3 | 8 | 12 | 14 | 20 |
| 3 | 9 | 12 | 14 | 20 |
| 4 | 6 | 12 | 14 | 20 |
| 4 | 7 | 12 | 14 | 20 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 4 | 8 | 12 | 14 | 20 |
| 4 | 9 | 12 | 14 | 20 |
| 5 | 6 | 12 | 14 | 20 |
| 5 | 7 | 12 | 14 | 20 |
| 5 | 8 | 12 | 14 | 20 |
| 5 | 9 | 12 | 14 | 20 |
| 1 | 6 | 13 | 14 | 20 |
| 1 | 7 | 13 | 14 | 20 |
| 1 | 8 | 13 | 14 | 20 |
| 1 | 9 | 13 | 14 | 20 |
| 2 | 6 | 13 | 14 | 20 |
| 2 | 7 | 13 | 14 | 20 |
| 2 | 8 | 13 | 14 | 20 |
| 2 | 9 | 13 | 14 | 20 |
| 3 | 6 | 13 | 14 | 20 |
| 3 | 7 | 13 | 14 | 20 |
| 3 | 8 | 13 | 14 | 20 |
| 3 | 9 | 13 | 14 | 20 |
| 4 | 6 | 13 | 14 | 20 |
| 4 | 7 | 13 | 14 | 20 |
| 4 | 8 | 13 | 14 | 20 |
| 4 | 9 | 13 | 14 | 20 |
| 5 | 6 | 13 | 14 | 20 |
| 5 | 7 | 13 | 14 | 20 |
| 5 | 8 | 13 | 14 | 20 |
| 5 | 9 | 13 | 14 | 20 |
| 1 | 6 | 10 | 15 | 20 |
| 1 | 7 | 10 | 15 | 20 |
| 1 | 8 | 10 | 15 | 20 |
| 1 | 9 | 10 | 15 | 20 |
| 2 | 6 | 10 | 15 | 20 |
| 2 | 7 | 10 | 15 | 20 |
| 2 | 8 | 10 | 15 | 20 |
| 2 | 9 | 10 | 15 | 20 |
| 3 | 6 | 10 | 15 | 20 |
| 3 | 7 | 10 | 15 | 20 |
| 3 | 8 | 10 | 15 | 20 |
| 3 | 9 | 10 | 15 | 20 |
| 4 | 6 | 10 | 15 | 20 |
| 4 | 7 | 10 | 15 | 20 |
| 4 | 8 | 10 | 15 | 20 |
| 4 | 9 | 10 | 15 | 20 |
| 5 | 6 | 10 | 15 | 20 |
| 5 | 7 | 10 | 15 | 20 |
| 5 | 8 | 10 | 15 | 20 |
| 5 | 9 | 10 | 15 | 20 |
| 1 | 6 | 11 | 15 | 20 |
| 1 | 7 | 11 | 15 | 20 |
| 1 | 8 | 11 | 15 | 20 |
| 1 | 9 | 11 | 15 | 20 |
| 2 | 6 | 11 | 15 | 20 |
| 2 | 7 | 11 | 15 | 20 |
| 2 | 8 | 11 | 15 | 20 |
| 2 | 9 | 11 | 15 | 20 |
| 3 | 6 | 11 | 15 | 20 |
| 3 | 7 | 11 | 15 | 20 |
| 3 | 8 | 11 | 15 | 20 |
| 3 | 9 | 11 | 15 | 20 |
| 4 | 6 | 11 | 15 | 20 |
| 4 | 7 | 11 | 15 | 20 |
| 4 | 8 | 11 | 15 | 20 |
| 4 | 9 | 11 | 15 | 20 |
| 5 | 6 | 11 | 15 | 20 |
| 5 | 7 | 11 | 15 | 20 |
| 5 | 8 | 11 | 15 | 20 |
| 5 | 9 | 11 | 15 | 20 |
| 1 | 6 | 12 | 15 | 20 |
| 1 | 7 | 12 | 15 | 20 |
| 1 | 8 | 12 | 15 | 20 |
| 1 | 9 | 12 | 15 | 20 |
| 2 | 6 | 12 | 15 | 20 |
| 2 | 7 | 12 | 15 | 20 |
| 2 | 8 | 12 | 15 | 20 |
| 2 | 9 | 12 | 15 | 20 |
| 3 | 6 | 12 | 15 | 20 |
| 3 | 7 | 12 | 15 | 20 |
| 3 | 8 | 12 | 15 | 20 |
| 3 | 9 | 12 | 15 | 20 |
| 4 | 6 | 12 | 15 | 20 |
| 4 | 7 | 12 | 15 | 20 |
| 4 | 8 | 12 | 15 | 20 |
| 4 | 9 | 12 | 15 | 20 |
| 5 | 6 | 12 | 15 | 20 |
| 5 | 7 | 12 | 15 | 20 |
| 5 | 8 | 12 | 15 | 20 |
| 5 | 9 | 12 | 15 | 20 |
| 1 | 6 | 13 | 15 | 20 |
| 1 | 7 | 13 | 15 | 20 |
| 1 | 8 | 13 | 15 | 20 |
| 1 | 9 | 13 | 15 | 20 |
| 2 | 6 | 13 | 15 | 20 |
| 2 | 7 | 13 | 15 | 20 |
| 2 | 8 | 13 | 15 | 20 |
| 2 | 9 | 13 | 15 | 20 |
| 3 | 6 | 13 | 15 | 20 |
| 3 | 7 | 13 | 15 | 20 |
| 3 | 8 | 13 | 15 | 20 |
| 3 | 9 | 13 | 15 | 20 |
| 4 | 6 | 13 | 15 | 20 |
| 4 | 7 | 13 | 15 | 20 |
| 4 | 8 | 13 | 15 | 20 |
| 4 | 9 | 13 | 15 | 20 |
| 5 | 6 | 13 | 15 | 20 |
| 5 | 7 | 13 | 15 | 20 |
| 5 | 8 | 13 | 15 | 20 |
| 5 | 9 | 13 | 15 | 20 |
| 1 | 6 | 10 | 16 | 20 |
| 1 | 7 | 10 | 16 | 20 |
| 1 | 8 | 10 | 16 | 20 |
| 1 | 9 | 10 | 16 | 20 |
| 2 | 6 | 10 | 16 | 20 |
| 2 | 7 | 10 | 16 | 20 |
| 2 | 8 | 10 | 16 | 20 |
| 2 | 9 | 10 | 16 | 20 |
| 3 | 6 | 10 | 16 | 20 |
| 3 | 7 | 10 | 16 | 20 |
| 3 | 8 | 10 | 16 | 20 |
| 3 | 9 | 10 | 16 | 20 |
| 4 | 6 | 10 | 16 | 20 |
| 4 | 7 | 10 | 16 | 20 |
| 4 | 8 | 10 | 16 | 20 |
| 4 | 9 | 10 | 16 | 20 |
| 5 | 6 | 10 | 16 | 20 |
| 5 | 7 | 10 | 16 | 20 |
| 5 | 8 | 10 | 16 | 20 |
| 5 | 9 | 10 | 16 | 20 |
| 1 | 6 | 11 | 16 | 20 |
| 1 | 7 | 11 | 16 | 20 |
| 1 | 8 | 11 | 16 | 20 |
| 1 | 9 | 11 | 16 | 20 |
| 2 | 6 | 11 | 16 | 20 |
| 2 | 7 | 11 | 16 | 20 |
| 2 | 8 | 11 | 16 | 20 |
| 2 | 9 | 11 | 16 | 20 |
| 3 | 6 | 11 | 16 | 20 |
| 3 | 7 | 11 | 16 | 20 |
| 3 | 8 | 11 | 16 | 20 |
| 3 | 9 | 11 | 16 | 20 |
| 4 | 6 | 11 | 16 | 20 |
| 4 | 7 | 11 | 16 | 20 |
| 4 | 8 | 11 | 16 | 20 |
| 4 | 9 | 11 | 16 | 20 |
| 5 | 6 | 11 | 16 | 20 |
| 5 | 7 | 11 | 16 | 20 |
| 5 | 8 | 11 | 16 | 20 |
| 5 | 9 | 11 | 16 | 20 |
| 1 | 6 | 12 | 16 | 20 |
| 1 | 7 | 12 | 16 | 20 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 1 | 8 | 12 | 16 | 20 |
| 1 | 9 | 12 | 16 | 20 |
| 2 | 6 | 12 | 16 | 20 |
| 2 | 7 | 12 | 16 | 20 |
| 2 | 8 | 12 | 16 | 20 |
| 2 | 9 | 12 | 16 | 20 |
| 3 | 6 | 12 | 16 | 20 |
| 3 | 7 | 12 | 16 | 20 |
| 3 | 8 | 12 | 16 | 20 |
| 3 | 9 | 12 | 16 | 20 |
| 4 | 6 | 12 | 16 | 20 |
| 4 | 7 | 12 | 16 | 20 |
| 4 | 8 | 12 | 16 | 20 |
| 4 | 9 | 12 | 16 | 20 |
| 5 | 6 | 12 | 16 | 20 |
| 5 | 7 | 12 | 16 | 20 |
| 5 | 8 | 12 | 16 | 20 |
| 5 | 9 | 12 | 16 | 20 |
| 1 | 6 | 13 | 16 | 20 |
| 1 | 7 | 13 | 16 | 20 |
| 1 | 8 | 13 | 16 | 20 |
| 1 | 9 | 13 | 16 | 20 |
| 2 | 6 | 13 | 16 | 20 |
| 2 | 7 | 13 | 16 | 20 |
| 2 | 8 | 13 | 16 | 20 |
| 2 | 9 | 13 | 16 | 20 |
| 3 | 6 | 13 | 16 | 20 |
| 3 | 7 | 13 | 16 | 20 |
| 3 | 8 | 13 | 16 | 20 |
| 3 | 9 | 13 | 16 | 20 |
| 4 | 6 | 13 | 16 | 20 |
| 4 | 7 | 13 | 16 | 20 |
| 4 | 8 | 13 | 16 | 20 |
| 4 | 9 | 13 | 16 | 20 |
| 5 | 6 | 13 | 16 | 20 |
| 5 | 7 | 13 | 16 | 20 |
| 5 | 8 | 13 | 16 | 20 |
| 5 | 9 | 13 | 16 | 20 |
| 1 | 6 | 10 | 17 | 20 |
| 1 | 7 | 10 | 17 | 20 |
| 1 | 8 | 10 | 17 | 20 |
| 1 | 9 | 10 | 17 | 20 |
| 2 | 6 | 10 | 17 | 20 |
| 2 | 7 | 10 | 17 | 20 |
| 2 | 8 | 10 | 17 | 20 |
| 2 | 9 | 10 | 17 | 20 |
| 3 | 6 | 10 | 17 | 20 |
| 3 | 7 | 10 | 17 | 20 |
| 3 | 8 | 10 | 17 | 20 |
| 3 | 9 | 10 | 17 | 20 |
| 4 | 6 | 10 | 17 | 20 |
| 4 | 7 | 10 | 17 | 20 |
| 4 | 8 | 10 | 17 | 20 |
| 4 | 9 | 10 | 17 | 20 |
| 5 | 6 | 10 | 17 | 20 |
| 5 | 7 | 10 | 17 | 20 |
| 5 | 8 | 10 | 17 | 20 |
| 5 | 9 | 10 | 17 | 20 |
| 1 | 6 | 11 | 17 | 20 |
| 1 | 7 | 11 | 17 | 20 |
| 1 | 8 | 11 | 17 | 20 |
| 1 | 9 | 11 | 17 | 20 |
| 2 | 6 | 11 | 17 | 20 |
| 2 | 7 | 11 | 17 | 20 |
| 2 | 8 | 11 | 17 | 20 |
| 2 | 9 | 11 | 17 | 20 |
| 3 | 6 | 11 | 17 | 20 |
| 3 | 7 | 11 | 17 | 20 |
| 3 | 8 | 11 | 17 | 20 |
| 3 | 9 | 11 | 17 | 20 |
| 4 | 6 | 11 | 17 | 20 |
| 4 | 7 | 11 | 17 | 20 |
| 4 | 8 | 11 | 17 | 20 |
| 4 | 9 | 11 | 17 | 20 |
| 5 | 6 | 11 | 17 | 20 |
| 5 | 7 | 11 | 17 | 20 |
| 5 | 8 | 11 | 17 | 20 |
| 5 | 9 | 11 | 17 | 20 |
| 1 | 6 | 12 | 17 | 20 |
| 1 | 7 | 12 | 17 | 20 |
| 1 | 8 | 12 | 17 | 20 |
| 1 | 9 | 12 | 17 | 20 |
| 2 | 6 | 12 | 17 | 20 |
| 2 | 7 | 12 | 17 | 20 |
| 2 | 8 | 12 | 17 | 20 |
| 2 | 9 | 12 | 17 | 20 |
| 3 | 6 | 12 | 17 | 20 |
| 3 | 7 | 12 | 17 | 20 |
| 3 | 8 | 12 | 17 | 20 |
| 3 | 9 | 12 | 17 | 20 |
| 4 | 6 | 12 | 17 | 20 |
| 4 | 7 | 12 | 17 | 20 |
| 4 | 8 | 12 | 17 | 20 |
| 4 | 9 | 12 | 17 | 20 |
| 5 | 6 | 12 | 17 | 20 |
| 5 | 7 | 12 | 17 | 20 |
| 5 | 8 | 12 | 17 | 20 |
| 5 | 9 | 12 | 17 | 20 |
| 1 | 6 | 13 | 17 | 20 |
| 1 | 7 | 13 | 17 | 20 |
| 1 | 8 | 13 | 17 | 20 |
| 1 | 9 | 13 | 17 | 20 |
| 2 | 6 | 13 | 17 | 20 |
| 2 | 7 | 13 | 17 | 20 |
| 2 | 8 | 13 | 17 | 20 |
| 2 | 9 | 13 | 17 | 20 |
| 3 | 6 | 13 | 17 | 20 |
| 3 | 7 | 13 | 17 | 20 |
| 3 | 8 | 13 | 17 | 20 |
| 3 | 9 | 13 | 17 | 20 |
| 4 | 6 | 13 | 17 | 20 |
| 4 | 7 | 13 | 17 | 20 |
| 4 | 8 | 13 | 17 | 20 |
| 4 | 9 | 13 | 17 | 20 |
| 5 | 6 | 13 | 17 | 20 |
| 5 | 7 | 13 | 17 | 20 |
| 5 | 8 | 13 | 17 | 20 |
| 5 | 9 | 13 | 17 | 20 |
| 1 | 6 | 10 | 14 | 21 |
| 1 | 7 | 10 | 14 | 21 |
| 1 | 8 | 10 | 14 | 21 |
| 1 | 9 | 10 | 14 | 21 |
| 2 | 6 | 10 | 14 | 21 |
| 2 | 7 | 10 | 14 | 21 |
| 2 | 8 | 10 | 14 | 21 |
| 2 | 9 | 10 | 14 | 21 |
| 3 | 6 | 10 | 14 | 21 |
| 3 | 7 | 10 | 14 | 21 |
| 3 | 8 | 10 | 14 | 21 |
| 3 | 9 | 10 | 14 | 21 |
| 4 | 6 | 10 | 14 | 21 |
| 4 | 7 | 10 | 14 | 21 |
| 4 | 8 | 10 | 14 | 21 |
| 4 | 9 | 10 | 14 | 21 |
| 5 | 6 | 10 | 14 | 21 |
| 5 | 7 | 10 | 14 | 21 |
| 5 | 8 | 10 | 14 | 21 |
| 5 | 9 | 10 | 14 | 21 |
| 1 | 6 | 11 | 14 | 21 |
| 1 | 7 | 11 | 14 | 21 |
| 1 | 8 | 11 | 14 | 21 |
| 1 | 9 | 11 | 14 | 21 |
| 2 | 6 | 11 | 14 | 21 |
| 2 | 7 | 11 | 14 | 21 |
| 2 | 8 | 11 | 14 | 21 |
| 2 | 9 | 11 | 14 | 21 |
| 3 | 6 | 11 | 14 | 21 |
| 3 | 7 | 11 | 14 | 21 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 3 | 8 | 11 | 14 | 21 |
| 3 | 9 | 11 | 14 | 21 |
| 4 | 6 | 11 | 14 | 21 |
| 4 | 7 | 11 | 14 | 21 |
| 4 | 8 | 11 | 14 | 21 |
| 4 | 9 | 11 | 14 | 21 |
| 5 | 6 | 11 | 14 | 21 |
| 5 | 7 | 11 | 14 | 21 |
| 5 | 8 | 11 | 14 | 21 |
| 5 | 9 | 11 | 14 | 21 |
| 1 | 6 | 12 | 14 | 21 |
| 1 | 7 | 12 | 14 | 21 |
| 1 | 8 | 12 | 14 | 21 |
| 1 | 9 | 12 | 14 | 21 |
| 2 | 6 | 12 | 14 | 21 |
| 2 | 7 | 12 | 14 | 21 |
| 2 | 8 | 12 | 14 | 21 |
| 2 | 9 | 12 | 14 | 21 |
| 3 | 6 | 12 | 14 | 21 |
| 3 | 7 | 12 | 14 | 21 |
| 3 | 8 | 12 | 14 | 21 |
| 3 | 9 | 12 | 14 | 21 |
| 4 | 6 | 12 | 14 | 21 |
| 4 | 7 | 12 | 14 | 21 |
| 4 | 8 | 12 | 14 | 21 |
| 4 | 9 | 12 | 14 | 21 |
| 5 | 6 | 12 | 14 | 21 |
| 5 | 7 | 12 | 14 | 21 |
| 5 | 8 | 12 | 14 | 21 |
| 5 | 9 | 12 | 14 | 21 |
| 1 | 6 | 13 | 14 | 21 |
| 1 | 7 | 13 | 14 | 21 |
| 1 | 8 | 13 | 14 | 21 |
| 1 | 9 | 13 | 14 | 21 |
| 2 | 6 | 13 | 14 | 21 |
| 2 | 7 | 13 | 14 | 21 |
| 2 | 8 | 13 | 14 | 21 |
| 2 | 9 | 13 | 14 | 21 |
| 3 | 6 | 13 | 14 | 21 |
| 3 | 7 | 13 | 14 | 21 |
| 3 | 8 | 13 | 14 | 21 |
| 3 | 9 | 13 | 14 | 21 |
| 4 | 6 | 13 | 14 | 21 |
| 4 | 7 | 13 | 14 | 21 |
| 4 | 8 | 13 | 14 | 21 |
| 4 | 9 | 13 | 14 | 21 |
| 5 | 6 | 13 | 14 | 21 |
| 5 | 7 | 13 | 14 | 21 |
| 5 | 8 | 13 | 14 | 21 |
| 5 | 9 | 13 | 14 | 21 |
| 1 | 6 | 10 | 15 | 21 |
| 1 | 7 | 10 | 15 | 21 |
| 1 | 8 | 10 | 15 | 21 |
| 1 | 9 | 10 | 15 | 21 |
| 2 | 6 | 10 | 15 | 21 |
| 2 | 7 | 10 | 15 | 21 |
| 2 | 8 | 10 | 15 | 21 |
| 2 | 9 | 10 | 15 | 21 |
| 3 | 6 | 10 | 15 | 21 |
| 3 | 7 | 10 | 15 | 21 |
| 3 | 8 | 10 | 15 | 21 |
| 3 | 9 | 10 | 15 | 21 |
| 4 | 6 | 10 | 15 | 21 |
| 4 | 7 | 10 | 15 | 21 |
| 4 | 8 | 10 | 15 | 21 |
| 4 | 9 | 10 | 15 | 21 |
| 5 | 6 | 10 | 15 | 21 |
| 5 | 7 | 10 | 15 | 21 |
| 5 | 8 | 10 | 15 | 21 |
| 5 | 9 | 10 | 15 | 21 |
| 1 | 6 | 11 | 15 | 21 |
| 1 | 7 | 11 | 15 | 21 |
| 1 | 8 | 11 | 15 | 21 |
| 1 | 9 | 11 | 15 | 21 |
| 2 | 6 | 11 | 15 | 21 |
| 2 | 7 | 11 | 15 | 21 |
| 2 | 8 | 11 | 15 | 21 |
| 2 | 9 | 11 | 15 | 21 |
| 3 | 6 | 11 | 15 | 21 |
| 3 | 7 | 11 | 15 | 21 |
| 3 | 8 | 11 | 15 | 21 |
| 3 | 9 | 11 | 15 | 21 |
| 4 | 6 | 11 | 15 | 21 |
| 4 | 7 | 11 | 15 | 21 |
| 4 | 8 | 11 | 15 | 21 |
| 4 | 9 | 11 | 15 | 21 |
| 5 | 6 | 11 | 15 | 21 |
| 5 | 7 | 11 | 15 | 21 |
| 5 | 8 | 11 | 15 | 21 |
| 5 | 9 | 11 | 15 | 21 |
| 1 | 6 | 12 | 15 | 21 |
| 1 | 7 | 12 | 15 | 21 |
| 1 | 8 | 12 | 15 | 21 |
| 1 | 9 | 12 | 15 | 21 |
| 2 | 6 | 12 | 15 | 21 |
| 2 | 7 | 12 | 15 | 21 |
| 2 | 8 | 12 | 15 | 21 |
| 2 | 9 | 12 | 15 | 21 |
| 3 | 6 | 12 | 15 | 21 |
| 3 | 7 | 12 | 15 | 21 |
| 3 | 8 | 12 | 15 | 21 |
| 3 | 9 | 12 | 15 | 21 |
| 4 | 6 | 12 | 15 | 21 |
| 4 | 7 | 12 | 15 | 21 |
| 4 | 8 | 12 | 15 | 21 |
| 4 | 9 | 12 | 15 | 21 |
| 5 | 6 | 12 | 15 | 21 |
| 5 | 7 | 12 | 15 | 21 |
| 5 | 8 | 12 | 15 | 21 |
| 5 | 9 | 12 | 15 | 21 |
| 1 | 6 | 13 | 15 | 21 |
| 1 | 7 | 13 | 15 | 21 |
| 1 | 8 | 13 | 15 | 21 |
| 1 | 9 | 13 | 15 | 21 |
| 2 | 6 | 13 | 15 | 21 |
| 2 | 7 | 13 | 15 | 21 |
| 2 | 8 | 13 | 15 | 21 |
| 2 | 9 | 13 | 15 | 21 |
| 3 | 6 | 13 | 15 | 21 |
| 3 | 7 | 13 | 15 | 21 |
| 3 | 8 | 13 | 15 | 21 |
| 3 | 9 | 13 | 15 | 21 |
| 4 | 6 | 13 | 15 | 21 |
| 4 | 7 | 13 | 15 | 21 |
| 4 | 8 | 13 | 15 | 21 |
| 4 | 9 | 13 | 15 | 21 |
| 5 | 6 | 13 | 15 | 21 |
| 5 | 7 | 13 | 15 | 21 |
| 5 | 8 | 13 | 15 | 21 |
| 5 | 9 | 13 | 15 | 21 |
| 1 | 6 | 10 | 16 | 21 |
| 1 | 7 | 10 | 16 | 21 |
| 1 | 8 | 10 | 16 | 21 |
| 1 | 9 | 10 | 16 | 21 |
| 2 | 6 | 10 | 16 | 21 |
| 2 | 7 | 10 | 16 | 21 |
| 2 | 8 | 10 | 16 | 21 |
| 2 | 9 | 10 | 16 | 21 |
| 3 | 6 | 10 | 16 | 21 |
| 3 | 7 | 10 | 16 | 21 |
| 3 | 8 | 10 | 16 | 21 |
| 3 | 9 | 10 | 16 | 21 |
| 4 | 6 | 10 | 16 | 21 |
| 4 | 7 | 10 | 16 | 21 |
| 4 | 8 | 10 | 16 | 21 |
| 4 | 9 | 10 | 16 | 21 |
| 5 | 6 | 10 | 16 | 21 |
| 5 | 7 | 10 | 16 | 21 |

TABLE 6-continued

Five-way combinations of hematopoietic stem cell population parameters for assessment

| First Parameter No. | Second Parameter No. | Third Parameter No. | Fourth Parameter No. | Fifth Parameter No. |
|---|---|---|---|---|
| 5 | 8 | 10 | 16 | 21 |
| 5 | 9 | 10 | 16 | 21 |
| 1 | 6 | 11 | 16 | 21 |
| 1 | 7 | 11 | 16 | 21 |
| 1 | 8 | 11 | 16 | 21 |
| 1 | 9 | 11 | 16 | 21 |
| 2 | 6 | 11 | 16 | 21 |
| 2 | 7 | 11 | 16 | 21 |
| 2 | 8 | 11 | 16 | 21 |
| 2 | 9 | 11 | 16 | 21 |
| 3 | 6 | 11 | 16 | 21 |
| 3 | 7 | 11 | 16 | 21 |
| 3 | 8 | 11 | 16 | 21 |
| 3 | 9 | 11 | 16 | 21 |
| 4 | 6 | 11 | 16 | 21 |
| 4 | 7 | 11 | 16 | 21 |
| 4 | 8 | 11 | 16 | 21 |
| 4 | 9 | 11 | 16 | 21 |
| 5 | 6 | 11 | 16 | 21 |
| 5 | 7 | 11 | 16 | 21 |
| 5 | 8 | 11 | 16 | 21 |
| 5 | 9 | 11 | 16 | 21 |
| 1 | 6 | 12 | 16 | 21 |
| 1 | 7 | 12 | 16 | 21 |
| 1 | 8 | 12 | 16 | 21 |
| 1 | 9 | 12 | 16 | 21 |
| 2 | 6 | 12 | 16 | 21 |
| 2 | 7 | 12 | 16 | 21 |
| 2 | 8 | 12 | 16 | 21 |
| 2 | 9 | 12 | 16 | 21 |
| 3 | 6 | 12 | 16 | 21 |
| 3 | 7 | 12 | 16 | 21 |
| 3 | 8 | 12 | 16 | 21 |
| 3 | 9 | 12 | 16 | 21 |
| 4 | 6 | 12 | 16 | 21 |
| 4 | 7 | 12 | 16 | 21 |
| 4 | 8 | 12 | 16 | 21 |
| 4 | 9 | 12 | 16 | 21 |
| 5 | 6 | 12 | 16 | 21 |
| 5 | 7 | 12 | 16 | 21 |
| 5 | 8 | 12 | 16 | 21 |
| 5 | 9 | 12 | 16 | 21 |
| 1 | 6 | 13 | 16 | 21 |
| 1 | 7 | 13 | 16 | 21 |
| 1 | 8 | 13 | 16 | 21 |
| 1 | 9 | 13 | 16 | 21 |
| 2 | 6 | 13 | 16 | 21 |
| 2 | 7 | 13 | 16 | 21 |
| 2 | 8 | 13 | 16 | 21 |
| 2 | 9 | 13 | 16 | 21 |
| 3 | 6 | 13 | 16 | 21 |
| 3 | 7 | 13 | 16 | 21 |
| 3 | 8 | 13 | 16 | 21 |
| 3 | 9 | 13 | 16 | 21 |
| 4 | 6 | 13 | 16 | 21 |
| 4 | 7 | 13 | 16 | 21 |
| 4 | 8 | 13 | 16 | 21 |
| 4 | 9 | 13 | 16 | 21 |
| 5 | 6 | 13 | 16 | 21 |
| 5 | 7 | 13 | 16 | 21 |
| 5 | 8 | 13 | 16 | 21 |
| 5 | 9 | 13 | 16 | 21 |
| 1 | 6 | 10 | 17 | 21 |
| 1 | 7 | 10 | 17 | 21 |
| 1 | 8 | 10 | 17 | 21 |
| 1 | 9 | 10 | 17 | 21 |
| 2 | 6 | 10 | 17 | 21 |
| 2 | 7 | 10 | 17 | 21 |
| 2 | 8 | 10 | 17 | 21 |
| 2 | 9 | 10 | 17 | 21 |
| 3 | 6 | 10 | 17 | 21 |
| 3 | 7 | 10 | 17 | 21 |
| 3 | 8 | 10 | 17 | 21 |
| 3 | 9 | 10 | 17 | 21 |
| 4 | 6 | 10 | 17 | 21 |
| 4 | 7 | 10 | 17 | 21 |
| 4 | 8 | 10 | 17 | 21 |
| 4 | 9 | 10 | 17 | 21 |
| 5 | 6 | 10 | 17 | 21 |
| 5 | 7 | 10 | 17 | 21 |
| 5 | 8 | 10 | 17 | 21 |
| 5 | 9 | 10 | 17 | 21 |
| 1 | 6 | 11 | 17 | 21 |
| 1 | 7 | 11 | 17 | 21 |
| 1 | 8 | 11 | 17 | 21 |
| 1 | 9 | 11 | 17 | 21 |
| 2 | 6 | 11 | 17 | 21 |
| 2 | 7 | 11 | 17 | 21 |
| 2 | 8 | 11 | 17 | 21 |
| 2 | 9 | 11 | 17 | 21 |
| 3 | 6 | 11 | 17 | 21 |
| 3 | 7 | 11 | 17 | 21 |
| 3 | 8 | 11 | 17 | 21 |
| 3 | 9 | 11 | 17 | 21 |
| 4 | 6 | 11 | 17 | 21 |
| 4 | 7 | 11 | 17 | 21 |
| 4 | 8 | 11 | 17 | 21 |
| 4 | 9 | 11 | 17 | 21 |
| 5 | 6 | 11 | 17 | 21 |
| 5 | 7 | 11 | 17 | 21 |
| 5 | 8 | 11 | 17 | 21 |
| 5 | 9 | 11 | 17 | 21 |
| 1 | 6 | 12 | 17 | 21 |
| 1 | 7 | 12 | 17 | 21 |
| 1 | 8 | 12 | 17 | 21 |
| 1 | 9 | 12 | 17 | 21 |
| 2 | 6 | 12 | 17 | 21 |
| 2 | 7 | 12 | 17 | 21 |
| 2 | 8 | 12 | 17 | 21 |
| 2 | 9 | 12 | 17 | 21 |
| 3 | 6 | 12 | 17 | 21 |
| 3 | 7 | 12 | 17 | 21 |
| 3 | 8 | 12 | 17 | 21 |
| 3 | 9 | 12 | 17 | 21 |
| 4 | 6 | 12 | 17 | 21 |
| 4 | 7 | 12 | 17 | 21 |
| 4 | 8 | 12 | 17 | 21 |
| 4 | 9 | 12 | 17 | 21 |
| 5 | 6 | 12 | 17 | 21 |
| 5 | 7 | 12 | 17 | 21 |
| 5 | 8 | 12 | 17 | 21 |
| 5 | 9 | 12 | 17 | 21 |
| 1 | 6 | 13 | 17 | 21 |
| 1 | 7 | 13 | 17 | 21 |
| 1 | 8 | 13 | 17 | 21 |
| 1 | 9 | 13 | 17 | 21 |
| 2 | 6 | 13 | 17 | 21 |
| 2 | 7 | 13 | 17 | 21 |
| 2 | 8 | 13 | 17 | 21 |
| 2 | 9 | 13 | 17 | 21 |
| 3 | 6 | 13 | 17 | 21 |
| 3 | 7 | 13 | 17 | 21 |
| 3 | 8 | 13 | 17 | 21 |
| 3 | 9 | 13 | 17 | 21 |
| 4 | 6 | 13 | 17 | 21 |
| 4 | 7 | 13 | 17 | 21 |
| 4 | 8 | 13 | 17 | 21 |
| 4 | 9 | 13 | 17 | 21 |
| 5 | 6 | 13 | 17 | 21 |
| 5 | 7 | 13 | 17 | 21 |
| 5 | 8 | 13 | 17 | 21 |
| 5 | 9 | 13 | 17 | 21 |

CXCR2 Agonists

Gro-β, Gro-β T, and Variants Thereof

Exemplary CXCR2 agonists that may be used in conjunction with the compositions and methods described herein are Gro-β and variants thereof. Gro-β (also referred to as growth-regulated protein β, chemokine (C-X-C motif) ligand 2 (CXCL2), and macrophage inflammatory protein 2-α (MIP2-α)) is a cytokine capable of mobilizing hematopoietic stem and progenitor cells, for example, by stimulating the release of proteases, and particularly MMP9, from peripheral neutrophils. Without being limited by mechanism, MMP9 may induce mobilization of hematopoietic stem and progenitor cells from stem cell niches, such as the bone marrow, to circulating peripheral blood by stimulating the degradation of proteins such as stem cell factor, its corresponding receptor, CD117, and CXCL12, all of which generally maintain hematopoietic stem and progenitor cells immobilized in bone marrow.

In addition to Gro-β, exemplary CXCR2 agonists that may be used in conjunction with the compositions and methods described herein are truncated forms of Gro-β, such as those that feature a deletion at the N-terminus of Gro-β of from 1 to 8 amino acids (e.g., peptides that feature an N-terminal deletion of 1 amino acids, 2 amino acids, 3 amino acids, 4 amino acids, 5 amino acids, 6 amino acids, 7 amino acids, or 8 amino acids). In some embodiments, CXCR2 agonists that may be used in conjunction with the compositions and methods described herein include Gro-β T, which is characterized by a deletion of the first four amino acids from the N-terminus of Gro-β. Gro-β T exhibits particularly advantageous biological properties, such as the ability to induce hematopoietic stem and progenitor cell mobilization with a potency superior to that of Gro-β by multiple orders of magnitude. Gro-β and Gro-β T are described, for example, in U.S. Pat. No. 6,080,398, the disclosure of which is incorporated herein by reference in its entirety.

In addition, exemplary CXCR2 agonists that may be used in conjunction with the compositions and methods described herein are variants of Gro-β containing an aspartic acid residue in place of the asparagine residue at position 69 of SEQ ID NO: 1. This peptide, referred to herein as Gro-β N69D, retains the hematopoietic stem and progenitor cell-mobilizing functionality of Gro-β, yet induces this effect with a superior potency. Similarly, CXCR2 agonists that may be used with the compositions and methods described herein include variants of Gro-β T containing an aspartic acid residue in place of the asparagine residue at position 65 of SEQ ID NO: 2. This peptide, referred to herein as Gro-β T N65D, not only retains hematopoietic stem and progenitor cell-mobilizing capacity, but exhibits a potency that is substantially greater than that of Gro-β T. Gro-β N69D and Gro-β T N65D are described, for example, in U.S. Pat. No. 6,447,766, the disclosure of which is incorporated herein by reference in its entirety.

The amino acid sequences of Gro-β, Gro-β T, Gro-β N69D, and Gro-β T N65D are set forth in TABLE 7, below.

TABLE 7

Amino acid sequences of Gro-β and select variants thereof

| SEQ ID NO. | Description | Amino Acid Sequence |
|---|---|---|
| 1 | Gro-β | APLATELRCQCLQTLQGIHLKN IQSVKVKSPGPHCAQTEVIATL KNGQKACLNPASPMVKKIIEKM LKNGKSN |
| 2 | Gro-β-T | TELRCQCLQTLQGIHLKNIQSV KVKSPGPHCAQTEVIATLKNGQ KACLNPASPMVKKIIEKMLKNG KSN |
| 3 | Gro-β N69D | APLATELRCQCLQTLQGIHLKN IQSVKVKSPGPHCAQTEVIATL KNGQKACLNPASPMVKKIIEKM LKDGKSN |
| 4 | Gro-β-T N65D | TELRCQCLQTLQGIHLKNIQSV KVKSPGPHCAQTEVIATLKNGQ KACLNPASPMVKKIIEKMLKDG KSN |

Additional CXCR2 agonists that may be used in conjunction with the compositions and methods described herein include other variants of Gro-β, such as peptides that have one or more amino acid substitutions, insertions, and/or deletions relative to Gro-β. In some embodiments, CXCR2 agonists that may be used in conjunction with the compositions and methods described herein include peptides having at least 85% sequence identity to the amino acid sequence of SEQ ID NO: 1 (e.g., a peptide having at least 85%, 90%, 95%, 96%, 97%, 98%, 99%, 99.5%, or 100% sequence identity to the amino acid sequence of SEQ ID NO: 1). In some embodiments, the amino acid sequence of the CXCR2 agonist differs from that of SEQ ID NO: 1 only by way of one or more conservative amino acid substitutions. In some embodiments, in some embodiments, the amino acid sequence of the CXCR2 agonist differs from that of SEQ ID NO: 1 by no more than 20, no more than 15, no more than 10, no more than 5, or no more than 1 nonconservative amino acid substitutions.

Additional examples of CXCR2 agonists useful in conjunction with the compositions and methods described herein are variants of Gro-β T, such as peptides that have one or more amino acid substitutions, insertions, and/or deletions relative to Gro-β T. In some embodiments, the CXCR2 agonist may be a peptide having at least 85% sequence identity to the amino acid sequence of SEQ ID NO: 2 (e.g., a peptide having at least 85%, 90%, 95%, 96%, 97%, 98%, 99%, 99.5%, or 100% sequence identity to the amino acid sequence of SEQ ID NO: 2). In some embodiments, the amino acid sequence of the CXCR2 agonist differs from that of SEQ ID NO: 2 only by way of one or more conservative amino acid substitutions. In some embodiments, in some embodiments, the amino acid sequence of the CXCR2 agonist differs from that of SEQ ID NO: 2 by no more than 20, no more than 15, no more than 10, no more than 5, or no more than 1 nonconservative amino acid substitutions.

Additional examples of CXCR2 agonists useful in conjunction with the compositions and methods described herein are variants of Gro-β N69D, such as peptides that have one or more amino acid substitutions, insertions, and/or deletions relative to Gro-β N69D. In some embodiments, the CXCR2 agonist may be a peptide having at least 85% sequence identity to the amino acid sequence of SEQ ID NO: 3 (e.g., a peptide having at least 85%, 90%, 95%, 96%, 97%, 98%, 99%, 99.%, or 100% sequence identity to the amino acid sequence of SEQ ID NO: 3). In some embodiments, the amino acid sequence of the CXCR2 agonist differs from that of SEQ ID NO: 3 only by way of one or more conservative amino acid substitutions. In some embodiments, in some embodiments, the amino acid sequence of the CXCR2 agonist differs from that of SEQ ID NO: 3 by no more than 20, no more than 15, no more than 10, no more than 5, or no more than 1 nonconservative amino acid substitutions.

Additional examples of CXCR2 agonists useful in conjunction with the compositions and methods described herein are variants of Gro-β T N65D, such as peptides that have one or more amino acid substitutions, insertions, and/or deletions relative to Gro-β T N65D. In some embodiments, the CXCR2 agonist may be a peptide having at least 85% sequence identity to the amino acid sequence of SEQ ID NO: 4 (e.g., a peptide having at least 85%, 90%, 95%, 96%, 97%, 98%, 99%, 99.%, or 100% sequence identity to the amino acid sequence of SEQ ID NO: 4). In some embodiments, the amino acid sequence of the CXCR2 agonist differs from that of SEQ ID NO: 4 only by way of one or more conservative amino acid substitutions. In some embodiments, in some embodiments, the amino acid sequence of the CXCR2 agonist differs from that of SEQ ID NO: 4 by no more than 20, no more than 15, no more than 10, no more than 5, or no more than 1 nonconservative amino acid substitutions.

Agonistic Anti-CXCR2 Antibodies and Antigen-Binding Fragments Thereof

In some embodiments, the CXCR2 agonist is an antibody or antigen-binding fragment thereof that binds CXCR2 and activates CXCR2 signal transduction. In some embodiments, the CXCR2 agonist may be an antibody or antigen-binding fragment thereof that binds the same epitope on CXCR2 as Gro-β or a variant or truncation thereof, such as Gro-β T, as assessed, for example, by way of a competitive CXCR2 binding assay. In some embodiments, the CXCR2 agonist is an antibody or an antigen-binding fragment thereof that competes with Gro-β or a variant or truncation thereof, such as Gro-β T, for binding to CXCR2.

In some embodiments of any of the above aspects, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from the group consisting of IgG, IgA, IgM, IgD, and IgE.

Synthetic CXCR2 Agonists

The peptidic CXCR2 agonists described herein, such as Gro-β, Gro-β T, and variants thereof, may be prepared synthetically, for instance, using solid phase peptide synthesis techniques. Systems and processes for performing solid phase peptide synthesis include those that are known in the art and have been described, for instance, in U.S. Pat. Nos. 9,169,287; 9,388,212; 9,206,222; 6,028,172; and 5,233,044, among others, the disclosures of each of which are incorporated herein by reference as they pertain to protocols and techniques for the synthesis of peptides on solid support. Solid phase peptide synthesis is a process in which amino acid residues are added to peptides that have been immobilized on a solid support, such as a polymeric resin (e.g., a hydrophilic resin, such as a polyethylene-glycol-containing resin, or hydrophobic resin, such as a polystyrene-based resin).

Peptides, such as those containing protecting groups at amino, hydroxy, thiol, and carboxy substituents, among others, may be bound to a solid support such that the peptide is effectively immobilized on the solid support. For example, the peptides may be bound to the solid support via their C termini, thereby immobilizing the peptides for subsequent reaction in at a resin-liquid interface.

The process of adding amino acid residues to immobilized peptides can include exposing a deprotection reagent to the immobilized peptides to remove at least a portion of the protection groups from at least a portion of the immobilized peptides. The deprotection reagent exposure step can be configured, for instance, such that side-chain protection groups are preserved, while N-terminal protection groups are removed. For instance, an exemplary amino protecting contains a fluorenylmethyloxycarbonyl (Fmoc) substituent. A deprotection reagent containing a strongly basic substance, such as piperidine (e.g., a piperidine solution in an appropriate organic solvent, such as dimethyl formamide (DMF)) may be exposed to the immobilized peptides such that the Fmoc protecting groups are removed from at least a portion of the immobilized peptides. Other protecting groups suitable for the protection of amino substituents include, for instance, the tert-butyloxycarbonyl (Boc) moiety. A deprotection reagent comprising a strong acid, such as trifluoroacetic acid (TFA) may be exposed to immobilized peptides containing a Boc-protected amino substituent so as to remove the Boc protecting group by an ionization process. In this way, peptides can be protected and deprotected at specific sites, such as at one or more side-chains or at the N- or C-terminus of an immobilized peptide so as to append chemical functionality regioselectively at one or more of these positions. This can be used, for instance, to derivatize a side-chain of an immobilized peptide, or to synthesize a peptide, e.g., from the C-terminus to the N-terminus.

The process of adding amino acid residues to immobilized peptides can include, for instance, exposing protected, activated amino acids to the immobilized peptides such that at least a portion of the activated amino acids are bonded to the immobilized peptides to form newly-bonded amino acid residues. For example, the peptides may be exposed to activated amino acids that react with the deprotected N-termini of the peptides so as to elongate the peptide chain by one amino acid. Amino acids can be activated for reaction with the deprotected peptides by reaction of the amino acid with an agent that enhances the electrophilicity of the backbone carbonyl carbon of the amino acid. For example, phosphonium and uronium salts can, in the presence of a tertiary base (e.g., diisopropylethylamine (DIPEA) and triethylamine (TEA), among others), convert protected amino acids into activated species (for example, BOP, PyBOP, HBTU, and TBTU all generate HOBt esters). Other reagents can be used to help prevent racemization that may be induced in the presence of a base. These reagents include carbodiimides (for example, DCC or WSCDI) with an added auxiliary nucleophile (for example, 1-hydroxy-benzotriazole (HOBO, 1-hydroxy-azabenzotriazole (HOAt), or HOSu) or derivatives thereof. Another reagent that can be utilized to prevent racemization is TBTU. The mixed anhydride method, using isobutyl chloroformate, with or without an added auxiliary nucleophile, can also be used, as well as the azide method, due to the low racemization associated with this reagent. These types of compounds can also increase the rate of carbodiimide-mediated couplings, as well as prevent dehydration of Asn and Gln residues. Typical additional reagents include also bases such as N,N-diisopropylethylamine (DIPEA), triethylamine (TEA) or N-methylmorpholine (NMM). These reagents are described in detail, for instance, in U.S. Pat. No. 8,546,350, the disclosure of which is incorporated herein in its entirety.

During the recombinant expression and folding of Gro-β and Gro-β T in aqueous solution, a particular C-terminal asparagine residue (Asn69 within Gro-β and Asn65 within Gro-β T) is prone to deamidation. This process effectuates the conversion of the asparagine residue to aspartic acid. Without wishing to be bound by any theory, the chemical synthesis of Gro-β and Gro-β T may overcome this problem, for instance, by providing conditions that reduce the exposure of this asparagine residue to nucleophilic solvent. When prepared synthetically (i.e., chemically synthesized), for instance, using, e.g., the solid phase peptide synthesis techniques described above, synthetic Gro-β, Gro-β T, and variants thereof that may be used in conjunction with the compositions and methods described herein may have a purity of, e.g., at least about 95% relative to the deamidated versions of these peptides (i.e., contain less than 5% of the corresponding deamidated peptide). For instance, synthetic Gro-β, Gro-β T, and variants thereof that may be used in conjunction with the compositions and methods described herein may have a purity of about 95%, 95.5%, 96%, 96.5%, 97%, 97.5%, 98%, 98.5%, 99%, 99.5%, 99.6%, 99.7%, 99.8%, 99.9%, 99.99%, or more, relative to the deamidated versions of these peptides (e.g., the Asn69 deamidated version of SEQ ID NO: 1 or the Asn65 deamidated version of SEQ ID NO: 2). For instance, synthetic Gro-β, Gro-β T, and variants thereof may have, for instance, a purity of from about 95% to about 99.99%, such as a purity of from about 95% to about 99.99%, about 96% to about 99.99%, about 97% to about 99.99%, about 98% to about 99.99%, about 99% to about 99.99%, about 99.9% to about 99.99%, about 95% to about 99.5%, about 96% to about 99.5%, about 95% to about 99%, or about 97% to about 99% relative to the deamidated versions of these peptides (e.g., the Asn69 deamidated version of SEQ ID NO: 1 or the Asn65 deamidated version of SEQ ID NO: 2).

CXCR4 Antagonists

Exemplary CXCR4 antagonists for use in conjunction with the compositions and methods described herein are compounds represented by formula (I)

Z-linker-Z'  (I)

or a pharmaceutically acceptable salt thereof, wherein Z is:
(i) a cyclic polyamine containing from 9 to 32 ring members, wherein from 2 to 8 of the ring members are nitrogen atoms separated from one another by 2 or more carbon atoms; or
(ii) an amine represented by formula (IA)

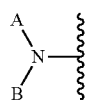
(IA)

wherein A includes a monocyclic or bicyclic fused ring system including at least one nitrogen atom and B is H or a substituent of from 1 to 20 atoms;

and wherein Z' is:
(i) a cyclic polyamine containing from 9 to 32 ring members, wherein from 2 to 8 of the ring members are nitrogen atoms separated from one another by 2 or more carbon atoms;
(ii) an amine represented by formula (IB)

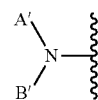
(IB)

wherein A' includes a monocyclic or bicyclic fused ring system including at least one nitrogen atom and B' is H or a substituent of from 1 to 20 atoms; or
(iii) a substituent represented by formula (IC)

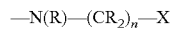
(IC)

wherein each R is independently H or $C_1$-$C_6$ alkyl, n is 1 or 2, and X is an aryl or heteroaryl group or a mercaptan;

wherein the linker is a bond, optionally substituted alkylene (e.g., optionally substituted $C_1$-$C_6$ alkylene), optionally substituted heteroalkylene (e.g., optionally substituted $C_1$-$C_6$ heteroalkylene), optionally substituted alkenylene (e.g., optionally substituted $C_2$-$C_6$ alkenylene), optionally substituted heteroalkenylene (e.g., optionally substituted $C_2$-$C_6$ heteroalkenylene), optionally substituted alkynylene (e.g., optionally substituted $C_2$-$C_6$ alkynylene), optionally substituted heteroalkynylene (e.g., optionally substituted $C_2$-$C_6$ heteroalkynylene), optionally substituted cycloalkylene, optionally substituted heterocycloalkylene, optionally substituted arylene, or optionally substituted heteroarylene.

In some embodiments, Z and Z' may each independently a cyclic polyamine containing from 9 to 32 ring members, of which from 2 to 8 are nitrogen atoms separated from one another by 2 or more carbon atoms. In some embodiments, Z and Z' are identical substituents. As an example, Z may be a cyclic polyamine including from 10 to 24 ring members. In some embodiments, Z may be a cyclic polyamine that contains 14 ring members. In some embodiments, Z includes 4 nitrogen atoms. In some embodiments, Z is 1,4,8,11-tetraazocyclotetradecane.

In some embodiments, the linker is represented by formula (ID)

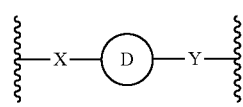
(ID)

wherein ring D is an optionally substituted aryl group, an optionally substituted heteroaryl group, an optionally substituted cycloalkyl group, or an optionally substituted heterocycloalkyl group; and
X and Y are each independently optionally substituted alkylene (e.g., optionally substituted $C_1$-$C_6$ alkylene), optionally substituted heteroalkylene (e.g., optionally substituted $C_1$-$C_6$ heteroalkylene), optionally substituted alkenylene (e.g., optionally substituted $C_2$-$C_6$ alkenylene), optionally substituted heteroalkenylene (e.g., optionally substituted $C_2$-$C_6$ heteroalkenylene), optionally substituted alkynylene (e.g., optionally substituted $C_2$-$C_6$ alkynylene), or optionally substituted heteroalkynylene (e.g., optionally substituted C₂-C₆ heteroalkynylene).

As an example, the linker may be represented by formula (IE)

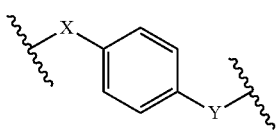

(IE)

wherein ring D is an optionally substituted aryl group, an optionally substituted heteroaryl group, an optionally substituted cycloalkyl group, or an optionally substituted heterocycloalkyl group; and X and Y are each independently optionally substituted alkylene (e.g., optionally substituted C₁-C₆ alkylene), optionally substituted heteroalkylene (e.g., optionally substituted C₁-C₆ heteroalkylene), optionally substituted C₂-C₆ alkenylene (e.g., optionally substituted C₂-C₆ alkenylene), optionally substituted heteroalkenylene (e.g., optionally substituted C₂-C₆ heteroalkenylene), optionally substituted alkynylene (e.g., optionally substituted C₂-C₆ alkynylene), or optionally substituted heteroalkynylene (e.g., optionally substituted C₂-C₆ heteroalkynylene). In some embodiments, X and Y are each independently optionally substituted C₁-C₆ alkylene. In some embodiments, X and Y are identical substituents. In some embodiments, X and Y may be each be methylene, ethylene, n-propylene, n-butylene, n-pentylene, or n-hexylene groups. In some embodiments, X and Y are each methylene groups.

The linker may be, for example, 1,3-phenylene, 2,6-pyridine, 3,5-pyridine, 2,5-thiophene, 4,4'-(2,2'-bipyrimidine), 2,9-(1,10-phenanthroline), or the like. In some embodiments, the linker is 1,4-phenylene-bis-(methylene).

CXCR4 antagonists useful in conjunction with the compositions and methods described herein include plerixafor (also referred to herein as "AMD3100" and "Mozibil"), or a pharmaceutically acceptable salt thereof, represented by formula (II), 1,1'-[1,4-phenylenebis(methylene)]-bis-1,4,8,11-tetra-azacyclotetradecane.

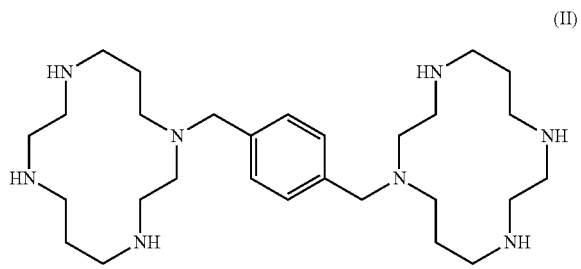 [SMILES: c1cc(CN2CCCNCCNCCCNCC2)ccc1CN1CCCNCCNCCCNCC1]

(II)

Additional CXCR4 antagonists that may be used in conjunction with the compositions and methods described herein include variants of plerixafor, such as a compound described in U.S. Pat. No. 5,583,131, the disclosure of which is incorporated herein by reference as it pertains to CXCR4 antagonists. In some embodiments, the CXCR4 antagonist may be a compound selected from the group consisting of: 1,1'-[1,3-phenylenebis(methylene)]-bis-1,4,8,11-tetra-azacyclotetradecane; 1,1'-[1,4-phenylene-bis-(methylene)]-bis-1,4,8,11-tetraazacyclotetradecane; bis-zinc or bis-copper complex of 1,1'-[1,4-phenylene-bis-(methylene)]-bis-1,4,8,11-tetraazacyclotetradecane; 1,1'-[3,3'-biphenylene-bis-(methylene)]-bis-1,4,8,11-tetraazacyclotetradecane; 11,11'-[1,4-phenylene-bis-(methylene)]-bis-1,4,7,11-tetraazacyclotetradecane; 1,11'-[1,4-phenylene-bis-(methylene)]-1,4,8,11-tetraazacyclotetradecane-1,4,7,11-tetraazacyclotetradecane; 1,1'-[2,6-pyridine-bis-(methylene)]-bis-1,4,8,11-tetraazacyclotetradecane; 1,1-[3,5-pyridine-bis-(methylene)]-bis-1,4,8,11-tetraazacyclotetradecane; 1,1'-[2,5-thiophene-bis-(methylene)]-bis-1,4,8,11-tetraazacyclotetradecane; 1,1'-[4,4'-(2,2'-bipyridine)-bis-(methylene)]-bis-1,4,8,11-tetraazacyclotetradecane; 1,1'-[2,9-(1,10-phenanthroline)-bis-(methylene)]-bis-1,4,8,11-tetraazacyclotetradecane; 1,1'-[1,3-phenylene-bis-(methylene)]-bis-1,4,7,10-tetraazacyclotetradecane; 1,1'-[1,4-phenylene-bis-(methylene)]-bis-1,4,7,10-tetraazacyclotetradecane; 1'-[5-nitro-1,3-phenylenebis(methylene)]bis-1,4,8,11-tetraazacyclotetradecane; 1',1'-[2,4,5,6-tetrachloro-1,3-phenylenebis(methylene)]bis-1,4,8,11-tetraazacyclotetradecane; 1,1'-[2,3,5,6-tetra-fluoro-1,4-phenylenebis(methylene)]bis-1,4,8,11-tetraazacyclotetradecane; 1,1'-[1,4-naphthylene-bis-(methylene)]bis-1,4,8,11-tetraazacyclotetradecane; 1,1'-[1,3-phenylenebis-(methylene)]bis-1,5,9-triazacyclododecane; 1,1'-[1,4-phenylene-bis-(methylene)]-1,5,9-triazacyclododecane; 1,1'-[2,5-dimethyl-1,4-phenylenebis-(methylene)]-bis-1,4,8,11-tetraazacyclotetradecane; 1,1'-[2,5-dichloro-1,4-phenylenebis-(methylene)]-bis-1,4,8,11-tetraazacyclotetradecane; 1,1'-[2-bromo-1,4-phenylenebis-(methylene)]-bis-1,4,8,11-tetraazacyclotetradecane; and 1,1'-[6-phenyl-2,4-pyridinebis-(methylene)]-bis-1,4,8,11-tetraazacyclotetradecane.

In some embodiments, the CXCR4 antagonist is a compound described in US 2006/0035829, the disclosure of which is incorporated herein by reference as it pertains to CXCR4 antagonists. In some embodiments, the CXCR4 antagonist may be a compound selected from the group consisting of: 3,7,11,17-tetraazabicyclo(13.3.1)heptadeca-1(17),13,15-triene; 4,7,10,17-tetrambicyclo(13.3.1)heptadeca-1(17),13,15-triene; 1,4,7,10-tetraazacyclotetradecane; 1,4,7-triazacyclotetradecane; and 4,7,10-triazabicyclo(13.3.1)heptadeca-1(17),13,15-triene.

The CXCR4 antagonist may be a compound described in WO 2001/044229, the disclosure of which is incorporated herein by reference as it pertains to CXCR4 antagonists. In some embodiments, the CXCR4 antagonist may be a compound selected from the group consisting of: N-[4-(11-fluoro-1,4,7-triazacyclotetradecanyl)-1,4-phenylenebis(methylene)]-2-(aminomethyl)pyridine; N-[4-(11,11-difluoro-1,4,7-triazacyclotetradecanyl)-1,4-phenylenebis(methylene)]-2-(aminomethyl)pyridine; N-[4-(1,4,7-triazacyclotetradecan-2-onyl)-1,4-phenylenebis(methylene)]-2-(aminomethyl)pyridine; N-[12-(5-oxa-1,9-diazacyclotetradecanyl)-1,4-phenylenebis(methylene)]-2-(aminomethyl)pyridine; N-[4-(11-oxa-1,4,7-triazacyclotetradecanyl)-1,4-phenylenebis(methylene)]-2-(aminomethyl)pyridine; N-[4-(11-thia-1,4,7-triazacyclotetradecanyl)-1,4-phenylenebis(methylene)]-2-(aminomethyl)pyridine; N-[4-(11-sulfoxo-1,4,7-triazacyclotetradecanyl)-1,4-phenylenebis(methylene)]-2-(aminomethyl)pyridine; N-[4-(11-sulfono-1,4,7-triazacyclotetradecanyl)-1,4-phenylenebis(methylene)]-2-(aminomethyl)pyridine; and N-[4-(3-carboxo-1,4,7-triazacyclotetradecanyl)-1,4-phenylenebis(methylene)]-2-(aminomethyl)pyridine.

Additional CXCR4 antagonists useful in conjunction with the compositions and methods described herein include compounds described in WO 2000/002870, the disclosure of which is incorporated herein by reference as it pertains to CXCR4 antagonists. In some embodiments, the CXCR4 antagonist may be a compound selected from the group consisting of: N-[1,4,8,11-tetraazacyclotetra-decanyl-1,4-phenylenebis-(methylene)]-2-(aminomethyl)pyridine; N-[1,4,8,11-tetraazacyclotetra-decanyl-1,4-phenylenebis(methylene)]-N-methyl-2-(aminomethyl)pyridine; N-[1,4,8,11-tetraazacyclotetra-decanyl-1,4-phenylenebis(methylene)]-4-(aminomethyl)pyridine; N-[1,4,8,11-tetraazacyclotetra-decanyl-1,4-phenylenebis(methylene)]-3-(aminomethyl)pyridine; N-[1,4,8,11-tetraazacyclotetra-decanyl-1,4-phenylenebis(methylene)]-(2-aminomethyl-5-methyl)pyrazine; N-[1,4,8,11-tetraazacyclotetra-decanyl-1,4-phenylenebis(methylene)]-2-(aminoethyl)pyridine; N-[1,4,8,11-tetraazacyclotetra-decanyl-1,4-phenylenebis(methylene)]-2-(aminomethyl)thiophene; N-[1,4,8,11-tetraazacyclotetra-decanyl-1,4-phenylenebis(methylene)]-2-(aminomethyl)mercaptan; N-[1,4,8,11-tetraazacyclotetra-decanyl-1,4-phenylenebis(methylene)]-2-amino benzylamine; N-[1,4,8,11-tetraazacyclotetra-decanyl-1,4-phenylenebis(methylene)]-4-amino benzylamine; N-[1,4,8,11-tetraazacyclotetra-decanyl-1,4-phenylenebis(methylene)]-4-(aminoethyl)imidazole; N-[1,4,8,11-tetraazacyclotetra-decanyl-1,4-phenylenebis(methylene)]-benzylamine; N-[4-(1,4,7-triazacyclotetra-decanyl)-1,4-phenylenebis(methylene)]-2-(aminomethyl)pyridine; N-[7-(4,7,10,17-tetraazabicyclo[13.3.1]heptadeca-1(17),13,15-trienyl)-1,4-phenylenebis(methylene)]-2-(aminomethyl)pyridine; N-[7-(4,7,10-triazabicyclo[13.3.1]heptadeca-1(17),13,15-trienyl)-1,4-phenylenebis(methylene)]-2-(aminomethyl)pyridine; N-[1-(1,4,7-triazacyclotetra-decanyl)-1,4-phenylenebis(methylene)]-2-(aminomethyl)pyridine; N-[4-[4,7,10,17-tetraazabicyclo[13.3.1]heptadeca-1(17),13,15-trienyl]-1,4-phenylenebis(methylene)]-2-(aminomethyl)pyridine; N-[4-[4,7,10-triazabicyclo[13.3.1]heptadeca-1 (17),13,15-trienyl]-1,4-phenylenebis(methylene)]-2-(aminomethyl)pyridine; N-[1,4,8,11-tetraazacyclotetradecanyl-1,4-phenylenebis(methylene)]-purine; 1-[1,4,8,11-tetraazacyclotetradecanyl-1,4-phenylenebis(methylene)]-4-phenylpiperazine; N-[4-(1,7-diazacyclotetradecanyl)-1,4-phenylenebis(methylene)]-2-(aminomethyl)pyridine; and N-[7-(4,10-diazabicyclo[13.3.1]heptadeca-1(17),13,15-trienyl)-1,4-phenylenebis(methylene)]-2-(aminomethyl)pyridine.

In some embodiments, the CXCR4 antagonist is a compound selected from the group consisting of: 1-[2,6-dimethoxypyrid-4-yl(methylene)]-1,4,8,11-tetraazacyclotetradecane; 1-[2-chloropyrid-4-yl(methylene)]-1,4,8,11-tetraazacyclotetradecane; 1-[2,6-dimethylpyrid-4-yl(methylene)]-1,4,8,11-tetraazacyclotetradecane; 1-[2-methylpyrid-4-yl(methylene)]-1,4,8,11-tetraazacyclotetradecane; 1-[2,6-dichloropyrid-4-yl(methylene)]-1,4,8,11-tetraazacyclotetradecane; 1-[2-chloropyrid-5-yl(methylene)]-1,4,8,11-tetraazacyclotetradecane; and 7-[4-methylphenyl(methylene)]-4,7,10,17-tetraazabicyclo[13.3.1]heptadeca-1(17),13,15-triene.

In some embodiments, the CXCR4 antagonist is a compound described in U.S. Pat. No. 5,698,546, the disclosure of which is incorporated herein by reference as it pertains to CXCR4 antagonists. In some embodiments, the CXCR4 antagonist may be a compound selected from the group consisting of: 7,7'-[1,4-phenylene-bis(methylene)]bis-3,7,11,17-tetraazabicyclo[13.3.1]heptadeca-1(17),13,15-triene; 7,7'-[1,4-phenylene-bis(methylene)]bis[15-chloro-3,7,11,17-tetraazabicyclo[13.3.1]heptadeca-1 (17),13,15-triene]; 7,7'-[1,4-phenylene-bis(methylene)]bis[15-methoxy-3,7,11,17-tetraazabicyclo[13.3.1]heptadeca-1(17),13,15-triene]; 7,7'-[1,4-phenylene-bis(methylene)]bis-3,7,11,17-tetraazabicyclo[13.3.1]-heptadeca-13,16-triene-15-one; 7,7'-[1,4-phenylene-bis(methylene)]bis-4,7,10,17-tetraazabicyclo[13.3.1]-heptadeca-1(17),13,15-triene; 8,8'-[1,4-phenylene-bis(methylene)]bis-4,8,12,19-tetraazabicyclo[15.3.1]nonadeca-1(19),15,17-triene; 6,6'-[1,4-phenylene-bis(methylene)]bis-3,6,9,15-tetraazabicyclo[11.3.1]pentadeca-1 (15),11,13-triene; 6,6'-[1,3-phenylene-bis(methylene)]bis-3,6,9,15-tetraazabicyclo[11.3.1]pentadeca-1 (15),11,13-triene; and 17,17'-[1,4-phenylene-bis(methylene)]bis-3,6,14,17,23,24-hexaazatricyclo[17.3.1.1$^{8,12}$]tetracosa-1(23),8,10,12(24),19,21-hexaene.

In some embodiments, the CXCR4 antagonist is a compound described in U.S. Pat. No. 5,021,409, the disclosure of which is incorporated herein by reference as it pertains to CXCR4 antagonists. In some embodiments, the CXCR4 antagonist may be a compound selected from the group consisting of: 2,2'-bicyclam, 6,6'-bicyclam; 3,3'-(bis-1,5,9,13-tetraaza cyclohexadecane); 3,3'-(bis-1,5,8,11,14-pentaazacyclohexadecane); methylene (or polymethylene) di-1-N-1,4,8,11-tetraazacyclotetradecane; 3,3'-bis-1,5,9,13-tetraazacyclohexadecane; 3,3'-bis-1,5,8,11,14-pentaazacyclohexadecane; 5,5'-bis-1,4,8,11-tetraazacyclotetradecane; 2,5'-bis-1,4,8,11-tetraazacyclotetradecane; 2,6'-bis-1,4,8,11-tetraazacyclotetradecane; 11,11'-(1,2-ethanediyl)bis-1,4,8,11-tetraazacyclotetradecane; 11,11'-(1,2-propanediyl)bis-1,4,8,11-tetraazacyclotetradecane; 11,11'-(1,2-butanediyl)bis-1,4,8,11-tetraazacyclotetradecane; 11,11'-(1,2-pentanediyl)bis-1,4,8,11-tetraazacyclotetradecane; and 11,11'-(1,2-hexanediyl)bis-1,4,8,11-tetraazacyclotetradecane.

In some embodiments, the CXCR4 antagonist is a compound described in WO 2000/056729, the disclosure of which is incorporated herein by reference as it pertains to CXCR4 antagonists. In some embodiments, the CXCR4 antagonist may be a compound selected from the group consisting of: N-(2-pyridinylmethyl)-N'-(6,7,8,9-tetrahydro-5H-cyclohepta[b]pyridin-9-yl)-1,4-benzenedimethanamine; N-(2-pyridinylmethyl)-N'-(5,6,7,8-tetrahydro-8-quinolinyl)-1,4-benzenedimethanamine; N-(2-pyridinylmethyl)-N'-(6,7-dihydro-5H-cyclopenta[b]pyridin-7-yl)-1,4-benzenedimethanamine; N-(2-pyridinylmethyl)-N'-(1,2,3,4-tetrahydro-1-naphthalenyl)-1,4-benzenedimethanamine; N-(2-pyridinylmethyl)-N'-(1-naphthalenyl)-1,4-benzenedimethanamine; N-(2-pyridinylmethyl)-N'-(8-quinolinyl)-1,4-benzenedimethanamine; N-(2-pyridinylmethyl)-N'-[2-[(2-pyridinylmethyl)amino]ethyl]-N'-(1-methyl-1,2,3,4-tetrahydro-8-quinolinyl)-1,4-benzenedimethanamine; N-(2-pyridinylmethyl)-N'-[2-[(1H-imidazol-2-ylmethyl)amino]ethyl]-N'-(1-methyl-1,2,3,4-tetrahydro-8-quinolinyl)-1,4-benzenedimethanamine; N-(2-pyridinylmethyl)-N'-(1,2,3,4-tetrahydro-8-quinolinyl)-1,4-benzenedimethanamine; N-(2-pyridinylmethyl)-N'-[2-[(1H-imidazol-2-ylmethyl)amino]ethyl]-N'-(1,2,3,4-tetrahydro-1-naphthalenyl)-1,4-benzenedimethanamine; N-(2-pyridinylmethyl)-N'-(2-phenyl-5,6,7,8-tetrahydro-8-quinolinyl)-1,4-benzenedimethanamine; N,N'-bis(2-pyridinylmethyl)-N'-(2-phenyl-5,6,7,8-tetrahydro-8-quinolinyl)-1,4-benzenedimethanamine;

N-(2-pyridinylmethyl)-N'-(5,6,7,8-tetrahydro-5-quinolinyl)-1,4-benzenedimethanamine; N-(2-pyridinylmethyl)-N'-(1H-imidazol-2-ylmethyl)-N'-(5,6,7,8-tetrahydro-5-quinolinyl)-1,4-benzenedimethanamine; N-(2-pyridinylmethyl)-N'-(1H-imidazol-2-ylmethyl)-N'-(5,6,7,8-tetrahydro-8-quinolinyl)-1,4-benzenedimethanamine; N-(2- pyridinylmethyl)-N'-[(2-amino-3-phenyl)propyl]-N'-(5,6,7,8-tetrahydro-8-quinolinyl)-1,4-benzenedimethanamine; N-(2-pyridinylmethyl)-N'-(1H-imidazol-4-ylmethyl)-N'-(5,6,7,8-tetrahydro-8-quinolinyl)-1,4-benzenedimethanamine; N-(2-pyridinylmethyl)-N'-(2-quinolinylmethyl)-N'-(5,6,7,8-tetrahydro-8-quinolinyl)-1,4-benzenedimethanamine; N-(2-pyridinylmethyl)-N'-(2-(2-naphthoyl)aminoethyl)-N'-(5,6,7,8-tetrahydro-8-quinolinyl)-1,4-benzenedimethanamine; N-(2-pyridinylmethyl)-N'—[(S)-(2-acetylamino-3-phenyl)propyl]-N'-(5,6,7,8-tetrahydro-8-quinolinyl)-1,4-benzenedimethanamine; N-(2-pyridinylmethyl)-N'—[(S)-(2-acetylamino-3-phenyl)propyl]-N'-(5,6,7,8-tetrahydro-8-quinolinyl)-1,4-benzenedimethanamine; N-(2-pyridinylmethyl)-N'-[3-((2-naphthalenylmethyl)amino)propyl]-N'-(5,6,7,8-tetrahydro-8-quinolinyl)-1,4-benzenedimethanamine; N-(2-pyridinylmethyl)-N'-[2-(S)-pyrollidinylmethyl]-N'-(5,6,7,8-tetrahydro-8-quinolinyl)-1,4-benzenedimethanamine; N-(2-pyridinylmethyl)-N'-[2-(R)-pyrollidinylmethyl]-N'-(5,6,7,8-tetrahydro-8-quinolinyl)-1,4-benzenedimethanamine; N-(2-pyridinylmethyl)-N'-[3-pyrazolylmethyl]-N'-(5,6,7,8-tetrahydro-8-quinolinyl)-1,4-benzenedimethanamine; N-(2-pyridinylmethyl)-N'-[2-pyrrolylmethyl]-N'-(5,6,7,8-tetrahydro-8-quinolinyl)-1,4-benzenedimethanamine; N-(2-pyridinylmethyl)-N'-[2-thiopheneylmethyl]-N'-(5,6,7,8-tetrahydro-8-quinolinyl)-1,4-benzenedimethanamine; N-(2-pyridinylmethyl)-N'-[2-thiazolylmethyl]-N'-(5,6,7,8-tetrahydro-8-quinolinyl)-1,4-benzenedimethanamine; N-(2-pyridinylmethyl)-N'-[2-furanylmethyl]-N'-(5,6,7,8-tetrahydro-8-quinolinyl)-1,4-benzenedimethanamine; N-(2-pyridinylmethyl)-N'-[2-[(phenylmethyl)amino]ethyl]-N'-(5,6,7,8-tetrahydro-8-quinolinyl)-1,4-benzenedimethanamine; N-(2-pyridinylmethyl)-N'-(2-aminoethyl)-N'-(5,6,7,8-tetrahydro-8-quinolinyl)-1,4-benzenedimethanamine; N-(2-pyridinylmethyl)-N'-3-pyrrolidinyl-N'-(5,6,7,8-tetrahydro-8-quinolinyl)-1,4-benzenedimethanamine; N-(2-pyridinylmethyl)-N'-4-piperidinyl-N'-(5,6,7,8-tetrahydro-8-quinolinyl)-1,4-benzenedimethanamine; N-(2-pyridinylmethyl)-N'-[2-[(phenyl)amino]ethyl]-N'-(5,6,7,8-tetrahydro-8-quinolinyl)-1,4-benzenedimethanamine; N-(2-pyridinylmethyl)-N'-(7-methoxy-1,2,3,4-tetrahydro-2-naphthalenyl)-1,4-benzenedimethanamine; N-(2-pyridinylmethyl)-N'-(6-methoxy-1,2,3,4-tetrahydro-2-naphthalenyl)-1,4-benzenedimethanamine; N-(2-pyridinylmethyl)-N'-(1-methyl-1,2,3,4-tetrahydro-2-naphthalenyl)-1,4-benzenedimethanamine; N-(2-pyridinylmethyl)-N'-(7-methoxy-3,4-dihydronaphthalenyl)-1-(aminomethyl)-4-benzamide; N-(2-pyridinylmethyl)-N'-(6-methoxy-3,4-dihydronaphthalenyl)-1-(aminomethyl)-4-benzamide; N-(2-pyridinylmethyl)-N'-(1H-imidazol-2-ylmethyl)-N'-(7-methoxy-1,2,3,4-tetrahydro-2-naphthalenyl)-1,4-benzenedimethanamine; N-(2-pyridinylmethyl)-N'-(8-hydroxy-1,2,3,4-tetrahydro-2-naphthalenyl)-1,4-benzenedimethanamine; N-(2-pyridinylmethyl)-N'-(1H-imidazol-2-ylmethyl)-N'-(8-hydroxy-1,2,3,4-tetrahydro-2-naphthalenyl)-1,4-benzenedimethanamine; N-(2-pyridinylmethyl)-N'-(8-Fluoro-1,2,3,4-tetrahydro-2-naphthalenyl)-1,4-benzenedimethanamine; N-(2-pyridinylmethyl)-N'-(1H-imidazol-2-ylmethyl)-N'-(8-Fluoro-1,2,3,4-tetrahydro-2-naphthalenyl)-1,4-benzenedimethanamine; N-(2-pyridinylmethyl)-N'-(5,6,7,8-tetrahydro-7-quinolinyl)-1,4-benzenedimethanamine; N-(2-pyridinylmethyl)-N'-(1H-imidazol-2-ylmethyl)-N'-(5,6,7,8-tetrahydro-7-quinolinyl)-1,4-benzenedimethanamine; N-(2-pyridinylmethyl)-N'-[2-[(2-naphthalenylmethyl)amino]ethyl]-N'-(5,6,7,8-tetrahydro-8-quinolinyl)-1,4-benzenedimethanamine; N-(2-pyridinylmethyl)-N'-[2-(isobutylamino)ethyl]-N'-(5,6,7,8-tetrahydro-8-quinolinyl)-1,4-benzenedimethanamine; N-(2-pyridinylmethyl)-N'-[2-[(2-pyridinylmethyl)amino]ethyl]-N'-(5,6,7,8-tetrahydro-8-quinolinyl)-1,4-benzenedimethanamine; N-(2-pyridinylmethyl)-N'-[2-[(2-furanylmethyl)amino]ethyl]-N'-(5,6,7,8-tetrahydro-8-quinolinyl)-1,4-benzenedimethanamine; N-(2-pyridinylmethyl)-N'-(2-guanidinoethyl)-N'-(5,6,7,8-tetrahydro-8-quinolinyl)-1,4-benzenedimethanamine; N-(2-pyridinylmethyl)-N'-[2-bis-[(2-methoxy)phenylmethyl]amino]ethyl]-N'-(5,6,7,8-tetrahydro-8-quinolinyl)-1,4-benzenedimethanamine; N-(2-pyridinylmethyl)-N'-[2-[(1H-imidazol-4-ylmethyl)amino]ethyl]-N'-(5,6,7,8-tetrahydro-8-quinolinyl)-1,4-benzenedimethanamine; N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine; N-(2-pyridinylmethyl)-N'-[2-(phenylureido)ethyl]-N'-(5,6,7,8-tetrahydro-8-quinolinyl)-1,4-benzenedimethanamine; N-(2-pyridinylmethyl)-N'—[[N"-(n-butyl)carboxamido]methyl]-N'-(5,6,7,8-tetrahydro-8-quinolinyl)-1,4-benzenedimethanamine; N-(2-pyridinylmethyl)-N'-(carboxamidomethyl)-N'-(5,6,7,8-tetrahydro-8-quinolinyl)-1,4-benzenedimethanamine; N-(2-pyridinylmethyl)-N'—[(N"-phenyl)carboxamidomethyl]-N'-(5,6,7,8-tetrahydro-8-quinolinyl)-1,4-benzenedimethanamine; N-(2-pyridinylmethyl)-N'-(carboxymethyl)-N'-(5,6,7,8-tetrahydro-8-quinolinyl)-1,4-benzenedimethanamine; N-(2-pyridinylmethyl)-N'-(phenylmethyl)-N'-(5,6,7,8-tetrahydro-8-quinolinyl)-1,4-benzenedimethanamine; N-(2-pyridinylmethyl)-N'-(1H-benzimidazol-2-ylmethyl)-N'-(5,6,7,8-tetrahydro-8-quinolinyl)-1,4-benzenedimethanamine; N-(2-pyridinylmethyl)-N'-(5,6-dimethyl-1H-benzimidazol-2-ylmethyl)-N'-(5,6,7,8-tetrahydro-8-quinolinyl)-1,4-benzenedimethanamine (hydrobromide salt); N-(2-pyridinylmethyl)-N'-(5-nitro-1H-benzimidazol-2-ylmethyl)-N'-(5,6,7,8-tetrahydro-8-quinolinyl)-1,4-benzenedimethanamine; N-(2-pyridinylmethyl)-N'-[(1H)-5-azabenzimidazol-2-ylmethyl]-N'-(5,6,7,8-tetrahydro-8-quinolinyl)-1,4-benzenedimethanamine; N-(2-pyridinylmethyl)-N-(4-phenyl-1H-imidazol-2-ylmethyl)-N'-(5,6,7,8-tetrahydro-8-quinolinyl)-1,4-benzenedimethanamine; N-(2-pyridinylmethyl)-N'-[2-(2-pyridinyl)ethyl]-N'-(5,6,7,8-tetrahydro-8-quinolinyl)-1,4-benzenedimethanamine; N-(2-pyridinylmethyl)-N'-(2-benzoxazolyl)-N'-(5,6,7,8-tetrahydro-8-quinolinyl)-1,4-benzenedimethanamine; N-(2-pyridinylmethyl)-N'-(trans-2-aminocyclohexyl)-N'-(5,6,7,8-tetrahydro-8-quinolinyl)-1,4-benzenedimethanamine; N-(2-pyridinylmethyl)-N'-(2-phenylethyl)-N'-(5,6,7,8-tetrahydro-8-quinolinyl)-1,4-benzenedimethanamine; N-(2-pyridinylmethyl)-N'-(3-phenylpropyl)-N'-(5,6,7,8-tetrahydro-8-quinolinyl)-1,4-benzenedimethanamine; N-(2-pyridinylmethyl)-N'-(trans-2-aminocyclopentyl)-N'-(5,6,7,8-tetrahydro-8-quinolinyl)-1,4-benzenedimethanamine; N-[[4-[[(2-pyridinylmethyl)amino]methyl]phenyl]methyl]-N-(5,6,7,8-tetrahydro-8-quinolinyl)-glycinamide; N-[[4-[[(2-pyridinylmethyl)amino]methyl]phenyl]methyl]-N-(5,6,7,8-tetrahydro-8-quinolinyl)-(L)-alaninamide; N-[[4-[[(2-pyridinylmethyl)amino]methyl]phenyl]methyl]-N-(5,6,7,8-tetrahydro-8-quinolinyl)-(L)-aspartamide; N-[[4-[[(2-pyridinylmethyl)amino]methyl]phenyl]methyl]-N-(5,6,7,8-tetrahydro-8-quinolinyl)-pyrazinamide; N-[[4-[[(2-pyridinylmethyl)amino]methyl]phenyl]methyl]-N-(5,6,7,8-tetrahydro-8-quinolinyl)-(L)-prolinamide; N-[[4-[[(2-pyridinylmethyl)amino]methyl]phenyl]methyl]-N-(5,6,7,8-tetrahydro-8-quinolinyl)-(L)-lysinamide; N-[[4-[[(2-pyridinylmethyl)

amino]methyl]phenyl]methyl]-N-(5,6,7,8-tetrahydro-8-quinolinyl)-benzamide; N-[[4-[[(2-pyridinylmethyl)amino]methyl]phenyl]methyl]-N-(5,6,7,8-tetrahydro-8-quinolinyl)-picolinamide; N'-Benzyl-N-[[4-[[(2-pyridinylmethyl)amino]methyl]phenyl]methyl]-N-(5,6,7,8-tetrahydro-8-quinolinyl)-urea; N'-phenyl-N-[[4-[[(2-pyridinylmethyl)amino]methyl]phenyl]methyl]-N-(5,6,7,8-tetrahydro-8-quinolinyl)-urea; N-(6,7,8,9-tetrahydro-5H-cyclohepta[bacteriapyridin-9-yl)-44 [(2-pyridinylmethyl)amino]methyl]benzamide; N-(5,6,7,8-tetrahydro-8-quinolinyl)-4-[[(2-pyridinylmethyl)amino]methyl]benzamide; N,N'-bis(2-pyridinylmethyl)-N'-(5,6,7,8-tetrahydro-8-quinolinyl)-1,4-benzenedimethanamine; N,N'-bis(2-pyridinylmethyl)-N'-(6,7,8,9-tetrahydro-5H-cyclohepta[bacteriapyridin-9-yl)-1,4-benzenedimethanamine; N,N'-bis(2-pyridinylmethyl)-N'-(6,7-dihydro-5H-cyclopenta[bacteriapyridin-7-yl)-1,4-benzenedimethanamine; N,N'-bis(2-pyridinylmethyl)-N'-(1,2,3,4-tetrahydro-1-naphthalenyl)-1,4-benzenedimethanamine; N,N'-bis(2-pyridinylmethyl)-N'-[(5,6,7,8-tetrahydro-8-quinolinyl)methyl]-1,4-benzenedimethanamine; N,N'-bis(2-pyridinylmethyl)-N'[(6,7-dihydro-5H-cyclopenta[bacteriapyridin-7-yl)methyl]-1,4-benzenedimethanamine; N-(2-pyridinylmethyl)-N-(2-methoxyethyl)-N'-(5,6,7,8-tetrahydro-8-quinolinyl)-1,4-benzenedimethanamine; N-(2-pyridinylmethyl)-N-[2-(4-methoxyphenyl)ethyl]-N'-(5,6,7,8-tetrahydro-8-quinolinyl)-1,4-benzenedimethanamine; N,N'-bis(2-pyridinylmethyl)-1,4-(5,6,7,8-tetrahydro-8-quinolinyl)benzenedimethanamine; N-[(2,3-dimethoxyphenyl)methyl]-N'-(2-pyridinylmethyl)-N-(5,6,7,8-tetrahydro-8-quinolinyl)-1,4-benzenedimethanamine; N,N'-bis(2-pyridinylmethyl)-N-[1-(N''-phenyl-N''-methylureido)-4-piperidinyl]-1,3-benzenedimethanamine; N,N'-bis(2-pyridinylmethyl)-N—[N''-p-toluenesulfonylphenylalanyl]-4-piperidinyl]-1,3-benzenedimethanamine; N,N'-bis(2-pyridinylmethyl)-N-[1-[3-(2-chlorophenyl)-5-methyl-isoxazol-4-oyl]-4-piperidinyl]-1,3-benzenedimethanamine; N-[(2-hydroxyphenyl)methyl]-N'-(2-pyridinylmethyl)-N-(6,7,8,9-tetrahydro-5H-cyclohepta[bacteriapyridin-9-yl)-1,4-benzenedimethanamine; N-[(4-cyanophenyl)methyl]-N'-(2-pyridinylmethyl)-N-(6,7,8,9-tetrahydro-5H-cyclohepta[bacteriapyridin-9-yl)-1,4-benzenedimethanamine; N-[(4-cyanophenyl)methyl]-N'-(2-pyridinylmethyl)-N-(5,6,7,8-tetrahydro-8-quinolinyl)-1,4-benzenedimethanamine; N-[(4-acetamidophenyl)methyl]-N'-(2-pyridinylmethyl)-N-(5,6,7,8-tetrahydro-8-quinolinyl)-1,4-benzenedimethanamine; N-[(4-phenoxyphenyl)methyl]-N'-(2-pyridinylmethyl)-N-(6,7,8,9-tetrahydro-5H-cyclohepta[bacteriapyridin-9-yl)-1,4-benzenedimethanamine; N-[(1-methyl-2-carboxamido)ethyl]-N,N'-bis(2-pyridinylmethyl)-1,3-benzenedimethanamine; N-[(4-benzyloxyphenyl)methyl]-M-(2-pyridinylmethyl)-N-(6,7,8,9-tetrahydro-5H-cyclohepta[bacteriapyridin-9-yl)-1,4-benzenedimethanamine; N-[(thiophene-2-yl)methyl]-N'-(2-pyridinylmethyl)-N-(6,7,8,9-tetrahydro-5H-cyclohepta[bacteriapyridin-9-yl)-1,4-benzenedimethanamine; N-[1-(benzyl)-3-pyrrolidinyl]-N,N'-bis(2-pyridinylmethyl)-1,3-benzenedimethanamine; N-[[1-methyl-3-(pyrazol-3-yl)]propyl]-N,N'-bis(2-pyridinylmethyl)-1,3-benzenedimethanamine; N-[1-(phenyl)ethyl]-N,N'-bis(2-pyridinylmethyl)-1,3-benzenedimethanamine; N-[(3,4-methylenedioxyphenyl)methyl]-N'-(2-pyridinylmethyl)-N-(6,7,8,9-tetrahydro-5H-cyclohepta[b]pyridin-9-yl)-1,4-benzenedimethanamine; N-[1-benzyl-3-carboxymethyl-4-piperidinyl]-N,N'-bis(2-pyridinylmethyl)-1,3-benzenedimethanamine; N-[(3,4-methylenedioxyphenyl)methyl]-N'-(2-pyridinylmethyl)-N-(5,6,7,8-tetrahydro-8-quinolinyl)-1,4-benzenedimethanamine; N-(3-pyridinylmethyl)-N'-(2-pyridinylmethyl)-N-(6,7,8,9-tetrahydro-5H-cyclohepta[b]pyridin-9-yl)-1,4-benzenedimethanamine; N-[[1-methyl-2-(2-tolyl)carboxamido]ethyl]-N,N'-bis(2-pyridinylmethyl)-1,3-benzenedimethanamine; N-[(1,5-dimethyl-2-phenyl-3-pyrazolinone-4-yl)methyl]-M-(2-pyridinylmethyl)-N-(5,6,7,8-tetrahydro-8-quinolinyl)-1,4-benzenedimethanamine; N-[(4-propoxyphenyl)methyl]-N'-(2-pyridinylmethyl)-N-(6,7,8,9-tetrahydro-5H-cyclohepta[b]pyridin-9-yl)-1,4-benzenedimethanamine; N-(1-phenyl-3,5-dimethylpyrazolin-4-ylmethyl)-N'-(2-pyridinylmethyl)-N-(5,6,7,8-tetrahydro-8-quinolinyl)-1,4-benzenedimethanamine; N—[H-imidazol-4-ylmethyl]-N,N'-bis(2-pyridinylmethyl)-1,3-benzenedimethanamine; N-[(3-methoxy-4,5-methylenedioxyphenyl)methyl]-N'-[2-pyridinylmethyl)-N-(6,7,8,9-tetrahydro-5H-cyclohepta[b]pyridin-9-yl)-1,4-benzenedimethanamine; N-[(3-cyanophenyl)methyl]-N'-(2-pyridinylmethyl)-N-(6,7,8,9-tetrahydro-5H-cyclohepta[b]pyridin-9-yl)-1,4-benzenedimethanamine; N-[(3-cyanophenyl)methyl]-N'-(2-pyridinylmethyl)-N-(5,6,7,8-tetrahydro-8-quinolinyl)-1,4-benzenedimethanamine; N-(5-ethylthiophene-2-ylmethyl)-N'-(2-pyridinylmethyl)-N-(6,7,8,9-tetrahydro-5H-cyclohepta[b]pyridin-9-yl)-1,4-benzenedimethanamine; N-(5-ethylthiophene-2-ylmethyl)-N'-(2-pyridinylmethyl)-N-(5,6,7,8-tetrahydro-8-quinolinyl)-1,4-benzenedimethanamine; N-[(2,6-difluorophenyl)methyl]-N'-(2-pyridinylmethyl)-N-(6,7,8,9-tetrahydro-5H-cyclohepta[b]pyridin-9-yl)-1,4-benzenedimethanamine; N-[(2,6-difluorophenyl)methyl]-N'-(2-pyridinylmethyl)-N-(5,6,7,8-tetrahydro-8-quinolinyl)-1,4-benzenedimethanamine; N-[(2-difluoromethoxyphenyl)methyl]-N'-(2-pyridinylmethyl)-N-(6,7,8,9-tetrahydro-5H-cyclohepta[b]pyridin-9-yl)-1,4-benzenedimethanamine; N-(2-difluoromethoxyphenylmethyl)-N'-(2-pyridinylmethyl)-N-(5,6,7,8-tetrahydro-8-quinolinyl)-1,4-benzenedimethanamine; N-(1,4-benzodioxan-6-ylmethyl)-N'-(2-pyridinylmethyl)-N-(6,7,8,9-tetrahydro-5H-cyclohepta[b]pyridin-9-yl)-1,4-benzenedimethanamine; N,N'-bis(2-pyridinylmethyl)-N-[1-(N''-phenyl-N''-methylureido)-4-piperidinyl]-1,4-benzenedimethanamine; N,N'-bis(2-pyridinylmethyl)-N—[N''-p-toluenesulfonylphenylalanyl]-4-piperidinyl]-1,4-benzenedimethanamine; N-[1-(3-pyridinecarboxamido)-4-piperidinyl]-N,N'-bis(2-pyridinylmethyl)-1,4-benzenedimethanamine; N-[1-(cyclopropylcarboxamido)-4-piperidinyl]-N,N'-bis(2-pyridinylmethyl)-1,4-benzenedimethanamine; N-[1-(1-phenylcyclopropylcarboxamido)-4-piperidinyl]-N,N'-bis(2-pyridinylmethyl)-1,4-benzenedimethanamine; N-(1,4-benzodioxan-6-ylmethyl)-N'-(2-pyridinylmethyl)-N-(5,6,7,8-tetrahydro-8-quinolinyl)-1,4-benzenedimethanamine; N-[1-[3-(2-chlorophenyl)-5-methyl-isoxazol-4-carboxamido]-4-piperidinyl]-N,N'-bis(2-pyridinylmethyl)-1,4-benzenedimethanamine; N-[1-(2-thiomethylpyridine-3-carboxamido)-4-piperidinyl]-N,N'-bis(2-pyridinylmethyl)-1,4-benzenedimethanamine; N-[(2,4-difluorophenyl)methyl]-N'-(2-pyridinylmethyl)-N-(5,6,7,8-tetrahydro-8-quinolinyl)-1,4-benzenedimethanamine; N-(1-methylpyrrol-2-ylmethyl)-N'-(2-pyridinylmethyl)-N-(5,6,7,8-tetrahydro-8-quinolinyl)-1,4-benzenedimethanamine; N-[(2-hydroxyphenyl)methyl]-N'-(2-pyridinylmethyl)-N-(5,6,7,8-tetrahydro-8-quinolinyl)-1,4-benzenedimethanamine; N-[(3-methoxy-4,5-methylenedioxyphenyl)methyl]-N'-(2-pyridinylmethyl)-N-(5,6,7,8-tetrahydro-8-quinolinyl)-1,4-benzenedimethanamine; N-(3- pyridinylmethyl)-N'-(2-pyridinylmethyl)-N-(5,6,7,8-tetrahydro-8-quinolinyl)-1,4-benzenedimethanamine; N-[2-(N'''-morpholinomethyl)-1-cyclopentyl]-N,N'-bis(2-pyridinylmethyl)-1,4-benzenedimethanamine; N-[(1-methyl-3-piperidinyl)propyl]-N,N'-bis(2-pyridinylmethyl)-1,4-benzenedimethanamine; N-(1-methylbenzimidazol-2-ylmethyl)-N'-(2-pyridinylmethyl)-N-(5,6,7,8-tetrahydro-8-quinolinyl)-1,4-benzenedimethanamine; N-[1-(benzyl)-3-pyrrolidinyl]-N,N'-bis(2-pyridinylmethyl)-1,4-benzenedimethanamine; N-[[(1-phenyl-3-(N'''-morpholino)]propyl]-N,N'-bis(2-pyridinylmethyl)-1,4-benzenedimethanamine; N-[1-(iso-propyl)-4-piperidinyl]-N,N'-bis(2-pyridinylmethyl)-1,4-benzenedimethanamine; N-[1-(ethoxycarbonyl)-4-piperidinyl]-N'-(2-pyridinylmethyl)-N-(5,6,7,8-tetrahydro-8-quinolinyl)-1,4-benzenedimethanamine; N-[(1-methyl-3-pyrazolyl)propyl]-N'-(2-pyridinylmethyl)-N-(5,6,7,8-tetrahydro-8-quinolinyl)-1,4-benzenedimethanamine; N-[1-methyl-2-(N'',N''-diethylcarboxamido)ethyl]-N,N'-bis(2-pyridinylmethyl)-1,4-benzenedimethanamine; N-[(1-methyl-2-phenylsulfonyl)ethyl]-M-(2-pyridinylmethyl)-N-(5,6,7,8-tetrahydro-8-quinolinyl)-1,4-benzenedimethanamine; N-[(2-chloro-4,5-methylenedioxyphenyl)methyl]-N'-(2-pyridinylmethyl)-N-(5,6,7,8-tetrahydro-8-quinolinyl)-1,4-benzenedimethanamine; N-[1-methyl-2-[N'''-(4-chlorophenyl)carboxamido]ethyl]-N'-(2-pyridinylmethyl)-N-(5,6,7,8-tetrahydro-8-quinolinyl)-1,4-benzenedimethanamine; N-(1-acetoxyindol-3-ylmethyl)-N'-(2-pyridinylmethyl)-N-(6,7,8,9-tetrahydro-5H-cyclohepta[b]pyridin-9-yl)-1,4-benzenedimethanamine; N-[(3-benzyloxy-4-methoxyphenyl)methyl]-N'-(2-pyridinylmethyl)-N-(6,7,8,9-tetrahydro-5H-cyclohepta[b]pyridin-9-yl)-1,4-benzenedimethanamine; N-(3-quinolylmethyl)-N'-(2-pyridinylmethyl)-N-(5,6,7,8-tetrahydro-8-quinolinyl)-1,4-benzenedimethanamine; N-[(8-hydroxy)-2-quinolylmethyl]-N'-(2-pyridinylmethyl)-N-(6,7,8,9-tetrahydro-5H-cyclohepta[b]pyridin-9-yl)-1,4-benzenedimethanamine; N-(2-quinolylmethyl)-N'-(2-pyridinylmethyl)-N-(6,7,8,9-tetrahydro-5H-cyclohepta[b]pyridin-9-yl)-1,4-benzenedimethanamine; N-[(4-acetamidophenyl)methyl]-N'-(2-pyridinylmethyl)-N-(6,7,8,9-tetrahydro-5H-cyclohepta[b]pyridin-9-yl)-1,4-benzenedimethanamine; N-[1H-imidazol-2-ylmethyl]-N,N'-bis(2-pyridinylmethyl)-1,4-benzenedimethanamine; N-(3-quinolylmethyl)-N'-(2-pyridinylmethyl)-N-(6,7,8,9-tetrahydro-5H-cyclohepta[b]pyridin-9-yl)-1,4-benzenedimethanamine; N-(2-thiazolylmethyl)-N'-(2-pyridinylmethyl)-N-(6,7,8,9-tetrahydro-5H-cyclohepta[b]pyridin-9-yl)-1,4-benzenedimethanamine; N-(4-pyridinylmethyl)-N'-(2-pyridinylmethyl)-N-(6,7,8,9-tetrahydro-5H-cyclohepta[b]pyridin-9-yl)-1,4-benzenedimethanamine; N-[(5-benzyloxy)benzo[b]pyrrol-3-ylmethyl]-N,N'-bis(2-pyridinylmethyl)-1,4-benzenedimethanamine; N-(1-methylpyrazol-2-ylmethyl)-N'-(2-pyridinylmethyl)-N-(6,7,8,9-tetrahydro-5H-cyclohepta[b]pyridin-9-yl)-1,4-benzenedimethanamine; N-[(4-methyl)-1H-imidazol-5-ylmethyl]-N,N'-bis(2-pyridinylmethyl)-1,4-benzenedimethanamine; N-[[(4-dimethylamino)-1-napthalenyl]methyl]-N,N'-bis(2-pyridinylmethyl)-1,4-benzenedimethanamine; N-[1,5-dimethyl-2-phenyl-3-pyrazolinone-4-ylmethyl]-N,N'-bis(2-pyridinylmethyl)-1,4-benzenedimethanamine; N-[1-[(1-acetyl-2-(R)-prolinyl]-4-piperidinyl]-N-[2-(2-pyridinyl)ethyl]-N'-(2-pyridinylmethyl)-1,3-benzenedimethanamine; N-[1-[2-acetamidobenzoyl-4-piperidinyl]-4-piperidinyl]-N-[2-(2-pyridinyl)ethyl]-N'-(2-pyridinylmethyl)-1,3-benzenedimethanamine; N-[(2-cyano-2-phenyl)ethyl]-M-(2-pyridinylmethyl)-N-(6,7,8,9-tetrahydro-5H-cyclohepta[b]pyridin-9-yl)-1,4-benzenedimethanamine; N—[(N''-acetyltryphanyl)-4-piperidinyl]-N-[2-(2-pyridinyl)ethyl]-N'-(2-pyridinylmethyl)-1,3-benzenedimethanamine; N—[(N''-benzoylvalinyl)-4-piperidinyl]-N-[2-(2-pyridinyl)ethyl]-N'-(2-pyridinylmethyl)-1,3-benzenedimethanamine; N-[(4-dimethylaminophenyl)methyl]-N'-(2-pyridinylmethyl)-N-(6,7,8,9-tetrahydro-5H-cyclohepta[b]pyridin-9-yl)-1,4-benzenedimethanamine; N-(4-pyridinylmethyl)-N'-(2-pyridinylmethyl)-N-(5,6,7,8-tetrahydro-8-quinolinyl)-1,4-benzenedimethanamine; N-(1-methylbenzimadazol-2-ylmethyl)-N'-(2-pyridinylmethyl)-N-(6,7,8,9-tetrahydro-5H-cyclohepta[b]pyridin-9-yl)-1,4-benzenedimethanamine; N-[1-butyl-4-piperidinyl]-N-[2-(2-pyridinyl)ethyl]-N'-(2-pyridinylmethyl)-1,3-benzenedimethanamine; N-[1-benzoyl-4-piperidinyl]-N-[2-(2-pyridinyl)ethyl]-N'-(2-pyridinylmethyl)-1,3-benzenedimethanamine; N-[1-(benzyl)-3-pyrrolidinyl]-N-[2-(2-pyridinyl)ethyl]-N'-(2-pyridinylmethyl)-1,3-benzenedimethanamine; N-[(1-methyl)benzo[b]pyrrol-3-ylmethyl]-N-[2-(2-pyridinyl)ethyl]-N'-(2-pyridinylmethyl)-1,3-benzenedimethanamine; N-[1H-imidazol-4-ylmethyl]-N-[2-(2-pyridinyl)ethyl]-N'-(2-pyridinylmethyl)-1,3-benzenedimethanamine; N-[1-(benzyl)-4-piperidinyl]-N-[2-(2-pyridinyl)ethyl]-N'-(2-pyridinylmethyl)-1,4-benzenedimethanamine; N-[1-methylbenzimidazol-2-ylmethyl]-N-[2-(2-pyridinyl)ethyl]-N'-(2-pyridinylmethyl)-1,4-benzenedimethanamine; N-[(2-phenyl)benzo[b]pyrrol-3-ylmethyl]-N-[2-(2-pyridinyl)ethyl]-N'-(2-pyridinylmethyl)-1,4-benzenedimethanamine; N-[(6-methylpyridin-2-yl)methyl]-N'-(2-pyridinylmethyl)-N-(5,6,7,8-tetrahydro-8-quinolinyl)-1,4-benzenedimethanamine; N-(3-methyl-1H-pyrazol-5-ylmethyl)-N'-(2-pyridinylmethyl)-N-(5,6,7,8-tetrahydro-8-quinolinyl)-1,3-benzenedimethanamine; N-[(2-methoxyphenyl)methyl]-N'-(2-pyridinylmethyl)-N-(5,6,7,8-tetrahydro-8-quinolinyl)-1,3-benzenedimethanamine; N-[(2-ethoxyphenyl)methyl]-N'-(2-pyridinylmethyl)-N-(6,7,8,9-tetrahydro-5H-cyclohepta[b]pyridin-9-yl)-1,3-benzenedimethanamine; N-(benzyloxyethyl)-N'-(2-pyridinylmethyl)-N-(5,6,7,8-tetrahydro-8-quinolinyl)-1,3-benzenedimethanamine; N-[(2-ethoxy-1-naphthalenyl)methyl]-N'-(2-pyridinylmethyl)-N-(5,6,7,8-tetrahydro-8-quinolinyl)-1,3-benzenedimethanamine; N-[(6-methylpyridin-2-yl)methyl]-N'-(2-pyridinylmethyl)-N-(5,6,7,8-tetrahydro-8-quinolinyl)-1,3-benzenedimethanamine; 1-[[4-[[(2-pyridinylmethyl)amino]methyl]phenyl]methyl]guanidine; N-(2-pyridinylmethyl)-N-(8-methyl-8-azabicyclo[3.2.1]octan-3-yl)-1,4-benzenedimethanamine; 1-[[4-[[(2-pyridinylmethyl)amino]methyl]phenyl]methyl]homopiperazine; 1-[[3-[[(2-pyridinylmethyl)amino]methyl]phenyl]methyl]homopiperazine; trans and cis-1-[[4-[[(2-pyridinylmethyl)amino]methyl]phenyl]methyl]-3,5-piperidinediamine; N,N'-[1,4-Phenylenebis(methylene)]bis-4-(2-pyrimidyl)piperazine; 1-[[4-[[(2-pyridinylmethyl)amino]methyl]phenyl]methyl]-1-(2-pyridinyl)methylamine; 2-(2-pyridinyl)-5-[[(2-pyridinylmethyl)amino]methyl]-1,2,3,4-tetrahydroisoquinoline; 1-[[4-[[(2-pyridinylmethyl)amino]methyl]phenyl]methyl]-3,4-diaminopyrrolidine; 1-[[4-[[(2-pyridinylmethyl)amino]methyl]phenyl]methyl]-3,4-diacetylaminopyrrolidine; [[4-[[(2-pyridinylmethyl)amino]methyl]phenyl]methyl]-2,5,8-triaza-3-oxabicyclo[4.3.0]nonane; and 8-[[4-[[(2-pyridinylmethyl)amino]methyl]phenyl]methyl]-2,5,8-triazabicyclo[4.3.0]nonane.

Additional CXCR4 antagonists that may be used to in conjunction with the compositions and methods described herein include those described in WO 2001/085196, WO 1999/050461, WO 2001/094420, and WO 2003/090512, the disclosures of each of which are incorporated herein by reference as they pertain to compounds that inhibit CXCR4 activity or expression.

Expansion of Hematopoietic Stem and Progenitor Cells

Prior to infusion into a patient, hematopoietic and progenitor cells may be expanded ex vivo, for example, by contacting the cells with an aryl hydrocarbon receptor antagonist. Aryl hydrocarbon receptor antagonists useful in conjunction with the compositions and methods described herein include those described in U.S. Pat. No. 9,580,426, the disclosure of which is incorporated herein by reference in its entirety.

In some embodiments, aryl hydrocarbon receptor antagonists include those represented by formula (III)

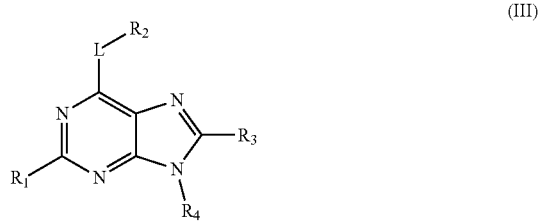

(III)

in which:
L is selected from —NR$_{5a}$(CH$_2$)$_{2-3}$, —NR$_{5a}$(CH$_2$)$_2$NR$_{5b}$—, —NR$_{5a}$(CH$_2$)$_2$S—, —NR$_{5a}$CH$_2$CH(OH)— and —NR$_{5a}$CH(CH$_3$)CH$_2$—; wherein R$_{5a}$ and R$_{5b}$ are independently selected from hydrogen and C$_{1-4}$ alkyl;
R$_1$ is selected from thiophenyl, 1H-benzoimidazolyl, isoquinolinyl, 1H-imidazopyridinyl, benzothiophenyl, pyrimidinyl, pyridinyl, pyrazinyl, pyridazinyl, and thiazolyl; In some embodiments, wherein the thiophenyl, 1H-benzoimidazolyl, isoquinolinyl, 1H-imidazopyridinyl, benzothiophenyl, pyrimidinyl, pyridinyl, pyrazinyl, pyridazinyl, or thiazolyl of R$_1$ can be optionally substituted by 1 to 3 radicals independently selected from cyano, hydroxy, C$_{1-4}$ alkyl, C$_{1-4}$ alkoxy, halo, halo-substituted-C$_{1-4}$ alkyl, halo-substituted-C$_{1-4}$alkoxy, amino, —C(O)R$_{8a}$, —S(O)$_{0-2}$R$_{8a}$, —C(O)OR$_{8a}$ and —C(O)NR$_{8a}$R$_{8b}$; wherein R$_{8a}$ and R$_{8b}$ are independently selected from hydrogen and C$_{1-4}$alkyl;
R$_2$ is selected from —S(O)$_2$NR$_{6a}$R$_{6b}$, —NR$_{6a}$C(O)R$_{6b}$—, —NR$_{6a}$C(O)NR$_{6b}$R$_{6c}$, phenyl, 1H-pyrrolopyridin-3-yl, 1H-pyrrolopyridin-5-yl, 1H-indolyl thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl; wherein R$_{6a}$, R$_{6b}$ and R$_{6c}$ are independently selected from hydrogen and C$_{1-4}$alkyl; and the phenyl, 1H-pyrrolopyridin-3-yl, 1H-pyrrolo[2,3-b]pyridin-5-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl or 1H-indazolyl of R$_2$ is optionally substituted with 1 to 3 radicals independently selected from hydroxy, halo, methyl, methoxy, amino, —O(CH$_2$)$_2$NR$_{7a}$R$_{7b}$, —S(O)$_2$NR$_{7a}$R$_{7b}$, —OS(O)$_2$NR$_{7a}$R$_b$ and —NR$_{7a}$S(O)$_2$R$_{7b}$; wherein R$_{7a}$ and R$_{7b}$ are independently selected from hydrogen and C$_{1-4}$ alkyl;
R$_3$ is selected from hydrogen, C$_{1-4}$alkyl and biphenyl; and
R$_4$ is selected from C$_{1-10}$ alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, and benzyl, (4-pentylphenyl)(phenyl)methyl and 1-(1-(2-oxo-6,9,12-trioxa-3-azatetradecan-14-yl)-1H-1,2,3-triazol-4-yl) ethyl wherein said alkyl, cyclopropyl, cyclohexyl, 2-(2-oxopyrrolidin-1-yl)ethyl, oxetan-3-yl, oxetan-2-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl or 1-(1-(2-oxo-6,9,12-trioxa-3-azatetradecan-14-yl)-1H-1,2,3-triazol-4-yl)ethyl can be optionally substituted with 1 to 3 radicals independently selected from hydroxy, C$_{1-4}$alkyl and halo-substituted-C$_{1-4}$alkyl; or a salt thereof.

In some embodiments, aryl hydrocarbon receptor antagonists useful in conjunction with the compositions and methods described herein include SR-1, represented by formula (1), below.

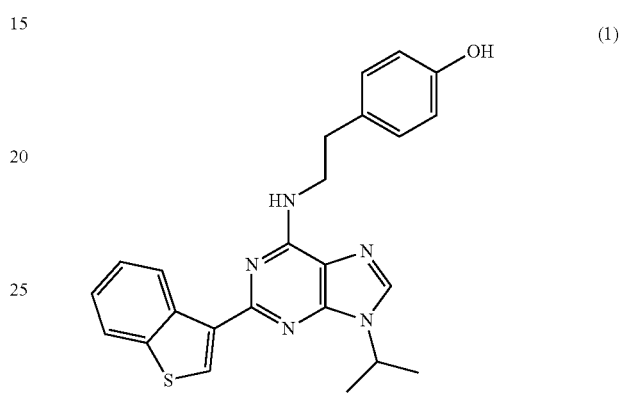

(1)

Methods for the Recombinant Expression of Peptides and Proteins

Peptides and proteins described herein (e.g., CXCR2 agonists, such as Gro-β, Gro-β T, Gro-β N69D, T N65D, and variants thereof) can be expressed in host cells, for example, by delivering to the host cell a nucleic acid encoding the corresponding peptide or protein. The sections that follow describe a variety of techniques that can be used for the purposes of introducing nucleic acids encoding peptides and proteins described herein to a host cell for the purposes of recombinant expression.

Transfection Techniques

Techniques that can be used to introduce a polynucleotide, such as nucleic acid encoding a CXCR2 agonist, such as Gro-β, Gro-β T, Gro-β N69D, Gro-β T N65D, or a variant thereof, into a cell (e.g., a mammalian cell, such as a human cell) are known in the art. In some embodiments, electroporation can be used to permeabilize mammalian cells (e.g., human cells) by the application of an electrostatic potential to the cell of interest. Mammalian cells, such as human cells, subjected to an external electric field in this manner are subsequently predisposed to the uptake of exogenous nucleic acids. Electroporation of mammalian cells is described in detail, e.g., in Chu et al. (1987) *Nucleic Acids Research* 15:1311, the disclosure of which is incorporated herein by reference. A similar technique, Nucleofection™, utilizes an applied electric field in order to stimulate the uptake of exogenous polynucleotides into the nucleus of a eukaryotic cell. Nucleofection and protocols useful for performing this technique are described in detail, e.g., in Distler et al. (2005) *Experimental Dermatology* 14:315, as well as in US 2010/0317114, the disclosures of each of which are incorporated herein by reference.

Additional techniques useful for the transfection of host cells for the purposes of recombinant peptide and protein expression include the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a human cell. Squeeze-poration is described in detail, e.g., in Sharei et al. (2013) *Journal of Visualized Experiments* 81:e50980, the disclosure of which is incorporated herein by reference.

Lipofection represents another technique useful for transfection of cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, for example, by direct fusion of the liposome with the cell membrane or by endocytosis of the complex. Lipofection is described in detail, for example, in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane are activated dendrimers (described, e.g., in Dennig (2003) *Topics in Current Chemistry* 228:227, the disclosure of which is incorporated herein by reference) and diethylaminoethyl (DEAE)-dextran, the use of which as a transfection agent is described in detail, for example, in Gulick et al. (1997) *Current Protocols in Molecular Biology* 40:1:9.2:9.2.1, the disclosure of which is incorporated herein by reference. Magnetic beads are another tool that can be used to transfect cells in a mild and efficient manner, as this methodology utilizes an applied magnetic field in order to direct the uptake of nucleic acids. This technology is described in detail, for example, in US 2010/0227406, the disclosure of which is incorporated herein by reference.

Another useful tool for inducing the uptake of exogenous nucleic acids by cells is laserfection, a technique that involves exposing a cell to electromagnetic radiation of a particular wavelength in order to gently permeabilize the cells and allow polynucleotides to penetrate the cell membrane. This technique is described in detail, e.g., in Rhodes et al. (2007) *Methods in Cell Biology* 82:309, the disclosure of which is incorporated herein by reference.

Microvesicles represent another potential vehicle that can be used to introduce a nucleic acid encoding a peptide or protein described herein into a host cell for the purpose of recombinant expression. In some embodiments, microvesicles that have been induced by the co-overexpression of the glycoprotein VSV-G with, e.g., a genome-modifying protein, such as a nuclease, can be used to efficiently deliver proteins into a cell that subsequently catalyze the site-specific cleavage of an endogenous polynucleotide sequence so as to prepare the genome of the cell for the covalent incorporation of a polynucleotide of interest, such as a gene or regulatory sequence. The use of such vesicles, also referred to as Gesicles, for the genetic modification of eukaryotic cells is described in detail, e.g., in Quinn et al., Genetic Modification of Target Cells by Direct Delivery of Active Protein [abstract]. In: Methylation changes in early embryonic genes in cancer [abstract], in: *Proceedings of the 18th Annual Meeting of the American Society of Gene and Cell Therapy;* 2015 May 13, Abstract No. 122.

Viral Vectors for Nucleic Acid Delivery

Viral genomes provide a rich source of vectors that can be used for the efficient delivery of exogenous nucleic acids encoding peptides and proteins described herein, such as CXCR2 agonists, including Gro-β, Gro-β T, Gro-β N69D, Gro-β T N65D, and variants thereof, into host cells for the purpose of recombinant expression. Viral genomes are particularly useful vectors for gene delivery because the polynucleotides contained within such genomes may be incorporated into the genome of a cell, for example, by way of generalized or specialized transduction. These processes may occur as part of the natural replication cycle of a viral vector, and may not require added proteins or reagents in order to induce gene integration. Examples of viral vectors that may be used to introduce a nucleic acid molecule encoding a peptide or protein described herein into a host cell for recombinant expression include parvovirus, such as adeno-associated virus (AAV), retrovirus, adenovirus (e.g., Ad5, Ad26, Ad34, Ad35, and Ad48), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding peptides and proteins described herein to host cells for recombinant expression purposes include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the disclosure of which is incorporated herein by reference as it pertains to viral vectors for use in gene delivery and recombinant protein and peptide expression.

Methods of Treatment

As described herein, hematopoietic stem cell transplant therapy can be administered to a subject in need of treatment so as to populate or repopulate one or more blood cell types, such as a blood cell lineage that is deficient or defective in a patient suffering from a stem cell disorder. Hematopoietic stem and progenitor cells exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis. Thus, hematopoietic stem and progenitor cells represent a useful therapeutic modality for the treatment of a wide array of disorders in which a patient has a deficiency or defect in a cell type of the hematopoietic lineage. The deficiency or defect may be caused, for example, by depletion of a population of endogenous cells of the hematopoietic system due to administration of a chemotherapeutic agent (e.g., in the case of a patient suffering from a cancer, such as a hematologic cancer described herein). The deficiency or defect may be caused, for example, by depletion of a population of endogenous hematopoietic cells due to the activity of self-reactive immune cells, such as T lymphocytes or B lymphocytes that cross-react with self antigens (e.g., in the case of a patient suffering from an autoimmune disorder, such as an autoimmune disorder described herein). Additionally or alternatively, the deficiency or defect in cellular activity may be caused by aberrant expression of an enzyme (e.g., in the case of a patient suffering from various metabolic disorders, such as a metabolic disorder described herein).

Thus, hematopoietic stem cells can be administered to a patient defective or deficient in one or more cell types of the hematopoietic lineage in order to re-constitute the defective or deficient population of cells in vivo, thereby treating the pathology associated with the defect or depletion in the endogenous blood cell population. Hematopoietic stem and progenitor cells can be used to treat, e.g., a non-malignant hemoglobinopathy (e.g., a hemoglobinopathy selected from the group consisting of sickle cell anemia, thalassemia, Fanconi anemia, aplastic anemia, and Wiskott-Aldrich syndrome). In these cases, for example, a CXCR4 antagonist and/or a CXCR2 agonist may be administered to a donor, such as a donor identified as likely to exhibit release of a population of hematopoietic stem and progenitor cells from a stem cell niche, such as the bone marrow, into circulating peripheral blood in response to such treatment. The hematopoietic stem and progenitor cells thus mobilized may then be withdrawn from the donor and administered to a patient, where the cells may home to a hematopoietic stem cell niche and re-constitute a population of cells that are damaged or deficient in the patient.

Additionally or alternatively, hematopoietic stem and progenitor cells can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). In these cases, for example, a CXCR4 antagonist and/or a CXCR2 agonist may be administered to a donor, such as a donor identified as likely to exhibit release of a population of hematopoietic stem and progenitor cells from a stem cell niche, such as the bone marrow, into circulating peripheral blood in response to such treatment. The hematopoietic stem and progenitor cells thus mobilized may then be withdrawn from the donor and administered to a patient, where the cells may home to a hematopoietic stem cell niche and re-constitute a population of immune cells (e.g., T lymphocytes, B lymphocytes, NK cells, or other immune cells) that are damaged or deficient in the patient.

Hematopoietic stem and progenitor cells can also be used to treat a metabolic disorder (e.g., a metabolic disorder selected from the group consisting of glycogen storage diseases, mucopolysaccharidoses, Gaucher's Disease, Hurlers Disease, sphingolipidoses, and metachromatic leukodystrophy). In these cases, for example, a CXCR4 antagonist and/or a CXCR2 agonist may be administered to a donor, such as a donor identified as likely to exhibit release of a population of hematopoietic stem and progenitor cells from a stem cell niche, such as the bone marrow, into circulating peripheral blood in response to such treatment. The hematopoietic stem and progenitor cells thus mobilized may then be withdrawn from the donor and administered to a patient, where the cells may home to a hematopoietic stem cell niche and re-constitute a population of hematopoietic cells that are damaged or deficient in the patient.

Additionally or alternatively, hematopoietic stem or progenitor cells can be used to treat a malignancy or proliferative disorder, such as a hematologic cancer or myeloproliferative disease. In the case of cancer treatment, for example, a CXCR4 antagonist and/or a CXCR2 agonist may be administered to a donor, such as a donor identified as likely to exhibit release of a population of hematopoietic stem and progenitor cells from a stem cell niche, such as the bone marrow, into circulating peripheral blood in response to such treatment. The hematopoietic stem and progenitor cells thus mobilized may then be withdrawn from the donor and administered to a patient, where the cells may home to a hematopoietic stem cell niche and re-constitute a population of cells that are damaged or deficient in the patient, such as a population of hematopoietic cells that is damaged or deficient due to the administration of one or more chemotherapeutic agents to the patient. In some embodiments, hematopoietic stem or progenitor cells may be infused into a patient in order to repopulate a population of cells depleted during cancer cell eradication, such as during systemic chemotherapy. Exemplary hematological cancers that can be treated by way of administration of hematopoietic stem and progenitor cells in accordance with the compositions and methods described herein are acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Hematopoietic stem or progenitor cells mobilized to the peripheral blood of a subject may be withdrawn (e.g., harvested or collected) from the subject by any suitable technique. For example, the hematopoietic stem or progenitor cells may be withdrawn by a blood draw. In some embodiments, hematopoietic stem or progenitor cells mobilized to a subject's peripheral blood as contemplated herein may be harvested (i.e., collected) using apheresis. In some embodiments, apheresis may be used to enrich a donor's blood with mobilized hematopoietic stem or progenitor cells.

Additional diseases that can be treated by the administration of hematopoietic stem and progenitor cells to a patient include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

In addition, administration of hematopoietic stem and progenitor cells can be used to treat autoimmune disorders. In some embodiments, upon infusion into a patient, transplanted hematopoietic stem and progenitor cells may home to a stem cell niche, such as the bone marrow, and establish productive hematopoiesis. This, in turn, can re-constitute a population of cells depleted during autoimmune cell eradication, which may occur due to the activity of self-reactive lymphocytes (e.g., self-reactive T lymphocytes and/or self-reactive B lymphocytes). Autoimmune diseases that can be treated by way of administering hematopoietic stem and progenitor cells to a patient include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatricial pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis.

In some embodiments, a method of harvesting hematopoietic stem cells from a human subject is provided. The method comprises administering a CXCR2 agonist and a CXCR4 antagonist to the human subject and harvesting the hematopoietic stem cells from peripheral blood of the human subject.

In some embodiments, a method of transplanting hematopoietic stem cells into a human patient in need thereof is provided. The method comprises administering a CXCR2 agonist and a CXCR4 antagonist to a hematopoietic stem cell donor, harvesting the hematopoietic stem cells from peripheral blood of the donor, and transplanting the harvested hematopoietic stem cells into the patient.

Selection of Donors and Patients

In some embodiments, the patient is the donor. In such cases, withdrawn hematopoietic stem or progenitor cells may be re-infused into the patient, such that the cells may subsequently home hematopoietic tissue and establish productive hematopoiesis, thereby populating or repopulating a line of cells that is defective or deficient in the patient (e.g., a population of megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes). In this scenario, the transplanted hematopoietic stem or progenitor cells are least likely to undergo graft rejection, as the infused cells are derived from the patient and express the same HLA class I and class II antigens as expressed by the patient.

Alternatively, the patient and the donor may be distinct. In some embodiments, the patient and the donor are related, and may, for example, be HLA-matched. As described herein, HLA-matched donor-recipient pairs have a decreased risk of graft rejection, as endogenous T cells and NK cells within the transplant recipient are less likely to recognize the incoming hematopoietic stem or progenitor cell graft as foreign, and are thus less likely to mount an immune response against the transplant. Exemplary HLA-matched donor-recipient pairs are donors and recipients that are genetically related, such as familial donor-recipient pairs (e.g., sibling donor-recipient pairs).

In some embodiments, the patient and the donor are HLA-mismatched, which occurs when at least one HLA antigen, in particular with respect to HLA-A, HLA-B and HLA-DR, is mismatched between the donor and recipient. To reduce the likelihood of graft rejection, for example, one haplotype may be matched between the donor and recipient, and the other may be mismatched.

$CD34^{dim}$ Cells

When the donor and patient are distinct, methods of treatment using hematopoietic stem cells comprising $CD34^{dim}$ cells are particularly useful, in part because $CD34^{dim}$ cells are capable of suppressing alloreactive T lymphocyte proliferation when administered to a recipient, thereby reducing the risk of graft vs. host disease (GVHD). (D'Aveni et al. (2015), supra.) In certain embodiments, administration of a CXCR2 agonist and a CXCR4 antagonist according to the methods disclosed herein mobilizes hematopoietic stem cells comprising $CD34^{dim}$ cells from the bone marrow of a donor into peripheral blood. The $CD34^{dim}$ cells are present in a higher amount in the peripheral blood as compared to peripheral blood from an unmobilized mammal. In certain embodiments, the $CD34^{dim}$ cells are present in a higher amount in the peripheral blood than if the hematopoietic stem cells were mobilized using the CXCR4 antagonist alone.

Accordingly, the methods disclosed herein are useful in performing an allogeneic hematopoietic stem cell transplant in a patient in need thereof. For example, the method can include infusing into the patient a therapeutically effective amount of allogeneic hematopoietic stem cells, wherein the hematopoietic stem cells were mobilized from bone marrow of a human donor into peripheral blood of the human donor using the methods herein. In certain embodiments, the method includes administering to the donor (i) a CXCR2 agonist selected from the group consisting of Gro-β, Gro-β T, and variants thereof at a dose of from about 50 μg/kg to about 1,000 μg/kg and (ii) a CXCR4 antagonist.

In addition, $CD34^{dim}$ cells have been shown to increase overall survival (OS), decrease non-relapse mortality (NRM, i.e., the time to death without relapse/recurrence), and lower the risk of infection (e.g., cytomegalovirus (CMV) infection) in a patient having a standard risk disease receiving an allogenic hematopoietic cell transplant. (Nakasone et al. "$CD34^+$ monocytes mobilized by G-CSF in donor PB and clinical outcomes after all-HCT from related donors," Poster presented at $44^{th}$ Annual Meeting of the European Society for Blood and Marrow Transplantation, Mar. 18-21, 2018, Lisbon, Portugal.)

Accordingly, in certain embodiments, the methods of treating a stem cell disorder in a human patient disclosed herein can include infusing into the patient a therapeutically effective amount of the hematopoietic stem cells mobilized by any one of the methods disclosed herein, wherein the mobilized hematopoietic stem cells comprise $CD34^{dim}$ cells, and wherein the treatment results in increased OS, decreased NRM, and/or lowered risk of infection (e.g., CMV infection).

In addition, the methods described herein can be used in preventing, reducing the risk of developing, or reducing the severity of a post-transplant infection in a patient in need thereof. The method can include infusing into the patient a therapeutically effective amount of hematopoietic stem cells, wherein the hematopoietic stem cells were mobilized from bone marrow of a human donor into peripheral blood of the human donor according to the methods described herein, for example, administering to the human donor (i) a CXCR2 agonist selected from the group consisting of Gro-β, Gro-β T, and variants thereof at a dose of from about 50 μg/kg to about 1,000 μg/kg and (ii) a CXCR4 antagonist. In certain embodiments, the infection is a CMV infection.

In addition, the disclosure relates to a method of preventing, reducing the risk of developing, or reducing the severity of graft versus host disease (GVHD) in a patient in need thereof, wherein the method includes infusing into the patient a therapeutically effective amount of hematopoietic stem cells, wherein the hematopoietic stem cells were mobilized from bone marrow of a mammalian donor into peripheral blood by the methods described herein, e.g., including administering to the mammalian donor a CXCR2 agonist and a CXCR4 antagonist.

In certain embodiments, the hematopoietic stem and progenitor cells mobilized from the bone marrow of a donor into peripheral blood comprise at least 1%, at least 2% at least 5% at least 10%, at least 15%, at least 20% or at least 20% or more $CD34^{dim}$ cells as compared to peripheral blood from an unmobilized mammal. In certain embodiments, the hematopoietic stem and progenitor cells mobilized from the bone marrow of a donor into peripheral blood comprise at from about 1% to about 5%, from about 1% to about 10%, from about 1% to about 15%, from about 1% to about 20%, from about 2% to about 25%, 2% to about 5%, from about 2% to about 10%, from about 2% to about 15%, from about 2% to about 20%, from about 2% to about 25%, from about 5% to about 10%, from about 5% to about 15%, from about 5% to about 20%, from about 5% to about 25%, from about 10% to about 15%, from about 10% to about 20%, from about 10% to about 25%, from about 15% to about 20%, from about 15% to about 25% $CD34^{dim}$ cells as compared to peripheral blood from an immobilized mammal.

In certain embodiments, the hematopoietic stem and progenitor cells mobilized from the bone marrow of a donor into peripheral blood comprise at least 1.5-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 20-fold, at least 30-fold, at least 50-fold more $CD34^{dim}$ cells as compared to peripheral blood from an unmobilized mammal. In certain embodiments, the hematopoietic stem and progenitor cells mobilized from the bone marrow of a donor into peripheral blood comprise between about 1.5-fold and 30-fold, between about 5-fold and about 25-fold, between about 10-fold and about 20-fold, or between about 12-fold and about 17-fold more $CD34^{dim}$ cells as compared to peripheral blood from an unmobilized mammal.

In certain embodiments, the hematopoietic stem and progenitor cells mobilized from the bone marrow of a donor into peripheral blood comprise at least 1%, at least 2% at least 5% at least 10%, at least 15%, at least 20% or at least 20% or more $CD34^{dim}$ cells than if the hematopoietic stem cells were mobilized using the CXCR4 antagonist alone. In certain embodiments, the hematopoietic stem and progenitor cells mobilized from the bone marrow of a donor into peripheral blood comprise at from about 1% to about 5%, from about 1% to about 10%, from about 1% to about 15%, from about 1% to about 20%, from about 2% to about 25%, 2% to about 5%, from about 2% to about 10%, from about 2% to about 15%, from about 2% to about 20%, from about 2% to about 25%, from about 5% to about 10%, from about 5% to about 15%, from about 5% to about 20%, from about 5% to about 25%, from about 10% to about 15%, from about 10% to about 20%, from about 10% to about 25%, from about 15% to about 20%, from about 15% to about 25% $CD34^{dim}$ cells than if the hematopoietic stem cells were mobilized using the CXCR4 antagonist alone.

In certain embodiments, the hematopoietic stem and progenitor cells mobilized from the bone marrow of a donor into peripheral blood comprise at least 1.5-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 20-fold, at least 30-fold, at least 50-fold more $CD34^{dim}$ cells than if the hematopoietic stem cells were mobilized using the CXCR4 antagonist alone. In certain embodiments, the hematopoietic stem and progenitor cells mobilized from the bone marrow of a donor into peripheral blood comprise between about 1.5-fold and 30-fold, between about 5-fold and about 25-fold, between about 10-fold and about 20-fold, or between about 12-fold and about 17-fold more $CD34^{dim}$ cells than if the hematopoietic stem cells were mobilized using the CXCR4 antagonist alone.

Methods of Genetic Modification of Hematopoietic Stem and Progenitor Cells

Prior to infusion into a patient, such as a patient having one or more stem cell disorders described herein, hematopoietic stem cells obtained from a donor (or progeny thereof) may be genetically modified, for example, by disrupting an endogenous gene. This strategy can be used, for example, to silence the expression of one or more major histocompatibility complex genes in a hematopoietic stem cell that is allogeneic with respect to the patient, thereby reducing the likelihood of graft rejection upon transplantation.

A wide array of methods has been established for the disruption of target genes in a population of cells. In some embodiments, one such method is through the use of a clustered regularly interspaced short palindromic repeats (CRISPR)/Cas system, a system that originally evolved as an adaptive defense mechanism in bacteria and archaea against viral infection. The CRISPR/Cas system includes palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can theoretically design a CRISPR/Cas system to cleave any target DNA molecule of interest. This technique has been exploited in order to edit eukaryotic genomes (Hwang et al. (2013) *Nature Biotechnology* 31:227, the disclosure of which is incorporated herein by reference) and can be used as an efficient means of site-specifically editing hematopoietic stem cell genomes in order to cleave DNA, for example, prior to the incorporation of a gene encoding a target protein. The use of CRISPR/Cas to modulate gene expression has been described in, e.g., U.S. Pat. No. 8,697,359, the disclosure of which is incorporated herein by reference. Alternative methods for site-specifically cleaving genomic DNA prior to the incorporation of a gene of interest in a hematopoietic stem cell include the use of zinc finger nucleases (ZFNs) and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. The use of ZFNs and TALENs in genome editing applications is described, e.g., in Urnov et al. (2010) *Nature Reviews Genetics* 11:636; and in Joung et al. (2013) *Nature Reviews Molecular Cell Biology* 14:49, the disclosure of both of which are incorporated herein by reference.

Additional genome editing techniques that can be used to incorporate polynucleotides encoding target genes into the genome of a hematopoietic stem cell include the use of ARCUS™ meganucleases that can be rationally designed so as to site-specifically cleave genomic DNA. The use of these enzymes for the incorporation of genes encoding target genes into the genome of a mammalian cell is advantageous in view of the defined structure-activity relationships that have been established for such enzymes. Single chain meganucleases can be modified at certain amino acid positions in order to create nucleases that selectively cleave DNA at desired locations, enabling the site-specific incorporation of a target gene into the nuclear DNA of a hematopoietic stem cell. These single-chain nucleases have been described extensively in, e.g., U.S. Pat. Nos. 8,021,867 and 8,445,251, the disclosures of each of which are incorporated herein by reference.

Kinetics of CXCR2 Agonist and CXCR4 Antagonist Dosing

For cases in which the donor is administered both a CXCR4 antagonist and a CXCR2 agonist, the two agents may be administered to the donor concurrently. In some embodiments, the CXCR4 antagonist and the CXCR2 agonist may be co-formulated with one another and administered in the same pharmaceutical composition. Alternatively, the CXCR4 antagonist and the CXCR2 agonist may be formulated in distinct pharmaceutical compositions and administered separately but simultaneously to the donor.

In some embodiments, the CXCR4 antagonist is administered to the donor prior to administration of the CXCR2 agonist. In some embodiments, the CXCR4 antagonist may be administered to the donor from about 30 minutes to about 180 minutes prior to administration of the CXCR2 agonist, such as from about 40 minutes to about 160 minutes, about 50 minutes to about 150 minutes, about 60 minutes to about 140 minutes, about 70 minutes to about 130 minutes, about 60 minutes to about 120 minutes, about 70 minutes to about 110 minutes, or about 80 minutes to about 100 minutes (e.g., about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, or about 180 minutes prior to administration of the CXCR2 agonist). In some embodiments, the CXCR4 antagonist is administered to the donor from about 30 minutes to about 60 minutes prior to administration of the CXCR2 agonist (e.g., about 30 minutes, about 35 minutes, about 40 minutes, about 45 minutes, about 50 minutes, about 55 minutes, or about 60 minutes prior to administration of the CXCR2 agonist). In some embodiments, the CXCR4 antagonist may be administered to the donor about 45 minutes prior to administration of the CXCR2 agonist.

Isolation of the population of hematopoietic stem or progenitor cells may commence from about 10 minutes to about 60 minutes following completion of the administration of the CXCR4 antagonist and the CXCR2 agonist (e.g., about 10 minutes to about 1.9 hours, about 20 minutes to about 1.8 hours, about 25 minutes to about 1.7 hours, about 30 minutes to about 1.6 hours, about 40 minutes to about 1.5 hours (e.g., about 10 minutes, about 15 minutes, about 20 minutes, about 25 minutes, about 30 minutes, about 35 minutes, about 40 minutes, about 45 minutes, about 50 minutes, about 55 minutes, about 60 minutes, or about 120 minutes following completion of the administration of the CXCR4 antagonist and the CXCR2 agonist). In some embodiments, isolation of the population of hematopoietic stem or progenitor cells may commence from about 10 minutes to about 20 minutes following completion of the administration of the CXCR4 antagonist and the CXCR2 agonist (e.g., about 10 minutes, about 11 minutes, about 12 minutes, about 13 minutes, about 14 minutes, about 15 minutes, about 16 minutes, about 17 minutes, about 18 minutes, about 19 minutes, or about 20 minutes following completion of the administration of the CXCR4 antagonist and the CXCR2 agonist). In some embodiments, isolation of the population of hematopoietic stem or progenitor cells commences about 15 minutes following completion of the administration of the CXCR4 antagonist and the CXCR2 agonist.

In some embodiments, the population of hematopoietic stem or progenitor cells is isolated from the donor over a period of from about 15 minutes to about 6 hours, such as from about 20 minutes to about 4.5 hours, about 30 minutes to about 4 hours, about 40 minutes to about 3.5 hours, about 50 minutes to about 3 hours, or about 1 hour to about 2 hours (e.g., over a period of about 15 minutes, about 20 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 180 minutes, about 240 minutes, about 300 minutes, or about 360 minutes). In some embodiments, the population of hematopoietic stem and progenitor cells may be isolated from the donor over a period of from about 30 minutes to about 1 hour (e.g., over a period of about 30 minutes, about 35 minutes, about 40 minutes, about 45 minutes, about 50 minutes, about 55 minutes, or about 60 minutes).

In some embodiments, the hematopoietic stem or progenitor cells may be harvested by apheresis. In some embodiments, the hematopoietic stem or progenitor cells may be harvested by drawing peripheral blood from the donor (i.e., subject).

Routes of Administration of CXCR2 Agonists and CXCR4 Antagonists

The CXCR4 antagonists and CXCR2 agonists described herein may be administered to a patient by a variety of routes, such as intravenously, subcutaneously, intramuscularly, or parenterally. The most suitable route for administration in any given case will depend on the particular agent administered, the patient, pharmaceutical formulation methods, administration methods (e.g., administration time and administration route), the patient's age, body weight, sex, severity of the diseases being treated, the patient's diet, and the patient's excretion rate. Preferably, the CXCR2 agonist (e.g., Gro-β, Gro-β T, or a variant thereof) may be administered to a donor intravenously. Under these conditions, CXCR2 agonists, such as those described herein, rapidly give rise to populations of cells that are enriched in $CD34^+$ $CD90^+$ $CD45RA^-$ cells (hematopoietic stem cells), and reduce the mobilization of other cell types, such as leukocytes, neutrophils, lymphocytes, and monocytes. This property is described in further detail in Example 1, below.

Pharmaceutical Compositions

The CXCR2 agonists and CXCR4 antagonists contemplated herein may each be formulated into a pharmaceutical composition for administration to a subject, such as a mammalian subject (e.g., a human subject). For instance, contemplated herein are pharmaceutical compositions comprising a CXCR2 agonist and/or a CXCR4 antagonist, in admixture with one or more suitable diluents, carriers, and/or excipients. Pharmaceutical compositions may include sterile aqueous suspensions. Conventional procedures and ingredients for the selection and preparation of suitable formulations are described, for example, in Remington: The Science and Practice of Pharmacy (2012, $22^{nd}$ ed.) and in The United States Pharmacopeia: The National Formulary (2015, USP 38 NF 33), the disclosure of which is incorporated herein by reference in its entirety.

A pharmaceutical composition may be administered to a subject, such as a human subject, alone or in combination with pharmaceutically acceptable carriers, the proportion of which may be determined by the quantity of active pharmaceutical ingredient (i.e., CXCR2 agonist and/or a CXCR4 antagonist), chosen route of administration, and standard pharmaceutical practice.

Administration and Dosing of CXCR2 Agonists and/or CXCR4 Antagonists

Contemplated CXCR2 agonists and CXCR4 antagonists, may be administered to a subject, such as a mammalian subject (e.g., a human subject), by one or more routes of administration. For instance, contemplated CXCR2 agonists and CXCR4 antagonists may be administered to a subject by intravenous, intraperitoneal, intramuscular, intraarterial, or subcutaneous infusion, among others.

Contemplated CXCR2 agonists and CXCR4 antagonists may be administered to a subject in one or more doses. For example, a CXCR2 agonist and/or CXCR4 antagonist may be administered as a single dose or in two, three, four, five, or more doses. When multiple doses are administered, subsequent doses may be provided during the same day or one or more days, weeks, months, or years following the initial dose. For instance, the contemplated CXCR2 agonists and CXCR4 antagonists described herein may be administered to a subject, such as a human subject one or more times daily, weekly, monthly, or yearly, depending on such factors as, for instance, the subject's age, body weight, sex, the subject's diet, and the subject's excretion rate. In certain embodiments, the contemplated CXCR2 agonists and CXCR4 antagonists are each administered in a single dose once per day.

Hematopoietic stem or progenitor cells and pharmaceutical compositions described herein may be administered to a subject in one or more doses. When multiple doses are administered, subsequent doses may be provided one or more days, weeks, months, or years following the initial dose. For instance, the hematopoietic stem cells and pharmaceutical compositions described herein may be administered to a subject, such as a human subject suffering from one or more diseases, conditions, or disorders described herein, one or more times daily, weekly, monthly, or yearly, depending on such factors as, for instance, the subject's age, body weight, sex, severity of the diseases being treated, the subject's diet, and the subject's excretion rate.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Figure 1B:
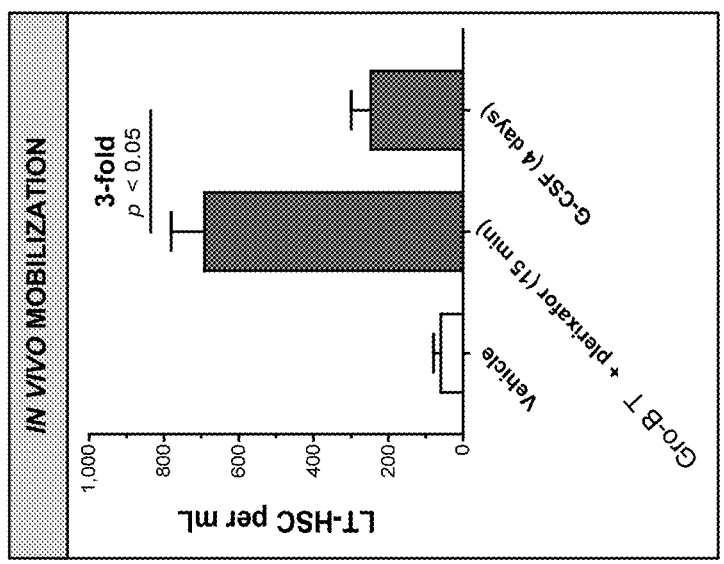
FIG. 1B provides a graph showing that grafts containing cells mobilized by Gro-β T and plerixaflor led to higher relative numbers of competitive repopulating units (CRU) at week 16 than did grafts containing cells mobilized by G-CSF alone.

Example 1. The Effects of Gro-β T on the Mobilization of Hematopoietic Stem Cells in Mice and Rhesus Monkeys Mobilized peripheral blood grafts are currently the predominant source of hematopoietic stem and progenitor cells (HSPC) for both autologous and allogeneic transplantation. The most common clinical hematopoietic stem cell mobilization protocol is five days of Filgrastim (G-CSF). This regimen requires daily injections, has been associated with bone pain and often results in unpredictably low yields. A rapid mobilization method that ideally only required a single treatment and had robust and predictable kinetics would be a significant improvement over the current standard of care. In mice, a unique CXCR2 agonist, T, induces rapid mobilization of stem and progenitor cells 15 minutes after a single injection. When co-administered with plerixafor (AMD3100), an inhibitor of CXCR4, a synergistic increase in mobilization results, and grafts are enriched in highly engraftable, long-term hematopoietic stem cells (see, e.g., FIG. 1A; LT-HSC=Lin-c-kit$^+$ Sca-1$^+$ CD150$^+$ CD48$^+$). Grafts containing cells mobilized by Gro-β T and plerixaflor led to higher relative numbers of competitive repopulating units (CRU) at week 16 than did grafts containing cells mobilized by G-CSF alone (FIG. 1B).

In this example, data are presented to demonstrate that combination treatment with Gro-β T and AMD3100 results in significantly enhanced mobilization of CD34$^+$ cells and colony forming units (CFU) compared to that achieved with AMD3100 alone in nonhuman primates (NHP).

Mobilization of hematopoietic stem cells was investigated in rhesus macaques using Gro-β T and plerixafor (also referred to as AMD3100) as described below.

Methods

Male rhesus macaques were treated with AMD3100 alone or in combination with Gro-β T. Blood was collected immediately prior to and 0.5, 1, 2, 4 and 24 hours after treatment and analyzed by multicolor flow cytometry to quantitate HSPC numbers. Additional aliquots of mobilized blood were plated in methylcellulose and CFU were enumerated seven days later.

Results

Figure 2A:
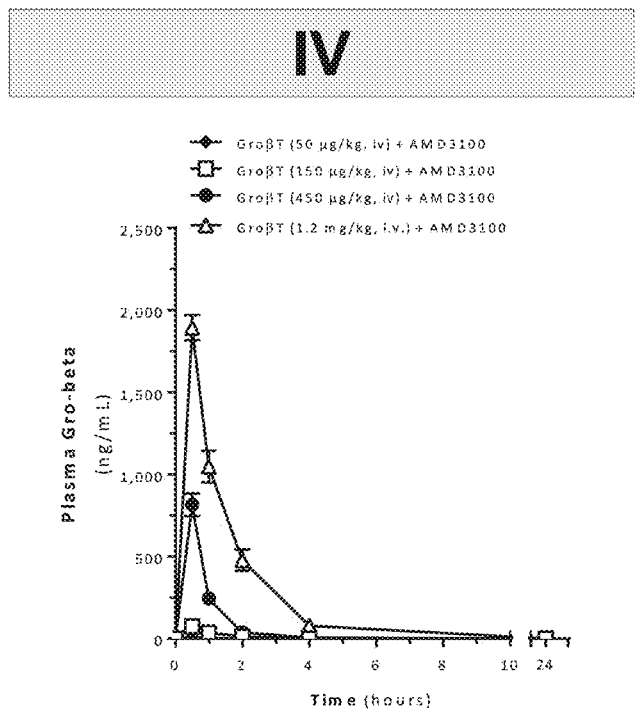
FIG. 2A is a graph demonstrating the pharmacokinetic profile of various dosages of Gro-β T when administered intravenously to Rhesus monkeys.
Figure 2B:
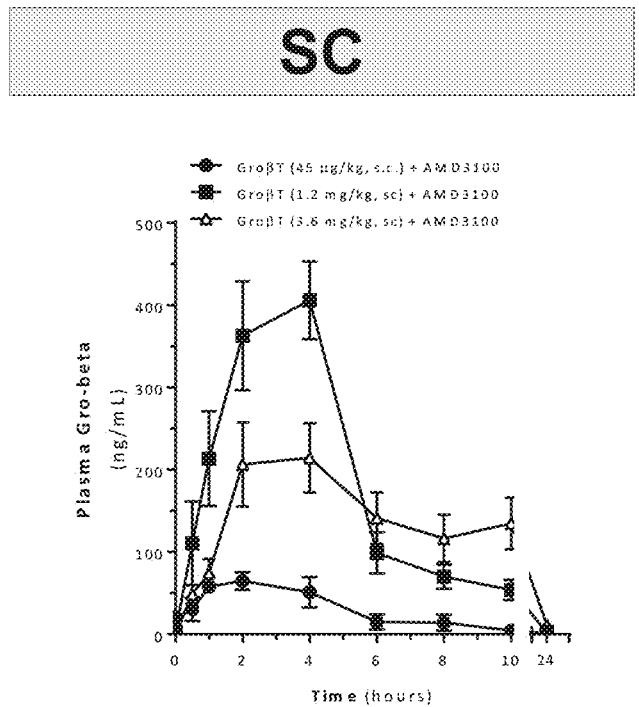
FIG. 2B is a graph demonstrating the pharmacokinetic profile of various dosages of Gro-β T when administered subcutaneously to Rhesus monkeys. In all experiments, Gro-β T was administered to subjects concurrently with plerixafor.
Figure 3A:
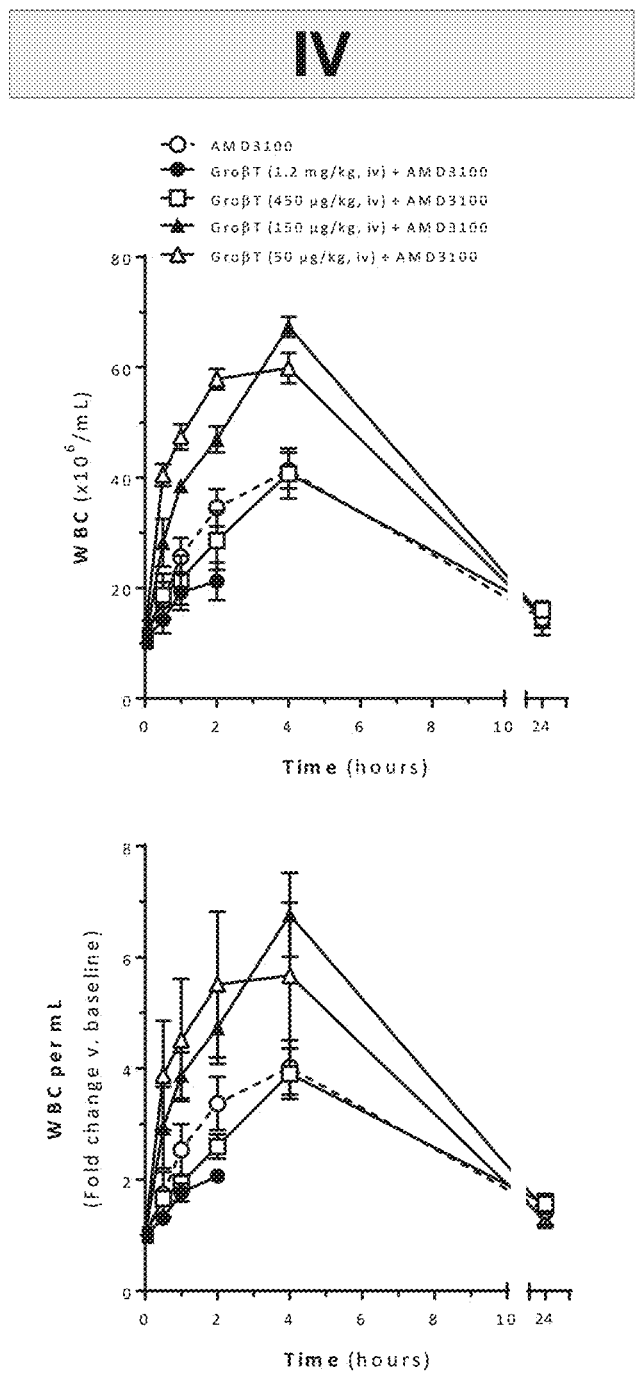
FIG. 3A shows a series of graphs demonstrating the mobilization response of leukocytes (white blood cells, "WBCs") to various dosages of Gro-β T upon intravenous administration to Rhesus monkeys. Leukocyte response is shown both in terms of the quantity of cells mobilized (top) and the fold change in leukocyte density relative to baseline leukocyte density prior to administration (bottom).
Figure 4A:
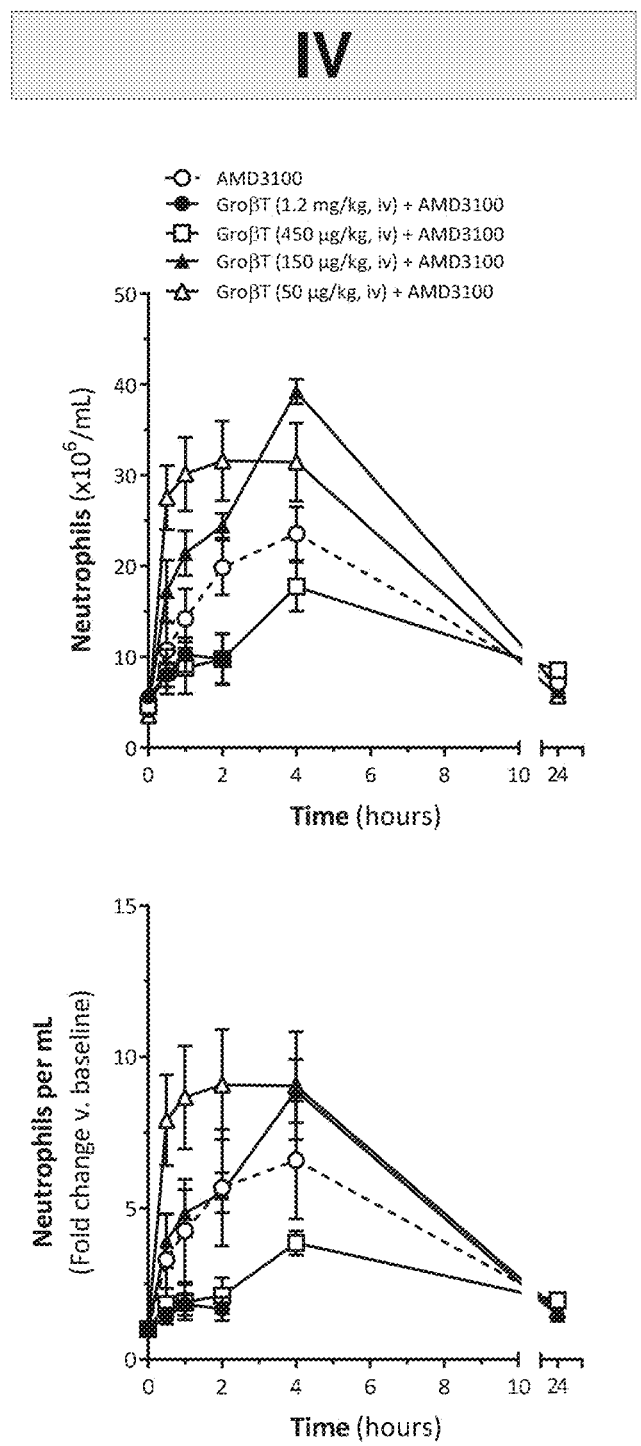
FIG. 4A shows a series of graphs demonstrating the mobilization response of neutrophils to various dosages of Gro-β T upon intravenous administration to Rhesus monkeys. Neutrophil response is shown both in terms of the quantity of cells mobilized (top) and the fold change in neutrophil density relative to baseline neutrophil density prior to administration (bottom).

FIG. 2A shows the pharmacokinetic profile of various dosages of Gro-β T when administered intravenously to Rhesus monkeys. FIG. 2B shows the pharmacokinetic profile of various dosages of Gro-β T when administered subcutaneously to Rhesus monkeys. In all experiments, Gro-β T was administered to subjects concurrently with plerixafor.

As shown in FIGS. 3-6, Gro-β T and AMD3100 mobilizes white blood cells into the peripheral blood. Animals were mobilized with AMD3100 alone or in combination with Gro-β T. Peripheral blood was collected at the time points shown and white blood cells enumerated on a HESKA Hematology Analyzer. Total number of white blood cells, neutrophils, lymphocytes and monocytes per μL of peripheral blood were determined. Data shown in FIGS. 2-5 are expressed as mean±SEM and represent 5 animals per group. Statistical significance was determined based on 2-way ANOVA with post-hoc Dunnett's multiple comparisons test (** $p<0.01$).

Figure 7B:
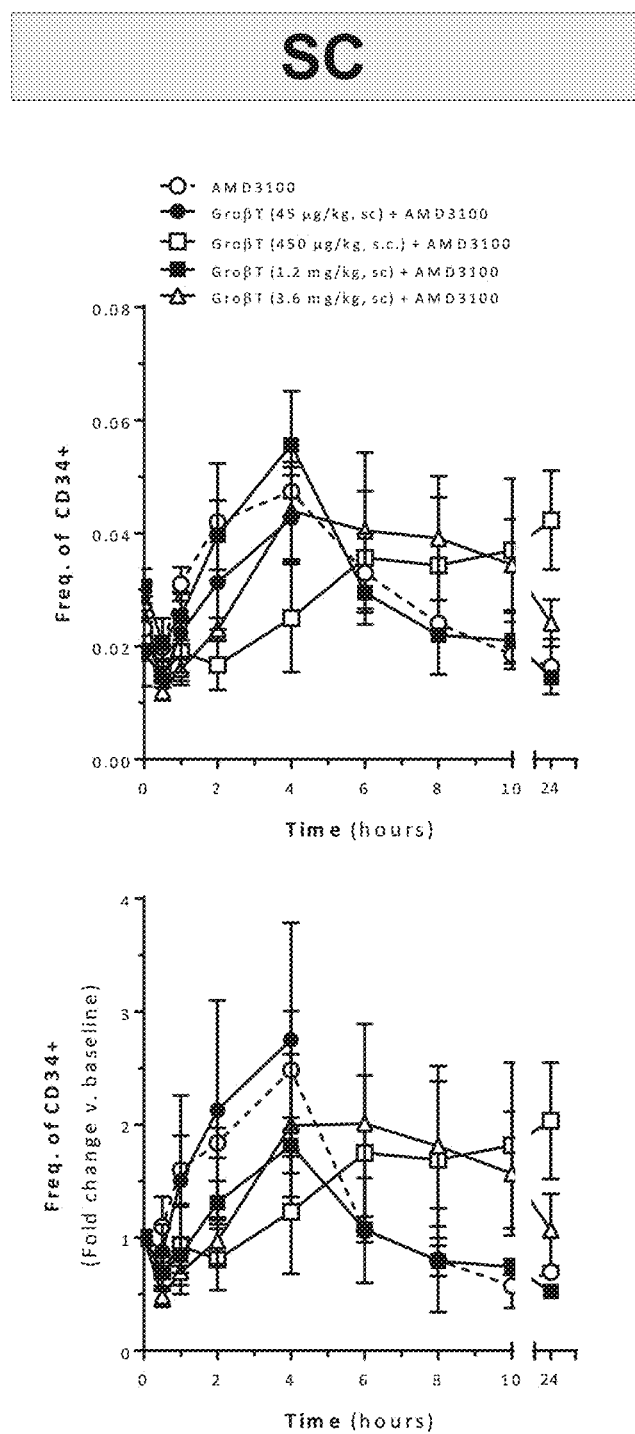
FIG. 7B shows a series of graphs demonstrating the mobilization response of $CD34^+$ cells to various dosages of Gro-β T upon subcutaneous administration to Rhesus monkeys. $CD34^+$ cell response is shown both in terms of the frequency of $CD34^+$ cells in the sample obtained from peripheral blood of the subjects (top) and the fold change in $CD34^+$ cell frequency relative to baseline $CD34^+$ cell frequency prior to administration (bottom). In all experiments, Gro-β T was administered to subjects concurrently with plerixafor.

Importantly, as shown in FIGS. 7 and 8, Gro-β T and AMD3100 induces robust mobilization of CD34$^+$ cells into the peripheral blood. The data shown in FIGS. 7 and 8 include the percentage of whole blood accounted for by CD34$^+$ hematopoietic stem and progenitor cells for each treatment group. Absolute numbers and fold change in CD34$^+$ cells per μL of peripheral blood were quantified with a single platform quantitative method. Data shown in FIGS. 7 and 8 are expressed as mean±SEM and represent 5 animals per group. Statistical significance was determined based on 2-way ANOVA with post-hoc Dunnett's multiple comparisons test (* $p<0.05$,  $p<0.01$, ** $p<0.0001$).

Figure 9B:
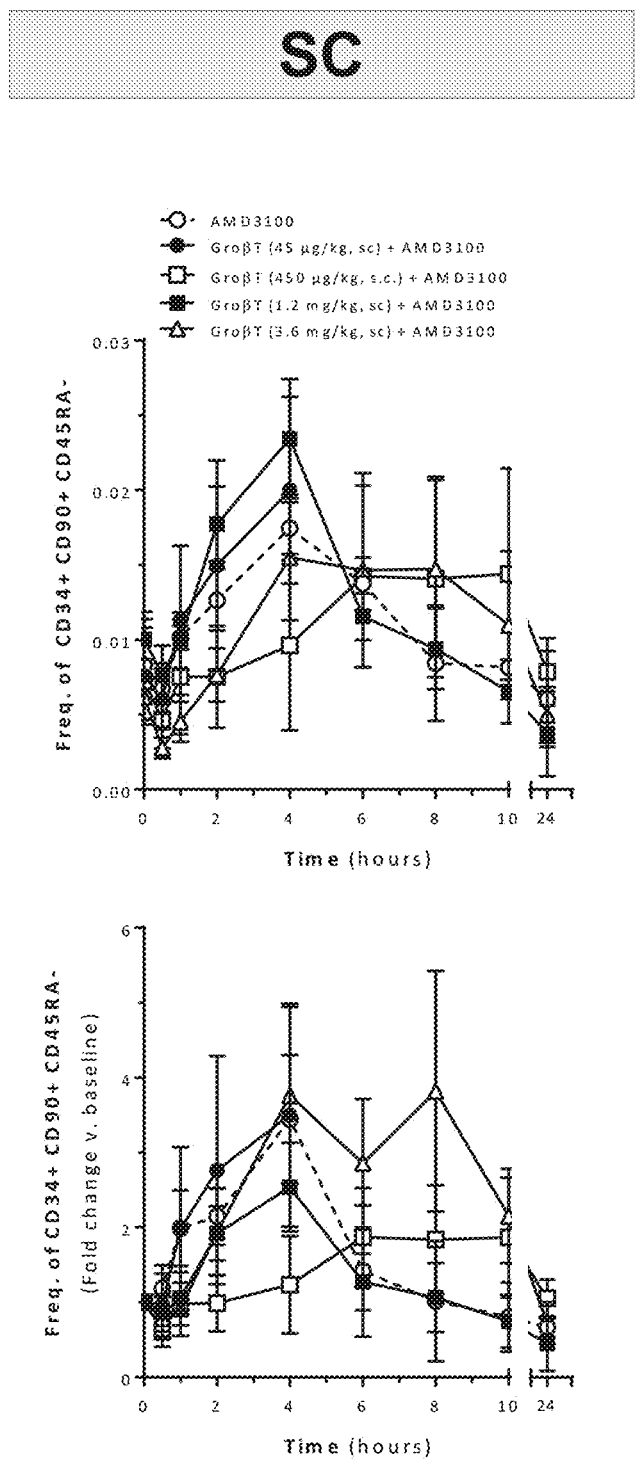
FIG. 9B shows a series of graphs demonstrating the mobilization response of hematopoietic stem cells ($CD34^+$ $CD90^+$ $CD45RA^-$ cells) to various dosages of Gro-β T upon subcutaneous administration to Rhesus monkeys. $CD34^+$ $CD90^+$ $CD45RA^-$ cell response is shown both in terms of the frequency of $CD34^+$ $CD90^+$ $CD45RA^-$ cells in the sample obtained from peripheral blood of the subjects (top) and the fold change in $CD34^+$ $CD90^+$ $CD45RA^-$ cell frequency relative to baseline $CD34^+$ $CD90^+$ $CD45RA^-$ cell frequency prior to administration (bottom). In all experiments, Gro-β T was administered to subjects concurrently with plerixafor.
Figure 10A:
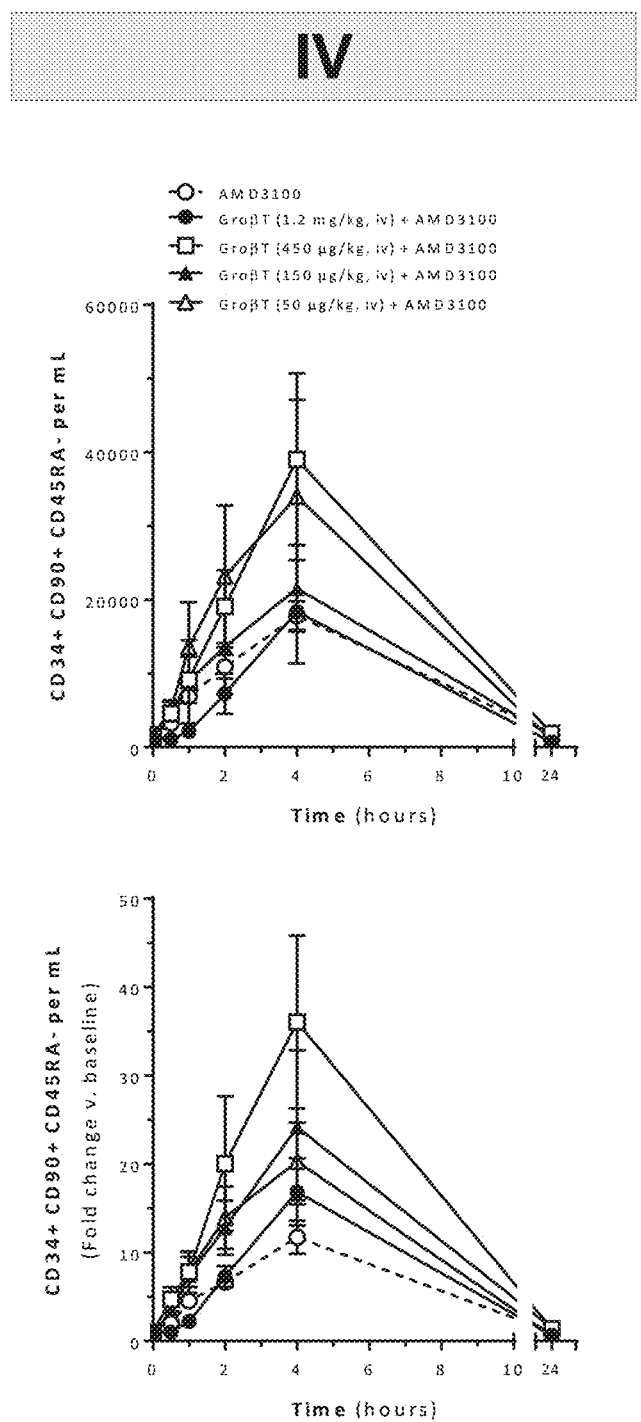
FIG. 10A shows a series of graphs demonstrating the mobilization response of hematopoietic stem cells ($CD34^+$ $CD90^+$ $CD45RA^-$ cells) to various dosages of Gro-β T upon intravenous administration to Rhesus monkeys. $CD34^+$ $CD90^+$ $CD45RA^-$ cell response is shown both in terms of the quantity of cells mobilized (top) and the fold change in $CD34^+$ $CD90^+$ $CD45RA^-$ cell density relative to baseline $CD34^+$ $CD90^+$ $CD45RA^-$ cell density prior to administration (bottom).
Figure 10B:
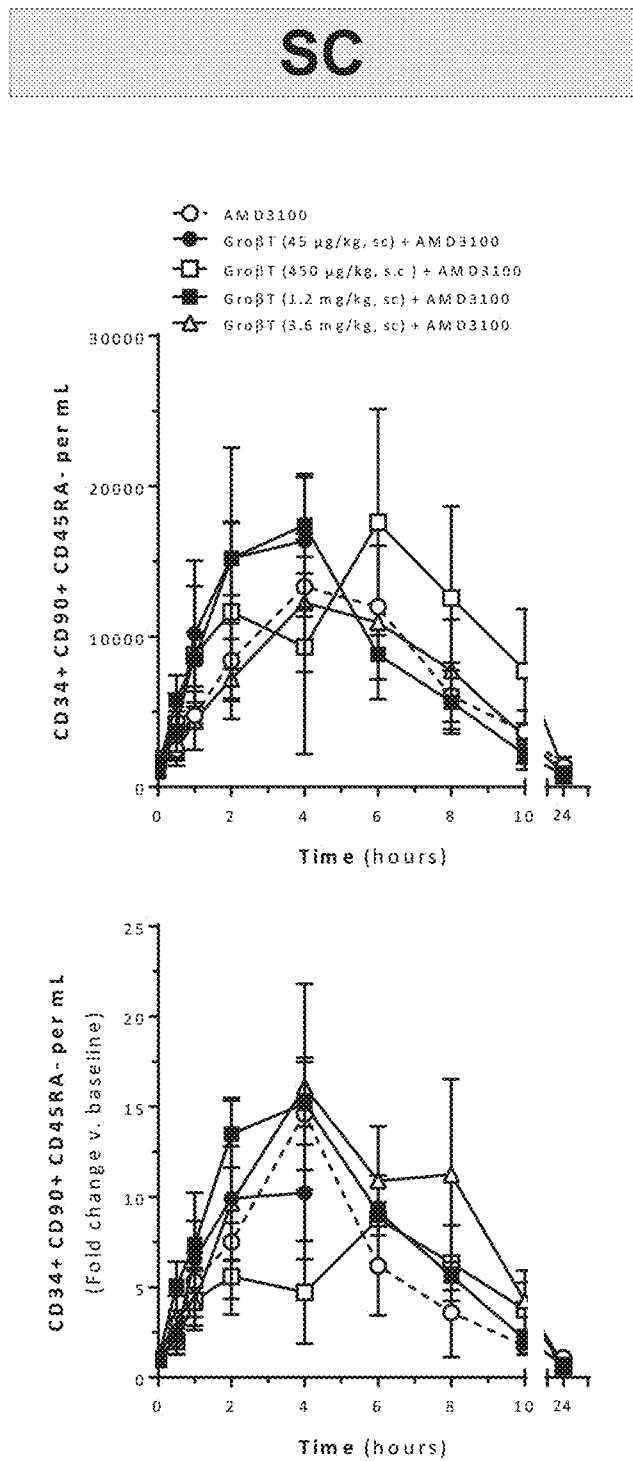
FIG. 10B shows a series of graphs demonstrating the mobilization response of hematopoietic stem cells ($CD34^+$ $CD90^+$ $CD45RA^-$ cells) to various dosages of Gro-β T upon subcutaneous administration to Rhesus monkeys. $CD34^+$ cell response is shown both in terms of the quantity of cells mobilized (top) and the fold change in $CD34^+$ $CD90^+$ $CD45RA^-$ cell density relative to baseline $CD34^+$ $CD90^+$ $CD45RA^-$ cell density prior to administration (bottom). In all experiments, Gro-β T was administered to subjects concurrently with plerixafor.

Additionally, as shown in FIGS. 9 and 10, CD34$^+$ cells mobilized in response to Gro-β T+AMD3100 are enriched for primitive CD34$^+$ CD90+CD45RA$^-$ stem and progenitor cells. The data shown in FIGS. 9 and 10 include the percentage of whole blood accounted for by CD34$^+$ CD90$^+$ CD45RA$^-$ hematopoietic stem and progenitor cells for each treatment group. Absolute numbers and fold change in CD34$^+$ CD90$^+$ CD45RA$^-$ cells per μL of peripheral blood are shown. Data shown in FIGS. 9 and 10 are expressed as mean±SEM and represent 5 animals per group. Statistical significance was determined based on 2-way ANOVA with post-hoc Dunnett's multiple comparisons test (* $p<0.05$. $p<0.01$, * $p<0.001$, **** $p<0.0001$).

Figure 12A:
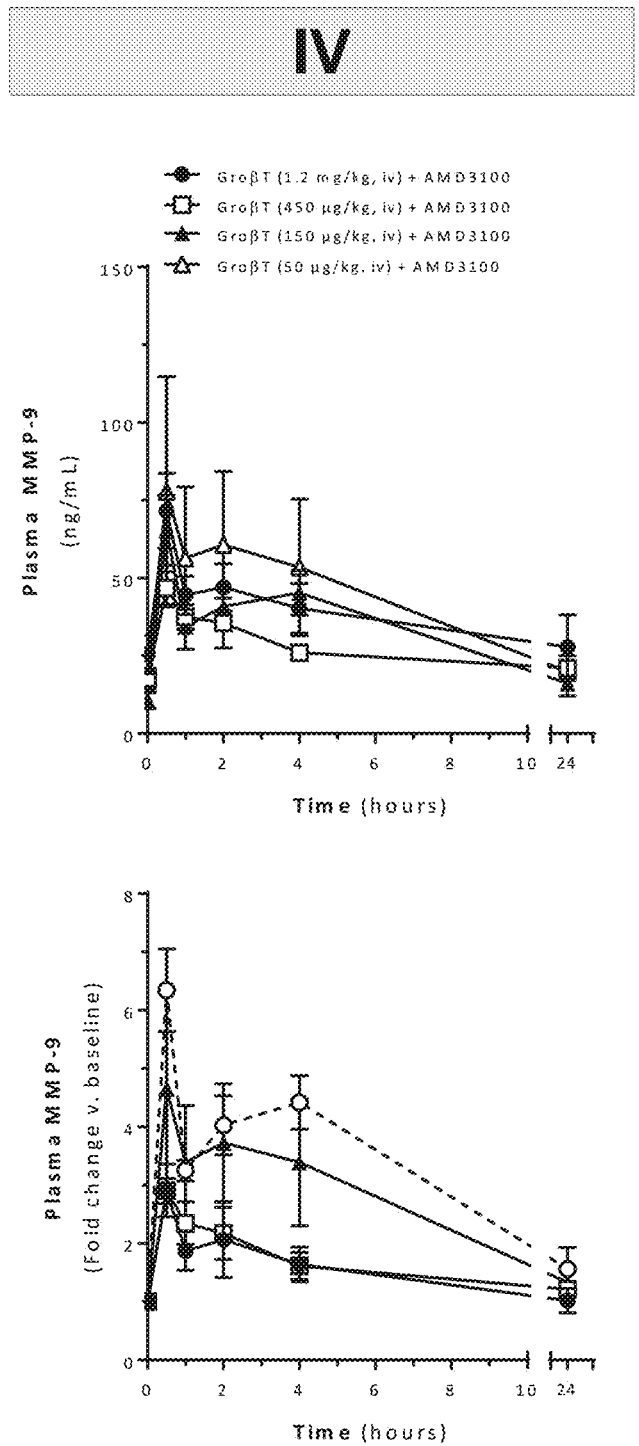
FIG. 12A shows a series of graphs demonstrating the response of plasma matrix metalloproteinase 9 (MMP9) to various dosages of Gro-β T upon intravenous administration to Rhesus monkeys. Plasma MMP9 response is shown both in terms of absolute concentration (top) and the fold change in plasma MMP9 concentration relative to baseline MMP9 concentration prior to administration (bottom).
Figure 12B:
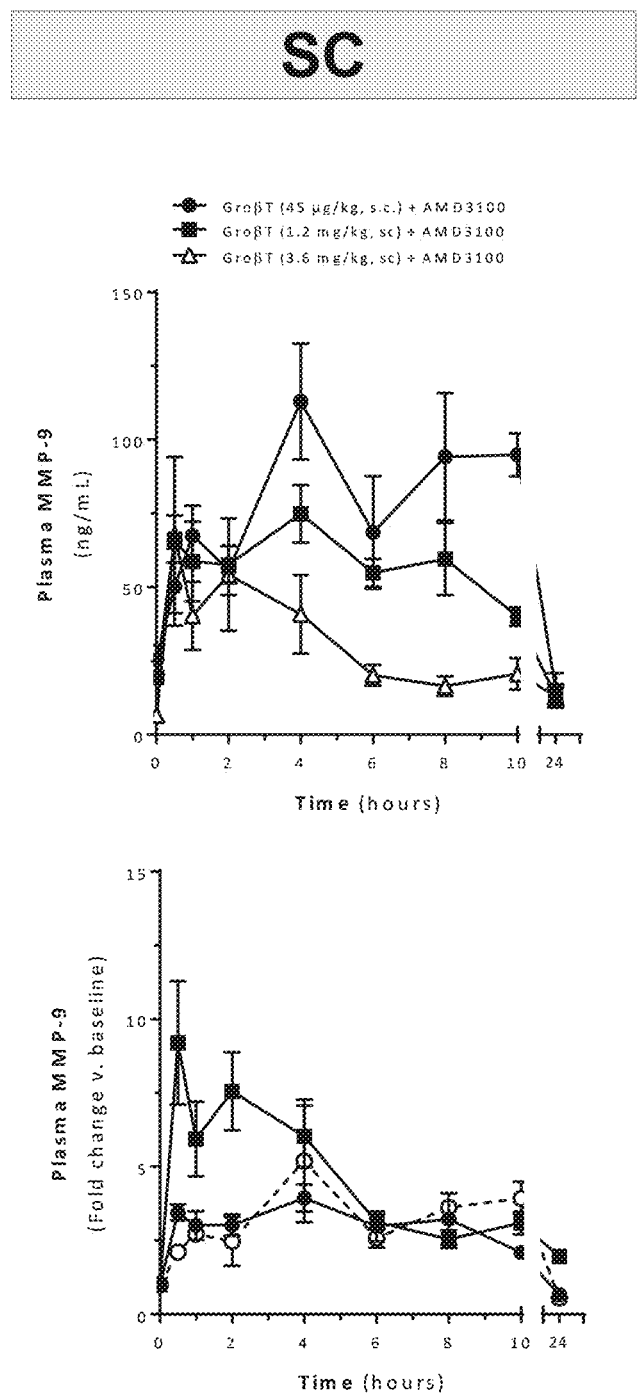
FIG. 12B shows a series of graphs demonstrating the response of plasma MMP9 to various dosages of Gro-β T upon subcutaneous administration to Rhesus monkeys. Plasma MMP9 response is shown both in terms of absolute concentration (top) and the fold change in plasma MMP9 concentration relative to baseline MMP9 concentration prior to administration (bottom). In all experiments, Gro-β T was administered to subjects concurrently with plerixafor.
Figure 13B:
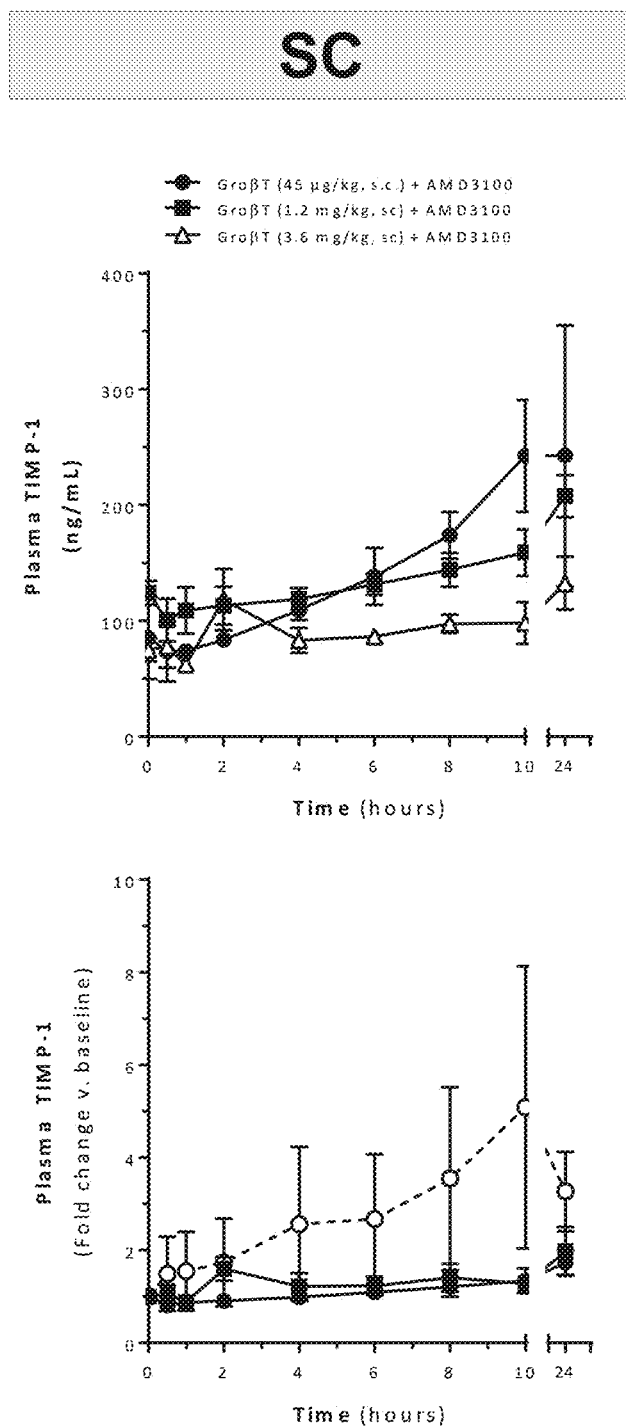
FIG. 13B shows a series of graphs demonstrating the response of plasma TIMP-1 to various dosages of Gro-β T upon subcutaneous administration to Rhesus monkeys. Plasma TIMP-1 response is shown both in terms of absolute concentration (top) and the fold change in plasma TIMP-1 concentration relative to baseline TIMP-1 concentration prior to administration (bottom). In all experiments, Gro-β T was administered to subjects concurrently with plerixafor.
Figure 14A:
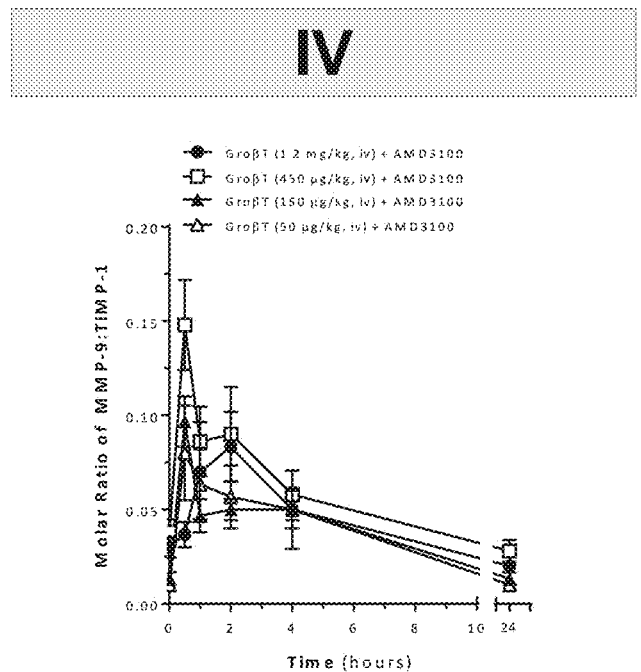
FIG. 14A is a graph showing the response of the molar ratio of plasma MMP9 to plasma TIMP-1 to various dosages of Gro-β T upon intravenous administration to Rhesus monkeys.
Figure 14B:
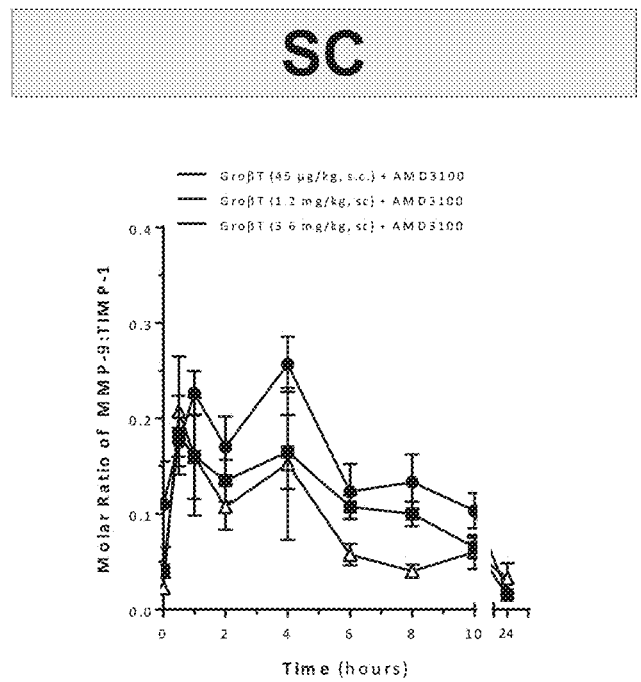
FIG. 14B is a graph showing the response of the molar ratio of plasma MMP9 to plasma TIMP-1 to various dosages of Gro-β T upon subcutaneous administration to Rhesus monkeys. In all experiments, Gro-β T was administered to subjects concurrently with plerixafor.

Further, as shown in FIG. 11, Gro-β T and AMD3100 mobilizes hematopoietic stem and progenitor cells with colony forming potential. The number of CFU per mL of peripheral blood was enumerated after seven days of culture in methylcellulose. Data shown in FIG. 11 are expressed as mean±SEM and represent 3-5 animals per group. Statistical significance was determined based on 2-way ANOVA with post-hoc Dunnett's multiple comparisons test (* $p<0.05$). The ratio of MMP-9 to TIMP-1 is additionally elevated following treatment with Gro-β T and AMD3100 (FIGS. 12-14).

Additional data summarizing the mobilization of CD34$^+$ cells (e.g., CD34$^+$ CD90$^+$ CD45RA$^-$ cells) in Rhesus monkeys using various doses of Gro-beta T and AMD3100 are reported in TABLES 8-11, below. Quantities are reported in TABLES 8-11 using the following notation: "Median value (Minimum value observed–maximum value observed)."

TABLE 8

Mobilization response observed in Rhesus monkeys upon administration of plerixafor (1 mg/kg, subcutaneously)

| Cell type | Quantity of cells observed 4 hours following sc administration of AMD3100: | Ratio of quantity of CD34$^+$ cells to other cell populations | Ratio of quantity of CD34$^+$ CD90$^+$ CD45RA$^-$ cells to other cell populations | Fold increase vs. baseline following sc administration of AMD3100: | Ratio of fold increase of CD34$^+$ cells to other cell populations | Ratio of fold increase of CD34$^+$ CD90$^+$ CD45RA$^-$ cells to other cell populations |
|---|---|---|---|---|---|---|
| CD34$^+$ | 41054 (23012-58496) | — | 0.352 (0.259-0.551) | 9.1 (7.8-16.5) | — | 1.4 (0.6-2.6) |
| CD34$^+$ CD90$^+$ CD54RA$^-$ | 14820 (6123-17893) | 2.838 (1.816-3.864) | — | 14.9 (5.3-23.3) | 0.7 (0.4-1.7) | — |
| WBCs | 3.90E+07 (3.16-4.97E+07) | 0.0009 (0.0006-0.0012) | 0.0003 (0.0002-0.0004) | 2.3 (1.6-4.6) | 2.3 (1.6-4.6) | 3.7 (1.0-7.9) |
| Neutrophils | 2.10E+07 (1.61-3.31E+07) | 0.0015 (0.0011-0.0021) | 0.0006 (0.0004-0.0007) | 5.0 (3.0-14.0) | 2.1 (0.6-3.6) | 3.0 (0.4-3.2) |
| Lymphocytes | 1.35E+07 (1.12-1.62E+07) | 0.0025 (0.0020-0.0043) | 0.0011 (0.0005-0.0013) | 2.5 (1.3-3.1) | 4.0 (2.9-8.2) | 5.7 (2.4-14.0) |
| Monocytes | 3.10E+06 (1.55-4.93E+06) | 0.0111 (0.0047-0.0377) | 0.0039 (0.0020-0.0115) | 7.9 (5.4-14.1) | 1.2 (0.6-2.0) | 1.6 (0.7-3.5) |

TABLE 9

Mobilization response observed in Rhesus monkeys upon administration of
Gro-β T (450 µg/kg, intravenously) and plerixafor (1 mg/kg, subcutaneously)

| Cell type | Quantity of cells observed 4 hours following iv administration of Gro-beta T at 450 µg/kg: | Ratio of quantity of $CD34^+$ cells to other cell populations | Ratio of quantity of $CD34^+$ $CD90^+$ $CD45RA^-$ cells to other cell populations | Fold increase vs. baseline following iv administration of Gro-beta T at 450 µg/kg: | Ratio of fold increase of $CD34^+$ cells to other cell populations | Ratio of fold increase of $CD34^+$ $CD90^+$ $CD45RA^-$ cells to other cell populations |
|---|---|---|---|---|---|---|
| $CD34^+$ | 47194 (38004-103119) | — | 0.676 (0.393-0.745) | 21.7 (11.2-27.2) | — | 1.2 (1.1-4.8) |
| $CD34^+$ $CD90^+$ $CD54RA^-$ | 25701 (16770-76870) | 1.479 (1.341-2.545) | — | 30.7 (18.3-73.9) | 0.8 (0.2-0.9) | — |
| WBCs | 3.84E+07 (2.72-5.27E+07) | 0.0014 (0.0008-0.0021) | 0.0009 (0.0003-0.0016) | 3.8 (2.7-5.4) | 5.1 (3.4-6.9) | 6.0 (5.5-26.9) |
| Neutrophils | 1.79E+07 (1.03-2.44E+07) | 0.0036 (0.0018-0.0058) | 0.0024 (0.0007-0.0043) | 3.4 (3.1-5.2) | 6.4 (2.1-8.1) | 8.2 (3.5-22.0) |
| Lymphocytes | 1.76E+07 (0.8-2.39E+07) | 0.0031 (0.0021-0.0094) | 0.0021 (0.0008-0.0069) | 3.2 (2.0-5.4) | 5.7 (4.8-8.4) | 9.3 (5.6-37.0) |
| Monocytes | 5.48E+06 (3.54-5.99E+06) | 0.0118 (0.0071-0.0174) | 0.0073 (0.0028-0.0130) | 11.7 (8.7-21.1) | 1.6 (1.1-2.3) | 1.9 (1.5-8.5) |

TABLE 10

Mobilization response observed in Rhesus monkeys upon administration of
Gro-β T (450 µg/kg, subcutaneously and plerixafor (1 mg/kg, subcutaneously)

| Cell type | Quantity of cells observed 6 hours following sc administration of Gro-beta T at 450 µg/kg: | Ratio of quantity of $CD34^+$ cells to other cell populations | Ratio of quantity of $CD34^+$ $CD90^+$ $CD45RA^-$ cells to other cell populations | Fold increase vs. baseline following sc administration of Gro-beta T at 450 µg/kg: | Ratio of fold increase of $CD34^+$ cells to other cell populations | Ratio of fold increase of $CD34^+$ $CD90^+$ $CD45RA^-$ cells to other cell populations |
|---|---|---|---|---|---|---|
| $CD34^+$ | 41178 (19413-72140) | — | 0.359 (0.318-0.441) | 6.3 (4.8-13.2) | — | 1.0 (1.0-1.3) |
| $CD34^+$ $CD90^+$ $CD54RA^-$ | 14782 (6177-31841) | 2.786 (2.266-3.143) | — | 6.6 (6.1-13.6) | 1.0 (0.8-1.0) | — |
| WBCs | 6.31E+07 (5.83-6.88E+07) | 0.0007 (0.0003-0.0011) | 0.0003 (0.0001-0.0005) | 5.4 (4.8-5.8) | 1.3 (0.9-2.3) | 1.4 (1.1-2.3) |
| Neutrophils | 4.00E+07 (3.64-4.98E+07) | 0.0011 (0.0004-0.0018) | 0.0004 (0.0001-0.0008) | 5.6 (4.8-6.1) | 1.3 (0.8-2.4) | 1.4 (1.0-2.4) |
| Lymphocytes | 1.85E+07 (1.57-1.97E+07) | 0.0022 (0.0012-0.0037) | 0.0008 (0.0004-0.0016) | 4.5 (3.9-5.7) | 1.4 (1.2-2.3) | 1.6 (1.5-2.4) |
| Monocytes | 2.23E+06 (2.05-2.60E+06) | 0.0185 (0.0075-0.0352) | 0.0066 (0.0024-0.0155) | 9.7 (7.4-17.1) | 0.7 (0.6-0.8) | 0.8 (0.7-0.8) |

TABLE 11

Mobilization response observed in Rhesus monkeys upon administration of Gro-β T (1.2 mg/kg, subcutaneously) and plerixafor (1 mg/kg, subcutaneously)

| Cell type | Quantity of cells observed 4 hours following sc administration of Gro-beta T at 1.2 mg/kg: | Ratio of quantity of CD34$^+$ cells to other cell populations | Ratio of quantity of CD34$^+$ CD90$^+$ CD45RA$^-$ cells to other cell populations | Fold increase vs. baseline following sc administration of Gro-beta T at 1.2 mg/kg: | Ratio of fold increase of CD34$^+$ cells to other cell populations | Ratio of fold increase of CD34$^+$ CD90$^+$ CD45RA$^-$ cells to other cell populations |
|---|---|---|---|---|---|---|
| CD34$^+$ | 36219 (26331-71704) | — | 0.449 (0.278-0.548) | 12.0 (7.2-15.0) | — | 1.3 (0.8-1.9) |
| CD34$^+$ CD90$^+$ CD54RA$^-$ | 17471 (7645-25964) | 2.232 (1.826-3.594) | — | 13.1 (10.3-23.9) | 0.8 (0.5-1.3) | — |
| WBCs | 4.94E+07 (4.07-6.66E+07) | 0.0008 (0.0005-0.0011) | 0.0003 (0.0001-0.0005) | 5.7 (4.5-9.7) | 1.8 (1.4-2.7) | 2.5 (1.1-4.2) |
| Neutrophils | 3.23E+07 (2.31-3.52E+07) | 0.0013 (0.0008-0.0023) | 0.0006 (0.0002-0.0008) | 9.7 (5.5-15.1) | 1.2 (0.7-1.9) | 1.6 (0.7-2.6) |
| Lymphocytes | 1.36E+07 (0.66-2.91E+07) | 0.0024 (0.0019-0.0068) | 0.0010 (0.0005-0.0037) | 3.3 (1.7-5.2) | 3.6 (2.4-8.9) | 4.9 (2.0-12.0) |
| Monocytes | 4.08E+06 (1.16-5.37E+06) | 0.0130 (0.0068-0.0237) | 0.0052 (0.0029-0.0078) | 13.7 (7.2-23.2) | 0.8 (0.5-2.1) | 1.1 (0.6-2.8) |

Conclusions

A single treatment of Gro-β T, in combination with AMD3100, induces robust mobilization of stem and progenitor cells within four hours of administration in nonhuman primates. Additionally, Gro-β T, in combination with AMD3100, results in 2-3 fold more CD34$^+$ CD90$^+$ CD45RA$^-$ stem and progenitor cells relative to AMD3100 alone, suggesting a significant graft quality improvement.

Further, as evidenced by these data, Gro-β T, in combination with AMD3100, may offer a more robust and safer alternative to G-CSF in autologous and allogeneic transplant, including diseases such as sickle cell disease (SCD) and multiple sclerosis (MS) where G-CSF is contraindicated or associated with adverse events.

Example 2. Determining Whether a Population of Hematopoietic Stem Cells Mobilized with a CXCR2 Agonist and/or a CXCR4 Antagonist is Suitable for Ex Vivo Expansion and/or Therapeutic Use Using the compositions and methods described herein, a practitioner of skill in the art may mobilize a population of hematopoietic stem or progenitor cells in a mammalian donor, such as a human donor. In some embodiments, the practitioner may administer a CXCR4 antagonist and a CXCR2 agonist in amounts sufficient to engender the release of a population of a population of hematopoietic stem cells into circulating peripheral blood while reducing the mobilization of other cells of the hematopoietic lineage, such as leukocytes, neutrophils, lymphocytes, and monocytes.

When administering a CXCR4 antagonist in combination with a CXCR2 agonist, the physician may administer the two agents to the donor simultaneously or at different times. In some embodiments, the CXCR4 antagonist may be administered to the donor from about 30 minutes to about 180 minutes prior to administration of the CXCR2 agonist, such as from about 40 minutes to about 160 minutes, about 50 minutes to about 150 minutes, about 60 minutes to about 140 minutes, about 70 minutes to about 130 minutes, about 60 minutes to about 120 minutes, about 70 minutes to about 110 minutes, or about 80 minutes to about 100 minutes (e.g., about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, or about 180 minutes prior to administration of the CXCR2 agonist).

To assess the efficacy of the mobilization regimen, a peripheral blood sample may be isolated from the subject following administration of the CXCR2 agonist and/or CXCR4 antagonist. The sample may then be characterized, for example, by acquiring an input value for each of one or more parameters of the sample, such as a parameter listed in TABLE 2. Exemplary parameters that may be used to assess the efficacy of the hematopoietic stem cell mobilization regimen are ratios of hematopoietic stem cells to cells of other types, such as leukocytes, neutrophils, lymphocytes, and monocytes, as well as the relative frequency of hematopoietic stem cells in the sample. Input values for these parameters may be acquired, for example, using immunophenotyping methods known in the art, such as flow cytometry and fluorescence activated cell sorting (FACS) techniques.

When acquiring and analyzing input values for more than one parameter listed in TABLE 2, one may analyze a combination of parameters. In some embodiments, one may analyze a ratio of hematopoietic stem cells to leukocytes, a ratio of hematopoietic stem cells to neutrophils, a ratio of hematopoietic stem cells to lymphocytes, a ratio of hematopoietic stem cells to monocytes, and/or the relative frequency of hematopoietic stem cells in a sample obtained from the peripheral blood of a donor following administration of a CXCR2 agonist and/or a CXCR4 antagonist. One may analyze, for example, a combination of parameters set forth in any one of TABLES 3-6.

Upon acquiring an input value for each of the one or more parameters, one may then compare the input value(s) to the reference criterion for each parameter. If the reference criterion is satisfied (e.g., if the ratio of hematopoietic stem cells to another hematopoietic cell type is sufficiently high, or if the relative frequency of hematopoietic stem cells in the sample obtained from the peripheral blood of the donor is sufficiently high), then the cells may be released for ex vivo expansion and/or for therapeutic use.

Example 3. Treatment of a Hematologic Disorder by Administration of a Hematopoietic Stem or Progenitor Cell Graft Using the compositions and methods described herein, a practitioner of skill in the art may treat a stem cell disorder, such as a hematologic pathology described herein, by administering to a patient a hematopoietic stem or progenitor cell graft. For example, a practitioner may identify a human donor of hematopoietic stem or progenitor cells as likely to respond to a mobilization regimen, as outlined in Example 1, and may subsequently mobilize a population of hematopoietic stem or progenitor cells accordingly, for example, as set forth in Example 2. Following mobilization, the physician may isolate a population of hematopoietic stem or progenitor cells from the donor. Isolation of the cells may commence, for example, from about 10 minutes to about 60 minutes following completion of the administration of a CXCR4 antagonist and/or a CXCR2 agonist, such as from about 15 minutes to about 55 minutes, about 20 minutes to about 50 minutes, about 25 minutes to about 45 minutes, or about 30 minutes to about 40 minutes following completion of the administration of these agents (e.g., about 10 minutes, about 15 minutes, about 20 minutes, about 25 minutes, about 30 minutes, about 35 minutes, about 40 minutes, about 45 minutes, about 50 minutes, about 55 minutes, or about 60 minutes following completion of the administration of the CXCR4 antagonist and the CXCR2 agonist).

The isolation procedure may be carried out over a period of from about 15 minutes to about 6 hours, such as from about 20 minutes to about 4.5 hours, about 30 minutes to about 4 hours, about 40 minutes to about 3.5 hours, about 50 minutes to about 3 hours, or about 1 hour to about 2 hours (e.g., over a period of about 15 minutes, about 20 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes). In some embodiments, the population of hematopoietic stem and progenitor cells may be isolated from the donor over a period of from about 30 minutes to about 1 hour (e.g., over a period of about 30 minutes, about 35 minutes, about 40 minutes, about 45 minutes, about 50 minutes, about 55 minutes, or about 60 minutes).

Following the isolation process, a patient may then receive an infusion (e.g., an intravenous infusion) of the mobilized and isolated hematopoietic stem or progenitor cells. The patient may be the donor, or may be a patient that is HLA-matched with respect to the donor, thereby reducing the likelihood of graft rejection. The patient may be one that is suffering, for example, from a cancer, such as a hematologic cancer described herein. Additionally or alternatively, the patient may be one that is suffering from an autoimmune disease or metabolic disorder described herein. The physician may administer the patient the mobilized and isolated hematopoietic stem or progenitor cells, for example, at a dosage of from $1\times10^3$ to $1\times10^9$ hematopoietic stem cells/kg (e.g., about $1\times10^5$ CD34$^+$ cells/kg to about $1\times10^7$ CD34$^+$ cells/kg, about $2\times10^5$ CD34$^+$ cells/kg to about $9\times10^6$ CD34$^+$ cells/kg, about $3\times10^5$ CD34$^+$ cells/kg to about $8\times10^6$ CD34$^+$ cells/kg, about $4\times10^5$ CD34$^+$ cells/kg to about $7\times10^6$ CD34$^+$ cells/kg, depending on various factors, such as the patient's age, weight, and the severity of the disease being treated.

The physician may monitor the engraftment of the hematopoietic stem cell transplant, for example, by withdrawing a blood sample from the patient and determining the increase in concentration of hematopoietic stem cells or cells of the hematopoietic lineage (such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes) following administration of the transplant. This analysis may be conducted, for example, from about 1 hour to about 6 months, from about 2 hours to about 5 months, from about 3 hours to about 4 months, from about 4 hours to about 3 months, from about 10 hours to about 7 days, from about 24 hours to about 96 hours, or more following hematopoietic stem cell transplant therapy (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or more). A finding that the concentration of hematopoietic stem cells or cells of the hematopoietic lineage has increased (e.g., by 1%, 2%, 3%, 4%, 5%, 6%, 7%, 8%, 9%, 10%, 20%, 30%, 40%, 50%, 60%, 70%, 80%, 90%, 100%, 200%, 500%, or more) following the transplant therapy relative to the concentration of the corresponding cell type prior to transplant therapy provides one indication that the hematopoietic stem or progenitor cell transplant therapy is efficacious in treating the stem cell disorder.

Example 4: Mobilization of CD34$^{dim}$ Cells Using a CXCR2 Agonist and/or a CXCR4 Antagonist In this example, data are presented to demonstrate that combination treatment with Gro-β T and AMD3100 (plerixafor) results in significantly enhanced mobilization of CD34$^{dim}$ cells compared to that achieved with AMD3100 alone in nonhuman primates (NHP).

Cells were mobilized according to the method of Example 1. A sample of peripheral blood was tested using a flow cytometer for the markers CD34, CD11b, CD14, CD16, CD45, and SSC.

Figure 15:
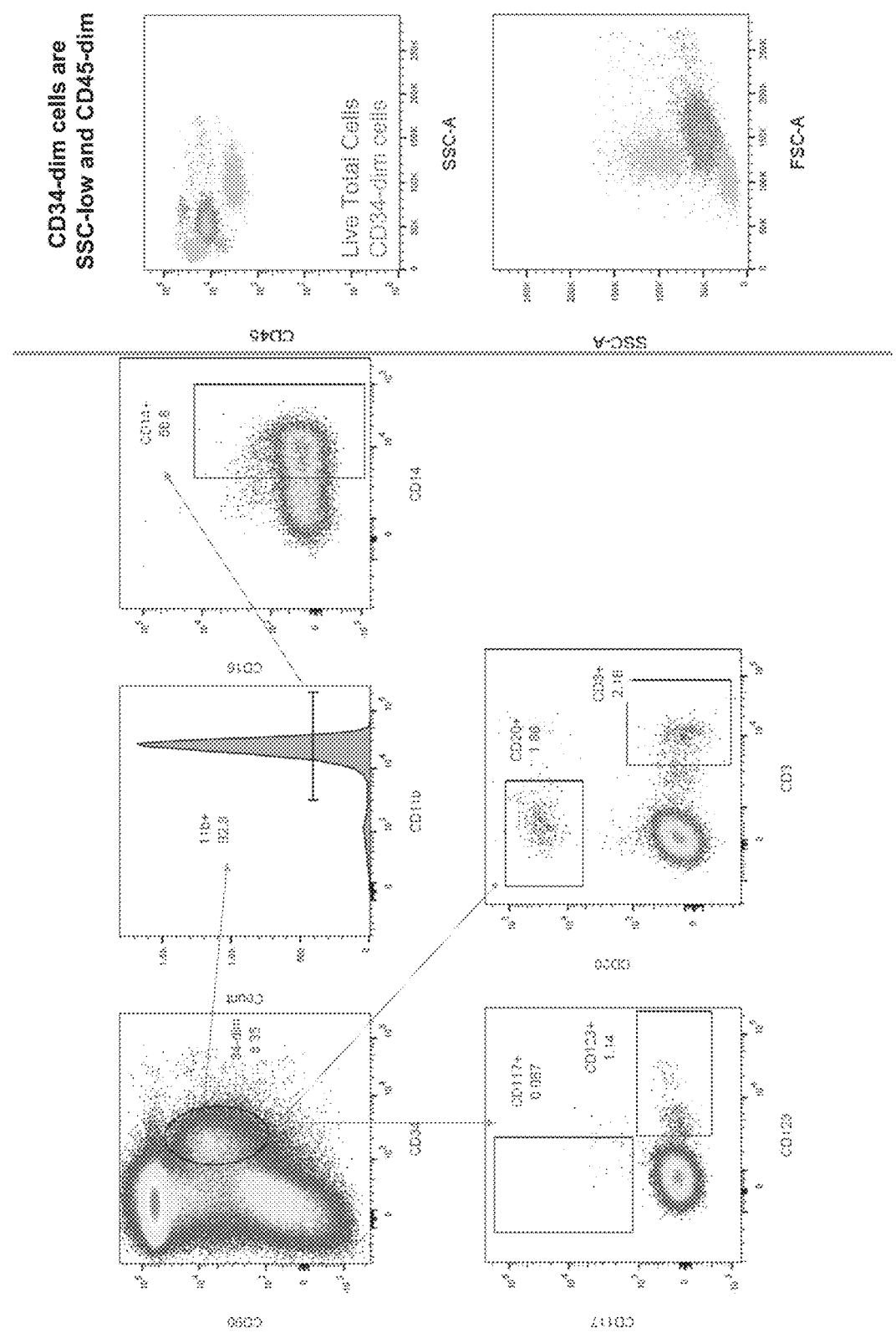
FIG. 15 provides representative flow plots from blood samples taken four hours post-mobilization from Rhesus monkeys. Intravenous administration of 450 µg/kg Gro-β T and subcutaneous administration of 1 mg/kg plerixafor (AMD3100) leads to the mobilization of a population of $CD34^{dim}$ cells.
Figure 16:
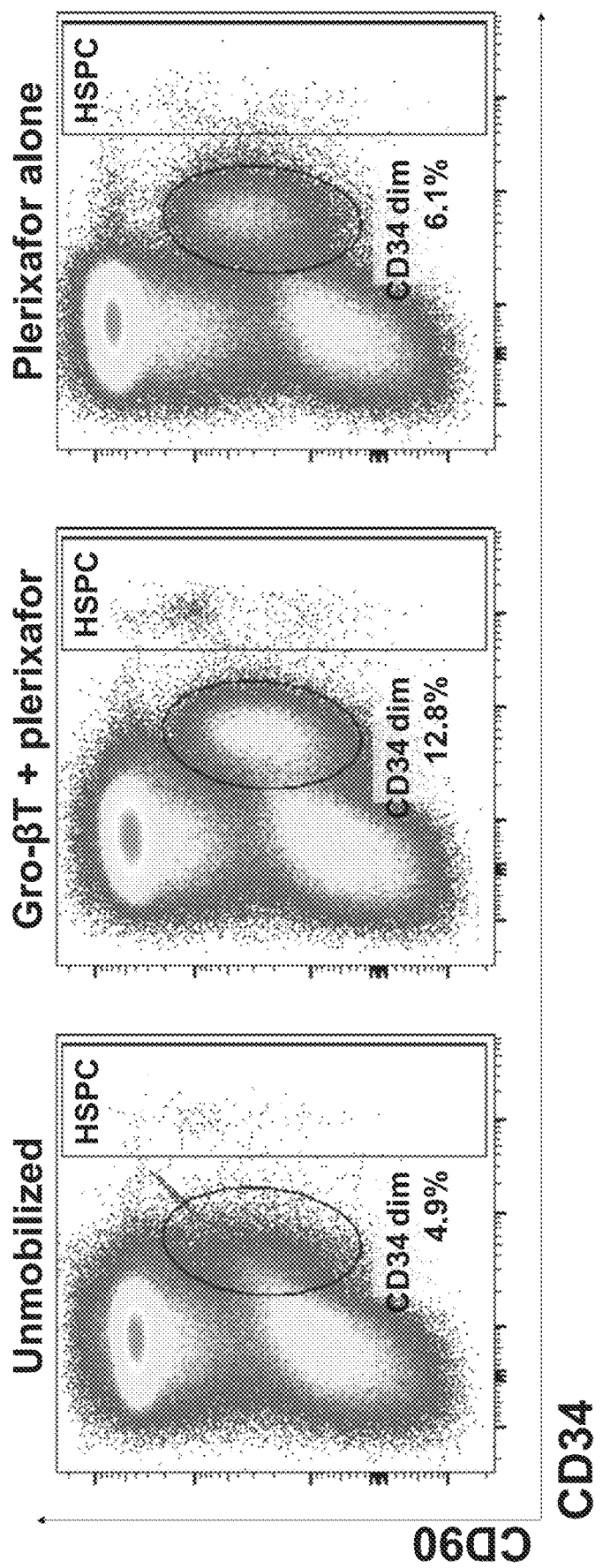
FIG. 16 provides representative flow plots from blood samples taken at baseline versus four hours post-mobilization from Rhesus monkeys. Mobilization was induced by (1) intravenous administration of 450 µg/kg Gro-β T and subcutaneous administration of 1 mg/kg plerixafor (AMD3100) or (2) subcutaneous administration of 1 mg/kg plerixafor (AMD3100). The combination of Gro-β T and plerixafor (as compared to plerixafor alone) leads to enhanced mobilization of $CD34^{dim}$ cells.

As shown in FIG. 15, intravenous administration of 450 μg/kg Gro-β T and subcutaneous administration of 1 mg/kg AMD3100 surprisingly leads to the mobilization of a population of cells that are CD34$^{dim}$ CD11b$^+$. Subpopulations within this population are CD14$^+$ CD16$^+$, CD14$^-$ CD16$^-$, and combinations thereof. FIG. 16 shows that mobilization of the CD34$^{dim}$ cells is significantly enhanced upon administration of the combination of Gro-β T and AMD3100 as compared to AMD3100 alone.

Example 5: Gro-β T in Combination with AMD3100 Mobilizes Immunosuppressive Monocytes that Inhibit Graft Vs. Host Disease This example demonstrates that combination treatment with Gro-β T and AMD3100 (plerixafor) results in significantly enhanced mobilization of CD34$^{'166}$ cells having immunosuppressive properties and that transplantation of this population of cells leads to a significantly reduced incidence of acute graft versus host disease (aGVHD) in a xenograft GVHD mouse model, as compared to transplantation of peripheral blood mononuclear cells having a lower concentration of CD34$^{dim}$ cells.

Figure 17:
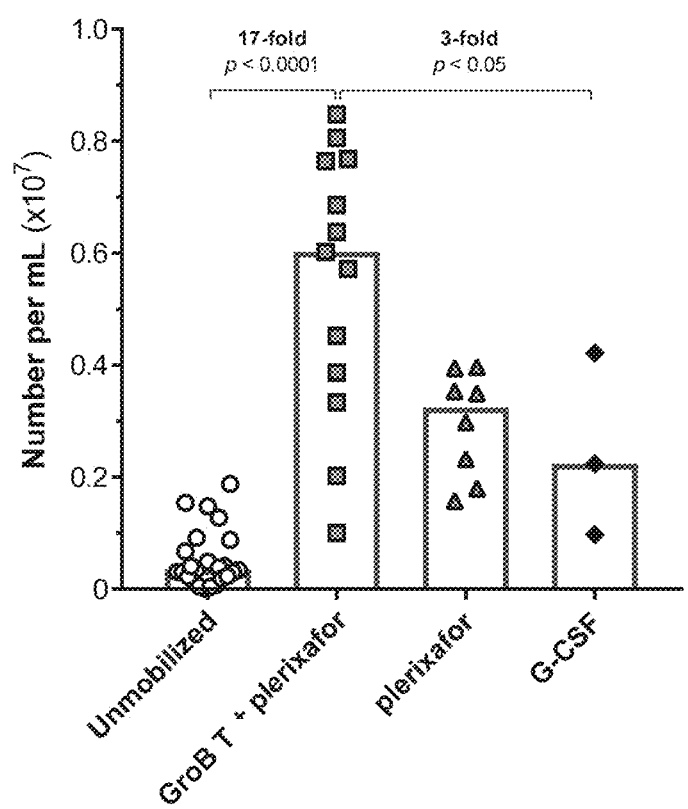
FIG. 17 is a graph quantifying the concentration of $CD34^{dim}$ cells in peripheral blood from untreated Rhesus monkeys ("Unmobilized"), Rhesus monkeys that have been treated with intravenous administration of 450 µg/kg Gro-β T and subcutaneous administration of 1 mg/kg plerixafor ("Gro-β T+plerixafor"), Rhesus monkeys that have been treated with subcutaneous administration of 1 mg/kg plerixafor ("plerixafor") and Rhesus monkeys that have been treated with subcutaneous administration of 50 µg/kg (q.d.×5) G-CSF ("G-CSF"). $CD34^{dim}$ cells were present at a significantly higher concentration in blood mobilized using Gro-β T plus plerixafor.

Rhesus macaques were treated with Gro-β T, AMD310C, Gro-β T and AMD3100, or G-CSF alone. A sample of peripheral blood was tested using a flow cytometry. Animals mobilized with Gro-β T and AMD3100 showed a more than fifteen-fold increase over baseline in the number of CD34$^{dim}$ cells at 4 hours post-treatment (p<0.0001, n=13, FIG. 17). By comparison, animals mobilized with G-CSF alone showed only about a nine-fold increase over baseline in the number of CD34$^{dim}$ cells at 4 hours after the last dose of G-CSF (p<0.0001, n=3, FIG. 17).

Figure 18:
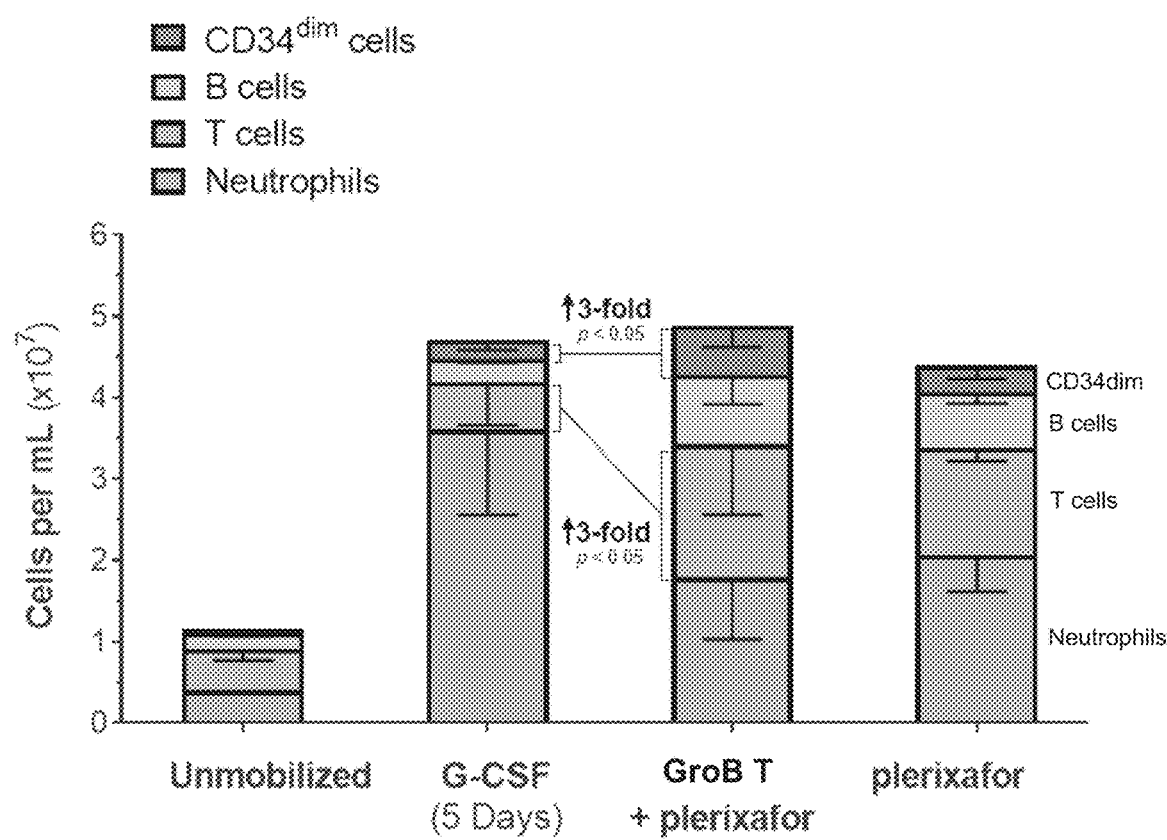
FIG. 18 is a graph depicting the composition of unmobilized cells and grafts mobilized by G-CSF, Gro-β T and AMD3100 and AMD3100 alone. As shown, grafts mobilized using Gro-β T and AMD3100 show a 3 fold increase in $CD34^{dim}$ cells and a 3 fold increase in T-cells as compared to grafts mobilized using G-CSF.

Further, the composition of unmobilized cells and grafts mobilized by G-CSF, Gro-β T and AMD3100 and AMD3100 alone is provided in FIG. 18. As shown, grafts mobilized using Gro-β T and AMD3100 show a 3 fold increase in CD34$^{dim}$ cells and a 3 fold increase in T-cells as compared to grafts mobilized using G-CSF.

Figure 19:
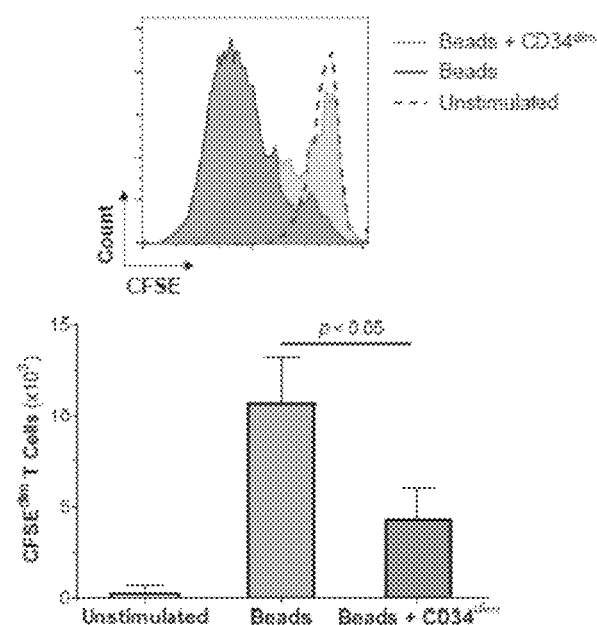
FIG. 19 provides graphs showing that Gro-β T and AMD3100 mobilized $CD34^{dim}$ cells suppressed T-cell proliferation as measured by carboxyfluorescein succinimidyl ester (CFSE) staining after four days in culture. "Beads" indicates stimulation of T-cells using anti-CD2/CD3/CD28 coated microbeads.

To determine if CD34$^{dim}$ cells had immunosuppressive properties, they were sorted from the peripheral blood of Rhesus macaques treated with Gro-β T and AMD3100. The CD34$^{dim}$ cells were co-cultured with carboxyfluorescein succinimidyl ester (CFSE)-labeled autologous T cells stimulated with anti-CD2/CD3/CD28-coated beads in vitro. As shown in FIG. 19, Gro-β T and AMD3100 mobilized CD34$^{dim}$ cells suppressed T-cell proliferation as measured by CFSE staining after four days.

To assess whether these immunosuppressive cells may prevent GVHD, we developed a xenograft GVHD model in NOD scid gamma (NSG) mice, which are immunodeficient mice. Gro-β T and AMD3100 mobilized peripheral blood (6×10$^6$ PBMCs) containing a high percentage of CD34$^{dim}$ cells were injected into sublethally irradiated NSG mice. This was compared to unmobilized primate PBMCs (6×10$^6$ PBMCs) containing a relatively low numbers of CD34$^{dim}$ cells and G-CSF mobilized primate PBMCs (6×10$^6$ PBMCs). As shown in the survival curve in FIG. 20, at day 24, all mice (13/13) transplanted with unmobilized PBMCs had died of aGVHD compared to 5/16 mice transplanted with AMD3100 mobilized PBMCs, 3/16 mice transplanted with G-CSF-mobilized PBMCs and none of the mice transplanted with Gro-β T and AMD3100-mobilized PBMCs. At day 60 post-transplant, 15/16 mice transplanted with Gro-β T and AMD3100 remained alive, whereas only 10/16 mice transplanted with AMD3100 mobilized peripheral blood and 11/16 mice transplanted with G-CSF mobilized peripheral blood remained alive (see FIG. 20). As shown in FIG. 21A, mice transplanted with unmobilized PBMCs ("Unmobilized") also demonstrated higher numbers of donor T-cells (approximately 160-fold higher, see FIG. 21A) compared to mice transplanted with Gro-β T and AMD3100 mobilized PBMCs ("Gro-β T+Plerixafor") at day 14 post-transplant (*p<0.01, n=6-8). Additionally, also as shown in FIG. 21A, mice transplanted with PBMCs mobilized with AMD3100 (i.e., plerixafor) alone ("Plerixafor") or PBMCs mobilized with G-CSF alone ("G-CSF") demonstrated higher numbers of T-cells (approximately 60-fold higher (p<0.05) and approximately 10-fold higher (p<0.01), respectively) as compared to mice transplanted with Gro-β T and AMD3100-mobilized PBMCs.

Figure 20:
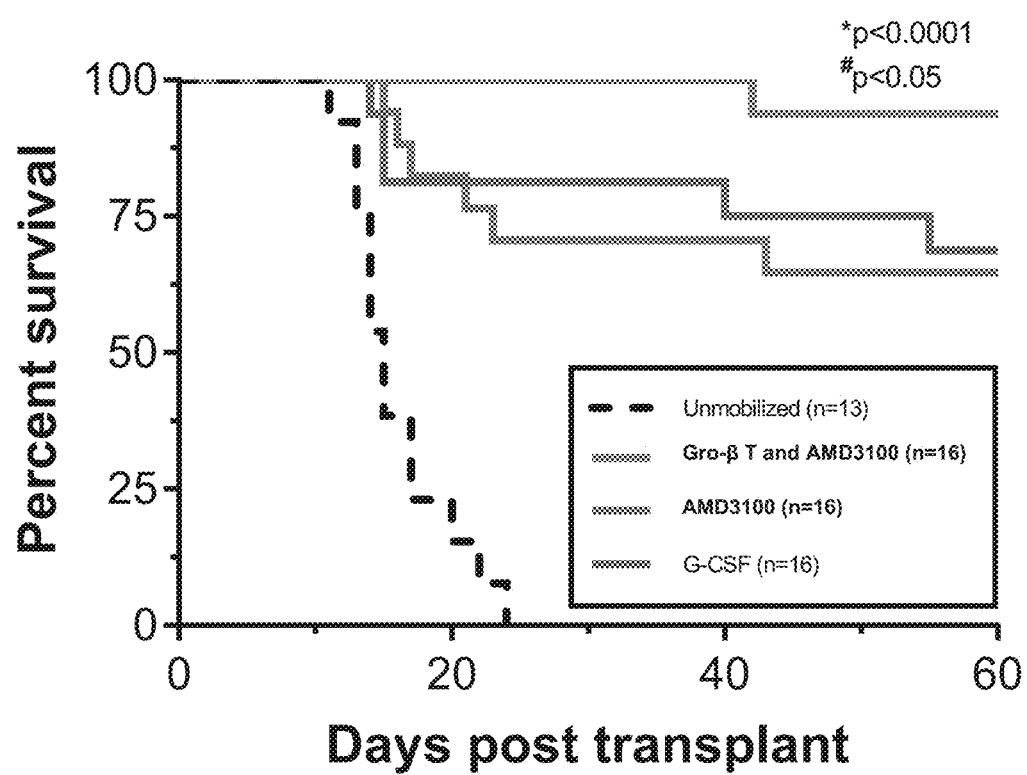
FIG. 20 provides a survival curve showing that by day 24, all mice (13/13) transplanted with unmobilized PBMCs had died of aGVHD compared to 5/16 mice transplanted with AMD3100 mobilized peripheral blood, 3/16 mice transplanted with G-CSF mobilized PBMCs and none of the mice transplanted with Gro-β T and AMD3100 mobilized PBMCs. At day 60 post-transplant, 15/16 mice transplanted with Gro-β T and AMD3100 remained alive, whereas only 10/16 mice transplanted with AMD3100 mobilized PBMCs and 11/16 mice transplanted with G-CSF mobilized PBMCs remained alive. $p<0.0001$ (comparing Gro-β T and AMD3100 v. unmobilized) and $p<0.05$ (comparing Gro-β T and AMD3100 v. AMD3100 alone).
Figure 21A:
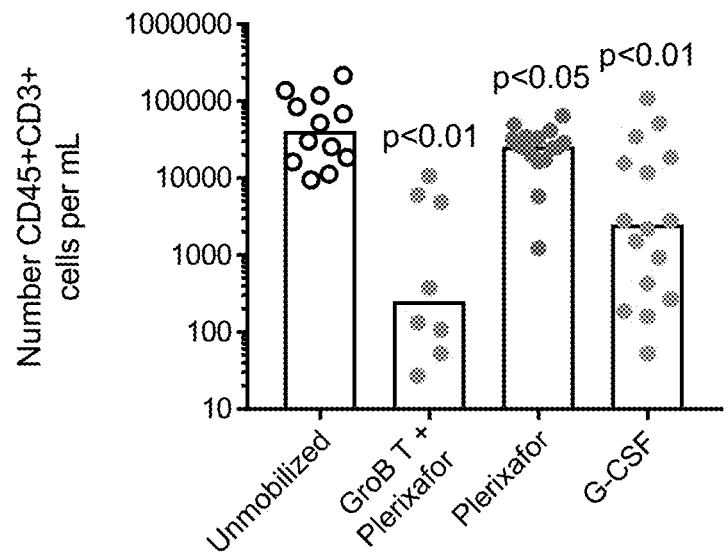
FIG. 21A shows rhesus CD45+CD3+ T-cell numbers in mice at day 14 post-transplant with unmobilized PBMCs, PBMCs mobilized with Gro-β T and plerixafor (i.e., AMD3100), PBMCs mobilized with plerixafor alone, and PBMCs mobilized with G-CSF alone.
Figure 21B:
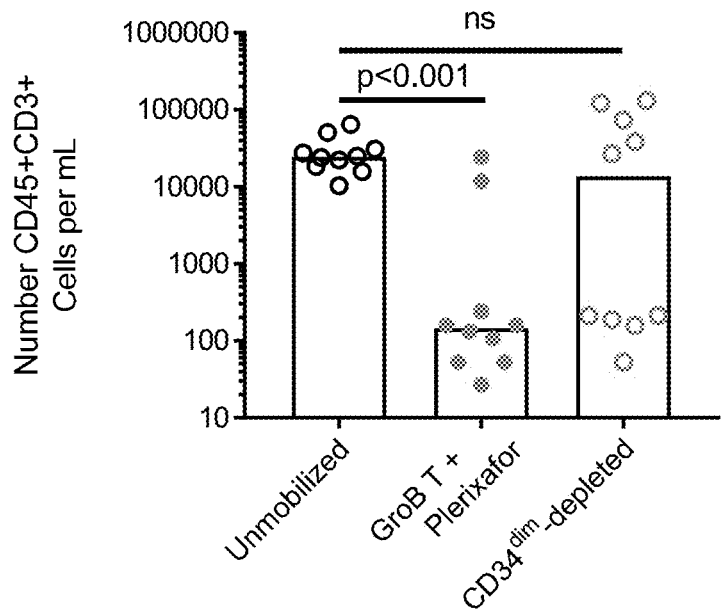
FIG. 21B shows T-cell numbers in mice at day 14 post-transplant with unmobilized PBMCs, Gro-β T and plerixafor (i.e., AMD3100) mobilized PBMCs, and Gro-β T and plerixafor mobilized PBMCs that have been depleted of CD34dim cells.
Figure 21C:
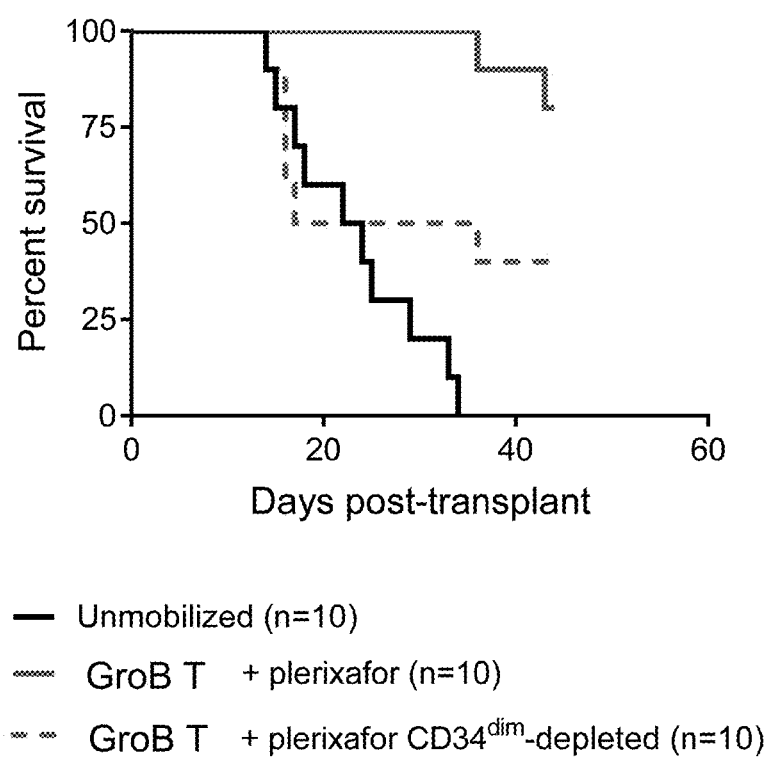
FIG. 21C provides a survival curve of mice transplanted with unmobilized PBMCs, Gro-β T and AMD3100 mobilized PBMCs, and Gro-β T and AMD3100 mobilized PBMCs that have been depleted of CD34dim cells.

To confirm that the CD34$^{dim}$ cells in the Gro-β T and AMD3100-mobilized graft were responsible for the protection against aGvHD in the NSG mouse xenotransplantation model shown in FIG. 20, additional cohorts of mice were transplanted with 6×10$^6$ PBMCs from Gro-β T and AMD3100-mobilized rhesus monkeys, where CD34$^{dim}$ cells were first depleted by fluorescence activated cell sorting and T cell numbers and survival were compared to cohorts transplanted with Gro-β T and AMD3100-mobilized PBMCs and cohorts transplanted with unmobilized PBMCs. As shown in FIG. 21B, at day 14 post-transplant, mice transplanted with Gro-β T and AMD3100-mobilized PBMCs ("Gro-β T+Plerixafor") had significantly reduced numbers of rhesus CD45+CD3+ T cells in peripheral blood as compared to mice transplanted with unmobilized PBMCs ("Umnobilized") (p<0.001, n=10/group). By contrast, mice transplanted with Gro-β T and AMD3100 mobilized PBMCs that were depleted of CD34dim cells showed no significant difference in T-cell numbers by day 14 post-transplant (n=10) as compared to mice transplanted with unmobilized PBMCs ("Unmobilized") (see FIG. 21B). As shown in FIG. 21C, by day 44 post transplant, 0/10 mice transplanted with unmobilized PBMCs ("Unmobilized") survived versus 8/10 mice transplanted with Gro-β T and AMD3100-mobilized PBMCs ("Gro-β T+plerixafor") (p<0.05) and only 4/10 mice transplanted with Gro-β T and AMD3100 mobilized PBMCs that were depleted of CD34dim cells ("Gro-β T+plerixafor CD34$^{dim}$-depleted") (no significant difference versus Unmobilized).

Accordingly, these data demonstrate that co-administration of Gro-β T and AMD3100 results not only in rapid and efficacious mobilization of highly enriched HSCs but that these HSCs are enriched in a CD34$^{dim}$ cell population with potent immunosuppressive activity compared to AMD3100 alone or the current standard of care, G-CSF, and that transplant of this CD34$^{dim}$ cell population can result in a reduced incidence of or risk for aGVHD.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A method of performing an allogeneic hematopoietic stem cell transplant in a patient in need thereof, the method comprising infusing into the patient a therapeutically effective amount of allogeneic hematopoietic stem cells, wherein the hematopoietic stem cells were mobilized from bone marrow of a human donor into peripheral blood of the human donor by a method comprising administering to the donor (i) Gro-β T and (ii) plerixafor or a pharmaceutically acceptable salt thereof, wherein the Gro-β T is administered between 30-180 minutes after the plerixafor or the pharmaceutically acceptable salt thereof.

2. The method of claim 1, wherein the Gro-β T is administered intravenously to the donor.

3. The method of claim 1, wherein the plerixafor or a pharmaceutically acceptable salt thereof is administered subcutaneously to the donor.

4. The method of claim 1, wherein the plerixafor or pharmaceutically acceptable salt thereof is administered to the donor at a dose of from about 50 μg/kg to about 500 μg/kg.

5. The method of claim 4, wherein the plerixafor or pharmaceutically acceptable salt thereof is administered to the donor at a dose of from about 200 μg/kg to about 300 μg/kg.

6. The method of claim 5, wherein the plerixafor or pharmaceutically acceptable salt thereof is administered to the donor at a dose of about 240 μg/kg.

7. The method of claim 1, wherein the method prevents, reduces the risk of developing, or reduces the severity of graft versus host disease (GVHD) in the patient.

8. A method of performing an allogeneic hematopoietic stem cell transplant in a patient in need thereof, the method comprising infusing into the patient a therapeutically effective amount of allogeneic hematopoietic stem cells, wherein the hematopoietic stem cells were mobilized from bone marrow of a human donor into peripheral blood of the human donor by a method comprising administering to the donor (i) Gro-β T at a dose of from about 50 μg/kg to about 150 μg/kg and (ii) plerixafor or a pharmaceutically acceptable salt thereof, wherein the plerixafor or pharmaceutically acceptable salt thereof is administered subcutaneously to the donor at a dose of about 240 μg/kg, wherein the Gro-β T is administered intravenously.

9. A method of performing an allogeneic hematopoietic stem cell transplant in a patient in need thereof, the method comprising infusing into the patient a therapeutically effective amount of allogeneic hematopoietic stem cells, wherein the hematopoietic stem cells were mobilized from bone marrow of a human donor into peripheral blood of the human donor by a method consisting essentially of administering to the donor (i) Gro-β T at a dose of from about 50 μg/kg to about 150 μg/kg and (ii) plerixafor or a pharmaceutically acceptable salt thereof, wherein the plerixafor or pharmaceutically acceptable salt thereof is administered subcutaneously to the donor at a dose of about 240 μg/kg, wherein the Gro-β T is administered intravenously.

10. The method of claim 1, wherein the Gro-β T is administered about 60 minutes after the plerixafor or the pharmaceutically acceptable salt thereof.

11. The method of claim 7, wherein the method significantly reduces the risk of developing and/or severity of graft versus host disease (GVHD) in the patient as compared to an identical method in which only the plerixafor or the pharmaceutically acceptable salt thereof is administered.

12. The method of claim 1, wherein the Gro-β T is administered between 40-160 minutes after the plerixafor or the pharmaceutically acceptable salt thereof.

13. The method of claim 1, wherein the Gro-β T is administered between 50-150 minutes after the plerixafor or the pharmaceutically acceptable salt thereof.

14. The method of claim 1, wherein the Gro-β T is administered between 60-140 minutes after the plerixafor or the pharmaceutically acceptable salt thereof.

15. The method of claim 1, wherein the Gro-β T is administered between 70-130 minutes after the plerixafor or the pharmaceutically acceptable salt thereof.

16. The method of claim 1, wherein the Gro-β T is administered about 120 minutes after the plerixafor or the pharmaceutically acceptable salt thereof.

17. The method of claim 1, wherein the plerixafor or pharmaceutically acceptable salt thereof is administered to the donor at a dose of about 160 μg/kg.

18. A method of performing an allogeneic hematopoietic stem cell transplant in a patient in need thereof, the method comprising infusing into the patient a therapeutically effective amount of allogeneic hematopoietic stem cells, wherein the hematopoietic stem cells were mobilized from bone marrow of a human donor into peripheral blood of the human donor by a method comprising administering to the donor (i) Gro-β T and (ii) plerixafor or a pharmaceutically acceptable salt thereof, wherein the Gro-β T is administered between 60-140 minutes after the plerixafor or the pharmaceutically acceptable salt thereof, wherein the plerixafor or pharmaceutically acceptable salt thereof is administered subcutaneously to the donor at a dose of about 240 µg/kg.

19. The method of claim 18, wherein the Gro-β T is administered intravenously to the donor.

20. The method of claim 18, wherein the method prevents, reduces the risk of developing, or reduces the severity of graft versus host disease (GVHD) in the patient.

21. The method of claim 20, wherein the method significantly reduces the risk of developing and/or severity of graft versus host disease (GVHD) in the patient as compared to an identical method in which only the plerixafor or the pharmaceutically acceptable salt thereof is administered.

22. The method of claim 18, wherein the Gro-β T is administered between 70-130 minutes after the plerixafor or the pharmaceutically acceptable salt thereof.

23. The method of claim 18, wherein the Gro-β T is administered about 120 minutes after the plerixafor or the pharmaceutically acceptable salt thereof.

* * * * *

SEQUENCE LISTING

<160> NUMBER OF SEQ ID NOS: 4

<210> SEQ ID NO 1
<211> LENGTH: 73
<212> TYPE: PRT
<213> ORGANISM: Homo sapiens

<400> SEQUENCE: 1

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
                20                  25                  30

Pro His Cys Ala Gln Thr Glu Val Ile Ala Thr Leu Lys Asn Gly Gln
            35                  40                  45

Lys Ala Cys Leu Asn Pro Ala Ser Pro Met Val Lys Lys Ile Ile Glu
        50                  55                  60

Lys Met Leu Lys Asn Gly Lys Ser Asn
65                  70

<210> SEQ ID NO 2
<211> LENGTH: 69
<212> TYPE: PRT
<213> ORGANISM: Artificial Sequence
<220> FEATURE:
<223> OTHER INFORMATION: Synthetic Construct

<400> SEQUENCE: 2

Thr Glu Leu Arg Cys Gln Cys Leu Gln Thr Leu Gln Gly Ile His Leu
1               5                   10                  15

Lys Asn Ile Gln Ser Val Lys Val Lys Ser Pro Gly Pro His Cys Ala
                20                  25                  30

Gln Thr Glu Val Ile Ala Thr Leu Lys Asn Gly Gln Lys Ala Cys Leu
            35                  40                  45

Asn Pro Ala Ser Pro Met Val Lys Lys Ile Ile Glu Lys Met Leu Lys
        50                  55                  60

Asn Gly Lys Ser Asn
65

<210> SEQ ID NO 3
<211> LENGTH: 73
<212> TYPE: PRT
<213> ORGANISM: Homo sapiens

<400> SEQUENCE: 3

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
                20                  25                  30

Pro His Cys Ala Gln Thr Glu Val Ile Ala Thr Leu Lys Asn Gly Gln
            35                  40                  45

Lys Ala Cys Leu Asn Pro Ala Ser Pro Met Val Lys Lys Ile Ile Glu
        50                  55                  60

Lys Met Leu Lys Asp Gly Lys Ser Asn
65                  70

<210> SEQ ID NO 4
<211> LENGTH: 69
<212> TYPE: PRT
<213> ORGANISM: Artificial Sequence
<220> FEATURE:

```
<223> OTHER INFORMATION: Synthetic Construct

<400> SEQUENCE: 4

Thr Glu Leu Arg Cys Gln Cys Leu Gln Thr Leu Gln Gly Ile His Leu
1               5                   10                  15

Lys Asn Ile Gln Ser Val Lys Val Lys Ser Pro Gly Pro His Cys Ala
            20                  25                  30

Gln Thr Glu Val Ile Ala Thr Leu Lys Asn Gly Gln Lys Ala Cys Leu
        35                  40                  45

Asn Pro Ala Ser Pro Met Val Lys Lys Ile Ile Glu Lys Met Leu Lys
    50                  55                  60

Asp Gly Lys Ser Asn
65
```